(12) United States Patent
Potter et al.

(10) Patent No.: US 7,098,343 B2
(45) Date of Patent: Aug. 29, 2006

(54) COMPOUND

(75) Inventors: Barry Victor Lloyd Potter, Oxford (GB); Lok Wai Lawrence Woo, Oxford (GB); Atul Purohit, Oxford (GB); Michael John Reed, Oxford (GB); Oliver Brook Sutcliffe, Oxford (GB); Christian Bubert, Oxford (GB)

(73) Assignee: Sterix, Limited (GB)

( * ) Notice: Subject to any disclaimer, the term of this patent is extended or adjusted under 35 U.S.C. 154(b) by 157 days.

(21) Appl. No.: 10/300,494

(22) Filed: Nov. 20, 2002

(65) Prior Publication Data
US 2004/0019016 A1 Jan. 29, 2004

Related U.S. Application Data
(60) Provisional application No. 60/346,483, filed on Jan. 7, 2002.

(30) Foreign Application Priority Data
Nov. 21, 2001 (GB) .............................. 0127923
Nov. 20, 2002 (GB) .............................. PCT/GB02/05214

(51) Int. Cl.
*C07D 249/08* (2006.01)

(52) U.S. Cl. ................... 548/264.8; 548/262.2

(58) Field of Classification Search ............. 548/262.2, 548/264.8
See application file for complete search history.

(56) References Cited

U.S. PATENT DOCUMENTS

| 4,263,396 A | 4/1981 | Klotzer |
| 4,981,506 A | 1/1991 | Bozarth |
| 5,538,976 A | 7/1996 | Okada et al. |
| 5,674,886 A | 10/1997 | Okada et al. |

FOREIGN PATENT DOCUMENTS

| EP | 0164268 | 12/1985 |
| EP | 0481562 | 4/1992 |
| EP | 0089834 | 9/1993 |
| EP | 0640595 | 3/1995 |
| EP | 0641785 | 3/1995 |
| EP | 1193250 A1 | 7/2000 |
| WO | 90/14338 | 11/1990 |
| WO | 01/44268 A1 | 6/2001 |
| WO | 02/32409 A2 | 4/2002 |
| WO | 2005/058842 A1 | 6/2005 |

OTHER PUBLICATIONS

Koizumi et al, "Preparation of phenyl sulfamate derivatives as steroid sulfatase inhibitors", Teikoku Hormone Mfg. Co., Ltd., Japan, p. 85, 2001.

*Primary Examiner*—Golam M. M. Shameem
(74) *Attorney, Agent, or Firm*—Frommer Lawrence & Haug; Thomas J. Kowalski; Angela Collison

(57) ABSTRACT

There is provided a compound of Formula I

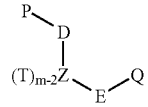

Formula I wherein each T is independently selected from H, hydrocarbyl, —F—R, and a bond with one of D, E, P or Q, or together with one of P and Q forms a ring; Z is a suitable atom the valency of which is m; D, E and F are each independently of each other an optional linker group, wherein when Z is nitrogen E is other than $CH_2$ and $C=O$; P, Q and R are independently of each other a ring system; and at least Q comprises a sulphamate group.

14 Claims, 4 Drawing Sheets

KEY ENZYMES IN STEROIDOGENESIS:-
1. SULPHATASE  2. AROMATASE  3. DEHYDROGENASE  4. 5α REDUCTASE

COMPOUND

CROSS REFERENCE TO RELATED APPLICATIONS

This application claims priority to provisional application Ser. No. 60/346,483, filed Jan. 7, 2002, British Patent Application serial number 0127923.1 filed Nov. 21, 2001 and PCT application number PCT/GB2002/005214 filed Nov. 20, 2002 which was filed in the UK claiming priority to both the U.S. provisional application Ser. No. 60/346,483 and British Patent Application serial number 0127923.1 entitled "Compound;" all of which are incorporated herein by reference, together with any documents therein cited and any documents cited or referenced in therein cited documents.

FIELD OF INVENTION

The present invention relates to a compound.

In particular the present invention relates to a compound and to a pharmaceutical composition comprising the compound. The present invention also relates to the use of the compound or composition in therapy applications.

BACKGROUND TO THE INVENTION

Evidence suggests that oestrogens are the major mitogens involved in promoting the growth of tumours in endocrine-dependent tissues, such as the breast and endometrium. Although plasma oestrogen concentrations are similar in women with or without breast cancer, breast tumour oestrone and oestradiol levels are significantly higher than in normal breast tissue or blood. In situ synthesis of oestrogen is thought to make an important contribution to the high levels of oestrogens in tumours and therefore inhibitors, in particular specific inhibitors, of oestrogen biosynthesis are of potential value for the treatment of endocrine-dependent tumours.

Over the past two decades, there has been considerable interest in the development of inhibitors of the aromatase pathway—which converts the androgen precursor androstenedione to oestrone. However, there is now evidence that the oestrone sulphatase (E1-STS) pathway, i.e. the hydrolysis of oestrone sulphate to oestrone (E1S to E1), and aromatase (i.e. conversion of androstenedione to oestrone) account for the production of oestrogens in breast tumours.

FIGS. 1 and 2 are schematic diagrams showing some of the enzymes involved in the in situ synthesis of oestrone from oestrone sulphate, oestradiol and androstenedione.

In FIG. 2, which schematically shows the origin of oestrogenic steroids in postmenopausal women, "ER" denotes Oestrogen Receptor, "DHA-S" denotes Dehydroepiandrosterone-Sulphate, "Adiol" denotes Androstenediol, "E1-STS" denotes Oestrone Sulphatase, "DHA-STS" denotes DHA-sulphatase, "Adiol-STS" denotes Adiol Sulphatase, and "17B-HSD" denotes Oestradiol 17B-hydroxysteroid dehydrogenase.

As can be seen, the main two enzymes that are involved in the peripheral synthesis of oestrogens are the aromatase enzyme and the enzyme oestrone sulphatase.

In short, the aromatase enzyme converts androstenedione, which is secreted in large amounts by the adrenal cortex, to oestrone. Recent reports have suggested that some flavones could inhibit aromatase activity.

Much of the oestrone so formed, however, is converted to oestrone sulphate (E1 S) and there is now a considerable body of evidence showing that E1S in plasma and tissue acts as a reservoir for the formation of oestrone by the action of oestrone sulphatase.

In this regard, it is now believed that the oestrone sulphatase (E1-STS) pathway—i.e. the hydrolysis of oestrone sulphate to oestrone (E1S to E1) is a major source of oestrogen in breast tumours. This theory is supported by a modest reduction of plasma oestrogen concentration in postmenopausal women with breast cancer treated by aromatase inhibitors, such as aminoglutethimide and 4-hydroxyandrostenedione and also by the fact that plasma E1S concentration in these aromatase inhibitor-treated patients remains relatively high. The long half-life of E1S in blood (10–12 h) compared with the unconjugated oestrogens (20 min) and high levels of steroid sulphatase activity in liver and, normal and malignant breast tissues, also lend support to this theory.

Thus, oestrogen formation in malignant breast and endometrial tissues via the sulphatase pathway makes a major contribution to the high concentration of oestrogens which are present in these tumours. However, inhibition of both the aromatase and sulphatase pathways could offer considerable therapeutic benefit.

PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters, such as N,N-dimethyl oestrone-3-sulphamate and, preferably, oestrone-3-sulphamate (otherwise known as "EMATE"). EMATE has the following structure:

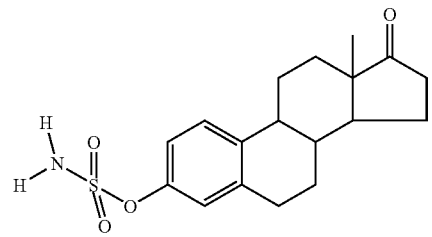

It is known that EMATE is a potent E1-STS inhibitor as it displays more than 99% inhibition of E1-STS activity in intact MCF-7 cells at 0.1 nM. EMATE also inhibits the E1-STS enzyme in a time- and concentration-dependent manner, indicating that it acts as an active site-directed inactivator. Although EMATE was originally designed for the inhibition of E1-STS, it also inhibits dehydroepiandrosterone sulphatase (DHA-STS), which is an enzyme that is believed to have a pivotal role in regulating the biosynthesis of the oestrogenic steroid androstenediol. Also, there is now evidence to suggest that androstenediol may be of even greater importance as a promoter of breast tumour growth. EMATE is also active in vivo as almost complete inhibition of rat liver E1-STS (99%) and DHA-STS (99%) activities resulted when it is administered either orally or subcutaneously. In addition, EMATE has been shown to have a memory enhancing effect in rats. Studies in mice have suggested an association between DHA-STS activity and the regulation of part of the immune response. It is thought that this may also occur in humans. The bridging O-atom of the sulphamate moiety in EMATE is important for inhibitory activity. Thus, when the 3-O-atom is replaced by other heteroatoms as in oestrone-3-N-sulphamate and oestrone-3-S-sulphamate, these analogues are weaker non-time-dependent inactivators.

In addition to oestrone, the other major steroid with oestrogenic properties which is produced by postmenopausal women is androstenediol (see FIG. 2).

Androstenediol, although an androgen, can bind to the oestrogen receptor (ER) and can stimulate the growth of ER positive breast cancer cells and the growth of carcinogen-induced mammary tumours in the rat. Importantly, in postmenopausal women 90% of the androstenediol produced originates from the androgen dehydroepiandrosterone sulphate (DHA-S) which is secreted in large amounts by the adrenal cortex. DHA-S is converted to DHA by DHA sulphatase, which may be the same as, or different from, the enzyme, oestrone sulphatase, which is responsible for the hydrolysis of E1S.

During the last 10–15 years considerable research has also been carried out to develop potent aromatase inhibitors, some of which are now marketed. However, in three recent reports of postmenopausal women with breast cancer who received aromatase inhibitor therapy, plasma E1S concentrations remained between 400–1000 pg/ml.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which.

Figure 1:
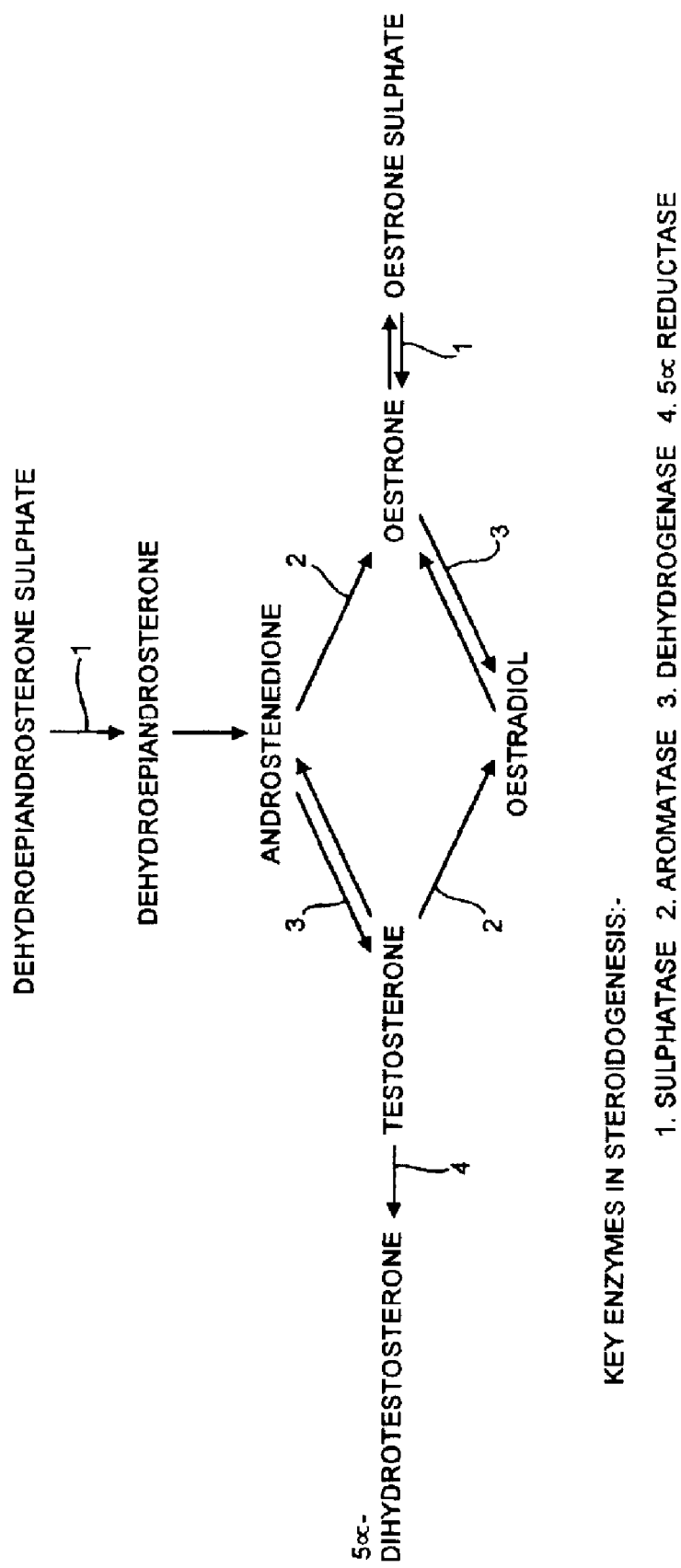
FIG. 1 is a scheme depicting the pathway of key enzymes in steroidogenesis.

In summation therefore in situ synthesis of oestrogen is thought to make an important contribution to the high levels of oestrogens in tumours and therefore specific inhibitors of oestrogen biosynthesis are of potential value for the treatment of endocrine-dependent tumours.

Moreover, even though oestrogen formation in malignant breast and endometrial tissues via the sulphatase pathway makes a major contribution to the high concentration of oestrogens, there are still other enzymatic pathways that contribute to in vivo synthesis of oestrogen.

The present invention seeks to provide novel compounds suitable for the inhibition of steroid sulphatase activity and aromatase activity.

SUMMARY ASPECTS OF THE PRESENT INVENTION

The present invention is based on the surprising finding that certain polycyclic compounds could be used as effective steroid sulphatase inhibitors and/or aromatase inhibitors and/or as agents that can influence cell cycling and/or as agents that can influence apoptosis.

In one aspect, the present invention is based on the surprising finding that certain polycyclic compounds could be used as effective steroid sulphatase inhibitors and/or aromatase inhibitors and/or as modulators of cell cycling and/or as modulators of apoptosis.

The polycyclic compounds comprise at least a central trivalent atom to which is attached either direct or indirectly via a linker at least two or three ring systems. At least one of the ring systems comprises a sulphamate group as a further substituent on the ring system.

The compounds of the present invention may comprise other substituents. These other substituents may, for example, further increase the activity of the compounds of the present invention and/or increase stability (ex vivo and/or in vivo).

DETAILED ASPECTS OF THE PRESENT INVENTION

According to one aspect of the present invention, there is provided a compound of Formula I

Formula I wherein each T is independently selected from H, hydrocarbyl, —F—R, and a bond with one of D, E, P or Q, or together with one of P and Q forms a ring; Z is a suitable atom the valency of which is m; D, E and F are each independently of each other an optional linker group, wherein when Z is nitrogen E is other than $CH_2$ and C=O; P, Q and R are independently of each other a ring system; and at least Q comprises a sulphamate group.

According to one aspect of the present invention, there is provided a method comprising (a) performing a steroid sulphatase (STS) assay and/or aromatase assay with one or more candidate compounds defined herein; (b) determining whether one or more of said candidate compounds is/are capable of modulating STS activity and/or aromatase activity and/or cell cycling and/or cell growth and/or apoptosis; and (c) selecting one or more of said candidate compounds that is/are capable of modulating STS activity and/or aromatase activity and/or cell cycling and/or cell growth and/or apoptosis.

According to one aspect of the present invention, there is provided a method comprising (a) performing a steroid sulphatase assay and/or aromatase assay with one or more candidate compounds as defined herein; (b) determining whether one or more of said candidate compounds is/are capable of inhibiting STS and/or aromatase activity; and (c) selecting one or more of said candidate compounds that is/are capable of inhibiting STS activity and/or aromatase activity and/or cell cycling and/or cell growth and/or apoptosis.

In any one of the methods of the present invention, one or more additional steps may be present. For example, the method may also include the step of modifying the identified candidate compound (such as by chemical and/or enzymatic techniques) and the optional additional step of testing that modified compound for STS inhibition effects (which may be to see if the effect is greater or different) and/or aromatase inhibition effects (which may be to see if the effect is greater or different). By way of further example, the method may also include the step of determining the structure (such as by use of crystallographic techniques) of the identified candidate compound and then performing computer modelling studies—such as to further increase its STS and/or aromatase inhibitory action. Thus, the present invention also encompasses a computer having a dataset (such as the crystallographic co-ordinates) for said identified candidate compound. The present invention also encompasses that identified candidate compound when presented on a computer screen for the analysis thereof—such as enzyme and/or protein binding studies.

According to one aspect of the present invention, there is provided a compound identified by the method of the present invention.

According to one aspect of the present invention, there is provided a compound according to the present invention for use in medicine.

According to one aspect of the present invention, there is provided a pharmaceutical composition comprising the compound according to the present invention optionally admixed with a pharmaceutically acceptable carrier, diluent, excipient or adjuvant.

According to one aspect of the present invention, there is provided the use of a compound according to the present invention in the manufacture of a medicament for use in the therapy of a condition or disease associated with STS and/or aromatase and/or cell cycling and/or apoptosis and/or cell growth.

According to one aspect of the present invention, there is provided the use of a compound according to the present invention in the manufacture of a medicament for use in the therapy of a condition or disease associated with adverse STS levels and/or adverse aromatase levels and/or cell cycling and/or apoptosis and/or cell growth.

According to one aspect of the present invention, there is provided the use of a compound according to the present invention in the manufacture of a medicament for inhibiting STS activity and/or inhibiting aromatase activity.

According to one aspect of the present invention, there is provided the use of a compound according to the present invention in the manufacture of a medicament for inhibiting STS activity and inhibiting aromatase activity.

According to one aspect of the present invention, there is provided the use of a compound in the manufacture of a medicament for use in the therapy of a condition or disease associated with aromatase and optionally associated with STS, wherein the compound is of Formula I

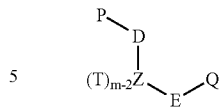

Formula I wherein each T is independently selected from H, hydrocarbyl, —F—R, and a bond with one of D, E, P or Q, or together with one of P and Q forms a ring; Z is a suitable atom the valency of which is m; D, E and F are each independently of each other an optional linker group, P, Q and R are independently of each other a ring system; and at least on of P, Q and R comprises a sulphamate group.

According to one aspect of the present invention, there is provided the use of a compound in the manufacture of a medicament for use in the therapy of a condition or disease associated with adverse aromatase levels and optionally associated with adverse STS levels, wherein the compound is of Formula I

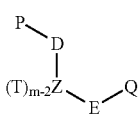

Formula I wherein each T is independently selected from H, hydrocarbyl, —F—R, and a bond with one of D, E, P or Q, or together with one of P and Q forms a ring; Z is a suitable atom the valency of which is m; D, E and F are each independently of each other an optional linker group, P, Q and R are independently of each other a ring system; and at least on of P, Q and R comprises a sulphamate group.

According to one aspect of the present invention, there is provided the use of a compound in the manufacture of a medicament for inhibiting aromatase activity and optionally for inhibiting STS activity, wherein the compound is of Formula I

Formula I wherein each T is independently selected from H, hydrocarbyl, —F—R, and a bond with one of D, E, P or Q, or together with one of P and Q forms a ring; Z is a suitable atom the valency of which is m; D, E and F are each independently of each other an optional linker group, P, Q and R are independently of each other a ring system; and at least on of P, Q and R comprises a sulphamate group.

The present invention also encompasses the novel compounds of the present invention (such as those presented herein), as well as processes for making same (such as the processes presented herein) as well as novel intermediates (such as those presented herein) for use in those processes.

For ease of reference, these and further aspects of the present invention are now discussed under appropriate section headings. However, the teachings under each section are not necessarily limited to each particular section.

Some Advantages

One key advantage of the present invention is that the compounds of the present invention can act as STS inhibitors.

One key advantage of the present invention is that the compounds of the present invention can act as aromatase inhibitors.

One key advantage of the present invention is that the compounds of the present invention can act as STS inhibitors and aromatase inhibitors.

Another advantage of the compounds of the present invention is that they may be potent in vivo.

Some of the compounds of the present invention may be non-oestrogenic compounds. Here, the term "non-oestrogenic" means exhibiting no or substantially no oestrogenic activity. Here, by the term "non-oestrogenic" means exhibiting no or substantially no systemic oestrogenic activity, such as that determined by Protocol 4.

Another advantage is that some of the compounds may not be capable of being metabolised to compounds which display or induce hormonal activity.

Some of the compounds of the present invention are also advantageous in that they may be orally active.

Some of the compounds of the present invention may useful for the prevention and/or treatment of cancer, such as breast cancer, as well as (or in the alternative) non-malignant conditions, such as the prevention and/or treatment of inflammatory conditions—such as conditions associated with any one or more of: autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders e.g. acne, psoriasis and contact dermatitis; graft versus host disease; eczema; asthma and organ rejection following transplantation. The compounds of the present invention are useful particularly when pharmaceuticals may need to be administered from an early age.

Thus, some of the compounds of the present invention are also believed to have therapeutic uses other than for the treatment of endocrine-dependent cancers, such as the treatment of autoimmune diseases.

The compounds of the present invention may also be useful as an inducer of apoptosis.

The compounds of the present invention may also be useful as a cell growth inhibitors.

Preferable Aspects

Z

As will be clear from Formula I, Z may be any atom which is capable of forming a bond or link with the optional linker groups D and/or E or ring systems P and/or Q and which is capable of forming a bond or link with the or each T. The valency of Z is denoted as m.

In one aspect Z is trivalent i.e. m=3.

In a preferred aspect $Z(T)_{m-2}$ is selected from Z(—F—R), ZH and Z-hydrocarbyl Suitable and preferred trivalent atoms include nitrogen (N), phosphorus (P) and boron (B). Preferably Z is Nitrogen.

In a preferred aspect $Z(T)_{m-2}$ is selected from N(—F—R), NH and N-hydrocarbyl In one aspect Z is tetravalent i.e. m=4.

In a preferred aspect $Z(T)_{m-2}$ is selected from ZH(—F—R), Z(—F—R)(—F—R), Z(—F—R)(hydrocarbyl), $ZH_2$, ZH-hydrocarbyl and Z(hydrocarbyl)(hydrocarbyl)

In a preferred aspect $Z(T)_{m-2}$ is selected from ZH(—F—R), $ZH_2$ and ZH-hydrocarbyl Suitable and preferred tetravalent atoms include carbon (C) and silicon (Si). Preferably Z is C. Thus preferably $Z(T)_{m-2}$ is selected from CH(—F—R), $CH_2$ and CH-hydrocarbyl

T

Each T of $Z(T)_{m-2}$ is independently selected from H, hydrocarbyl, a bond with one of D, E, P or Q, and —F—R, or together with one of P and Q forms a ring.

In one aspect each T of $Z(T)_{m-2}$ is independently selected from H, hydrocarbyl and —F—R.

When T is a hydrocarbyl group it may be selected from $C_1$–$C_{10}$ hydrocarbyl,
$C_1$–$C_5$ hydrocarbyl
$C_1$–$C_3$ hydrocarbyl.
hydrocarbon groups
$C_1$–$C_{10}$ hydrocarbon
$C_1$–$C_5$ hydrocarbon
$C_1$–$C_3$ hydrocarbon.
alkyl groups
$C_1$–$C_{10}$ alkyl
$C_1$–$C_5$ alkyl
$C_1$–$C_3$ alkyl.

The hydrocarbyl/hydrocarbon/alkyl of T may be straight chain or branched and/or may be saturated or unsaturated.

The hydrocarbyl/hydrocarbon/alkyl of T may be straight or branched hydrocarbon groups containing at least one hetero atom in the group.

Optional Linker—D, E and F

Independently of each other linker groups D, E and F may or may not be present. If present D, E or F may be selected from C=O and hydrocarbyl groups.

The term "hydrocarbyl group" as used herein means a group comprising at least C and H and may optionally comprise one or more other suitable substituents. Examples of such substituents may include halo, alkoxy, nitro, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

A typical hydrocarbyl group is a hydrocarbon group. Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

Preferably D, E and F are independently selected from $C_1$–$C_{10}$ hydrocarbyl, $C_1$–$C_5$ hydrocarbyl or $C_1$–$C_3$ hydrocarbyl.

Preferably D, E and F are independently selected from hydrocarbon groups, preferably $C_1$–$C_{10}$ hydrocarbon, $C_1$–$C_5$ hydrocarbon or $C_1$–$C_3$ hydrocarbon.

Preferably D, E and F are independently selected from alkyl groups, $C_1$–$C_{10}$ alkyl, $C_1$–$C_5$ alkyl or $C_1$–$C_3$ alkyl.

The hydrocarbyl/hydrocarbon/alkyl of D, E and F may be straight chain or branched and/or may be saturated or unsaturated.

In one preferred aspect D, E and F are independently selected from straight or branched hydrocarbon groups containing at least one hetero atom in the group.

In a preferred aspect D, E and F are independently selected from hydrocarbon groups and a group of the formula

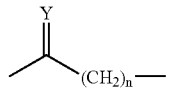

wherein n is 1 to 6 and Y=O, S or $CH_2$.

In a preferred aspect D, E and F are independently selected linear or branched hydrocarbon groups having a carbon chain of from 1 to 6 carbon atoms and a group of the formula

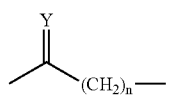

wherein n is 1 to 6 and Y=O, S or $CH_2$

In one preferred aspect only one of optional linker groups D, E and F is present. It will be understood that by only one it is meant that one of the linkers is present and the other optional linker group(s) is/are not present.

In one preferred aspect E (and preferably D and/or F) is selected from hydrocarbyl groups comprising at least two carbons or wherein the total number of carbons and hetero atoms is at least two.

In one preferred aspect E (and preferably D and/or F) is selected from hydrocarbyl groups containing at least one hetero atom in the group. Preferably the hetero atom is selected from sulphur, nitrogen and oxygen.

In one preferred aspect E (and preferably D and/or F) is selected from straight or branched hydrocarbon groups containing at least one hetero atom in the group. Preferably the hetero atom is selected from sulphur, nitrogen and oxygen.

In one preferred aspect E (and preferably D and/or F) is selected from hydrocarbon groups comprising at least 2 carbons and a group of the formula

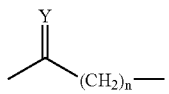

wherein n is 1 to 6 and Y=Oxygen, Sulphur or $CH_2$.

In one preferred aspect E (and preferably D and/or F) is selected from linear or branched hydrocarbon groups having a carbon chain of from 2 to 6 carbon atoms and a group of the formula

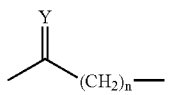

wherein n is 1 to 6 and Y=Oxygen, Sulphur or $CH_2$.

In one preferred aspect E (and preferably D and/or F) is selected from straight or branched alkyl groups, preferably $C_{1-10}$ alkyl, more preferably $C_{1-5}$ alkyl, containing at least one hetero atom in the group. Preferably the hetero atom is selected from sulphur, nitrogen and oxygen.

In one preferred aspect E (and preferably D and/or F) is selected from straight chain alkyl groups, preferably $C_{1-10}$ alkyl, more preferably $C_{1-5}$ alkyl, containing at least one hetero atom in the group. Preferably the hetero atom is selected from sulphur, nitrogen and oxygen.

When E (or D and/or F) contains a hetero atom, preferably the hetero atom is attached to the ring Q (or D or R in the case of D and F).

In a highly preferred aspect the compound of the present invention is of the formula

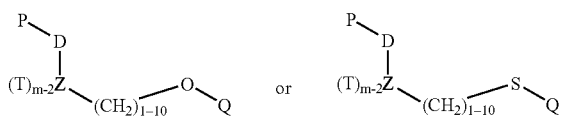

In a highly preferred aspect the compound of the present invention is of the formula

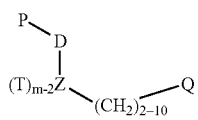

Rings—P, Q and R

The present compound comprises two or three ring systems each of which is attached directly or indirectly via linker D, E or F to Z. For each of P, Q and R the ring system need not be a cyclic structure. In this regard, the ring system may be a linear structure that may have the ability to conform to a ring like structure when in in vivo. However in preferred aspects each ring system is a cyclic structure.

In a preferred aspect, P, Q and R are independently selected from cyclic groups.

At least one of the cyclic groups P, Q and R may be a heterocyclic group (a heterocycle) or a non-heterocyclic group. Suitable hetero atoms of a heterocyclic group include N, S and O.

At least one of the cyclic groups P, Q and R may be ring systems comprising carbon and optionally one or more hetero atoms.

In a preferred aspect at least one of P, Q and R is, or P, Q and R are independently selected from a ring system comprising carbon and optionally one, two or three hetero atoms. Preferably at least one of P, Q and R is, or P, Q and R are independently selected from a ring system comprising carbon and one or more hetero atoms.

When hetero atoms are present in a ring system to provide a heterocyclic group, the hetero atoms may be present in any amount. In one preferred aspect at least one of P, Q and R is, or P, Q and R are independently selected from, a ring system comprising carbon and one or more hetero atoms selected from N, S and O.

When one of P, Q and R is a heterocyclic group the other of P, Q and R may or may not be heterocyclic groups. In a preferred aspect one of P, Q and R is a ring system comprising carbon and one or more hetero atoms and the other of P, Q and R are independently carbocyclic ring systems. It will be understood that by carbocyclic it is meant a ring system in which the ring contains only carbon atoms together with optional substituents on the ring. In this aspect preferably one of P, Q and R is a ring system comprising carbon and one or more hetero atoms selected from N, S and O and two of P, Q and R are independently carbocyclic ring systems.

In one aspect of the invention at least one of P, Q and R, or P, Q and R are independently selected a saturated ring structure or an unsaturated ring structure (such as an aryl group).

In one aspect of the invention at least one of P, Q and R, or P, Q and R are independently selected a saturated ring structure such a cycloalkyl group.

Preferably, at least one P, Q and R is an aryl ring.

In one aspect of the invention at least one of P, Q and R, or P, Q and R are independently selected from substituted or unsubstituted aromatic rings.

In one aspect of the invention at least one of P, Q and R is or comprises a substituted or unsubstituted aromatic ring.

In one aspect one of P, Q or R may be a polycyclic group, which need not be a fused polycycle. The term "polycyclic" includes fused and non-fused ring structures including combinations thereof. If the ring system of P, Q or R is polycyclic some or all of the ring components of the ring system may be fused together or joined via one or more suitable spacer groups.

The ring size of any of P, Q and R may be chosen by one skilled in the art to achieve compounds having desired activity. Typically P, Q and R are independently ring systems comprising from 3 to 10 members, such as ring systems comprising from 5, 6 or 7 members.

Heterocyclic ring systems for use in the present invention include imidazole, tetrazole, pyrazole, triazole, such as 1H-1,2,3-triazole, 1H-1,2,4-triazole, 4H-1,2,4-triazole; optionally substituted 5- or 6-membered heterocyclic group containing 1 to 3 hetero atoms each selected from N, O and S, optionally substituted aryl (monocyclic or polycyclic aromatic), pyridazine, pyrimidine, triazine such as 1,3,5 triazine, and optionally substituted bicyclic condensed heterocyclic group consisting of the above heterocyclic group condensed with benzene.

In a highly preferred aspect at least one of P, Q and R is, or P, Q and R are independently selected from triazole, in particular 1H-1,2,3-triazole, 1H-1,2,4-triazole, 4H-1,2,4-triazole In a highly preferred aspect at least one of P, Q and R is 4H-1,2,4-triazole.

In a highly preferred aspect at least one of P, Q and R is triazole, in particular 1H-1,2,3-triazole, 1H-1,2,4-triazole, 4H-1,2,4-triazole and the other of P, Q and R are substituted or unsubstituted benzyl rings.

In a highly preferred aspect at least one of P, Q and R is 4H-1,2,4-triazole and the other of P, Q and R are substituted or unsubstituted benzyl rings.

In the above aspects the triazole may be linked to X via a C in the triazole ring or a N in the triazole ring. In one aspect the triazole is linked to X via a C in the triazole ring.

In a preferred aspect P is a ring system comprising carbon and one or more hetero atoms and Q and R, if present, are independently carbocyclic ring systems.

In a preferred aspect P is a ring system comprising carbon and one or more hetero atoms selected from N, S and O and Q and R, if present, are independently carbocyclic ring systems.

In a preferred aspect Q and R, if present, are independently carbocyclic ring systems, and P is a ring system selected from imidazole, tetrazole, pyrazole, triazole, such as 1H-1,2,3-triazole, 1H-1,2,4-triazole, 4H-1,2,4-triazole; optionally substituted 5- or 6-membered heterocyclic group containing 1 to 3 hetero atoms each selected from N, O and S, optionally substituted aryl (monocyclic or polycyclic aromatic), pyridazine, pyrimidine, triazine such as 1,3,5 triazine, and optionally substituted bicyclic condensed heterocyclic group consisting of the above heterocyclic group condensed with benzene.

In a preferred aspect Q and R, if present, are independently carbocyclic ring systems, and P is a ring system selected from triazoles, in particular 1H-1,2,3-triazole, 1H-1,2,4-triazole, 4H-1,2,4-triazole In a preferred aspect Q and R, if present, are independently carbocyclic ring systems, and P is 4H-1,2,4-triazole.

In a preferred aspect P is a ring system comprising carbon and one or more hetero atoms and Q and R, if present, are independently optionally substituted benzyl rings.

In a preferred aspect P is a ring system comprising carbon and one or more hetero atoms selected from N, S and O and Q and R, if present, are independently optionally substituted benzyl rings.

In a preferred aspect Q and R, if present, are independently optionally substituted benzyl rings, and P is a ring system selected from imidazole, tetrazole, pyrazole, triazole, such as 1H-1,2,3-triazole, 1H-1,2,4-triazole, 4H-1,2,4-triazole; optionally substituted 5- or 6-membered heterocyclic group containing 1 to 3 hetero atoms each selected from N, O and S, optionally substituted aryl (monocyclic or polycyclic aromatic), pyridazine, pyrimidine, triazine such as 1,3,5 triazine, and optionally substituted bicyclic condensed heterocyclic group consisting of the above heterocyclic group condensed with benzene.

In a preferred aspect Q and R, if present, are independently optionally substituted benzyl rings, and P is a ring system selected from triazoles, in particular 1H-1,2,3-triazole, 1H-1,2,4-triazole, 4H-1,2,4-triazole In a preferred aspect Q and R, if present, are independently optionally substituted benzyl rings, and P is 4H-1,2,4-triazole.

The ring systems P, Q and R may be substituted by one or more substituents. Preferred substituents (other than the required sulphamate group) include hydrocarbyl, oxyhydrocarbyl, halo and cyano (—C≡N) groups. The ring systems P, Q and R may also be substituted by one or more substituents selected from phosphonate groups, thiophosphonate groups, sulphonate groups and sulphonamide groups.

The term "oxyhydrocarbyl" group as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms. Suitable hetero atoms will be apparent to those skilled in the art and include, for instance, sulphur and nitrogen.

In one embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Typically, the oxyhydrocarbyl group is of the formula $C_{1-6}O$ (such as a $C_{1-3}O$).

Preferably Q is substituted with one or more halo atoms. Preferably the halo atoms are at a position ortho to the sulphamate group, Preferably R, particularly when it is a carbocyclic group, is substituted with a cyano (—C≡N) group.

Further Preferred Compounds

In one preferred aspect the compound of the present invention is of the Formula II

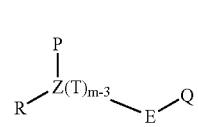

Formula II wherein each T is independently selected from H, hydrocarbyl, —F—R', and a bond with one of E, P or Q, or together with one of P and Q forms a ring; Z is a suitable atom the valency of which is m; when Z is Nitrogen E is an optional linker group other than $CH_2$ and C=O; P, Q, R and R' are independently of each other a ring system; and Q comprises a sulphamate group.

In one preferred aspect the compound of the present invention is of the Formula III

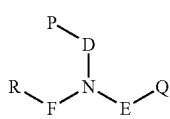

Formula III wherein D, E and F are each independently of each other an optional linker group, wherein E is other than CH$_2$ and C=O; P, Q and R are independently of each other a ring system; and at least Q comprises a sulphamate group.

In one preferred aspect the compound of the present invention is of the Formula IIIa

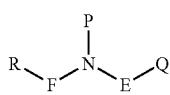

Formula IIIa wherein E and F are each independently of each other an optional linker group, wherein E is other than CH$_2$ and C=O; P, Q and R are independently of each other a ring system; and at least Q comprises a sulphamate group.

In one preferred aspect the compound of the present invention is of the Formula IIIb

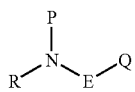

Formula IIIb wherein E is an optional linker group, wherein E is other than CH$_2$ and C=O; P, Q and R are independently of each other a ring system; and at least Q comprises a sulphamate group.

In one preferred aspect the compound of the present invention is of the Formula IIIc

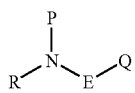

Formula IIIc wherein E is a linker group, wherein E is other than CH$_2$ and C=O; P, Q and R are independently of each other a ring system; and at least Q comprises a sulphamate group.

In one preferred aspect the compound of the present invention is of the Formula IIId

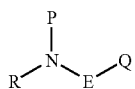

Formula IIId wherein E is a straight chain or branched hydrocarbon group, preferably a C$_1$–C$_{10}$ hydrocarbon group containing at least two carbons or at least one hetero atom in the group; P, Q and R are independently of each other a ring system; and at least Q comprises a sulphamate group.

In one preferred aspect the compound of the present invention is of the Formula IV

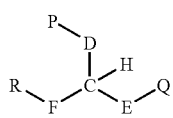

Formula IV wherein D, E and F are each independently of each other an optional linker group, P, Q and R are independently of each other a ring system; and at least Q comprises a sulphamate group.

In one preferred aspect the compound of the present invention is of the Formula IVa

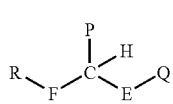

Formula IVa wherein E and F are each independently of each other an optional linker group, P, Q and R are independently of each other a ring system; and at least Q comprises a sulphamate group.

In one preferred aspect the compound of the present invention is of the Formula IVb

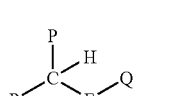

Formula IVb wherein E is an optional linker group, P, Q and R are independently of each other a ring system; and at least Q comprises a sulphamate group.

In one preferred aspect the compound of the present invention is of the Formula IVc

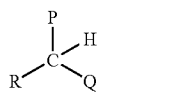

Formula IVc wherein P, Q and R are independently of each other a ring system; and at least Q comprises a sulphamate group.

In formulae II, III, IIIa, IIIb, IIIc, IIId, IV, IVa, IVb, IVc, preferably one of P, Q and R is a ring system comprising carbon and one or more hetero atoms and two of P, Q and R are independently selected from carbocyclic ring systems.

In formulae II, III, IIIa, IIIb, IIIc, IIId, IV, IVa, IVb, IVc, preferably one of P, Q and R is a ring system comprising carbon and one or more hetero atoms selected from Nitrogen, Sulphur and Oxygen and two of P, Q and R are independently selected from carbocyclic ring systems.

In formulae II, III, IIIa, IIIb, IIIc, IIId, IV, IVa, IVb, and IVc, preferably one of P, Q and R is 4H-1,2,4-triazole and two of P, Q and R are independently selected from substituted or unsubstituted benzyl rings.

In one preferred aspect the compound of the present invention is of the Formula V

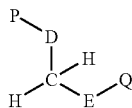

Formula V wherein D and E are each independently of each other an optional linker group, P and Q are independently of each other a ring system; and at least Q comprises a sulphamate group.

In one preferred aspect the compound of the present invention is of the Formula Va

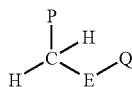

Formula Va wherein E is an optional linker group, P and Q are independently of each other a ring system; and at least Q comprises a sulphamate group.

In one preferred aspect the compound of the present invention is of the Formula Vb

Formula Vb wherein P and Q are independently of each other a ring system; and at least Q comprises a sulphamate group.

In formulae V, Va, and Vb, preferably one of P and Q is a ring system comprising carbon and one or more hetero atoms and the other of P and Q is a carbocyclic ring system.

In formulae V, Va, and Vb, preferably one of P and Q is a ring system comprising carbon and one or more hetero atoms selected from Nitrogen, Sulphur and Oxygen and the other of P and Q is a carbocyclic ring system.

In formulae V, Va, and Vb, preferably one of P and Q is 4H-1,2,4-triazole and the other of P and Q is a substituted or unsubstituted benzyl ring.

In a particularly preferred aspect the compound of the present invention is of Formula VI

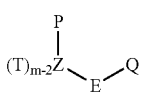

Formula VI wherein each T is independently selected from H, hydrocarbyl, a bond with one of D, E, P or Q and —R, or together with one of P and Q forms a ring, and wherein m is the valency of Z; E is an optional linker group; wherein P, Q and R are each independently of each other a ring system; and Q comprises a sulphamate group.

A highly preferred compound of the present invention is a compound selected from compounds of the formula

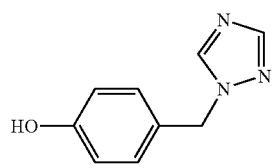

STX269  4-[1,2,4]Triazol-1-ylmethylphenol (LWO02015A, STX269)

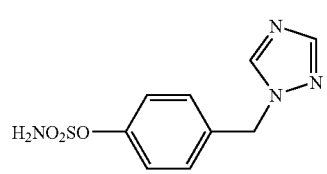

STX270  Sulfamic acid 4-[1,2,4]triazol-1-ylmethylphenyl ester (LWO02017A, STX270)

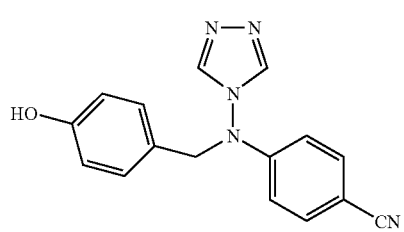

STX265  4-[(4-Hydroxylbenzyl)-[1,2,4]triazol-4-ylamino]benzonitrile (LWO02030, STX265)

-continued

| | | |
|---|---|---|
| 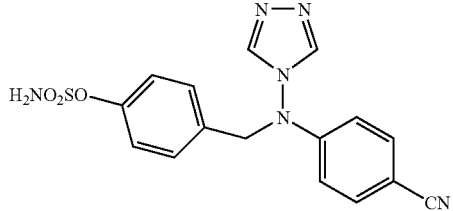 | STX258 | Sulfamic acid 4-{[(4-cyanophenyl)-[1,2,4]triazol-4-ylamino]methyl}phenyl ester (LWO02031, STX258) |
| 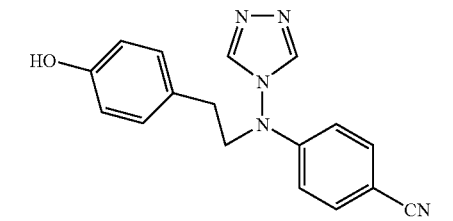 | STX290 | 4-{[2-(4-Hydroxyphenyl)ethyl]-[1,2,4]triazol-4-yl-amino}benzonitrile (LWO02063, STX290) |
| 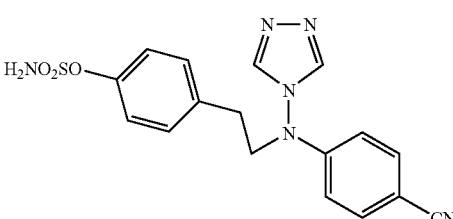 | STX273 | Sulfamic acid 4-{2-[(4-cyanophenyl)-[1,2,4]triazol-4-ylamino]ethyl}phenyl ester (LWO02066, STX273) |
| 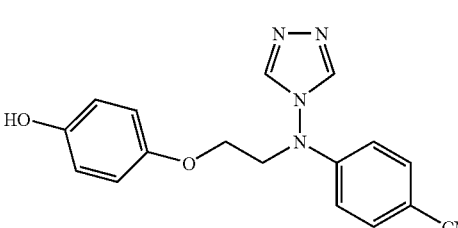 | STX291 | 4-{[2-(4-Hydroxyphenoxy)ethyl]-[1,2,4]triazol-4-yl-amino}benzonitrile (LWO02076, STX291) |
| 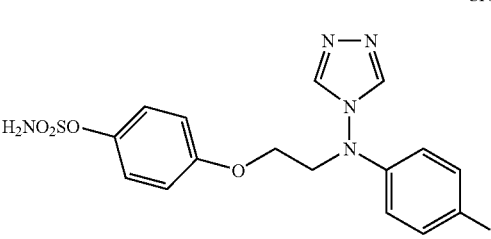 | STX292 | Sulfamic acid 4-{2-[(4-cyanophenyl)-[1,2,4]triazol-4-yl-amino]ethoxy}phenyl ester (LWO02077, STX292) |
| 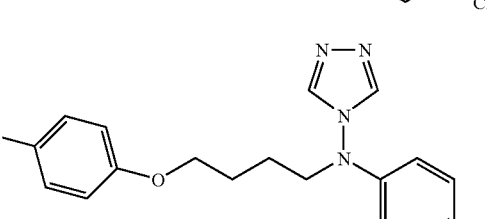 | STX287 | 4-{[4-(4-Hydroxyphenoxy)butyl]-[1,2,4]triazol-4-ylamino}benzonitrile (LWO02067, STX287) |
| 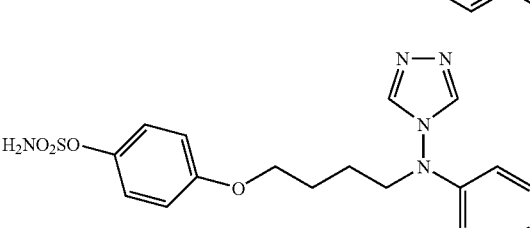 | STX288 | Sulfamic acid 4-{4-[(4-cyanophenyl)-[1,2,4]triazol-4-ylamino]buto |

-continued

| | | |
|---|---|---|
| 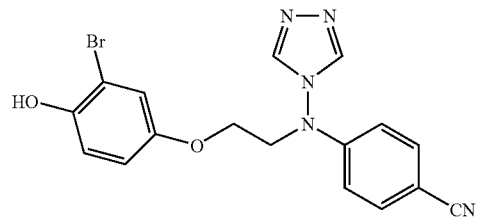 | STX300 | 4-{[2-(3-Bromo-4-hydroxyphenoxy)ethyl]-[1,2,4]triazot-4-ylamino}benzonitrile (STX300) |
| 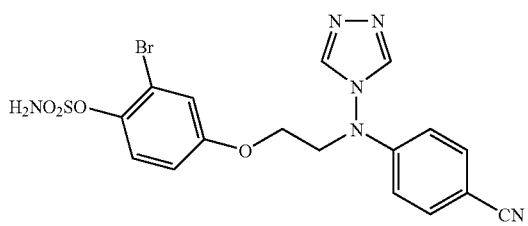 | STX301 | Sulfamic acid 2-bromo-4-{2-[(4-cyanophenyl)-[1,2,4]triazol-4-ylamino]ethoxy}phenyl ester (STX301) |
| 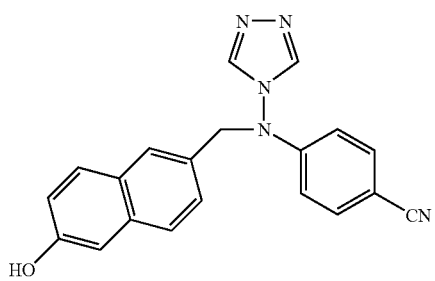 | STX335 | 4-[(6-Hydroxy-naphthalen-2-ylmethyl)-[1,2,4]triazol-4-yl-amino]-benzonitrile (JRL01012, STX 335) |
| 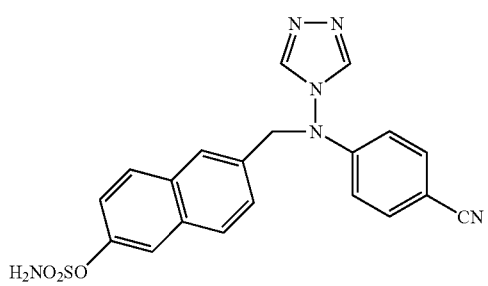 | STX336 | Sulfamic acid 6-{[(4-cyano-phenyl)-[1,2,4]triazol-4-yl-amino]-methyl}-naphthalen-2-yl ester (JRL01014, STX 336) |
| 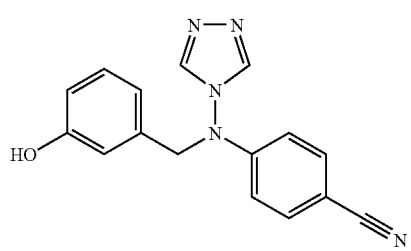 | STX333 | 4-[(3-Hydroxybenzyl)(4-cyanophenyl)amino]-4H-[1,2,4]triazole (OBS01022, STX333) |
| 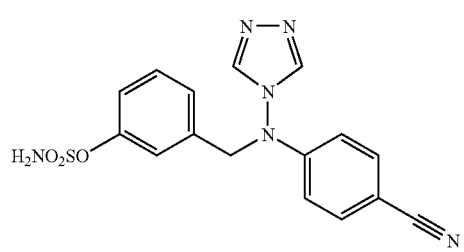 | STX334 | 4-[(3-O-Sulfamoylbenzyl)(4-cyanophenyl)amino]-4H-[1,2,4]triazole (OBS01030, STX334) |

-continued

| | | |
|---|---|---|
| 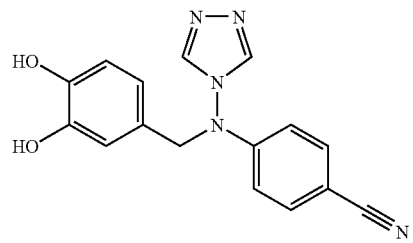 | STX355 | 4-{(3,4-Bis(hydroxybenzyl)(4-cyanophenyl)amino]-4H-[1,2,4]triazole (OBS01067, STX355) |
| 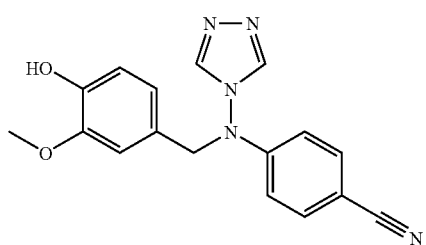 | STX362 | 4-[(3-Hydroxy-4-methoxybenzyl)(4-cyanophenyl)amino]-4H-[1,2,4]triazole (OBS01076, STX362) |
| 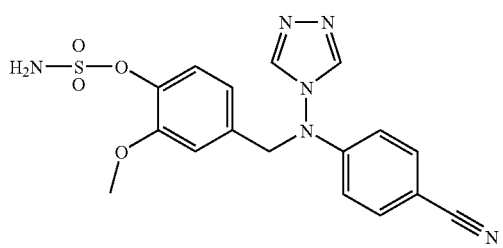 | STX660 | 4-[(4-Methoxy-3-O-sulfamoylbenzyl)(4-cyanophenyl)amino]-4H-[1,2,4]triazole (OBS01135, STX660) |
| 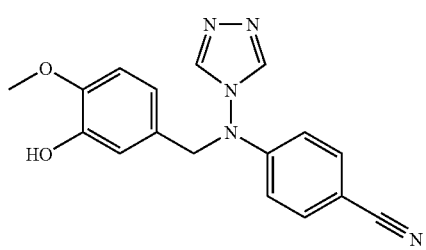 | STX363 | 4-[(3-Hydroxy-4-methoxybenzyl)(4-cyanophenyl)amino]-4H-[1,2,4]triazole (OBS01080, STX363) |
| 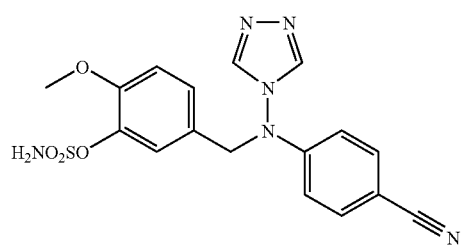 | STX661 | 4-[(4-Methoxy-3-O-sulfamoylbenzyl)(4-cyanophenyl)amino]-4H-[1,2,4]triazole (OBS01137, STX661) |
| 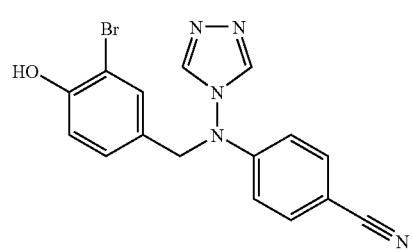 | STX405 | 4-[(3-Bromo-4-hydroxybenzyl)(4-cyanophenyl)amino]-4H-1,2,4]triazole (OBS01132, STX405) |

-continued

| | | |
|---|---|---|
| 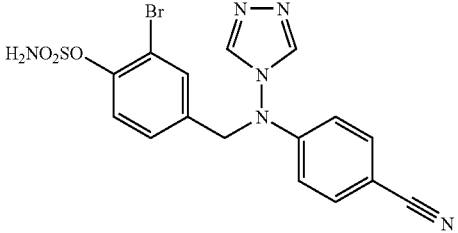 | STX681 | 4-[(3-Bromo-4-O-sulfamoylbenzyl)(4-cyanophenyl)amino]-4H-[1,2,4]triazole (OBS01141, STX681) |
| 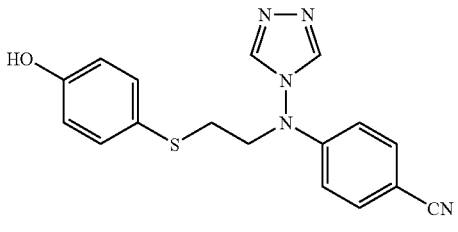 | STX456 | 4-{[2-(4-Hydroxy-phenylsulfanyl)-ethyl]-1,2,4]triazol-4-yl-amino}-benzonitrile (CAB02137, STX456) |
| 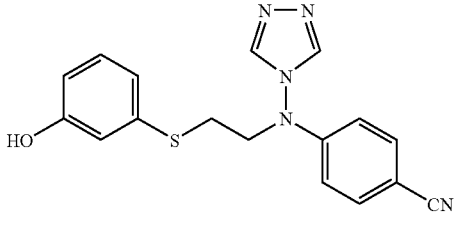 | STX512 | 4-{[2-(3-Hydroxy-phenylsulfanyl)-ethyl]-1,2,4]triazol-4-yl-amino}-benzonitrile (CAB02149, STX512) |
| 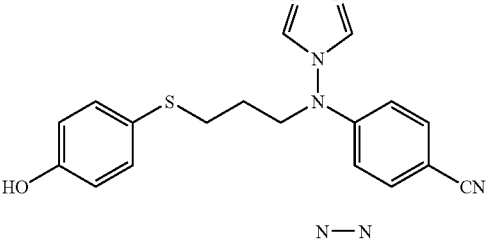 | STX596 | 4-{[3-(4-Hydroxy-phenylsulfanyl)-propyl]-1,2,4]triazol-4-yl-amino}-benzonitrile (CAB0182, STX596) |
| 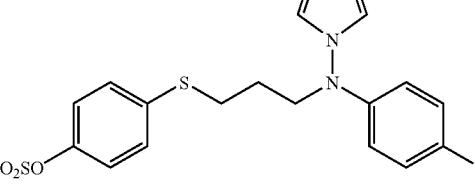 | STX597 | Sulfamic acid 4-{3-[(4-cyano-phenyl)-[1,2,4]triazol-4-yl-amino]-propylsulfanyl}-phenyl ester (CAB02184, STX597) |
| 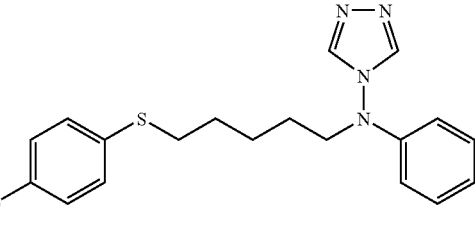 | STX698 | 4-{[5-(4-Hydroxy-phenylsulfanyl)-pentyl]-[1,2,4]triazol-4-yl-amino-benzonitrile (CAB03014, STX698) |
| 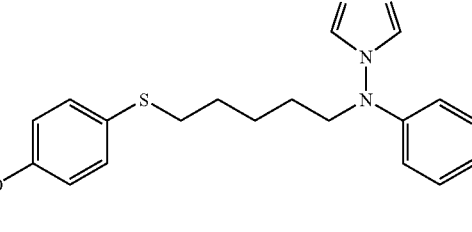 | STX699 | Sulfamic acid 4-{5-[(4-cyano-phenyl)-[1,2,4]triazol-4-yl-amino]-pentylsulfanyl}-phenyl ester (CAB03025, STX699) |

| | | |
|---|---|---|
| | STX625 | 4-{[10-(4-Hydroxy-phenylsulfanyl)-decyl]-[1,2,4]triazol-4-yl-amino-benzonitrile (CAB03011, STX625) |
| | STX655 | Sulfamic acid 4-{10-[(4-cyano-phenyl)-[1,2,4]triazol-4-yl-amino]-decylsulfanyl}-phenyl ester (CAB03012, STX655) |
| | STX435 | 4-[(3,5-Dichloro-4-hydroxy-benzyl)-[1,2,4]triazol-4-yl-amino]-benzonitrile (CAB02120, STX435) |
| | STX447 | 4-[(3-Chloro-4-hydroxy-benzyl)-[1,2,4]triazol-4-yl-amino]-benzonitrile (CAB02130, STX447) |
| | STX694 | Sulfamic acid 2-chloro-4-{[(4-cyano-phenyl)-[1,2,4]triazol-4-yl-amino[-methyl}-phen |
| | STX483 | 4-[(4-Chloro-3-hydroxy-benzyl)-[1,2,4]triazol-4-yl-amino]-benzonitrile (CAB02141, STX483) |
| | STX559 | Sulfamicacid-2-chloro-5-{[(4-cyano-phenyl)-[1,2,4]triazol-4-yl-amino]-methyl}-phenyl ester (CAB02176, STX559)) |

| | | |
|---|---|---|
| 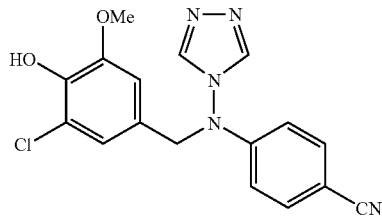 | STX600 | 4-[(3-chloro-4-hydroxy-5-methoxy-benzyl)-[1,2,4]triazol-4-yl-amino]-benzonitrile (CAB02179, STX600) |
| 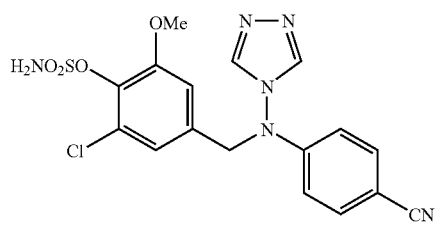 | STX601 | Sulfamicacid-2-chloro-4-{[(4-cyano-phenyl)-[1,2,4]triazol-4-yl-amino]-methyl}-6-methoxy-phenyl ester (CAB02181, STX601) |
| 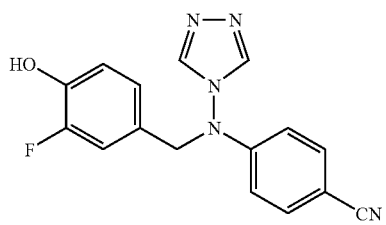 | STX696 | 4-[(3-Fluoro-4-hydroxy-benzyl)-[1,2,4]triazol-4-yl-amino]-benzonitrile (CAB03020, STX696) |
| 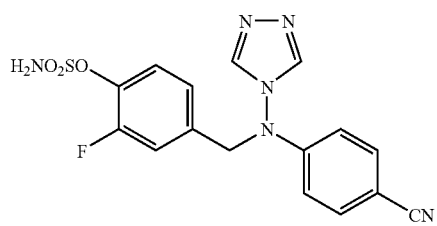 | STX700 | Sulfamicacid-4-{[(4-cyano-phenyl)-[1,2,4]triazol-4-yl-amino]-methyl}-2-fluoro-phenyl ester (CAB03021, STX700) |
| 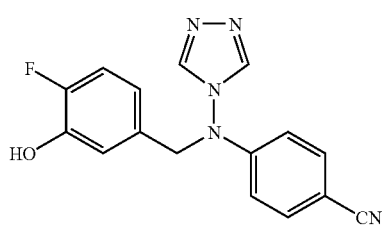 | STX488 | 4-[(4-Fluoro-3-hydroxy-benzyl)-[1,2,4]triazol-4-yl-amino]-benzonitrile (CAB02154, STX488) |
| 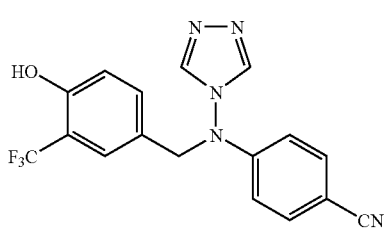 | STX781 | 4-[(4-Hydroxy-3-trifluoromethyl-benzyl)-[1,2,4]triazol-4-yl-amino]-benzonitrile (CAB03059, STX781) |

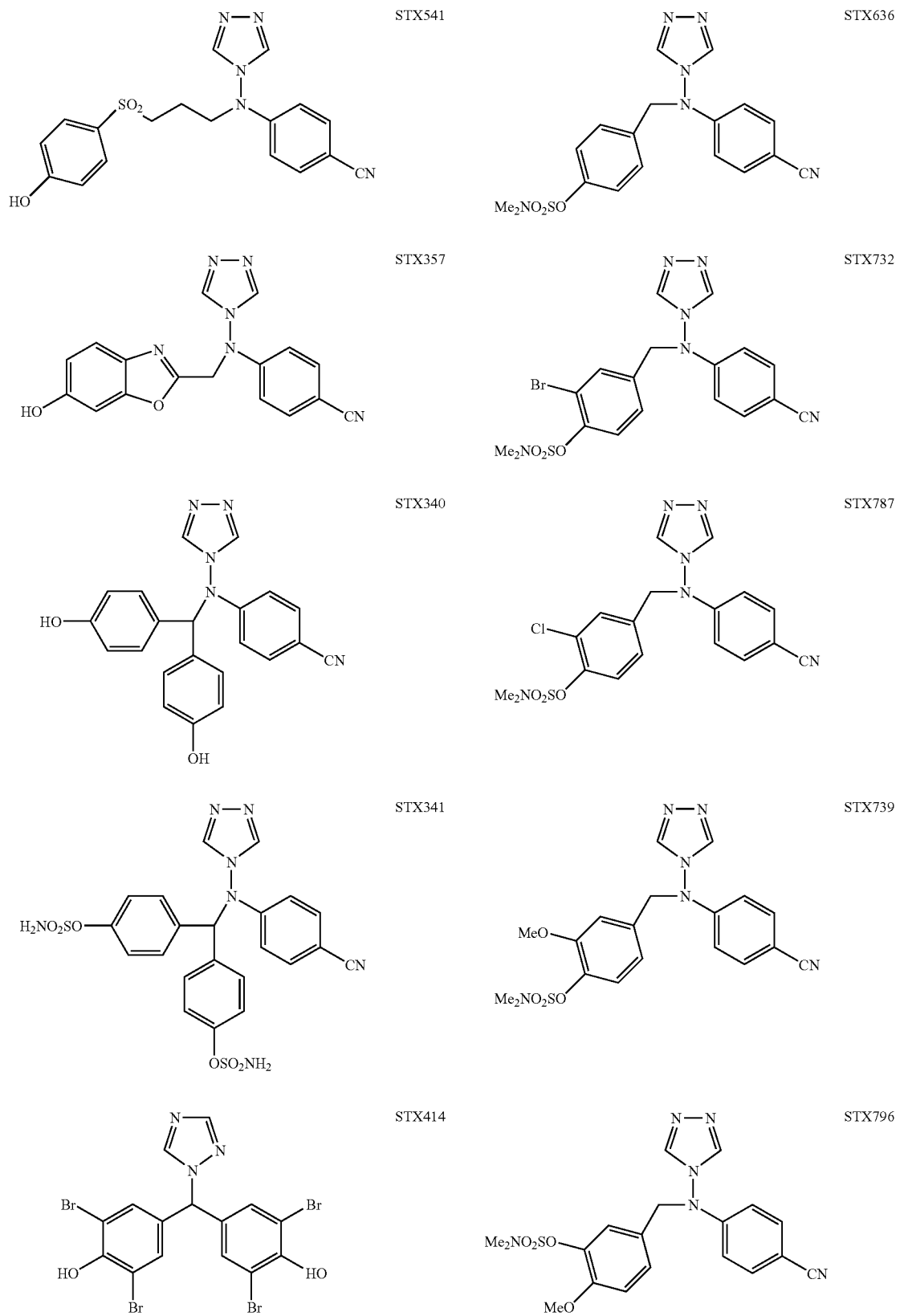

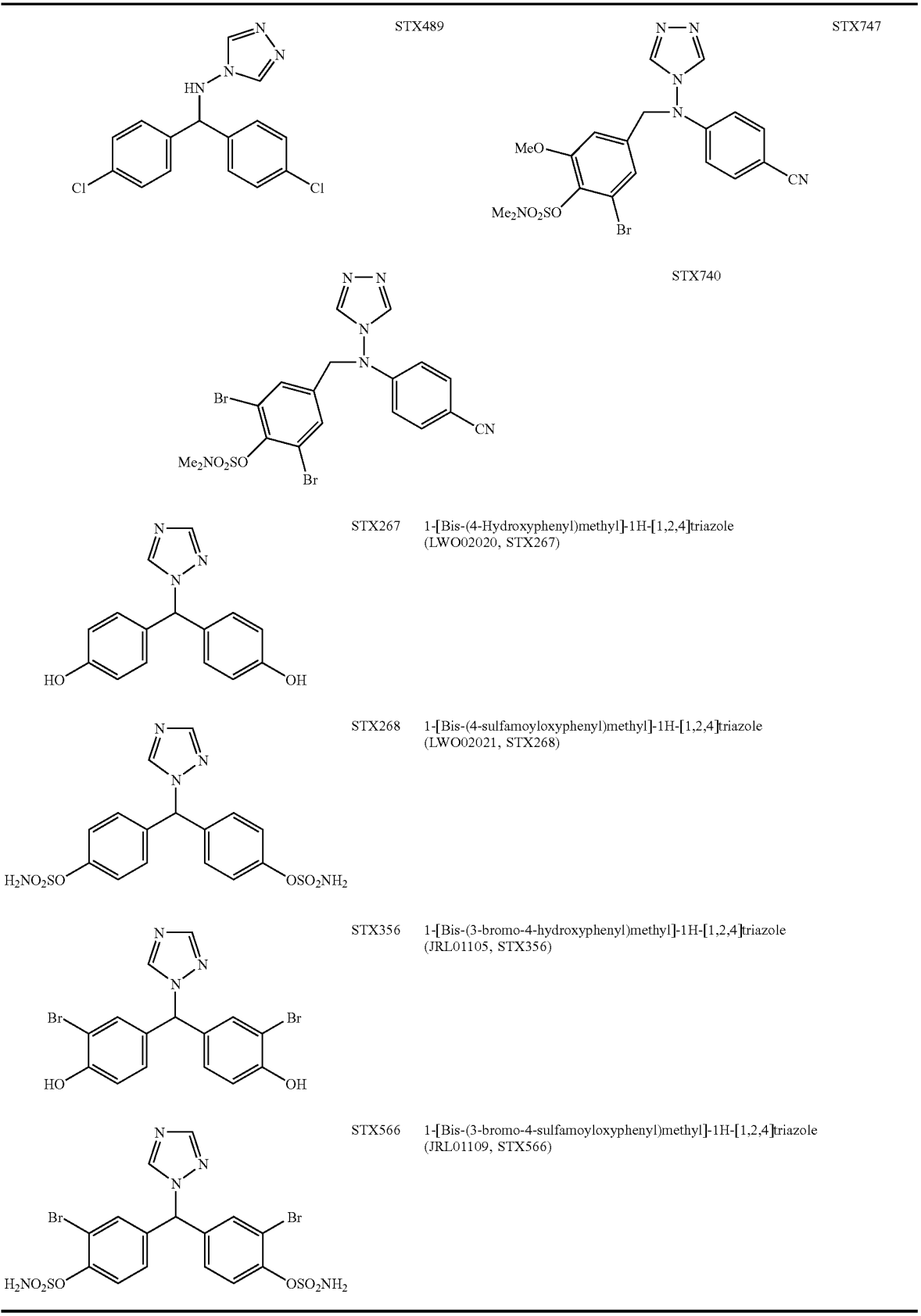

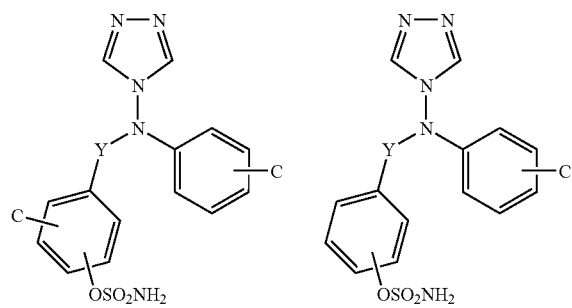

X = H, F, Cl, Br, I, CN or bicyclic heterocycles

Ar—Y—N = CO, (CH$_2$)n, CO(CH$_2$)n, (CH$_2$)nCO,

CS(CH$_2$)n, (CH$_2$)nCS, O(CH$_2$)n, S(CH$_2$)n, SO(CH$_2$)n, SO$_2$(CH$_2$)n

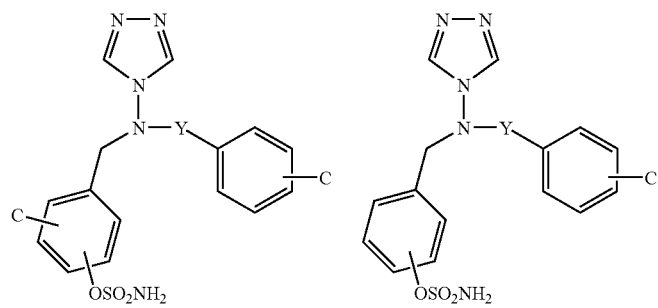

X = H, F, Cl, Br, I, CN or bicyclic heterocycles

N—Y—Ar = CO, (CH$_2$)n, CO(CH$_2$)n, (CH$_2$)nCO,

CS(CH$_2$)n, (CH$_2$)nCS, (CH$_2$)nO, (CH$_2$)nS, (CH$_2$)nSO, (CH$_2$)nSO$_2$

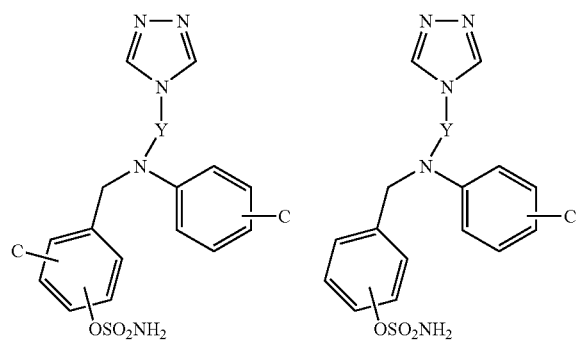

X = H, F, Cl, Br, I, CN or bicyclic heterocycles

Y = (CH$_2$)n, CO(CH$_2$)n, (CH$_2$)nCO, CS(CH$_2$)n, (CH$_2$)nCS,

SO(CH$_2$)n, SO$_2$(CH$_2$)n, (CH$_2$)nSO, (CH$_2$)nSO$_2$,

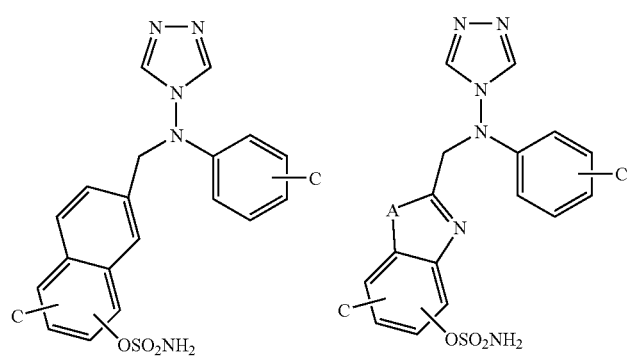

A = CH$_2$, O, S, NH or other bicyclic heterocycles

X = H, F, Cl, Br, I, CN or other bicyclic heterocycles

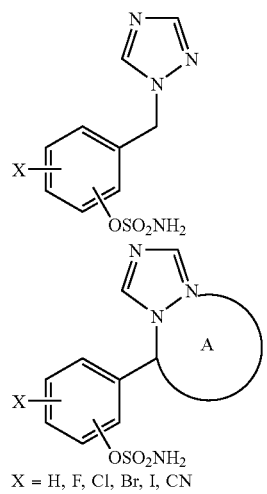

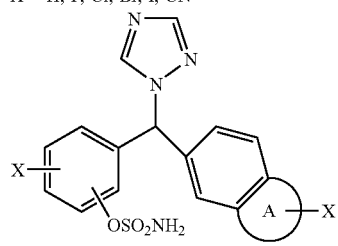

X = H, F, Cl, Br, I, CN

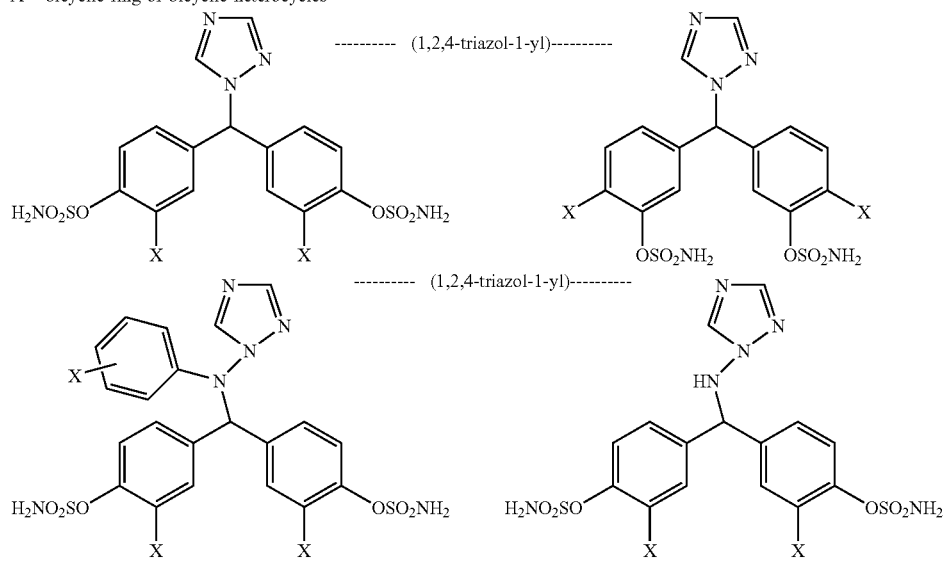

A = bicyclic ring or bicyclic heterocycles

Further Aspects

In a further aspect of the present invention we have found that one may provide a compound of Formula I

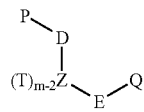

Formula I wherein each T is independently selected from H, hydrocarbyl, —F—R, and a bond with one of D, E, P or Q, or together with one of P and Q forms a ring; Z is a suitable atom the valency of which is m; D, E and F are each independently of each other an optional linker group, P, Q and R are independently of each other a ring system; and at least on of P, Q and R comprises a sulphamate group, wherein when Z is N (an optionally when Z is other than N) the sulphamate group is of the formula:

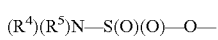

wherein $R^4$ and $R^5$ are independently selected from alkyl, cycloalkyl, alkenyl, acyl and aryl, or combinations thereof, or together represent alkylene, wherein the or each alkyl or cycloalkyl or alkenyl or optionally contain one or more hetero atoms or groups. Preferably $R^4$ and $R^5$ are independently selected from alkyl groups, such as $C_{1-10}$ alkyl, $C_{1-5}$ alkyl, methyl and ethyl. Preferably $R^4$ and $R^5$ are both ethyl.

In a further aspect of the present invention we have found that one may provide a compound of Formula I

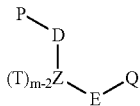

Formula I wherein each T is independently selected from H, hydrocarbyl, —F—R, and a bond with one of D, E, P or Q, or together with one of P and Q forms a ring; Z is a suitable atom the valency of which is m; D, E and F are each independently of each other an optional linker group, P, Q and R are independently of each other a ring system; and at least on of P, Q and R comprises a sulphamate group and wherein when Z is N (an optionally when Z is other than N)R is substituted by a halogen.

Sulphamate Group

At least Q one of the compound of the present invention comprises a sulphamate group.

For some compounds of the present invention, it is highly preferred that the compound comprises at least two or more sulphamate groups.

For some compounds of the present invention, it is highly preferred that the compound comprises at least two sulphamate groups, wherein said sulphamate groups are not on the same ring.

For some applications, preferably the compounds have no, or a minimal, oestrogenic effect.

For some applications, preferably the compounds have an oestrogenic effect.

For some applications, preferably the compounds have a reversible action.

For some applications, preferably the compounds have an irreversible action.

In one embodiment, the compounds of the present invention are useful for the treatment of breast cancer.

The present invention also covers novel intermediates that are useful to prepare the compounds of the present invention. For example, the present invention covers novel alcohol precursors for the compounds. By way of further example, the present invention covers bis protected precursors for the compounds. Examples of each of these precursors are presented herein. The present invention also encompasses a process comprising each or both of those precursors for the synthesis of the compounds of the present invention.

Steroid Sulphatase

Steroid sulphatase—which is sometimes referred to as steroid sulphatase or steryl sulphatase or "STS" for short—hydrolyses several sulphated steroids, such as oestrone sulphate, dehydroepiandrosterone sulphate and cholesterol sulphate. STS has been allocated the enzyme number EC 3.1.6.2.

STS has been cloned and expressed. For example see Stein et al (J. Biol. Chem. 264:13865–13872 (1989)) and Yen et al (Cell 49:443–454(1987)).

STS is an enzyme that has been implicated in a number of disease conditions.

By way of example, workers have found that a total deficiency in STS produces ichthyosis. According to some workers, STS deficiency is fairly prevalent in Japan. The same workers (Sakura et al, J Inherit Metab Dis 1997 Nov.; 20(6):807–10) have also reported that allergic diseases—such as bronchial asthma, allergic rhinitis, or atopic dermatitis—may be associated with a steroid sulphatase deficiency.

In addition to disease states being brought on through a total lack of STS activity, an increased level of STS activity may also bring about disease conditions. By way of example, and as indicated above, there is strong evidence to support a role of STS in breast cancer growth and metastasis.

STS has also been implicated in other disease conditions. By way of example, Le Roy et al (Behav Genet 1999 Mar.;29(2):131–6) have determined that there may be a genetic correlation between steroid sulphatase concentration and initiation of attack behaviour in mice. The authors conclude that sulphatation of steroids may be the prime mover of a complex network, including genes shown to be implicated in aggression by mutagenesis.

STS Inhibition

It is believed that some disease conditions associated with STS activity are due to conversion of a nonactive, sulphated oestrone to an active, nonsulphated oestrone. In disease conditions associated with STS activity, it would be desirable to inhibit STS activity.

Here, the term "inhibit" includes reduce and/or eliminate and/or mask and/or prevent the detrimental action of STS.

STS Inhibitor

In accordance with the present invention, the compound of the present invention is capable of acting as an STS inhibitor.

Here, the term "inhibitor" as used herein with respect to the compound of the present invention means a compound that can inhibit STS activity—such as reduce and/or eliminate and/or mask and/or prevent the detrimental action of STS. The STS inhibitor may act as an antagonist.

The ability of compounds to inhibit oestrone sulphatase activity can be assessed using either intact JEG3 choriocarcinoma cells or placental microsomes. In addition, an animal model may be used. Details on suitable Assay Protocols are presented in following sections. It is to be noted that other assays could be used to determine STS activity and thus STS inhibition. For example, reference may also be made to the teachings of WO-A-99/50453.

In one aspect, for some applications, the compound is further characterised by the feature that if the sulphamate group were to be substituted by a sulphate group to form a sulphate derivative, then the sulphate derivative would be hydrolysable by an enzyme having steroid sulphatase (E.C. 3.1.6.2) activity—i.e. when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a Km value of less than 200 mmolar, preferably less than 150 mmolar, preferably less than 100 mmolar, preferably less than 75 mmolar, preferably less than 50 mmolar, when incubated with steroid sulphatase EC 3.1.6.2 at pH 7.4 and 37° C.

In a preferred embodiment, the compound of the present invention is not hydrolysable by an enzyme having steroid sulphatase (E.C. 3.1.6.2) activity.

For some applications, preferably the compound of the present invention has at least about a 100 fold selectivity to a desired target (e.g. STS and/or aromatase), preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

It is to be noted that the compound of the present invention may have other beneficial properties in addition to or in the alternative to its ability to inhibit STS and/or aromatase activity.

Sulphamate Group

The term "sulphamate" as used herein includes an ester of sulphamic acid, or an ester of an N-substituted derivative of sulphamic acid, or a salt thereof.

If $R^3$ is a sulphamate group then the compound of the present invention is referred to as a sulphamate compound.

Typically, the sulphamate group has the formula:

$$(R^4)(R^5)N—S(O)(O)—O—$$

wherein preferably $R^4$ and $R^5$ are independently selected from H, alkyl, cycloalkyl, alkenyl, acyl and aryl, or combinations thereof, or together represent alkylene, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^4$ and/or $R^5$ is alkyl, the preferred values are those where $R^4$ and $R^5$ are each independently selected from lower alkyl groups containing from 1 to 6 carbon atoms, that is to say methyl, ethyl, propyl etc. $R^4$ and $R^5$ may both be methyl. When $R^4$ and/or $R^5$ is aryl, typical values are phenyl and tolyl (PhCH$_3$; o). Where $R^4$ and $R^5$ represent cycloalkyl, typical values are cyclopropyl, cyclopentyl, cyclohexyl etc. When joined together $R^4$ and $R^5$ typically represent an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl, acyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the sulphamate group may form a ring structure by being fused to (or associated with) one or more atoms in or on group X.

In some embodiments, there may be more than one sulphamate group. By way of example, there may be two sulphamates (i.e. bis-sulphamate compounds).

In some preferred embodiments, at least one of $R^4$ and $R^5$ is H.

In some further preferred embodiments, each of $R^4$ and $R^5$ is H.

Phosphonate Group

If the compound of the present invention comprises a phosphonate group then the compound of the present invention is referred to as a phosphonate compound.

Typically, the phosphonate group has the formula:

$$(R^6)—P(O)(OH)—O—$$

wherein preferably $R^6$ is H, alkyl, cycloalkyl, alkenyl, acyl or aryl, or combinations thereof, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^6$ is alkyl, $R^6$ may be a lower alkyl groups containing from 1 to 6 carbon atoms, that is to say methyl, ethyl, propyl etc. By way of example, $R^6$ may be methyl. When $R^6$ is aryl, typical values are phenyl and tolyl (PhCH$_3$; o). Where $R^6$ represents cycloalkyl, typical values are cyclopropyl, cyclopentyl, cyclohexyl etc. $R^6$ may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl, acyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the phosphonate group may form a ring structure by being fused to (or associated with) one or more atoms in or on group X.

In some embodiments, there may be more than one phosphonate group. By way of example, there may be two phosphonates (i.e. bis-phosphonate compounds). If these compounds are based on a steroidal nucleus, preferably the second (or at least one of the additional) phosphonate group is located at position 17 of the steroidal nucleus. These groups need not be the same.

Thiophosphonate Group

If the compound of the present invention comprises a thiophosphonate group then the compound of the present invention is referred to as a thiophosphonate compound.

Typically, the thiophosphonate group has the formula:

$$(R^7)—P(S)(OH)—O—$$

wherein preferably $R^7$ is H, alkyl, cycloalkyl, alkenyl, acyl or aryl, or combinations thereof, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^7$ is alkyl, $R^7$ may be a lower alkyl groups containing from 1 to 6 carbon atoms, that is to say methyl, ethyl, propyl etc. By way of example, $R^7$ may be methyl. When $R^7$ is aryl, typical values are phenyl and tolyl (PhCH$_3$;o). Where $R^7$ represents cycloalkyl, typical values are cyclopropyl, cyclopentyl, cyclohexyl etc. $R^7$ may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl, acyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the thiophosphonate group may form a ring structure by being fused to (or associated with) one or more atoms in or on group X.

In some embodiments, there may be more than one thiophosphonate group. By way of example, there may be two thiophosphonates (i.e. bis-thiophosphonate compounds). If these compounds are based on a steroidal nucleus, preferably the second (or at least one of the additional) thiophosphonate group is located at position 17 of the steroidal nucleus. These groups need not be the same.

Sulphonate Group

If the compound of the present invention comprises a sulphonate group then the compound of the present invention is referred to as a sulphonate compound.

Typically, the sulphonate group has the formula:

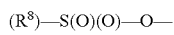

$(R^8)$—S(O)(O)—O— wherein preferably $R^8$ is H, alkyl, cycloalkyl, alkenyl, acyl or aryl, or combinations thereof, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^8$ is alkyl, $R^8$ may be a lower alkyl groups containing from 1 to 6 carbon atoms, that is to say methyl, ethyl, propyl etc. By way of example, $R^8$ may be methyl. When $R^8$ is aryl, typical values are phenyl and tolyl ($PhCH_3$; o). Where $R^8$ represents cycloalkyl, typical values are cyclopropyl, cyclopentyl, cyclohexyl etc. $R^8$ may even comprise an alkylene group providing a chain of 4 to 6 carbon atoms, optionally interrupted by one or more hetero-atoms or groups, e.g. to provide a 5 membered heterocycle, e.g. morpholino, pyrrolidino or piperidino.

Within the values alkyl, cycloalkyl, alkenyl, acyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the sulphonate group may form a ring structure by being fused to (or associated with) one or more atoms in or on group X.

In some embodiments, there may be more than one sulphonate group. By way of example, there may be two sulphonates (i.e. bis-sulphonate compounds). If these compounds are based on a steroidal nucleus, preferably the second (or at least one of the additional) sulphonate group is located at position 17 of the steroidal nucleus. These groups need not be the same.

Other Substituents

The compound of the present invention may have substituents other than those of formula I. By way of example, these other substituents may be one or more of: one or more sulphamate group(s), one or more phosphonate group(s), one or more thiophosphonate group(s), one or more sulphonate group(s), one or more sulphonamide group(s), one or more halo groups, one or more O groups, one or more hydroxy groups, one or more amino groups, one or more sulphur containing group(s), one or more hydrocarbyl group (s)—such as an oxyhydrocarbyl group.

Assay for Determining STS Activity Using Cancer Cells

Protocol 1
Inhibition of Steroid Sulphatase Activity in JEG3 Cells

Steroid sulphatase activity is measured in vitro using intact JEG3 choriocarcinoma cells. This cell line may be used to study the control of human breast cancer cell growth. It possesses significant steroid sulphatase activity (Boivin et al., J. Med. Chem., 2000, 43: 4465–4478) and is available in from the American Type Culture Collection (ATCC).

Cells are maintained in Minimal Essential Medium (MEM) (Flow Laboratories, Irvine, Scotland) containing 20 mM HEPES, 5% foetal bovine serum, 2 mM glutamine, non-essential amino acids and 0.075% sodium bicarbonate. Up to 30 replicate 25 cm2 tissue culture flasks are seeded with approximately $1 \times 10^5$ cells/flask using the above medium. Cells are grown to 80% confluency and the medium is changed every third day.

Intact monolayers of JEG3 cells in triplicate 25 cm² tissue culture flasks are washed with Earle's Balanced Salt Solution (EBSS from ICN Flow, High Wycombe, U.K.) and incubated for 3–4 hours at 37° C. with 5 pmol ($7 \times 10^5$ dpm) [6,7-3H]oestrone-3-sulphate (specific activity 60 Ci/mmol from New England Nuclear, Boston, Mass., U.S.A.) in serum-free MEM (2.5 ml) together with oestrone-3-sulphamate (11 concentrations: 0; 1 fM; 0.01 pM; 0.1 pM; 1 pM; 0.01 nM; 0.1 nM; 1 nM; 0.01 mM; 0.1 mM; 1 mM). After incubation each flask is cooled and the medium (1 ml) is pipetted into separate tubes containing [14C]oestrone ($7 \times 10^3$ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C] oestrone and <0.1% [3H]oestrone-3-sulphate is removed from the aqueous phase by this treatment. A portion (2 ml) of the organic phase is removed, evaporated and the 3H and 14C content of the residue determined by scintillation spectrometry. The mass of oestrone-3-sulphate hydrolysed was calculated from the 3H counts obtained (corrected for the volumes of the medium and organic phase used, and for recovery of [14C] oestrone added) and the specific activity of the substrate. Each batch of experiments includes incubations of microsomes prepared from a sulphatase-positive human placenta (positive control) and flasks without cells (to assess apparent non-enzymatic hydrolysis of the substrate). The number of cell nuclei per flask is determined using a Coulter Counter after treating the cell monolayers with Zaponin. One flask in each batch is used to assess cell membrane status and viability using the Trypan Blue exclusion method (Phillips, H. J. (1973) In: Tissue culture and applications, [eds: Kruse, D. F. & Patterson, M. K.]; pp. 406–408; Academic Press, New York).

Results for steroid sulphatase activity are expressed as the mean ±1 S.D. of the total product (oestrone+oestradiol) formed during the incubation period (3–4 hours) calculated for 106 cells and, for values showing statistical significance, as a percentage reduction (inhibition) over incubations containing no oestrone-3-sulphamate. Unpaired Student's t-test was used to test the statistical significance of results.

Assay for Determining STS Activity Using Placental Microsomes

Protocol 2
Inhibition of Steroid Sulphatase Activity in Placental Microsomes

Sulphatase-positive human placenta from normal term pregnancies are thoroughly minced with scissors and washed once with cold phosphate buffer (pH 7.4, 50 mM) then re-suspended in cold phosphate buffer (5 ml/g tissue). Homogenisation is accomplished with an Ultra-Turrax homogeniser, using three 10 second bursts separated by 2 minute cooling periods in ice. Nuclei and cell debris are removed by centrifuging (4° C.) at 2000 g for 30 minutes and portions (2 ml) of the supernatant are stored at 20° C. The protein concentration of the supernatants is determined by the method of Bradford (Anal. Biochem., 72, 248–254 (1976)).

Incubations (1 ml) are carried out using a protein concentration of 100 mg/ml, substrate concentration of 20 mM [6,7-3H]oestrone-3-sulphate (specific activity 60 Ci/mmol from New England Nuclear, Boston, Mass., U.S.A.) and an incubation time of 20 minutes at 37° C. If necessary eight concentrations of compounds are employed: 0 (i.e. control); 0.05 mM; 0.1 mM; 0.2 mM; 0.4 mM; 0.6 mM; 0.8 mM; 1.0 mM. After incubation each sample is cooled and the medium (1 ml) was pipetted into separate tubes containing [14C] oestrone (7×10³ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C] oestrone and <0.1% [3H]oestrone-3-sulphate is removed from the aqueous phase by this treatment. A portion (2 ml) of the organic phase was removed, evaporated and the 3H and 14C content of the residue determined by scintillation spectrometry. The mass of oestrone-3-sulphate hydrolysed is calculated from the 3H counts obtained (corrected for the volumes of the medium and organic phase used, and for recovery of [14C]oestrone added) and the specific activity of the substrate.

Animal Assay Model for Determining STS Activity

Protocol 3
Inhibition of Oestrone Sulphatase Activity In Vivo

The compounds of the present invention may be studied using an animal model, in particular in ovariectomised rats. In this model compounds which are oestrogenic stimulate uterine growth.

The compound (0.1 mg/Kg/day for five days) is administered orally to rats with another group of animals receiving vehicle only (propylene glycol). At the end of the study samples of liver tissue were obtained and oestrone sulphatase activity assayed using 3H oestrone sulphate as the substrate as previously described (see PCT/GB95/02638).

Animal Assay Model for Determining Oestrogenic Activity

Protocol 4

The compounds of the present invention may be studied using an animal model, in particular in ovariectomised rats. In this model, compounds which are oestrogenic stimulate uterine growth.

The compound (0.1 mg/Kg/day for five days) was administered orally to rats with another group of animals receiving vehicle only (propylene glycol). At the end of the study uteri were obtained and weighed with the results being expressed as uterine weight/whole body weight×100.

Compounds having no significant effect on uterine growth are not oestrogenic.

Biotechnological Assays for Determining STS Activity

Protocol 5

The ability of compounds to inhibit oestrone sulphatase activity can also be assessed using amino acid sequences or nucleotide sequences encoding STS, or active fragments, derivatives, homologues or variants thereof in, for example, high-through put screens.

Any one or more of appropriate targets—such as an amino acid sequence and/or nucleotide sequence—may be used for identifying an agent capable of modulating STS in any of a variety of drug screening techniques. The target employed in such a test may be free in solution, affixed to a solid support, borne on a cell surface, or located intracellularly. The abolition of target activity or the formation of binding complexes between the target and the agent being tested may be measured.

The assay of the present invention may be a screen, whereby a number of agents are tested. In one aspect, the assay method of the present invention is a high through put screen.

Techniques for drug screening may be based on the method described in Geysen, European Patent Application 84/03564, published on Sep. 13, 1984. In summary, large numbers of different small peptide test compounds are synthesised on a solid substrate, such as plastic pins or some other surface. The peptide test compounds are reacted with a suitable target or fragment thereof and washed. Bound entities are then detected—such as by appropriately adapting methods well known in the art. A purified target can also be coated directly onto plates for use in a drug screening techniques. Alternatively, non-neutralising antibodies can be used to capture the peptide and immobilise it on a solid support.

This invention also contemplates the use of competitive drug screening assays in which neutralising antibodies capable of binding a target specifically compete with a test compound for binding to a target.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

In one preferred aspect, the present invention relates to a method of identifying agents that selectively modulate STS, which compounds have the formula (I).

Assay for Determining Aromatase Activity Using JEG3 Cells

Protocol 6

Aromatase activity is measured in JEG3 choriocarcinoma cells, obtained from the ATCC. This cell line possesses significant aromatase activity and is widely used to study the control of human aromatase activity (Bhatnager et al., J. Steroid Biochem. Molec. Biol. 2001, 76: 199–202). Cells are maintained in Minimal Essential Medium (MEM, Flow Laboratories, Irvine, Scotland) containing 20 mM HEPES, 10% foetal bovine serum, 2 mM glutamine, non-essential amino acids and 0.075% sodium bicarbonate. Intact monolayers of JEG3 cells ($2.5 \times 10^6$ cells) in triplicate 25 cm² tissue culture flasks are washed with Earle's Balanced salt solution (EBSS, from ICN Flow, High Wycombe, UK) and incubated with [1β-³H] androstenedione (2–5 nM, 26 Ci/mmol, New England Nuclear, Boston, Mass., USA) for 30 min with inhibitors over the range of 10 pm–10 µM. During the aromatase reaction, $^3H_2O$ is liberated which can he quantified using a liquid scintillation spectrometer (Beckman-Coulter, High Wycombe, Bucks. UK). This $^3H_2O$-release method has been widely used to measure aromatase activity (Newton et al., J. Steroid Biochem. 1986,24: 1033–1039). The number of cell nuclei per flask is determined using a Coulter Counter after treating the cell monolayers with Z aponin.

Results for aromatase activity are expressed as the mean ±1 S.D. of the product formed during the incubation period (30 min) calculated for $10^6$ cells and, for values showing a statistical significance, as a percentage reduction (inhibition) over incubations containing no aromatase inhibitor. Unpaired Student's t test was used to test the statistical significance of results. $IC_{50}$ values were calculated as the concentration of inhibitor required to obtain a 50% inhibition of aromatase activity.

Animal Assays for Determining Aromatase Activity

Protocol 7
(i) Inhibition of PMSG-induced Oestrogen Synthesis

The ability of compounds to inhibit aromatase activity in vivo was tested using a pregnant mare serum gonadotrophin (PMSG)-induced oestrogen synthesis assay. For this, female rats (250 g) were injected with PMSG (200 IU, s.c.). After 72 h rats were administered vehicle (propylene glycol) or various doses of test compounds orally. At 2 h after dosing blood samples were obtained by cardiac puncture (under anaesthesia). Plasma oestradiol levels were measured in control groups and groups receiving drugs. The efficacy of aromatase inhibition was determined by measurement of plasma oestradiol concentrations by radioimmunoassay. This method has been widely used to determine the effectiveness of aromatase inhibitors in vivo (Wouters et al., J. Steroid Biochem., 1989, 32: 781–788).

(ii) Inhibition of Androstenedione Stimulated Uterine Growth in Ovariectomised Rats Female rats (250 g) were ovariectomised and used to determine the effectiveness of aromatase inhibition on androstenedione stimulated uterine growth. Administration of androstenedione (30 mg/kg/d) for a 2-week period results in a significant increase in uterine growth in ovariectomised animals. This increase in uterine growth is stimulated by oestrogen which is derived from the administered androstenedione as a result of the action of the aromatase enzyme. By co-administration of compounds with androstenedione the extent of aromatase inhibition can be determined by measurements of uterine weights in treated and untreated animals.

Reporters

A wide variety of reporters may be used in the assay methods (as well as screens) of the present invention with preferred reporters providing conveniently detectable signals (e.g. by spectroscopy). By way of example, a reporter gene may encode an enzyme which catalyses a reaction which alters light absorption properties.

Other protocols include enzyme-linked immunosorbent assay (ELISA), radioimmunoassay (RIA) and fluorescent activated cell sorting (FACS). A two-site, monoclonal-based immunoassay utilising monoclonal antibodies reactive to two non-interfering epitopes may even be used. These and other assays are described, among other places, in Hampton R et al (1990, Serological Methods, A Laboratory Manual, APS Press, St Paul Minn.) and Maddox DE et al (1983, J Exp Med 15 8:1211).

Examples of reporter molecules include but are not limited to (β-galactosidase, invertase, green fluorescent protein, luciferase, chloramphenicol, acetyltransferase, (-glucuronidase, exo-glucanase and glucoamylase. Alternatively, radiolabelled or fluorescent tag-labelled nucleotides can be incorporated into nascent transcripts which are then identified when bound to oligonucleotide probes.

By way of further examples, a number of companies such as Pharmacia Biotech (Piscataway, N.J.), Promega (Madison, Wis.), and US Biochemical Corp (Cleveland, Ohio) supply commercial kits and protocols for assay procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241.

Host Cells

The term "host cell"—in relation to the present invention includes any cell that could comprise the target for the agent of the present invention.

Thus, a further embodiment of the present invention provides host cells transformed or transfected with a polynucleotide that is or expresses the target of the present invention. Preferably said polynucleotide is carried in a vector for the replication and expression of polynucleotides that are to be the target or are to express the target. The cells will be chosen to be compatible with the said vector and may for example be prokaryotic (for example bacterial), fungal, yeast or plant cells.

The gram negative bacterium *E. coli* is widely used as a host for heterologous gene expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus *Bacillus* are very suitable as heterologous hosts because of their capability to secrete proteins into the culture medium. Other bacteria suitable as hosts are those from the genera *Streptomyces* and *Pseudomonas*.

Depending on the nature of the polynucleotide encoding the polypeptide of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

Examples of suitable expression hosts within the scope of the present invention are fungi such as *Aspergillus* species (such as those described in EP-A-0184438 and EP-A-0284603) and *Trichoderma* species; bacteria such as *Bacillus* species (such as those described in EP-A-0134048 and EP-A-0253455), *Streptomyces* species and *Pseudomonas* species; and yeasts such as *Kluyveromyces* species (such as those described in EP-A-0096430 and EP-A-0301670) and *Saccharomyces* species. By way of example, typical expression hosts may be selected from *Aspergillus niger, Aspergillus niger* var. *tubigenis, Aspergillus niger* var. *awamori, Aspergillus aculeatis, Aspergillus nidulans, Aspergillus orvzae, Trichoderma reesei, Bacillus subtilis, Bacillus licheniformis, Bacillus amyloliquefaciens, Kluyveromyces lactis* and *Saccharomyces cerevisiae*.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

Organism

The term "organism" in relation to the present invention includes any organism that could comprise the target according to the present invention and/or products obtained therefrom. Examples of organisms may include a fungus, yeast or a plant.

The term "transgenic organism" in relation to the present invention includes any organism that comprises the target according to the present invention and/or products obtained.

Transformation of Host Cells/Host Organisms

As indicated earlier, the host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

If a prokaryotic host is used then the nucleotide sequence may need to be suitably modified before transformation—such as by removal of introns.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al (1987, Yeast Biotechnology, D R Berry et al, eds, pp 401–429, Allen and Unwin, London) and by King et al (1989, Molecular and Cell Biology of Yeasts, E F Walton and G T Yarronton, eds, pp 107–133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae*.

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic *Saccharomyces*, expression constructs are prepared by inserting the nucleotide sequence into a construct designed for expression in yeast. Several types of constructs used for heterologous expression have been developed. The constructs contain a promoter active in yeast fused to the nucleotide sequence, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic *Saccharomyces* according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153,163–168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, e.g. G418.

Another host organism is a plant. The basic principle in the construction of genetically modified plants is to insert genetic information in the plant genome so as to obtain a stable maintenance of the inserted genetic material. Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech March/April 1994 17–27). Further teachings on plant transformation may be found in EP-A-0449375.

Thus, the present invention also provides a method of transforming a host cell with a nucleotide sequence that is to be the target or is to express the target. Host cells transformed with the nucleotide sequence may be cultured under conditions suitable for the expression of the encoded protein. The protein produced by a recombinant cell may be displayed on the surface of the cell. If desired, and as will be understood by those of skill in the art, expression vectors containing coding sequences can be designed with signal sequences which direct secretion of the coding sequences through a particular prokaryotic or eukaryotic cell membrane. Other recombinant constructions may join the coding sequence to nucleotide sequence encoding a polypeptide domain which will facilitate purification of soluble proteins (Kroll D J et al (1993) DNA Cell Biol 12:441–53).

Variants/Homologues/Derivatives

In addition to the specific amino acid sequences and nucleotide sequences mentioned herein, the present invention also encompasses the use of variants, homologue and derivatives thereof. Here, the term "homology" can be equated with "identity".

In the present context, an homologous sequence is taken to include an amino acid sequence which may be at least 75, 85 or 90% identical, preferably at least 95 or 98% identical. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403–410) and the GENEWORKS suite of comparison tools. Both BLAST and FASTA are available for offline and online searching (see Ausubel et al., 1999 ibid, pages 7–58 to 7–60). However it is preferred to use the GCG Bestfit program.

A further useful reference is that found in FEMS Microbiol Lett May 15, 1999;174(2):247–50 (and a published erratum appears in FEMS Microbiol Lett Aug. 1, 1999;177 (1):187–8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Expression Vectors

The nucleotide sequence for use as the target or for expressing the target can be incorporated into a recombinant replicable vector. The vector may be used to replicate and express the nucleotide sequence in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The protein produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Fusion Proteins

The target amino acid sequence may be produced as a fusion protein, for example to aid in extraction and purification. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the activity of the target.

The fusion protein may comprise an antigen or an antigenic determinant fused to the substance of the present invention. In this embodiment, the fusion protein may be a non-naturally occurring fusion protein comprising a substance which may act as an adjuvant in the sense of providing a generalised stimulation of the immune system. The antigen or antigenic determinant may be attached to either the amino or carboxy terminus of the substance.

In another embodiment of the invention, the amino acid sequence may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

Therapy

The compounds of the present invention may be used as therapeutic agents—i.e. in therapy applications.

The term "therapy" includes curative effects, alleviation effects, and prophylactic effects.

The therapy may be on humans or animals, preferably female animals.

Pharmaceutical Compositions

In one aspect, the present invention provides a pharmaceutical composition, which comprises a compound according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Combination Pharmaceutical

The compound of the present invention may be used in combination with one or more other active agents, such as one or more other pharmaceutically active agents.

By way of example, the compounds of the present invention may be used in combination with other STS inhibitors and/or other inhibitors such as an aromatase inhibitor (such as for example, 4-hydroxyandrostenedione (4-OHA)) and/or steroids—such as the naturally occurring neurosteroids dehydroepiandrosterone sulfate (DHEAS) and pregnenolone sulfate (PS) and/or other structurally similar organic compounds. Examples of other STS inhibitors may be found in the above references. By way of example, STS inhibitors for use in the present invention include EMATE, and either or both of the 2-ethyl and 2-methoxy 17-deoxy compounds that are analogous to compound 5 presented herein.

In addition, or in the alternative, the compound of the present invention may be used in combination with a biological response modifier.

The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc. For some applications, preferably, the biological response modifier is a cytokine. Examples of cytokines include: interleukins (IL)—such as IL-1, IL-2, IL-3, IL-4, IL-5, IL-6, IL-7, IL-8, IL-9, IL-10, IL-11, IL-12, IL-19; Tumour Necrosis Factor (TNF)—such as TNF-α; Interferon alpha, beta and gamma; TGF-β. For some applications, preferably the cytokine is tumour necrosis factor (TNF). For some applications, the TNF may be any type of TNF—such as TNF-α, TNF-β, including derivatives or mixtures thereof. More preferably the cytokine is TNF-α. Teachings on TNF may be found in the art—such as WO-A-98/08870 and WO-A-98/13348.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous, subcutaneous, intraocular or transdermal administration. Depending upon the need, the agent may be administered at a dose of from 0.01 to 30 mg/kg body weight, such as from 0.1 to 10 mg/kg, more preferably from 0.1 to 1 mg/kg body weight.

By way of further example, the agents of the present invention may be administered in accordance with a regimen of 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Aside from the typical modes of delivery—indicated above—the term "administered" also includes delivery by techniques such as lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Thus, for pharmaceutical administration, the STS inhibitors of the present invention can be formulated in any suitable manner utilising conventional pharmaceutical formulating techniques and pharmaceutical carriers, adjuvants, excipients, diluents etc. and usually for parenteral administration. Approximate effective dose rates may be in the range from 1 to 1000 mg/day, such as from 10 to 900 mg/day or even from 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

Cell Cycling

The compounds of the present invention may be useful in the method of treatment of a cell cycling disorder.

As discussed in "Molecular Cell Biology" 3rd Ed. Lodish et al. pages 177–181 different eukaryotic cells can grow and divide at quite different rates. Yeast cells, for example, can divide every 120 min., and the first divisions of fertilised eggs in the embryonic cells of sea urchins and insects take only 1530 min. because one large pre-existing cell is subdivided. However, most growing plant and animal cells take 10–20 hours to double in number, and some duplicate at a much slower rate. Many cells in adults, such as nerve cells and striated muscle cells, do not divide at all; others, like the fibroblasts that assist in healing wounds, grow on demand but are otherwise quiescent.

Still, every eukaryotic cell that divides must be ready to donate equal genetic material to two daughter cells. DNA synthesis in eukaryotes does not occur throughout the cell division cycle but is restricted to a part of it before cell division.

The relationship between eukaryotic DNA synthesis and cell division has been thoroughly analysed in cultures of mammalian cells that were all capable of growth and division. In contrast to bacteria, it was found, eukaryotic cells spend only a part of their time in DNA synthesis, and it is completed hours before cell division (mitosis). Thus a gap of time occurs after DNA synthesis and before cell division; another gap was found to occur after division and before the next round of DNA synthesis. This analysis led to the conclusion that the eukaryotic cell cycle consists of an M (mitotic) phase, a $G_1$ phase (the first gap), the S (DNA synthesis) phase, a $G_2$ phase (the second gap), and back to M. The phases between mitoses ($G_1$, S, and $G_2$) are known collectively as the interphase.

Many nondividing cells in tissues (for example, all quiescent fibroblasts) suspend the cycle after mitosis and just prior to DNA synthesis; such "resting" cells are said to have exited from the cell cycle and to be in the $G_0$ state.

It is possible to identify cells when they are in one of the three interphase stages of the cell cycle, by using a fluorescence-activated cell sorter (FACS) to measure their relative DNA content: a cell that is in $G_1$ (before DNA synthesis) has a defined amount x of DNA; during S (DNA replication), it has between x and 2x; and when in $G_2$ (or M), it has 2x of DNA.

The stages of mitosis and cytokinesis in an animal cell are as follows (a) Interphase. The $G_2$ stage of interphase immediately precedes the beginning of mitosis. Chromosomal DNA has been replicated and bound to protein during the S phase, but chromosomes are not yet seen as distinct structures. The nucleolus is the only nuclear substructure that is visible under light microscope. In a diploid cell before DNA replication there are two morphologic chromosomes of each type, and the cell is said to be 2n. In $G_2$, after DNA replication, the cell is 4n. There are four copies of each chromosomal DNA. Since the sister chromosomes have not yet separated from each other, they are called sister chromatids.

b) Early prophase. Centrioles, each with a newly formed daughter centriole, begin moving toward opposite poles of the cell; the chromosomes can be seen as long threads. The nuclear membrane begins to disaggregate into small vesicles.

(c) Middle and late prophase. Chromosome condensation is completed; each visible chromosome structure is composed of two chromatids held together at their centromeres. Each chromatid contains one of the two newly replicated daughter DNA molecules. The microtubular spindle begins to radiate from the regions just adjacent to the centrioles, which are moving closer to their poles. Some spindle fibres reach from pole to pole; most go to chromatids and attach at kinetochores.

(d) Metaphase. The chromosomes move toward the equator of the cell, where they become aligned in the equatorial plane. The sister chromatids have not yet separated.

(e) Anaphase. The two sister chromatids separate into independent chromosomes. Each contains a centromere that is linked by a spindle fibre to one pole, to which it moves. Thus one copy of each chromosome is donated to each daughter cell. Simultaneously, the cell elongates, as do the pole-to-pole spindles. Cytokinesis begins as the cleavage furrow starts to form.

(f) Telophase. New membranes form around the daughter nuclei; the chromosomes uncoil and become less distinct, the nucleolus becomes visible again, and the nuclear membrane forms around each daughter nucleus. Cytokinesis is nearly complete, and the spindle disappears as the microtubules and other fibres depolymerise. Throughout mitosis the "daughter" centriole at each pole grows until it is full-length. At telophase the duplication of each of the original centrioles is completed, and new daughter centrioles will be generated during the next interphase.

(g) Interphase. Upon the completion of cytokinesis, the cell enters the $G_1$ phase of the cell cycle and proceeds again around the cycle.

It will be appreciated that cell cycling is an extremely important cell process. Deviations from normal cell cycling can result in a number of medical disorders. Increased and/or unrestricted cell cycling may result in cancer. Reduced cell cycling may result in degenerative conditions. Use of the compound of the present invention may provide a means to treat such disorders and conditions.

Thus, the compound of the present invention may be suitable for use in the treatment of cell cycling disorders such as cancers, including hormone dependent and hormone independent cancers.

In addition, the compound of the present invention may be suitable for the treatment of cancers such as breast cancer, ovarian cancer, endometrial cancer, sarcomas, melanomas, prostate cancer, pancreatic cancer etc. and other solid tumours.

For some applications, cell cycling is inhibited and/or prevented and/or arrested, preferably wherein cell cycling is prevented and/or arrested. In one aspect cell cycling may be inhibited and/or prevented and/or arrested in the $G_2/M$ phase. In one aspect cell cycling may be irreversibly prevented and/or inhibited and/or arrested, preferably wherein cell cycling is irreversibly prevented and/or arrested.

By the term "irreversibly prevented and/or inhibited and/or arrested" it is meant after application of a compound of the present invention, on removal of the compound the effects of the compound, namely prevention and/or inhibition and/or arrest of cell cycling, are still observable. More particularly by the term "irreversibly prevented and/or inhibited and/or arrested" it is meant that when assayed in accordance with the cell cycling assay protocol presented herein, cells treated with a compound of interest show less growth after Stage 2 of the protocol I than control cells. Details on this protocol are presented below.

Thus, the present invention provides compounds which: cause inhibition of growth of oestrogen receptor positive (ER+) and ER negative (ER−) breast cancer cells in vitro by preventing and/or inhibiting and/or arresting cell cycling; and/or cause regression of nitroso-methyl urea (NMU)-induced mammary tumours in intact animals (i.e. not ovariectomised), and/or prevent and/or inhibit and/or arrest cell cycling in cancer cells; and/or act in vivo by preventing and/or inhibiting and/or arresting cell cycling and/or act as a cell cycling agonist.

Cell Cycling Assay

Protocol 7

Procedure

Stage 1

MCF-7 breast cancer cells are seeded into multi-well culture plates at a density of 105 cells/well. Cells were allowed to attach and grown until about 30% confluent when they are treated as follows:

Control—no treatment

Compound of Interest (COI) 20 μM

Cells are grown for 6 days in growth medium containing the COI with changes of medium/CO every 3 days. At the end of this period cell numbers were counted using a Coulter cell counter.

Stage 2

After treatment of cells for a 6-day period with the COI cells are re-seeded at a density of $10^4$ cells/well. No further treatments are added. Cells are allowed to continue to grow for a further 6 days in the presence of growth medium. At the end of this period cell numbers are again counted.

Cancer

As indicated, the compounds of the present invention may be useful in the treatment of a cell cycling disorder. A particular cell cycling disorder is cancer.

Cancer remains a major cause of mortality in most Western countries. Cancer therapies developed so far have included blocking the action or synthesis of hormones to inhibit the growth of hormone-dependent tumours. However, more aggressive chemotherapy is currently employed for the treatment of hormone-independent tumours.

Hence, the development of a pharmaceutical for anti-cancer treatment of hormone dependent and/or hormone independent tumours, yet lacking some or all of the side-effects associated with chemotherapy, would represent a major therapeutic advance.

It is known that oestrogens undergo a number of hydroxylation and conjugation reactions after their synthesis. Until recently it was thought that such reactions were part of a metabolic process that ultimately rendered oestrogens water soluble and enhanced their elimination from the body. It is now evident that some hydroxy metabolites (e.g. 2-hydroxy and 16alpha-hydroxy) and conjugates (e.g. oestrone sulphate, E1S) are important in determining some of the complex actions that oestrogens have in the body.

Workers have investigated the formation of 2- and 16-hydroxylated oestrogens in relation to conditions that alter the risk of breast cancer. There is now evidence that factors which increase 2-hydroxylase activity are associated with a reduced cancer risk, while those increasing 16alpha-hydroxylation may enhance the risk of breast cancer. Further interest in the biological role of estrogen metabolites has been stimulated by the growing body of evidence that 2-methoxyoestradiol is an endogenous metabolite with anti-mitotic properties. 2-MeOE2 is formed from 2-hydroxy estradiol (2-OHE2) by catechol estrogen methyl transferase, an enzyme that is widely distributed throughout the body.

Workers have shown that in vivo 2-MeOE2 inhibits the growth of tumours arising from the subcutaneous injection of Meth A sarcoma, B16 melanoma or MDA-MB-435 estrogen receptor negative (ER−) breast cancer cells. It also inhibits endothelial cell proliferation and migration, and in vitro angiogenesis. It was suggested that the ability of 2-MeOE2 to inhibit tumour growth in vivo may be due to its ability to inhibit tumour-induced angiogenesis rather than direct inhibition of the proliferation of tumour cells.

The mechanism by which 2-MeOE2 exerts its potent anti-mitogenic and anti-angiogenic effects is still being elucidated. There is evidence that at high concentrations it can inhibit microtubule polymerisation and act as a weak inhibitor of colchicine binding to tubulin. Recently, however, at concentrations that block mitosis, tubulin filaments in cells were not found to be depolymerised but to have an identical morphology to that seen after taxol treatment. It is possible, therefore, that like taxol, a drug that is used for breast and ovarian breast cancer therapy, 2-MeOE2 acts by stabilising microtubule dynamics.

While the identification of 2-MeOE2 as a new therapy for cancer represents an important advance, the bioavailability of orally administered oestrogens is poor. Furthermore, they can undergo extensive metabolism during their first pass through the liver. As part of a research programme to develop a steroid sulphatase inhibitor for breast cancer therapy, oestrone-3-O-sulphamate (EMATE) was identified as a potent active site-directed inhibitor. Unexpectedly, EMATE proved to possess potent oestrogenic properties with its oral uterotrophic activity in rats being a 100-times higher than that of estradiol. Its enhanced oestrogenicity is thought to result from its absorption by red blood cells (rbcs) which protects it from inactivation during its passage through the liver and which act as a reservoir for its slow release for a prolonged period of time. A number of A-ring modified analogues were synthesised and tested, including 2-methoxyoestrone-3-O-sulphamate. While this compound was equipotent with EMATE as a steroid sulphatase inhibitor, it was devoid of oestrogenicity.

We believe that the compound of the present invention provides a means for the treatment of cancers and, especially, breast cancer.

In addition or in the alternative the compound of the present invention may be useful in the blocking the growth of cancers including leukaemias and solid tumours such as breast, endometrium, prostate, ovary and pancreatic tumours.

Therapy Concerning Oestrogen

We believe that some of the compounds of the present invention may be useful in the control of oestrogen levels in the body—in particular in females. Thus, some of the compounds may be useful as providing a means of fertility control—such as an oral contraceptive tablet, pill, solution or lozenge. Alternatively, the compound could be in the form of an implant or as a patch.

Thus, the compounds of the present invention may be useful in treating hormonal conditions associated with oestrogen.

In addition or in the alternative the compound of the present invention may be useful in treating hormonal conditions in addition to those associated with oestrogen. Hence, the compound of the present invention may also be capable of affecting hormonal activity and may also be capable of affecting an immune response.

Neurodegenerative Diseases

We believe that some of the compounds of the present invention may be useful in the treatment of neurodenerative diseases, and similar conditions.

By way of example, it is believed that STS inhibitors may be useful in the enhancing the memory function of patients suffering from illnesses such as amnesia, head injuries, Alzheimer's disease, epileptic dementia, presenile dementia, post traumatic dementia, senile dementia, vascular dementia and post-stroke dementia or individuals otherwise seeking memory enhancement.

TH1

We believe that some of the compounds of the present invention may be useful in TH1 implications.

By way of example, it is believed that the presence of STS inhibitors within the macrophage or other antigen presenting cells may lead to a decreased ability of sensitised T cells to mount a TH1 (high IL-2, IFNγ low IL-4) response. The normal regulatory influence of other steroids such as glucocorticoids would therefore predominate.

Inflamatory Conditions

We believe that some of the compounds of the present invention may be useful in treating inflammatory conditions—such as conditions associated with any one or more of: autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease; skin disorders e.g. psoriasis and contact dermatitis; graft versus host disease; eczema; asthma and organ rejection following transplantation.

By way of example, it is believed that STS inhibitors may prevent the normal physiological effect of DHEA or related steroids on immune and/or inflammatory responses.

The compounds of the present invention may be useful in the manufacture of a medicament for revealing an endogenous glucocorticoid-like effect.

Other Therapies

It is also to be understood that the compound/composition of the present invention may have other important medical implications.

For example, the compound or composition of the present invention may be useful in the treatment of the disorders listed in WO-A-99/52890—viz:

In addition, or in the alternative, the compound or composition of the present invention may be useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the compound or composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Compound Preparation

The compounds of the present invention may be prepared by reacting an appropriate alcohol with a suitable chloride. By way of example, the sulphamate compounds of the present invention may be prepared by reacting an appropriate alcohol with a suitable sulfamoyl chloride, of the formula $R^4R^5NSO_2Cl$.

Typical conditions for carrying out the reaction are as follows.

Sodium hydride and a sulfamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporated with toluene affords a crude residue which is further purified by flash chromatography.

Preferably, the alcohol is derivatised, as appropriate, prior to reaction with the sulfamoyl chloride. Where necessary, functional groups in the alcohol may be protected in known manner and the protecting group or groups removed at the end of the reaction.

Preferably, the sulphamate compounds are prepared according to the teachings of Page et al (1990 Tetrahedron 46; 2059–2068).

The phosphonate compounds may be prepared by suitably combining the teachings of Page et al (1990 Tetrahedron 46; 2059–2068) and PCT/GB92/01586.

The sulphonate compounds may be prepared by suitably adapting the teachings of Page et al (1990 Tetrahedron 46; 2059–2068) and PCT/GB92/01586.

The thiophosphonate compounds may be prepared by suitably adapting the teachings of Page et al (1990 Tetrahedron 46; 2059–2068) and PCT/GB91/00270.

Preferred preparations are also presented in the following text.

Summary

In summation, the present invention provides novel compounds for use as steroid sulphatase inhibitors and/or aromatase inhibitors and/or modulators of apoptosis and/or modulators of cell cycling and/or cell growth, and pharmaceutical compositions containing them.

EXAMPLES

Figure 2:
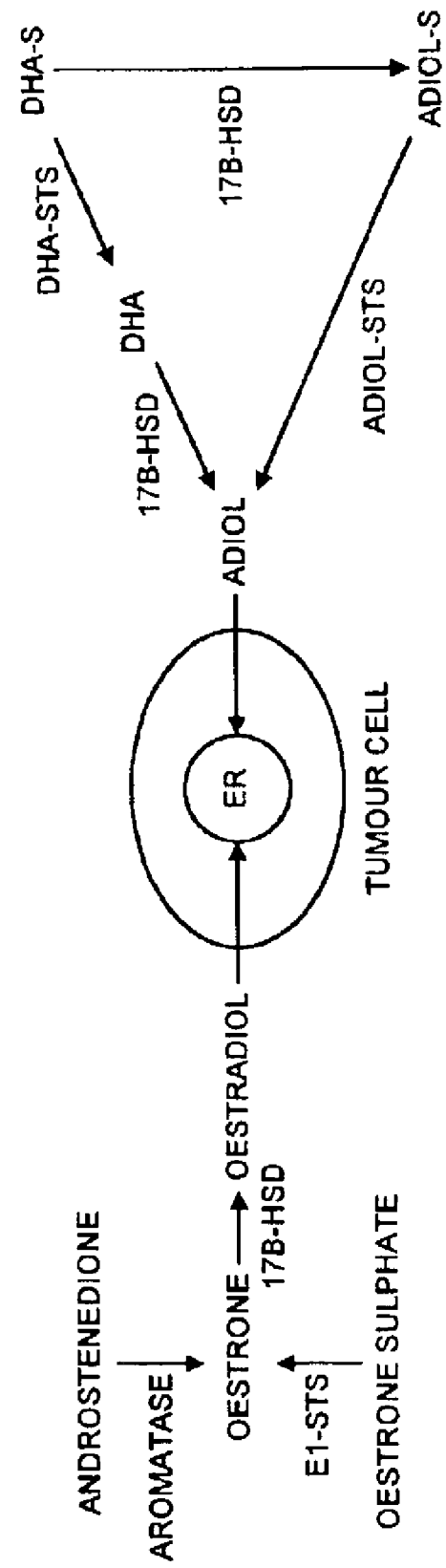
FIG. 2 is a scheme depicting the pathway of oestrogenic steroids in postmenopausal women.
Figure 3:
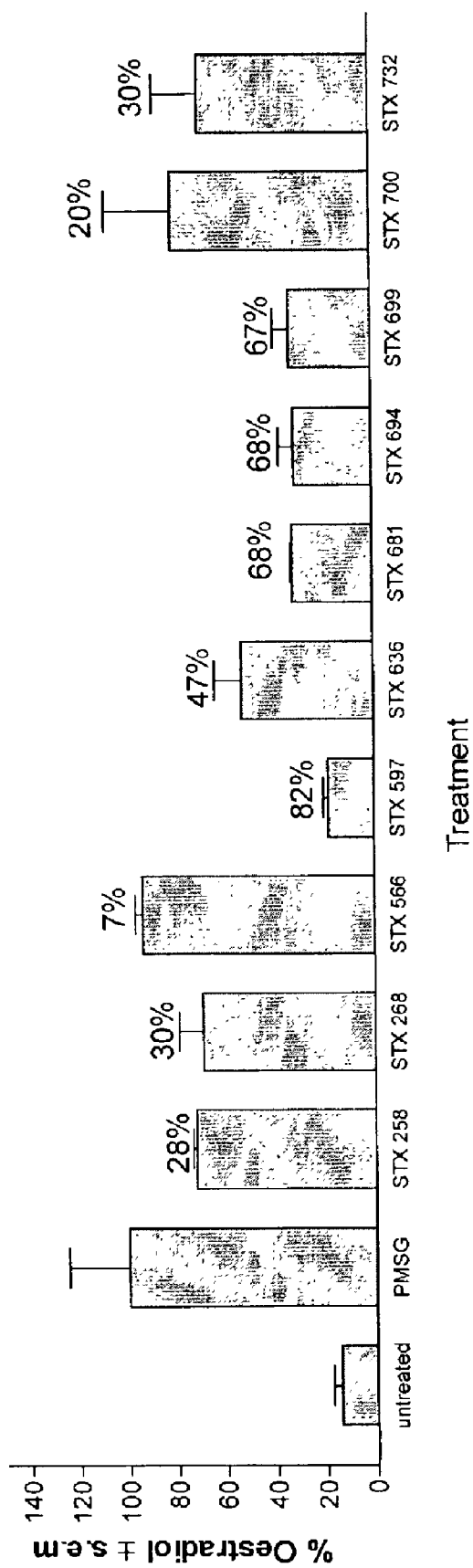
FIG. 3 is a bar graph depicting the effect of various dual aromatase-sulphatase inhibitors given orally at 10 mg/kg on PMSG-induced plasma oestradiol after 3 hour during in the DASI model.

The present invention will now be described in further detail by way of example only with reference to the accompanying figure in which:

FIG. 1 shows a summary scheme;

FIG. 2 shows a summary scheme;

FIG. 3 shows a graph; and

Figure 4:
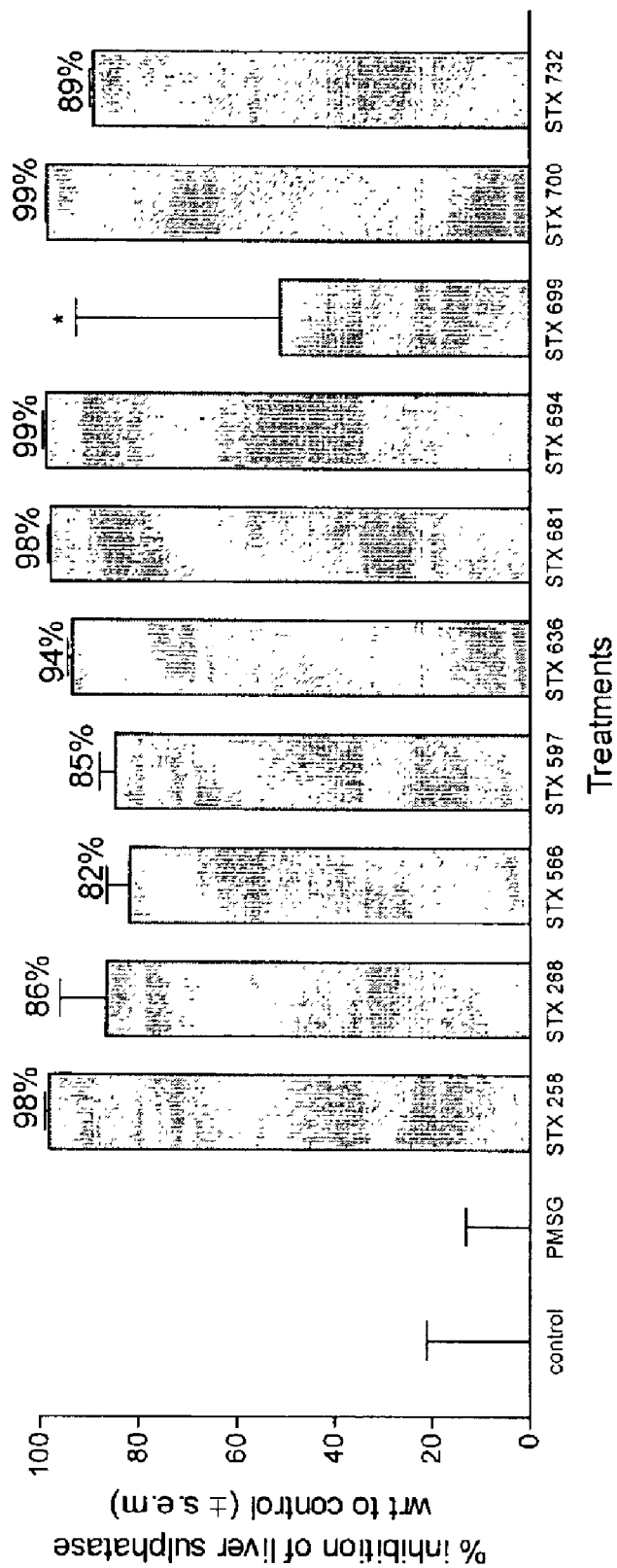
FIG. 4 is a bar graph depicting the effect of various dual-aromatase-sulphatase inhibitors given orally at 10 mg/kg on rat liver sulphatase activity after 3 hour in the in vivo DASI model.

FIG. 4 shows a graph.

The present invention will now be described only by way of example. However, it is to be understood that the examples also present preferred compounds of the present invention, as well as preferred routes for making same and useful intermediates in the preparation of same.

Synthetic Routes

Compounds in accordance with the present invention were synthesised in accordance with the synthetic routes and schemes.

Compounds of Formula III 4-([1,2,4]Triazol-4-ylamino)benzonitrile (LWO02023)

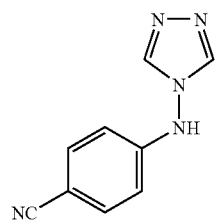

To a mixture of potassium tert-butoxide (6.7 g, 59.47 mmol) in anhydrous methyl sulfoxide (DMSO, 20 mL) was added at 10–15° C. portionwise a solution of 4-amino-4H-1,2,4-triazole (5.0 g, 59.47 mmol) in anhydrous DMSO (10 mL). After stirring the resulting thick light yellow suspension at room temperature under nitrogen for 60 min, this was cooled to ice/water temperature and a solution of 4-fluorobenzonitrile (3.60 g, 29.74 mmol) in anhydrous DMSO (10 mL) was added dropwise over a period of 5 min.

The orange suspension that formed was stirred at room temperature under nitrogen for 1 h before it was poured into water (500 mL). The pH of the clear yellow mixture that formed was brought to neutral by using 5M HCL followed by saturated aqueous sodium bicarbonate solution if required. This mixture was allowed to stand at room temperature uncovered for 7 days at which yellow crystals were deposited. Upon filtration, washings exhaustively with water and air-drying overnight, 4-([1,2,4]triazol-4-ylamino) benzonitrile (2.08 g, 11.23 mmol, 37.8%) was collected; m.p. 200–204° C.; $\delta_H$ (400 MHz, DMSO-$d_6$) 6.55 (2H, AA'BB'), 7.69 (2H, AA'BB'), 8.85 (2H, s, C3'-H and C5'-H) and 10.23 (1H, br s, exchanged with $D_2O$, NH).

4-[(4-Benzyloxybenzyl)-[1,2,4]triazol-4-ylamino] benzonitrile (LWO02029)

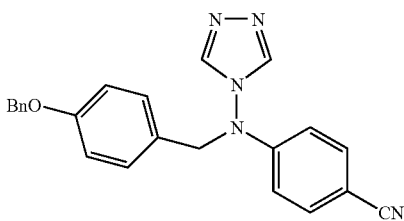

To a stirred solution of LWO02023 (700 mg, 3.780 mmol) in DMF (10 mL) at ice/water temperature was added sodium hydride (60% in mineral oil, 151 mg, 3.780 mmol). After stirring at room temperature under an atmosphere of nitrogen for 30 min, 4-benzyloxybenzyl chloride (968 mg, 4.158 mmol) was added in one portion and the resulting orange/brown mixture was heated at 80–90° C. for 3 h. The yellow suspension thus formed at room temperature was diluted with water (200 mL) and the white precipitate that formed was collected, washed exhaustively with water and air-dried to give 4-[(4-benzyloxybenzyl)-[1,2,4]triazol-4-ylamino] benzonitrile (1.35 g, 3.539 mmol, 94%) as white powder; m.p. 206–211° C.; $R_f$ 0.37 (neat ethyl acetate), c.f. 0.83 (4-benzyloxybenzyl chloride); $\delta_H$ (400 MHz, DMSO-$d_6$) 4.98 (2H, s $CH_2N$), 5.06 (2H, s, $CH_2O$), 6.77 (2H, AA'BB'), 6.95 (2H, AA'BB'), 7.21 (2H, AA'BB'), 7.30–7.46 (5H, m, Bn), 7.76 (2H, AA'BB') and 8.75 (2H, s, C3'-H and C5'-H); LRMS (FAB+): 763.3[7, (2M+H)$^+$], 382.2[100, (M+H)$^+$], 313.1[48, (M+H-triazole)$^+$]; (FAB–): 687.3[28, (M+2NBA)$^-$], 534.2[100, (M+NBA)$^-$]; HRMS (FAB+) 382.16648 $C_{23}H_{20}N_5O$ requires 382.16679.

4-[(4-Hydroxylbenzyl)-[1,2,4]triazol-4-ylamino] benzonitrile (LWO02030, STX265)

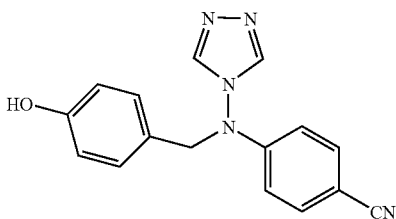

To a stirred solution of 4-[(4-benzyloxybenzyl)-[1,2,4] triazol-4-ylamino]benzonitrile (705 mg, 1.848 mmol) in distilled THF (120 mL) was added in succession absolute ethanol (30 mL) and Pd/C (10%, 40 mg). The black suspension was then stirred under an atmosphere of hydrogen (balloon) for 3 days. Upon removal by filtration and washings of the supported catalyst exhaustively with distilled THF, the filtrate was evaporated to give a slight wet light yellow residue (529 mg). The crude was recrystallised from DMF/ethyl acetate (1:10, 33 mL) to give 4-[(4-hydroxylbenzyl)-[1,2,4]triazol-4-ylamino]benzonitrile as yellow crystals (138 mg, 473.7 μmol, 25.6%); m.p. 228–230° C.; $R_f$ 0.24 (neat ethyl acetate), c.f. 0.40 (S.M.); $\delta_H$ (400 MHz, DMSO-$d_6$) 4.91 (2H, s $CH_2N$), 6.67 (2H, AA'BB'), 6.77 (2H, AA'BB'), 7.06 (2H, AA'BB'), 7.76 (2H, AA'BB'), 8.71 (2H, s, C3'-H and C5'-H) and 9.49 (1H, s, exchanged with $D_2O$, OH); LRMS (FAB+): 583.3[9, (2M+H)$^+$], 445.2[13, (M+H+NBA)$^+$], 292.2[100, (M+H)$^+$], 223.1 [50, (M-triazole)$^+$]; (FAB–): 444.2[36, (M+NBA)$^-$], 184.1 [100, (M-$C_7H_7O$)$^-$]; HRMS (FAB+) 292.11871 $C_{16}H_{14}N_5O$ requires 292.11984.

Sulfamic Acid 4-{[(4-cyanophenyl)-[1,2,4]triazol-4-ylamino]methyl}phenyl ester (LWO02031, STX258)

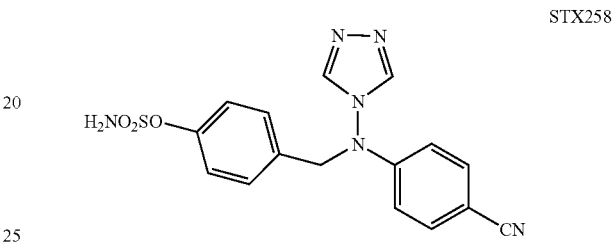

To a stirred solution of 4-[(4-hydroxylbenzyl)-[1,2,4] triazol-4-ylamino]benzonitrile (265 mg, 715.4 μmol) in anhydrous N,N-dimethylacetamide (DMA, 20 mL) was added at room temperature a solution of sulfamoyl chloride in toluene (ca. 0.68 M, 3.6 mL) and the resulting mixture stirred under an atmosphere of nitrogen overnight. Ethyl acetate (100 mL) was added to the reaction mixture and the organic layer that separated was washed with brine (100 mL, 4×50 mL), dried (MgSO4) and evaporated to give a light brown syrup/residue (ca. 400 mg). This crude was fractionated by flash chromatography (chloroform/methanol, 7:1 to 3.5:1, gradient) and the third fraction that isolated gave sulfamic acid 4-{[(4-cyanophenyl)-[1,2,4]triazol-4-ylamino]methyl}phenyl ester as a pale beige residue (150 mg, 405.0 μmol, 57%); m.p. 80–95° C.; $R_f$ 0.57 (chloroform/methanol, 5:1), c.f. 0.67 (S.M.); $\delta_H$ (400 MHz, DMSO-$d_6$) 5.10 (2H, s $CH_2N$), 6.74 (2H, AA'BB'), 7.23 (2H, AA'BB'), 7.42 (2H, AA'BB'), 7.77 (2H, AA'BB'), 8.03 (2H, br s, exchanged with $D_2O$, $H_2NSO_2$) and 8.85 (2H, s, C3'-H and C5'-H); LRMS (FAB+): 371.1[100, (M+H)$^+$], 302.1[30, (M-triazole)$^+$]; (FAB–): 523.2[30, (M+NBA)$^-$], 369.1[100, (M–H)$^-$], 184.1[34, (M-Bn-OSO$_2NH_2$)$^-$]; HRMS (FAB+) 371.09116 $C_{16}H_{15}N_6O_3S$ requires 371.09264.

2-(4-Benzyloxyphenyl)ethanol (LWO02057)

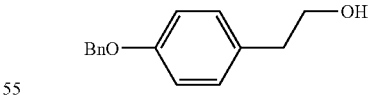

To a stirred solution of 4-hydroxyphenethyl alcohol (3.0 g, 22.16 mmol) in anhydrous DMF (50 mL) at ice/water temperature was added sodium hydride (60% in mineral oil, 886 mg, 22.16 mmol). After stirring at room temperature for 10 min, benzyl bromide (3.86 g, 22.16 mmol) was added and the reaction mixture was heated at 50° C. for 30 min. Upon cooling to room temperature, ethyl acetate (250 mL) was added and the organic layer that separated was washed with brine (500 mL, 4×100 mL), dried (MgSO$_4$) and evaporated to give a white residue (6.05 g). The crude was first dissolved in hot isopropanol (10 mL) and hexane (10 mL)

was then added dropwise. Upon cooling, 2-(4-benzyloxyphenyl)ethanol was isolated as soft white crystals (2.45 g, 10.73 mmol). A second crop of the product (2.04 g, 8.936 mmol, total yield: 89%) was obtained from the residue of the mother liquor upon recrystallisation from hot hexane (ca. 150 mL); $R_f$ 0.71 (neat ethyl acetate), 0.63 (S.M.); $\delta_H$ (400 MHz, DMSO-$d_6$) 2.64 (2H, t, J7.2 Hz, C$\underline{H}_2$CH$_2$OH), 3.54 (2H, m, reduced to t after D$_2$O exchange, CH$_2$C$\underline{H}_2$OH), 4.59 (1H, t, J5.2 Hz, exchanged with D$_2$O, OH), 5.06 (2H, S, CH$_2$O), 6.90 (2H, AA'BB'), 7.11 (2H, AA'BB') and 7.28–7.46 (5H, m, Bn); LRMS (FAB+): 228.0[94, M$^+$], 91.0[100, Bn$^+$].

1-Bromo-2-(4-benzyloxyphenyl)ethane (LWO02060)

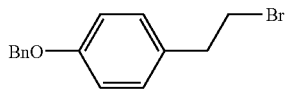

To a stirred solution of 2-(4-benzyloxyphenyl)ethanol (2.02 g, 8.848 mmol) in anhydrous distilled THF (30 mL) at ice/water temperature and under an atmosphere of nitrogen was added phosphorus tribromide (2.47 g, 8.848 mmol). After stirring at room temperature for 30 min, the reaction mixture was evaporated and the pale yellow liquid thus obtained was diluted with ethyl acetate (100 mL). The organic layer that separated was washed with brine (100 mL, 4×50 mL), dried (MgSO$_4$) and evaporated to give a light orange brown syrup (3.21 g) which turned light yellow upon standing overnight. This crude was fractionated by flash chromatography (chloroform/ethyl acetate, 1:2 to 1:1, gradient) and the first fraction that separated gave 1-bromo-2-(4-benzyloxyphenyl)ethane as a yellow solid (990 mg, 3.40 mmol, 38.4%); $R_f$ 0.82 (neat ethyl acetate), 0.68 (S.M.); $\delta_H$ (400 MHz, DMSO-$d_6$) 3.04 (2H, t, J 7.2 Hz, C$\underline{H}_2$CH$_2$Br), 3.67 (2H, t, J 7.4 Hz, CH$_2$C$\underline{H}_2$Br), 5.08 (2H, S, CH$_2$O), 6.95 (2H, AA'BB'), 7.20 (2H, AA'BB') and 7.30–7.48 (5H, m, Bn); LRMS (FAB+): 289.9(9), 73.0(100), (FAB−) 233.9 (100).

4-{[2-(4-Benzyloxyphenyl)ethyl]-[1,2,4]triazol-4-yl-amino}benzonitrile (LWO02061)

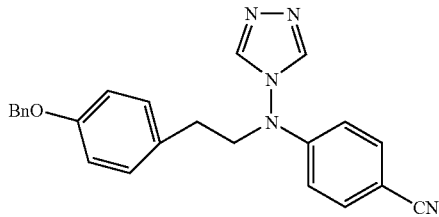

To a stirred solution of 4-([1,2,4]triazol-4-ylamino) benzonitrile (549 mg, 2.966 mmol) in DMF (10 mL) at ice/water temperature was added sodium hydride (60% in mineral oil, 137 mg, 3.426 mmol). After stirring at room temperature under an atmosphere of nitrogen for 30 min, 1-bromo-2-(4-benzyloxyphenyl)ethane (950 mg, 3.263 mmol) was added in one portion and the resulting dark brown mixture was heated at 70° C. for 3 h.

The reddish brown mixture that formed was diluted with ice/water (200 mL) and the precipitate that formed was collected, washed exhaustively with water and air-dried to give a light orange yellow residue (1.21 g). This crude was fractionated by flash chromatography (dry loading, ethyl acetate as eluant) and the second fraction that separated gave 4-{[2-(4-benzyloxyphenyl)ethyl]-[1,2,4]triazol-4-yl-amino}benzonitrile as a yellow syrup which solidified upon standing overnight at room temperature to a light yellow wax (590 mg, 1.492 mmol, 50.3%); $R_f$ 0.40 (neat ethyl acetate), c.f. 0.85 (1-bromo-2-(4-benzyloxyphenyl)ethane); $\delta_H$ (400 MHz, DMSO-$d_6$) 2.74 (2H, t, J~7.6 Hz, C$\underline{H}_2$CH$_2$N), 4.04 (2H, t, J~7.4 Hz, CH$_2$C$\underline{H}_2$N), 5.08 (2H, s, CH$_2$O), 6.59 (2H, AA'BB'), 6.94 (2H, AA'BB'), 7.20 (2H, AA'BB'), 7.28–7.46 (5H, m, Bn), 7.70 (2H, AA'BB') and 8.83 (2H, s, C3'-H and C5'-H); LRMS (FAB+): 396.1[100, (M+H)$^+$], 369.3[5, (M−CN)$^+$], 91.0[82, Bn$^+$]; (FAB−): 701.4[25, (M+2NBA)$^−$], 548.3[100, (M+NBA)$^−$], 441.2[35, (M+NBA−OBn)$^−$]; HRMS (FAB+) 396.18192 C$_{24}$H$_{22}$N$_5$O requires 396.18244.

4-{[2-(4-Hydroxyphenyl)ethyl]-[1,2,4]triazol-4-yl-amino}benzonitrile (LWO02063, STX290)

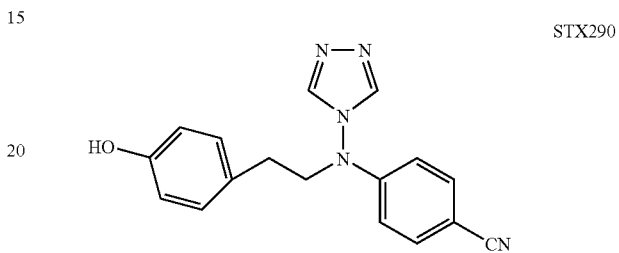

To a stirred solution of 4-{[2-(4-benzyloxyphenyl)ethyl]-[1,2,4]triazol-4-yl-amino}benzonitrile (536 mg, 1.355 mmol) in distilled THF (15 mL) was added in succession absolute ethanol (30 mL) and Pd/C (10%, 54 mg). The black suspension was then stirred under an atmosphere of hydrogen (balloon) for 3 days. Upon removal by filtration and washings of the supported catalyst exhaustively with distilled THF, the filtrate was evaporated to give a pale yellow syrup which solidified upon standing at room temperature to a light yellow wax (192 mg). This crude was fractionated by flash chromatography (ethyl acetate) and the second fraction that separated gave 4-{[2-(4-hydroxyphenyl)ethyl]-[1,2,4]triazol-4-yl-amino}benzonitrile as a pale yellow waxy residue (115 mg, 376.6 μmol, 28%); $R_f$ 0.46 (neat ethyl acetate), c.f. 0.59 (S.M.); $\delta_H$ (400 MHz, DMSO-$d_6$) 2.70 (2H, t, J 7.4 Hz, C$\underline{H}_2$CH$_2$N), 4.01 (2H, t, J~7.6 Hz, CH$_2$N), 6.59 (2H, AA'BB'), 6.69 (2H, AA'BB'), 7.06 (2H, AA'BB'), 7.71 (2H, AA'BB'), 8.78 (2H, s, C3'-H and C5'-H) and 9.29 (1H, s, exchanged with D$_2$O, OH); LRMS (FAB+): 611.2[12, (2M+H)$^+$], 459.1[8, (M+H+NBA)$^+$], 306.0[100, (M+H)$^+$]; (FAB−): 763.5[18, (2M+NBA)$^−$], 609.4[45, (2M−H)$^−$], 184.0[100, (HOPhCH$_2$CH$_2$)$^−$]; HRMS (FAB+) 306.13477 C$_{17}$H$_{16}$N$_5$O requires 306.13549.

Sulfamic Acid 4-{2-[(4-cyanophenyl)-[1,2,4]triazol-4-ylamino]ethyl}phenyl ester (LWO02066, STX273)

STX273

To a stirred solution of 4-{[2-(4-hydroxyphenyl)ethyl]-[1,2,4]triazol-4-yl-amino}benzonitrile (81 mg, 265.2 μmol) in anhydrous N,N-dimethylacetamide (DMA, 5 mL) was added at room temperature a solution of sulfamoyl chloride in toluene (ca. 0.68 M, 1.2 mL) and the resulting mixture was stirred under an atmosphere of nitrogen overnight. Ethyl acetate (50 mL) was then added to the reaction mixture and the organic layer that separated was washed with brine (100 mL, 4×50 mL), dried (MgSO4), filtered and evaporated to give a light brown syrup/residue (ca. 100 mg). This crude was dissolved in acetone (20 mL) and then concentrated to approximately 3 mL. Hexane (1.5 mL) was then added dropwise and upon standing gave sulfamic acid 4-{2-[(4-cyanophenyl)-[1,2,4]triazol-4-ylamino]ethyl}phenyl ester as white crystals (52 mg, 135.3 μmol, 51%); $R_f$ 0.33 (ethyl acetate), c.f. 0.41 (S.M.); $\delta_H$ (400 MHz, DMSO-$d_6$) 2.84 (2H, t, J 7 Hz, C$\underline{H}_2$CH$_2$N), 4.09 (2H, t, J~7 Hz, CH$_2$N), 6.63 (2H, AA'BB'), 7.20 (2H, AA'BB'), 7.38 (2H, AA'BB'), 7.72 (2H, AA'BB'), 7.97 (2H, br s, exchanged with D$_2$O, OSO$_2$NH$_2$) and 8.87 (2H, s, C3'-H and C5'-H); LRMS (FAB+): 385.0[100, (M+H)$^+$]; (FAB−): 537.2[40, (M+NBA)$^-$], 383.1[100, (M−H)$^-$]; HRMS (FAB+) 385.10752 C$_{17}$H$_{17}$N$_6$O$_3$S requires 385.10829.

1-Benzyloxy-4-(2-bromoethoxy)benzene (LWO02068)

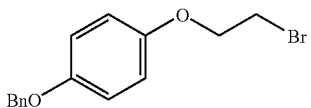

This compound was prepared from 4-(benzyloxy)phenol and 1,2-dibromoethane in the same manner as described by Zhou et. Al. (1999) J. Med. Chem. 42: 2993–3000.

4-{[2-(4-Benzyloxyphenoxy)ethyl]-[1,2,4]triazol-4-yl-amino}benzonitrile (LWO02075)

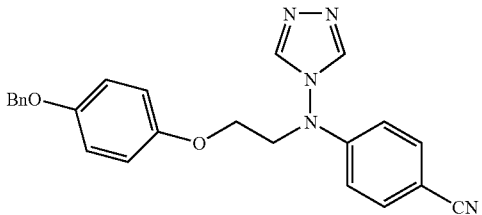

To a stirred solution of 4-([1,2,4]triazol-4-ylamino)benzonitrile (1.0 g, 5.40 mmol) in DMF (15 mL) at ice/water temperature was added sodium hydride (60% in mineral oil, 238 mg, 5.94 mmol). After stirring at room temperature under an atmosphere of nitrogen for 10 min, 1-benzyloxy-4-(2-bromoethoxy)benzene (1.82 g, 5.94 mmol) was added in one portion and the resulting dark brown mixture was heated at 50° C. for 18 h. The reaction mixture was then passed through a short column of silica and the filter cake was washed with ethyl acetate (10×20 mL). The combined filtrate was washed with brine (200 mL, 4×50 mL), dried (MgSO$_4$), filtered and evaporated to give a light yellow brown residue (2.28 g). This crude was recrystallised from hot ethyl acetate to give 4-{[2-(4-benzyloxyphenoxy)ethyl]-[1,2,4]triazol-4-yl-amino}benzonitrile (690 mg, 1.677 mmol) as fluffy creamy crystals. A second crop of the product (915 mg, 2.224 mmol, total yield, 72%) was obtained from the residue of the mother liquor upon recrystallisation from hot ethyl acetate and hexane; m.p. 160–162° C.; Rf 0.45 (neat ethyl acetate), c.f. 0.89 (1-benzyloxy-4-(2-bromoethoxy)benzene); $\delta_H$ (400 MHz, DMSO-$d_6$) 4.08 (2H, m, CH$_2$), 4.23 (2H, m, CH$_2$), 5.03 (2H, s, CH$_2$O), 6.67 (2H, AA'BB'), 6.82 (2H, AA'BB'), 6.93 (2H, AA'BB'), 7.28–7.46 (5H, m, Bn), 7.74 (2H, AA'BB') and 8.91 (2H, s, C3'-H and C5'-H). Found C, 69.7; H, 5.16; N, 16.7; C$_{24}$H$_{21}$N$_5$O$_2$ requires C, 70.06; H, 5.14; N, 17.02%.

4-{[2-(4-Hydroxyphenoxy)ethyl]-[1,2,4]triazol-4-yl-amino}benzonitrile (LWO02076, STX291)

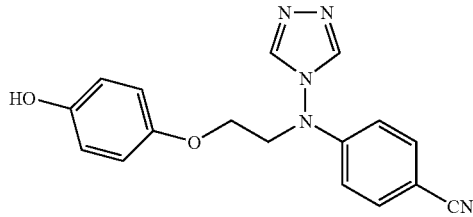

To a stirred solution of 4-{[2-(4-benzyloxyphenoxy)ethyl]-[1,2,4]triazol-4-yl-amino}benzonitrile (670 mg, 1.628 mmol) in distilled THF (70 mL) was added in succession absolute ethanol (30 mL) and Pd/C (10%, 67 mg). The black suspension was then stirred under an atmosphere of hydrogen (balloon) for 3 days. Upon removal by filtration and washings of the supported catalyst exhaustively with distilled THF, the filtrate was evaporated to give a light yellow residue (491 mg). This crude was dissolved in hot acetone (25 mL) and hexane (15 mL) was then added dropwise. Upon cooling, 4-{[2-(4-hydroxyphenoxy)ethyl]-[1,2,4]triazol-4-yl-amino}benzonitrile was separated as light green yellow crystals (310 mg, 964.1 μmol, 59%); m.p. 184–195° C.; $R_f$ 0.31 (neat ethyl acetate), c.f. 0.45 (S.M.); $\delta_H$ (400 MHz, DMSO-$d_6$) 4.03 (2H, t, J 4.6–5.1 Hz, CH$_2$), 4.21 (2H, t, J 5.1 Hz, CH$_2$), 6.62–6.73 (6H, m, Ar), 7.73 (2H, AA'BB'), 8.89 (2H, s, C3'-H and C5'-H) and 8.95 (1H, s, exchanged with D$_2$O, OH); LRMS (FAB+): 643.2[12, (2M−H)$^+$], 475.1[100, (M+H+NBA)$^+$], 322.1[100, (M+H)$^+$], 253.1[20, (M-triazole)$^+$]; (FAB−): 795.1[10, (2M+NBA)$^-$], 641.2[30, (2M−H)$^-$], 474.2[90, (M+NBA)$^-$], 320.1[100, (M−H)$^-$]; HRMS (FAB+) 322.12984 C$_{17}$H$_{16}$N$_5$O$_2$ requires 322.13040.

Sulfamic Acid 4-{2-[(4-cyanophenyl)-[1,2,4]triazol-4-yl-amino]ethoxy}phenyl ester (LWO02077, STX292)

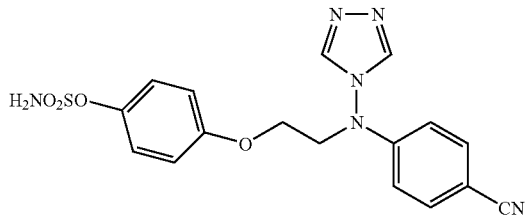

To a stirred solution of 4-{[2-(4-hydroxyphenoxy)ethyl]-[1,2,4]triazol-4-yl-amino}benzonitrile (212 mg, 659.7 μmol) in anhydrous N,N-dimethylacetamide (DMA, 5 mL) was added at room temperature a solution of sulfamoyl chloride in toluene (ca. 0.68 M, 2 mL) and the resulting mixture was stirred under an atmosphere of nitrogen for 1.5 h. Ethyl acetate (100 mL) was then added to the reaction mixture and the organic layer that separated was washed with brine (100 mL, 4×50 mL), dried (MgSO4), filtered and evaporated to give a white fluffy residue (299 mg). This crude was fractionated by flash chromatography (ethyl acetate, then ethyl acetate/acetone 2:1 after the second fraction was eluted) and upon evaporation of the third fraction that isolated gave sulfamic acid 4-{2-[(4-cyanophenyl)-[1,2,4]triazol-4-yl-amino]ethoxy}phenyl ester as white fluffy residue (218 mg, 544.4 μmol, 83%); $R_f$ 0.21 (ethyl acetate), c.f. 0.30 (S.M.); $\delta_H$ (400 MHz, DMSO-$d_6$) 4.14 (2H, m, CH$_2$), 4.28 (2H, m, CH$_2$), 6.68 (2H, AA'BB'), 6.94 (2H, AA'BB'), 7.18 (2H, AA'BB'), 7.75 (2H, AA'BB'), 7.89 (2H, br s, exchanged with D$_2$O, OSO$_2$NH$_2$) and 8.93 (2H, s, C3'-H and C5'-H); LRMS (FAB+): 401.0 [100, (M+H)$^+$]; (FAB−): 799.1[8, (2M−H)$^−$], 553.2[35, (M+NBA)$^−$], 399.1[100, (M−H)$^−$]; HRMS (FAB+) 401.10471 C$_{17}$H$_{17}$N$_6$O$_4$S requires 401.10320.

1-Benzyloxy-4-(4-bromobutoxy)benzene (LWO02064)

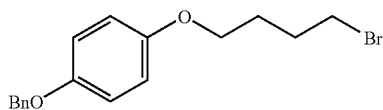

To a solution of 4-(benzyloxy)phenol (3.0 g, 15.13 mmol) and 1,4-dibromobutane (16.34 g, 75.65 mmol) in acetonitrile (25 mL) was added anhydrous potassium carbonate (5.23 g, 37.83 mmol). The suspension was then refluxed for 18 h. After cooling to room temperature, the suspension was filtered through a short column of silica and the filter cake washed exhaustively with ethyl acetate. The filtrate was evaporated to give a yellow liquid (17.63 g) which upon standing gave a mass of white crystals. These crystals were then triturated with hexane and collected by filtration. Upon drying in the air, 1-benzyloxy-4-(4-bromobutoxy)benzene was obtained as creamy crystals (2.87 g, 8.561 mmol, 57%); m.p. 73–75° C.; R$_f$ 0.84 (chloroform), c.f. 0.16 (S.M.); $\delta_H$ (400 MHz, DMSO-$d_6$) 1.80 (2H, m, CH$_2$), 1.95 (2H, m, CH$_2$), 3.60 (2H, t, J=6.6 Hz, CH$_2$Br), 3.92 (2H, t, J 6.2 Hz, OCH$_2$CH$_2$), 5.03 (2H, s, CH$_2$O), 6.86 (2H, AA'BB'), 6.92 (2H, AA'BB') and 7.28–7.46 (5H, m, Bn). Found C 60.8, H 5.71; C$_{17}$H$_{19}$BrO$_2$ requires C 60.91, H 5.71%.

4-{[4-(4-Benzyloxyphenoxy)butyl]-[1,2,4]triazol-4-ylamino}benzonitrile (LWO02065)

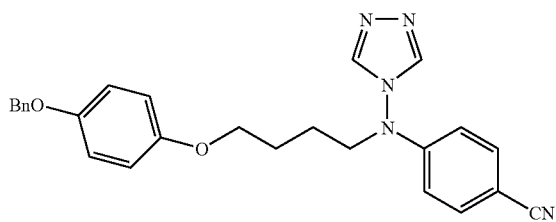

To a stirred solution of 4-([1,2,4]triazol-4-ylamino)benzonitrile (1.0 g, 5.40 mmol) in DMF (15 mL) at ice/water temperature was added sodium hydride (60% in mineral oil, 238 mg, 5.94 mmol). After stirring at room temperature under an atmosphere of nitrogen for 10 min, 1-benzyloxy-4-(4-bromobutoxy)benzene (1.99 g, 5.94 mmol) was added in one portion and the resulting dark brown mixture was heated at 50° C. for 18 h. The cooled reaction mixture was then passed through a short column of silica and the filter cake was washed with ethyl acetate (10×20 mL). The combined filtrate was washed with brine (200 mL, 4×50 mL), dried (MgSO$_4$), filtered and evaporated to give a yellow orange residue (2.50 g). This crude was dissolved in hot ethyl acetate (10 mL) and hexane (2 mL) was then added dropwise. Upon cooling to room temperature, 4-{[4-(4-benzyloxyphenoxy)butyl]-[1,2,4]triazol-4-ylamino}benzonitrile was obtained as creamy/pale yellow crystals (1.42 g, 3.231 mmol). A second crop of the product (363 mg, 825.9 µmol, total yield, 75%) was obtained from the residue of the mother liquor upon recrystallisation from hot ethyl acetate; m.p. 124.5–126.5° C.; Rf 0.45 (neat ethyl acetate), c.f. 0.88 (1-benzyloxy-4-(4-bromobutoxy)benzene); $\delta_H$ (400 MHz, DMSO-$d_6$) 1.58 (2H, quasi quintet, CH$_2$), 1.78 (2H, quasi quintet, CH$_2$), 3.90 (4H, quasi q, OCH$_2$CH$_2$CH$_2$CH$_2$N), 5.03 (2H, s, CH$_2$O), 6.65 (2H, AA'BB'), 6.84 (2H, AA'BB'), 6.92 (2H, AA'BB'), 7.28–7.45 (5H, m, Bn), 7.72 (2H, AA'BB') and 8.98 (2H, s, C3'-H and C5'-H). Found C, 71.05; H, 5.74; N, 15.8; C$_{26}$H$_{25}$N$_5$O$_2$ requires C 71.05, H 5.73, N 15.93%.

4-{[4-(4-Hydroxyphenoxy)butyl]-[1,2,4]triazol-4-ylamino}benzonitrile (LWO02067, STX287)

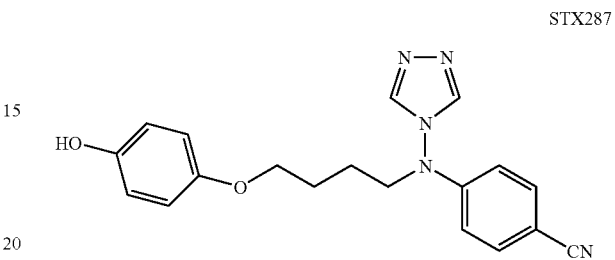

To a stirred solution of 4-{[4-(4-benzyloxyphenoxy)butyl]-[1,2,4]triazol-4-ylamino}benzonitrile (800 mg, 1.820 mmol) in distilled THF (10 mL) was added in succession absolute ethanol (30 mL) and Pd/C (10%, 80 mg). The black suspension was then stirred under an atmosphere of hydrogen (balloon) for 2 days. Upon removal by filtration and washings of the supported catalyst exhaustively with distilled THF, the filtrate was evaporated to give a light yellow frothy residue/syrup (481 mg). This crude was fractionated by flash chromatography (ethyl acetate to acetone, gradient) and the second fraction that separated upon evaporation gave a soft pale yellow residue (323 mg) which was further purified by recrystallisation from acetone/hexane to give 4-{[4-(4-hydroxyphenoxy)butyl]-[1,2,4]triazol-4-ylamino}benzonitrile as fine pale yellow crystals (280 mg, 801.4 µmol, 44%); m.p. 156–159° C.; R$_f$ 0.42 (neat ethyl acetate), c.f. 0.51 (S.M.); $\delta_H$ (400 MHz, DMSO-$d_6$) 1.58 (2H, m), 1.76 (2H, m), 3.87 (4H, m, OCH$_2$CH$_2$CH$_2$CH$_2$N), 6.61–6.75 (6H, m, Ar), 7.73 (2H, AA'BB'), 8.91 (1H, s, exchanged with D$_2$O, OH) and 8.99 (2H, s, C3'-H and C5'-H). Found C 65.4, H 5.54, N 19.6; C$_{19}$H$_{19}$NSO$_2$ requires C, 65.32; H, 5.48; N, 20.04%.

Sulfamic Acid 4-{4-[(4-cyanophenyl)-[1,2,4]triazol-4-ylamino]butoxy}phenyl ester (LWO02069, STX288)

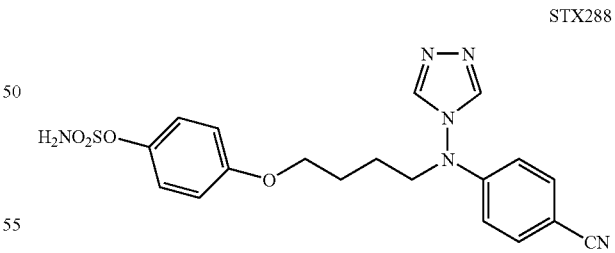

To a stirred solution of 4-{[4-(4-hydroxyphenoxy)butyl]-[1,2,4]triazol-4-ylamino}benzonitrile (210 mg, 601 µmol) in anhydrous N,N-dimethylacetamide (DMA, 5 mL) was added at room temperature a solution of sulfamoyl chloride in toluene (ca. 0.68 M, 1.8 mL) and the resulting mixture was stirred under an atmosphere of nitrogen for 1.5 h. Ethyl acetate (100 mL) was then added to the reaction mixture and the organic layer that separated was washed with brine (50 mL, 4×20 mL), dried (MgSO4), filtered and evaporated to give a creamy residue (291 mg) which was purified by recrystallisation from acetone/hexane to give sulfamic acid 4-{4-[(4-cyanophenyl)-[1,2,4]triazol-4-ylamino]butoxy}phenyl ester as pale yellow crystals (218 mg, 508.8 µmol, 85%); m.p. 164–172° C.; $R_f$ 0.43 (ethyl acetate), c.f. 0.48 (S.M.); $\delta_H$ (400 MHz, DMSO-$d_6$) 1.60 (2H, m, $CH_2$), 1.82 (2H, m, $CH_2$), 3.90 (2H, t, J 7.4 Hz, $CH_2$), 3.98 (2H, t, J 6.2 Hz, $CH_2$), 6.66 (2H, AA'BB'), 6.97 (2H, AA'BB'), 7.18 (2H, AA'BB'), 7.73 (2H, AA'BB'), 8.91 (2H, br s, exchanged with $D_2O$, $OSO_2NH_2$) and 8.99 (2H, s, C3'-H and C5'-H); LRMS (FAB+): 429.0[100, (M+H)$^+$]; (FAB-): 427.1[100, (M-H)$^-$]; HRMS (FAB+) 429.13567 $C_{19}H_{21}N_6O_4S$ requires 429.13450.

3-Bromo-4-hydroxybenzaldehyde (LWO02081)

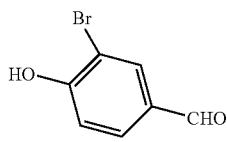

To a stirred solution of 4-hydroxybenzaldehyde *8.0 g, 64.20 mmol) in chloroform (400 mL) at 40° C. was added portionwise a solution of bromine (3.3 mL) in chloroform (10 mL). The resulting reddish brown mixture was stirred at 40° C. for 2 h, cooled and evaporated to give a purple residue which was dissolved in ethyl acetate (200 mL). The organic layer that separated was washed with brine (4×100 mL), dried ($MgSO_4$), filtered and evaporated to give a light pink/brown residue (12.95 g). The crude was purified by recrystallisation from hot toluene twice to give 3-bromo-4-hydroxybenzaldehyde as light orange/brown crystals (8.88 g, 44.17 mmol, 69%); m.p. 115–128° C.; $R_f$ 0.42 (chloroform/ethyl acetate, 4:1), c.f. 0.36 (S.M.); $\delta_H$ (400 MHz, DMSO-$d_6$) 7.11 (1H, d, J 8.2 Hz, C5-H), 7.76 (1H, dd, J 1.95 and 8.2 Hz, C6-H), 8.04 (1H, d, J 2 Hz, C2-H), 9.78 (1H, s, CHO) and 11.53 (1H, s, exchanged with $D_2O$, OH). This product was used for the next reaction without further purification.

4-Benzyloxy-3-bromobenzaldehyde (LWO02082)

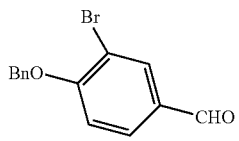

To a stirred solution of 3-bromo-4-hydroxybenzaldehyde (8.0 g, 39.80 mmol) in anhydrous DMF (50 mL) at ice/water temperature was added sodium hydride (60% in mineral oil, 1.67 g, 41.79 mmol). After stirring at room temperature for 10 min, benzyl bromide (7.64 g, 43.78 mmol) was added and the reaction mixture was heated at 80° C. for 2 h. Upon cooling to room temperature, ethyl acetate (300 mL) was added and the organic layer that separated was washed with brine (500 mL, 4×50 mL), dried ($MgSO_4$), filtered and evaporated to give a light beige residue (13.09 g). The crude was purified by recrystallisation from isopropanol/hexane to give 4-benzyloxy-3-bromobenzaldehyde as fine light yellow crystals (9.52 g, 32.70 mmol, 82%); m.p. 95–96.5° C. [Lit.[1] (ethanol), m.p. 95° C.]; $R_f$ 0.75 (ethyl acetate/hexane, 1:1), 0.52 (S.M.); $\delta_H$ (400 MHz, DMSO-$d_6$) 5.35 (2H, s, $CH_2$), 7.33–7.53 (6H, m, Bn and C5-H), 7.93 (1H, dd, J 2 and 8.4 Hz, C6-H), 8.13 (1H, d, J 1.9 Hz, C2-H) and 9.87 (1H, s, CHO).

[1] Buu-Hoi et. Al. (1953) J. Org. Chem. 18: 121–125.

4-Benzyloxy-3-bromophenol (LWO02085)

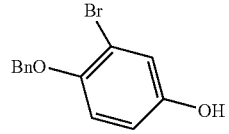

To a stirred solution of 4-benzyloxy-3-bromobenzaldehyde (4.5 g, 15.46 mmol) in chloroform (30 mL) at room temperature was added m-chloroperoxybenzoic acid (57–86%, 5.62 g) and the resulting suspension was stirred for 4 h. Ethyl acetate (200 mL) was then added and the organic layer that separated was washed with saturated aqueous sodium bicarbonate (1×100 mL, 3×50 mL) followed by brine (2×50 mL), dried ($MgSO_4$), filtered and evaporated to give a clear brown oil which upon standing at room temperature overnight gave some light yellow deposits (6.05 g). To this crude in methanol (45 mL) at room temperature was added 1 M NaOH (aq) (30 mL). After stirring for 2 h, the resulting brown mixture was acidified with 5 M HCl followed by dilution with ethyl acetate (200 mL). The organic layer that separated was washed with brine (100 mL, 4×50 mL), dried ($MgSO_4$), filtered and evaporated to give a brown oil (5.33 g). Upon fractionation by flash chromatography (ethyl acetate/hexane, 1:2 to 1:1 gradient), the fourth fraction that isolated gave 4-benzyloxy-3-bromophenol as a light golden yellow oil which solidified upon standing at room temperature to form a light brown wax (3.92 g, 14.04 mmol, 91%); $R_f$ 0.48 (ethyl acetate/hexane, 1:2), 0.61 (4-benzyloxy-3-bromobenzaldehyde); $\delta_H$ (400 MHz, DMSO-$d_6$) 5.07 (2H, s, $CH_2O$), 6.72 (1H, dd, J 2.7 and 8.9 Hz, C6-H), 6.98 (1H, d, J 3.1 Hz, C2-H), 7.02 (1H, d, J 8.9 Hz, C5-H), 7.28–7.50 (5H, m, Bn) and 9.39 (1H, br s, exchanged with $D_2O$, OH); LRMS (FAB+): 278.0[35, (79M)$^+$], 91.0[100, Bn$^+$]; (FAB-): 433.1[83, ($^{81}$M+NBA)$^-$], 276.9[84, (79M-H)$^-$], 187.9 [100, (81M-H-Bn)$^-$]; HRMS (FAB+) 277.99390 $C_{13}H_{11}^{79}BrO_2$ requires 277.99424, (FAB+) 279.99213 $C_{13}H_{18}^{81}BrO_2$ requires 279.99219. The product was not further purified before use.

2-(4-Benzyloxy-3-bromophenoxy)ethanol (LWO02086)

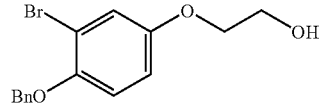

To a solution of 4-benzyloxy-3-bromophenol (2.0 g, 7.165 mmol) in anhydrous DMF (10 mL) at room temperature was added anhydrous potassium carbonate (1.04 g) followed by 2-bromoethanol (990 mg, 7.523 mmol). The resulting suspension was stirred under an atmosphere of nitrogen at 80° C. overnight. After cooling, ethyl acetate (100 mL) was added and the organic layer that separated was washed with brine (150 mL, 4×50 mL), dried ($MgSO_4$), filtered and evaporated to give a brown syrup (2.51 g). This crude was fractionated by flash chromatography (chloroform/ethyl acetate, 6:1 to 2:1 gradient) and the third fraction that separated upon evaporation gave 2-(4-benzyloxy-3-bromophenoxy)ethanol (1.58 g, 4.889 mmol, 68%); $R_f$ 0.49 (chloroform/ethyl acetate, 4:1), c.f. 0.68 (S.M.); $\delta_H$ (400 MHz, DMSO-$d_6$) 3.67 (2H, ~q, J~5 Hz, C$\underline{H}_2$OH), 3.94 (2H, t, J 5.1 Hz, C$\underline{H}_2$CH$_2$OH), 4.86 (1H, t, J 5.5 Hz, exchanged with $D_2O$, OH), 5.13 (2H, s, $CH_2O$), 6.92 (1H, dd, J 3.1 and 8.9 Hz, C6-H), 7.12 (1H, d, J 9 Hz, C5-H), 7.19 (1H, d, J 3.1 Hz, C2-H) and 7.30–7.50 (5H, m, Bn); LRMS (FAB+): 322.0[45, (79M)$^+$], 91.0[100, Bn$^+$]; (FAB−): 475.2[24, ($^{79}$M+NBA)$^-$], 323.1 [100, ($^{81}$M−H)$^-$], 231.9(100); HRMS (FAB+) 324.01846 $C_{15}H_{15}{}^{81}BrO_3$ requires 324.01841.

2-Bromo-1-(4-benzyloxy-3-bromophenoxy)ethane (LWO02087)

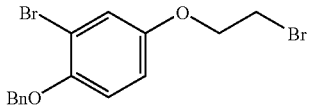

To a solution of 2-(4-benzyloxy-3-bromophenoxy)ethanol (1.44 g, 4.456 mmol) in anhydrous dichloromethane (15 mL) at ice/water temperature was added carbon tetrabromide (1.88 g, 5.570 mmol) followed by triphenylphosphine (1.77 g, 6.684 mmol) portionwise over a period of 5 min. After stirring under an atmosphere of nitrogen at ice/water temperature for 15 min, the reaction mixture was evaporated to give a pale orange syrup (5.22 g). This crude was fractionated by flash chromatography (chloroform/ethyl acetate, 4:1) and the first fraction that separated upon evaporation gave 2-bromo-1-(4-benzyloxy-3-bromophenoxy)ethane as a pale yellow liquid (1.81 g, 4.688 mmol); $R_f$ 0.79 (chloroform/ethyl acetate, 4:1), c.f. 0.32 (S.M.); $\delta_H$ (400 MHz, DMSO-$d_6$) 3.76 (2H, t, J 5.5 Hz, C$\underline{H}_2$Br), 4.28 (2H, ~t, J 4–5 Hz, OC$\underline{H}_2$CH$_2$), 5.14 (2H, s, CH$_2$O), 6.96 (1H, dd, J 3.1 and 8.9 Hz, C6-H), 7.13 (1H, d, J 8.9 Hz, C5-H), 7.24 (1H, d, J 2.7 Hz, C2-H) and 7.30–7.50 (5H, m, Bn); LRMS (FAB+): 385.9[36, M$^+$], 91.0[100, Bn$^+$]; (FAB−): 385.0[29, (M−H)$^-$], 231.9(100); HRMS (FAB+) 385.93362 $C_{15}H_{14}O_2{}^{79}Br^{81}Br$ requires 385.93401.

4-{[2-(4-Benzyloxy-3-bromophenoxy)ethyl]-[1,2,4]triazol-4-ylamino}benzonitrile (LWO02088)

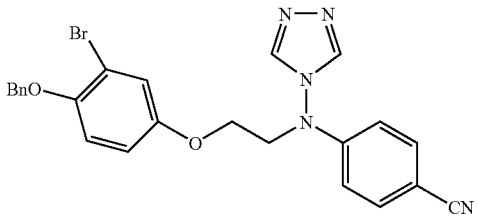

To a stirred solution of 4-([1,2,4]triazol-4-ylamino)benzonitrile (741 mg, 4.001 mmol) in anhydrous DMF (10 mL) at ice/water temperature was added sodium hydride (60% in mineral oil, 176 mg, 4.401 mmol). After stirring at room temperature under an atmosphere of nitrogen for 10 min, a solution of 2-bromo-1-(4-benzyloxy-3-bromophenoxy)ethane (1.70 g, 4.401 mmol) in DMF (5 mL) was added. The resulting mixture was heated at 60° C. for 2 h, then cooled and diluted with ethyl acetate (500 mL). The organic layer that separated was washed with brine (200 mL, 4×100 mL), dried (MgSO$_4$), filtered and evaporated to give a light brown residue (2.04 g). This crude was purified by recrystallisation from hot ethyl acetate and upon cooling gave 4-{[2-(4-benzyloxy-3-bromophenoxy)ethyl]-[1,2,4]triazol-4-ylamino}benzonitrile as fluffy pale beige powder (1.20 g, 2.447 mmol, 61%); m.p. 163–166° C.; $R_f$ 0.30 (ethyl acetate), c.f. 0.75 [2-bromo-1-(4-benzyloxy-3-bromophenoxy)ethane]; $\delta_H$ (400 MHz, DMSO-$d_6$) 4.11 (2H, t, J 4–5 Hz, CH$_2$N), 4.23 (2H, t, J 4–5 Hz, CH$_2$O), 5.13 (2H, s, CH$_2$O), 6.66 (2H, AA'BB'), 6.86 (1H, dd, J 2.7 and 8.9 Hz, C6'-H), 7.12 (1H, d, J 8.9 Hz, C5'-H), 7.16 (1H, d, J 2.7 Hz, C2'-H), 7.30–7.48 (5H, m, Bn), 7.74 (2H, AA'BB') and 8.94 (2H, s, C3"-H and C5"-H). Found C, 58.6; H, 4.17; N, 14.38; $C_{24}H_{20}BrN_5O_2$ requires C 58.79, H 4.11, N 14.28%.

4-{[2-(3-Bromo-4-hydroxyphenoxy)ethyl]-[1,2,4]triazol-4-ylamino}benzonitrile (STX300) and 4-{[2-(4-Hydroxyphenoxy)ethyl]-[1,2,4]triazol-4-ylamino}benzonitrile (STX291) (LWO02089)

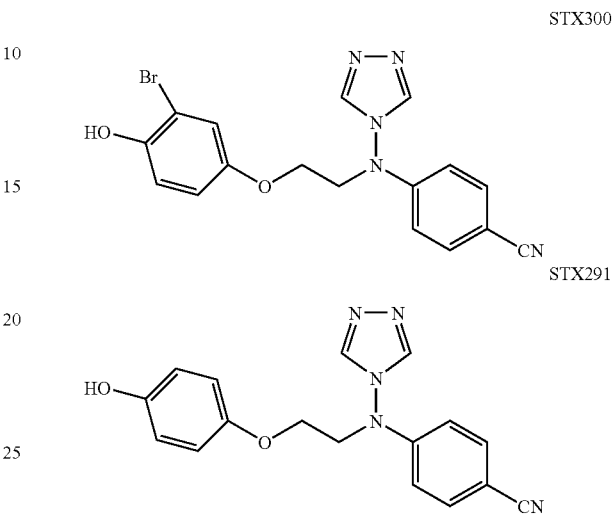

To a stirred solution of 4-{[2-(4-benzyloxy-3-bromophenoxy)ethyl]-[1,2,4]triazol-4-ylamino}benzonitrile (902 mg, 1.839 mmol) in distilled THF (45 mL) was added in succession absolute ethanol (45 mL) and Pd/C (10%, 90 mg). The black suspension was then stirred under an atmosphere of hydrogen (balloon) for 2 days. Upon removal by filtration and washings of the supported catalyst exhaustively with distilled THF, the filtrate was evaporated to give a beige residue (860 mg). This crude in DMF (10 mL) was fractionated by flash chromatography (ethyl acetate/acetone, 4:1 to acetone, gradient) and the third fraction that separated upon evaporation gave a wet creamy residue which was triturated with ether (50 mL). The precipitate that formed was filtered, washed exhaustively with water and air-dried overnight to give LWO02089 as off-white powder (453 mg); $R_f$ 0.40 (ethyl acetate), c.f. 0.50 (S.M.); $\delta_H$ (400 MHz, DMSO-$d_6$) 4.03 (~0.4H, t, J 4.6–5.1 Hz, CH$_2$N of STX291), 4.06 (1.6H, t, J 4.6–5.1 Hz, CH$_2$N of STX300), 4.21 (2H, t, J 4.6–5.1 Hz, OC$\underline{H}_2$CH$_2$N of STX291 and STX300), 6.65 (~2H, AA'BB' of STX291 and STX300), 6.71 (~0.4H, AA'BB' of STX291), 6.74 (~0.8H, dd, J 2.8–3.1 and 8.8 Hz, C6'-H of STX300), 6.85 (~0.8H, d, J 8.9 Hz, C5'-H of STX300), 7.04 (0.8H, d, J 3.1 Hz, C2'-H of STX300), 7.74 (2H, AA'BB' of STX291 and STX300), 8.91 (~0.4H, s, C3"-H and C5"-H of STX291), 8.93 (~1.6H, s, C3"-H and C5"-H of STX300), 8.98 (~0.2H, br s, exchanged with D$_2$O, OH of STX291) and 9.74 (~0.8H, br s, exchanged with D$_2$O, OH of STX300) This implies that the product contains approx. 20% of STX291; LRMS (FAB+): 553.0[18, ($^{79}$M+H+NBA)$^+$], 475.1[12, (STX291+H+NBA)$^+$], 400.0[100, ($^{79}$M+H)$^+$], 322.1[85, (STX291+H)$^+$], 252.1[50, ($^{79}$M−$^{79}$Br-triazole)$^+$]; (FAB−): 552.0[60, (79M+NBA)$^-$], 475.3 [32, (STX291+H+NBA)$^-$], 398.1[100, ($^{79}$M−H)$^-$]; HRMS (FAB+) 400.04045 $C_{17}H_{15}{}^{79}BrN_5O_2$ requires 400.04091, (FAB+) 322.12936 $C_{17}H_{16}N_5O_2$ requires 322.13040.

Sulfamic Acid 2-bromo-4-{2-[(4-cyanophenyl)-[1,2,4]triazol-4-ylamino]ethoxy}phenyl ester (STX301) and Sulfamic Acid 4-{2-[(4-cyanophenyl)-[1,2,4]triazol-4-ylamino]ethoxy}phenyl ester (STX292) (LWO02090)

STX301

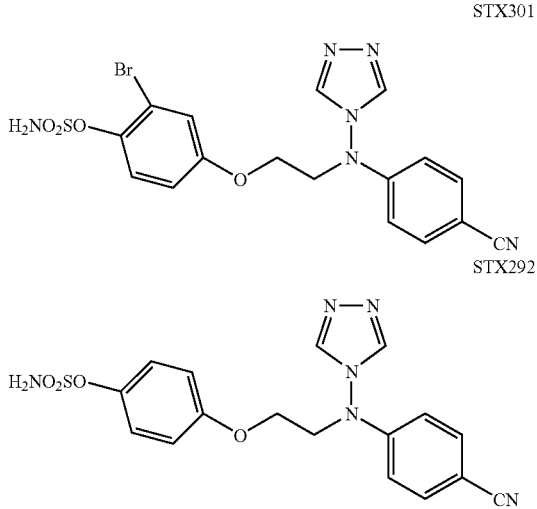

STX292

To a stirred solution of LWO02089 (289 mg, 699.5 μmol) in anhydrous N,N-dimethylacetamide (DMA, 10 mL) was added at room temperature a solution of sulfamoyl chloride in toluene (ca. 0.59 M, 4.7 mL) and the resulting mixture was stirred under an atmosphere of nitrogen overnight. Ethyl acetate (100 mL) was then added to the reaction mixture and the organic layer that separated was washed with brine (100 mL, 4×50 mL), dried (MgSO4), filtered and evaporated to give a white fluffy residue (347 mg). This crude in ethyl acetate was filtered through a short column of silica and the combined filtrate upon evaporation gave LWO02090 as a white fluffy residue (310 mg, 646.8 μmol, 92.5%); $R_f$ 0.29 (ethyl acetate), c.f. 0.35 (S.M.); $\delta_H$ (400 MHz, DMSO-$d_6$) 4.14 (~0.4H, t, J 4.6–5.1 Hz, CH$_2$N of STX292), 4.17 (~1.6H, t, J 4.7 Hz, CH$_2$N of STX301), 4.27 (2H, t, J 3.9–4.6 Hz, OCH$_2$CH$_2$N of STX292 and STX301), 6.68 (2H, AA'BB' of STX292 and STX301), 6.91–6.99 (~1.2H, mixture of AA'BB' and dd of STX292 and C6'-H of STX301), 7.18 (~0.4H, AA'BB' of STX292), 7.25 (0.8H, d, J 3.1 Hz, C2'-H of STX301), 7.37 (~0.8H, d, J 8.9 Hz, C5'-H of STX301), 7.75 (2H, AA'BB' of STX292 and STX301), 7.91 (~0.4H, br s, exchanged with D$_2$O, SO$_2$NH$_2$ of STX292), 8.16 (~1.6H, br s, exchanged with D$_2$O, SO$_2$NH$_2$ of STX301), 8.94 (~0.4H, s, C3"-H and C5"-H of STX292) and 8.99 (~1.6H, s, C3"-H and C5"-H of STX301) This implies that the product contains approx. 20% of STX292; LRMS (FAB+): 481.0[100, ($^{81}$M+H)$^+$], 401.1[73, (STX292+H)$^+$], (FAB–): 631.1[35, ($^{79}$M+NBA)$^-$], 477.1[100, ($^{79}$M–H)$^-$], 399.1[64, (STX292-H)$^-$]; HRMS (FAB+) 479.01430 C$_{17}$H$_{15}$$^{79}$BrN$_6$O$_4$S requires 479.01371, (FAB+) 401.10349 C$_{17}$H$_{17}$N$_6$O$_4$S requires 401.10320.

6-Benzyloxy-naphthalene-2-carboxylic acid benzyl ester (JRL01001)

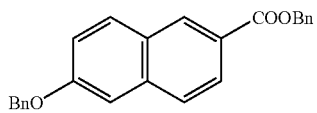

To a stirred suspension of NaH (60%, 1.37 g, 34.3 mmol) in DMF (40 mL) at 0° C. under nitrogen was added 6-hydroxy-2-naphthoic acid (3.0 g, 15.6 mmol). The resulting brown mixture was stirred for 30 min before benzyl bromide (5.99 g, 34.3 mmol) was added. After stirring overnight, the reaction mixture was poured into water and the aqueous layer was extracted with ethyl acetate (3×100 mL). The combined organic extracts was washed with brine (4×100 mL), dried (Na$_2$SO$_4$) and evaporated to give the crude product which upon fractionation with flash chromatography (hexane/ethyl acetate, 10:1) gave JRL01001 as a white solid (4.3 g, 75%); $R_f$ (hexane/ethyl acetate, 10:1) 0.42; $\delta_H$ (400 MHz, CDCl$_3$) 5.19 (2H, s), 5.41 (2H, s), 7.20–7.60 (12H, m), 7.74 (1H, d, J 8.6 Hz), 7.85 (1H, d, J 9.0 Hz), 8.06 (1H, dd, J 1.9 and 8.6 Hz) and 8.57 (1H, s); $\delta_C$ (100 MHz, CDCl$_3$) 67.1 (t), 70.5 (t), 107.2 (d), 120.2 (d), 125.5 (s), 126.3 (d), 127.2 (d), 127.5 (d), 128.2 (s), 128.4 (d), 128.5 (d), 128.6 (d), 128.9 (d), 131.2 (d), 136.5 (s), 136.7 (s), 137.4 (s), 158.6 (s), 166.8 (s).

(6-Benzyloxy-naphthalen-2-yl)-methanol (JRL01003)

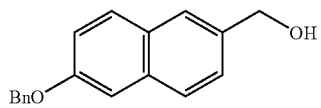

To a stirred suspension of LiAlH$_4$ (240 mg, 6.0 mmol) in THF (100 mL) at room temperature under nitrogen was added a solution of JRL01001 (1.99 g, 5.4 mmol) in THF. After 2 h of stirring at which time no starting material was detected by TLC, the reaction mixture was evaporated. The residue obtained was treated with ethyl acetate (100 mL) and the organic layer resulted was washed with dilute ammonium chloride solution (50 mL) and brine (3×50 mL), dried (Na$_2$SO$_4$) and evaporated. The crude product thus obtained was recrystallised from hot ethanol to give JRL01003 as white solid (1.16 g, 81%); m.p. 138.0–138.5° C.; $R_f$ 0.26 (hexane/ethyl acetate, 2:1); $\delta_H$ (400 MHz, CDCl$_3$) 1.82 (1H, t, J 5.9 Hz), 4.79 (2H, d, J 5.9 Hz), 5.16 (2H, s) and 7.20–7.80 (11H, m); $\delta_C$ (100 MHz, CDCl$_3$) 65.8 (t), 70.3 (t), 107.3 (d), 119.5 (d), 125.7 (d), 126.0 (d), 127.4 (d), 127.7 (d), 128.2 (d), 128.8 (d), 129.1 (s), 129.6 (d), 134.2 (s), 136.2 (s), 137.0 (s), 157.0 (s). Found: C 81.77, H 6.11; C$_{18}$H$_{16}$O$_2$ requires C 81.79, H 6.10%.

2-Benzyloxy-6-bromomethyl-naphthalene (JRL01006)

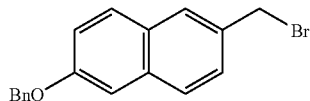

To a stirred solution of JRL01003 (1.29 g, 4.9 mmol) in dry CH$_2$Cl$_2$ (60 mL) at 0° C. under nitrogen was added PBr$_3$ (1.33 g, 4.9 mmol). A white suspension was formed initially but it turned into a pale yellow mixture subsequently. After stirring the reaction mixture for 2 h at 0° C. and at room temperature for 1 h, it was poured onto ice/water. The organic layer was separated and the aqueous layer extracted with dichloromethane (3×50 mL). The combined organic extracts was dried (Na$_2$SO$_4$) and evaporated to give JRL01006 as a white solid (1.51 g, 94%); $R_f$ 0.28 (hexane/ethyl acetate, 10:1); $\delta_H$ (400 MHz, CDCl$_3$) 4.65 (2H, s), 5.17 (2H, s), 7.10–7.30 (2H, m), 7.30–7.50 (6H, m) and 7.68–7.78 (3H, m); LRMS (FAB+) 327.9 [25, (M+H)$^+$], 247 (45), 91.0 [100, (Bn$^+$)].

4-[(6-Benzyloxy-naphthalen-2-ylmethyl)-[1,2,4]triazol-4-yl-amino]-benzonitrile (JRL01010)

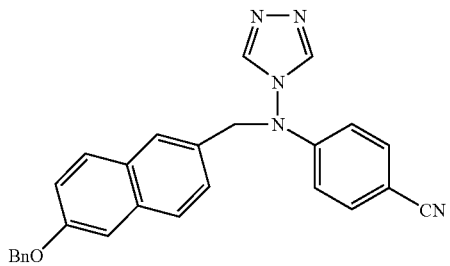

To a stirred solution of NaH (60%, 144 mg, 3.6 mmol) in DMF (10 mL) at 0° C. under nitrogen was added 4-([1,2,4]triazol-4-ylamino)benzonitrile (LWO02023, 667 mg, 3.6 mmol) in DMF (10 mL). A white suspension/mixture was resulted initially but it turned orange subsequently. After stirring at 40–50° C. for 1 h under nitrogen, the reaction mixture was cooled to room temperature and JRL01006 (1.21 g, 3.7 mmol) was added. The solution was stirred at room temperature overnight under nitrogen and then diluted with dichloromethane (100 mL). The organic layer was washed with brine (4×50 mL), dried ($Na_2SO_4$) and evaporated to give JRL0110 as a pale yellow solid (994 mg, 64%); $R_f$ 0.42 (ethyl acetate); $\delta_H$ (400 MHz, $CDCl_3$) 5.00 (2H, s), 5.20 (2H, s), 6.72 (2H, AA'BB'), 7.20–7.80 (13H, m) and 8.10 (2H, s); LRMS (FAB+) 432.1 [70, $(M+H)^+$], 363.1 [50, $(M-triazole)^+$], 247.1 (35), 91.0 [100, $(Bn)^+$].

4-[(6-Hydroxy-naphthalen-2-ylmethyl)-[1,2,4]triazol-4-yl-amino]-benzonitrile (JRL01012, STX 335)

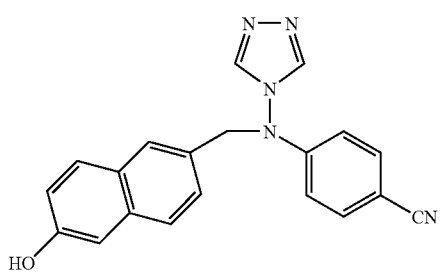

STX335

To a stirred solution of JRL0110 (906 mg, 2.1 mmol) in THF/MeOH (1:1, 180 mL) was added Pd—C (10%, 250 mg). After stirring the suspension under an atmosphere of hydrogen (balloon) overnight, it was filtered through Celite and the filtrate evaporated to give a grey crude product. Upon trituration in hot ethyl acetate, the pale grey solid that resulted was filtered and dried to give JRL01012 (STX335, 444 mg, 62%); m.p. 281–284° C.; $R_f$ 0.26 (ethyl acetate); $\delta_H$ (400 MHz, DMSO-$d_6$) 5.18 (2H, s), 6.80 (2H, AA'BB'), 7.07 (2H, m), 7.34 (1H, d, J 8.2 Hz), 7.60–7.70 (3H, m), 7.76 (2H AA'BB'), 8.80 (2H, s) and 9.79 (1H, s); LRMS (FAB) 342.1 [100, $(M+H)^+$], 274.1 [37, (M+H-triazole)$^+$], 158.0 (25); HRMS (FAB+) 342.13594, $C_{20}H_{16}N_5O$ requires 342.13549.

Sulfamic Acid 6-{[(4-cyano-phenyl)-[1,2,4]triazol-4-yl-amino]-methyl}-naphthalen-2-yl ester (JRL01014, STX 336)

STX336

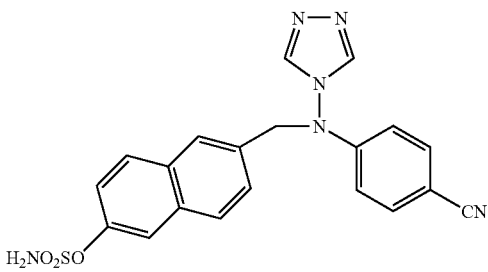

To a stirred solution of JRL01012 (181 mg, 530 μmol) in DMA (2 mL) under nitrogen was added sulfamoyl chloride (1.2 mmol). After stirring overnight at room temperature, the reaction mixture was diluted with ethyl acetate (30 mL). The organic layer was then washed with brine (4×30 mL), dried ($Na_2SO_4$) and evaporated to give JRL01014 (STX336, 189 mg, 85%) as a white solid. An amount of 70 mg of this solid was recrystallised from acetone/hexane to obtain white crystals (40 mg); m.p. 125–127° C.; $R_f$ 0.23 (ethyl acetate); $\delta_H$ (400 MHz, DMSO-$d_6$) 5.23 (2H, s), 6.80 (2H, AA'BB'), 7.42 (1H, dd, J 2.3 and 9.0 Hz), 7.55 (1H, br dd, J 8.6 Hz),; 7.74–7.82 (3H, m), 7.85 (1H, s), 7.94 (2H, m), 8.04 (2H, br s, $H_2NSO_2O$) and 8.84 (2H, s); LRMS (FAB+) 421.1 [100, $(M+H)^+$], 352.0 [58, $(M-triazole)^+$], 341.1 (10), 236.0 (25), 158.0 (10); HRMS (FAB+) 421.10766, $C_{20}H_{17}N_6O_3S$ requires 421.10829.

3-Benzyoxybenzyl bromide (OBS01018)

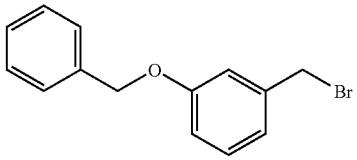

Using the procedure reported by K. Thakkar et al., *J. Med. Chem.*, 1993, 36 (20), 2950.

Phosphorus tribromide (1.96 mL, 20.6 mmol) was added to a solution of 3-benzyloxybenzyl alcohol (4.29 g, 20 mmol) in anhydrous dichloromethane (90 mL) at 0° C. The mixture was stirred at 0° C. for 2 h and then at room temperature for 1 h. The reaction was poured onto ice/water (400 mL) and allowed to warm to room temperature. The aqueous solution was extracted with $Et_2O$ (5×100 mL) and the combined ethereal solution dried ($MgSO_4$). Concentration in vacuo gave a light yellow oil which crystallised on standing to give OBS01018 as colourless needles (4.93 g, 89%). TLC [$SiO_2$, EtOAc-n-hexane (1:1)] $R_f$=0.9; m.p. 55–56° C. [Lit. (Petroleum ether): 55° C.]; $^1$H-NMR (400 MHz, $CDCl_3$) 4.44 (2H, s), 5.05 (2H, s); 6.78 (1H, d, J=2), 6.93 (1H, m), 7.22 (1H, t, J=8), 7.40 (5H, m).

4-[(3-Benzyloxybenzyl)(4-cyanophenyl)amino]-4H-[1,2,4]triazole (OBS01019, STX675)

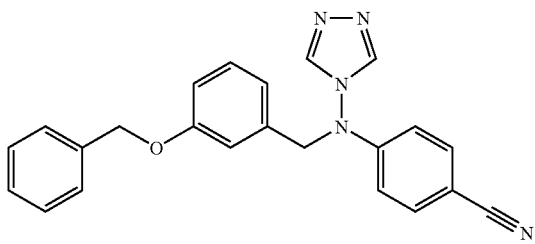

To a suspension of NaH (60% dispersion in oil, 0.22 g, 5.4 mmol) in anhydrous DMF (20 mL) at room temperature was added a solution of 4-[(4-cyanophenyl)amino]-4H-[1,2,4]triazole (see LWO02023) (1.0 g, 5.4 mmol) in anhydrous DMF (4 mL) and the mixture stirred under a positive flow of dry nitrogen for 1 h. The orange-yellow suspension was then treated with a solution of OBS01018 (1.57 g, 5.66 mmol) in anhydrous DMF (5 mL) and the mixture was stirred at room temperature overnight. The mixture was transferred to a separating funnel and diluted with EtOAc (100 mL). The organic layer was washed with water (4×100 mL), brine (100 mL), and dried (MgSO$_4$). Concentration in vacuo gave a residue which was recrystallised from i-PrOH to give OBS01019 as a white solid (0.58 g, 28%). TLC [SiO$_2$, EtOAc-n-hexane (1:1)] R$_f$=0.15 (blue fluorescence at 254 nm); $^1$H-NMR (400 MHz, CDCl$_3$) 4.85 (2H, s), 5.03 (2H, s); 6.62 (2H, AA'BB'), 6.77 (1H, d, J=7.8), 6.79 (1H, d, J=2.4), 6.96 (1H, dd, J=7.8, 2.4), 7.26 (1H, t, J=7.8), 7.34–7.37 (5H, m), 7.57 (2H, AA'BB'), 8.04 (2H, s); LC-MS: t$_R$=6.81 min, M+H=382 (Waters 2790 Alliance HPLC/ZQ MicroMass spectrometer with PDA detector using APCI, gradient elution: 5:95 MeCN/H$_2$O—95:5 MeCN/H$_2$O over 10 mins then 95:5 MeCN/H$_2$O—5:95 MeCN/H$_2$O using Waters "Symmetry" C18 (packing: 3.5 µm), 100 mm column); HPLC (Waters 717+ Autosampler with PDA detector, using Waters "Symmetry" C18 (packing: 3.5 µm), 4.6×150 mm column, 90:10 MeOH/H$_2$O) t$_R$=2.27 min (98% purity).

4-[(3-Hydroxybenzyl)(4-cyanophenyl)amino]-4H-[1,2,4]triazole (OBS01022, STX333)

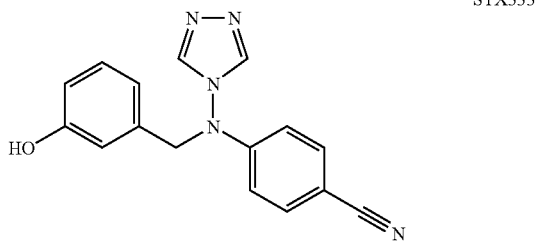

To a solution of OBS01019 (0.4 g, 1.05 mmol) in THF-MeOH (1:1) (20 mL) was added a slurry of Pd—C (10%, 0.24 g, 2.26 mmol) in THF (2 mL) and the suspension stirred under an atmosphere of hydrogen (balloon) for 21 h. The suspension was filtered through Celite and the combined filtrates concentrated in vacuo to give a brown residue which solidified on standing. Recrystallisation from EtOH gave OBS01022 (STX333) as a white solid (0.27 g, 88%). TLC [SiO$_2$, EtOAc-n-hexane (1:1)] R$_f$=0.6; $^1$H-NMR (400 MHz, d$_6$-DMSO) 4.97 (2H, s), 6.68 (2H, d, AA'BB'), 6.72–6.75 (3H, m), 7.11 (1H, m), 7.76 (2H, AA'BB'), 8.77 (2H, s), 9.49 (1H, bs). MS (FAB+)=292 (M+H, 100%), 223 (M+H-triazole, 42); Acc. MS for C$_{16}$H$_{13}$N$_5$O (Required, 292.1192; Found, 292.1198); HPLC (Waters 717+ Autosampler with PDA detector, using Waters "Symmetry" C18 (packing: 3.5 µm), 4.6×150 mm column, 70:30 MeOH/H$_2$O) t$_R$=2.22 min (92% purity).

4-[(3-O-Sulfamoylbenzyl)(4-cyanophenyl)amino]-4H-[1,2,4]triazole (OBS01030, STX334)

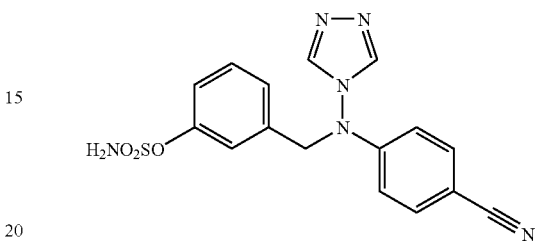

To an ice-cooled solution of OBS01022 (100 mg, 340 µmol) in DMA (2 mL) was added sulfamoyl chloride (0.59 M solution toluene, 1.2 mL, 0.69 mmol) in DMA (2 mL) and the mixture stirred under nitrogen overnight. The mixture was diluted with EtOAc (30 mL) and washed with brine (3×100 mL). The organic solution was dried (Na$_2$SO$_4$) and concentrated in vacuo to give a colourless residue which solidified on standing. Recrystallisation from acetone-petroleum ether (40–60) gave OBS01030 (STX334) as a colourless solid (0.06 g, 47%). TLC [SiO$_2$, EtOAc-n-hexane (1:1)] R$_f$=0.55; $^1$H-NMR (400 MHz, d$_6$-DMSO) 5.11 (2H, s), 6.74 (2H, d, J=8.6), 7.20–7.27 (3H, m), 7.40 (1H, t, J=7.8), 7.77 (2H, d, J=8.6), 7.98 (2H, br s), 8.81 (2H, s). MS (FAB+)=371 (M+H, 100%), 302 (M+H-triazole, 28); Acc. MS for C$_{16}$H$_{15}$N$_6$O$_3$S (Required, 371.0946; Found, 371.0926); HPLC (Waters 717+ Autosampler with PDA detector, using Waters "Symmetry" C18 (packing: 3.5 µm), 4.6×150 mm column, 70:30 MeOH/H$_2$O) t$_R$=2.13 min (99% purity).

3,4-Bis(benzyloxy)benzaldehyde (OBS 01058)

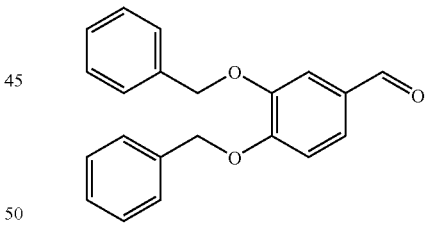

Using the procedure reported by A. F. Barrero et al., Tetrahedron, 1998, 54, 5635. To a suspension of 3,4-dihydroxybenzaldehyde (6.9 g, 50 mmol) and potassium carbonate (14.5 g) in acetone (150 mL) was added benzyl bromide (11.96 mL, 101 mmol) and the mixture heated at reflux for 15 h. The reaction was cooled and the solvent removed in vacuo to give a light brown residue. The residue was redissolved in Et$_2$O (200 mL), washed with water (3×200 mL) and dried (Na$_2$SO$_4$). Concetration in vacuo gave a pale yellow solid which was recrystallised from EtOH to give OBS01058 as a white powder (13.84 g, 87%). TLC [SiO$_2$, EtOAc-n-hexane (1:1)] R$_f$=0.7; m.p. 93–94° C. [Lit. (EtOH): 93–94° C.]; $^1$H-NMR (400 MHz, d$_6$-DMSO) 5.22 (2H, s), 5.28 (2H, s), 7.29 (1H, d, J=8.4), 7.30–7.48 (10H, m), 7.51 (1H, d, J=2), 7.55 (1H, dd, J=2, 8.4), 9.81 (1H, s).

3,4-Bis(benzyloxy)benzyl alcohol (OBS01060)

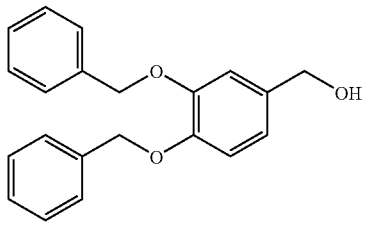

Reference: L. Lisowski et al., *Bioorg. Med. Chem. Lett.*, 2001, 11(16), 2205

To a solution of OBS01058 (3.18 g, 10 mmol) in anhydrous THF (50 mL) was added sodium borohydride (378 mg, 10 mmol) and the mixture stirred at room temperature for 4 h. The reaction was quenched with cautious addition of water (CARE !!), filtered through Celite and concentrated in vacuo to give a yellow oil. The oil was recrystallised from MeOH to give OBS01060 as colourless needles (2.97 g, 93%). TLC [$SiO_2$, EtOAc-n-hexane (1:1)] $R_f$=0.45; m.p. 65–67° C. [Lit. (MeOH): 65–66° C.]; $^1$H-NMR (400 MHz, $CDCl_3$) 4.58 (2H, d, J=5), 5.16 (2H, s), 5.17 (2H, s), 6.86 (1H, dd, J=2, 8.2), 6.91 (1H, d, J=8.2), 7.00 (1H, d, J=2), 7.29–7.39 and 7.43–7.47 (10H, m), OH signal too broad to be observed.

3,4-Bis(benzyloxy)benzyl bromide (OBS01061)

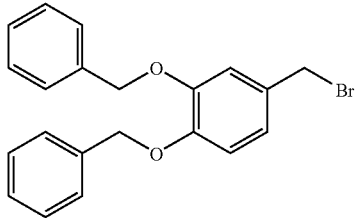

Reference: K. Thakkar et al., *J. Med. Chem.*, 1993, 36(20), 2950.

Phosphorus tribromide (0.98 mL, 10.3 mmol) was added to a solution of OBS01060 (3.20 g, 10 mmol) in anhydrous DCM (45 mL) at 0° C. The mixture was stirred at 0° C. for 2 h and then at room temperature for 1 h. The reaction was poured onto ice water (200 mL) and allowed to warm to room temperature. The aqueous solution was extracted with $Et_2O$ (5×50 mL) and the combined ethereal solution dried ($MgSO_4$). Concentration in vacuo gave a colourless oil which solidified on standing to give OBS01061 as a white solid (3.10 g, 78%). TLC [$SiO_2$, EtOAc-n-hexane (1:1)] $R_f$=0.89; m.p. 72–75° C. [Lit: 72–75° C.]; $^1$H-NMR (400 MHz, $CDCl_3$) 4.53 (2H, s), 5.15 (2H, s), 5.17 (2H, s), 6.83 (1H, dd, J=2, 8.2), 6.90 (1H, d, J=8.2), 6.99 (11H, d, J=2), 7.52 (10H, m).

4-[(3,4-Bis(benzyloxy)benzyl)(4-cyanophenyl)amino]-4H-[1,2,4]triazole (OBS01066, STX676)

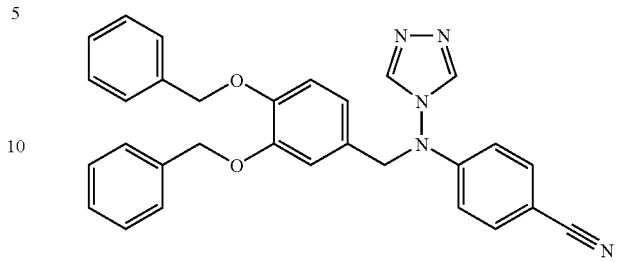

STX676

To a suspension of NaH (60% dispersion in oil, 0.22 g, 5.4 mmol) in anhydrous DMF (20 mL) at room temperature was added a solution of 4-[(4-cyanophenyl)amino]-4H-[1,2,4]triazole (1.0 g, 5.4 mmol) in anhydrous DMF (4 mL) and the mixture stirred under nitrogen for 1 h. The orange-yellow suspension was then treated with a solution of OBS01061 (2.07 g, 5.67 mmol) in anhydrous DMF (5 mL) and the mixture stirred at room temperature overnight. The mixture was transferred to a separating funnel and diluted with EtOAc (100 mL). The organic layer was washed with water (4×100 mL), brine (100 mL), and dried ($MgSO_4$). Concentration in vacuo gave a residue which was recystallised from EtOH to give OBS01066 (STX676) as an off-white solid (1.66 g, 63%). TLC [$SiO_2$, EtOAc-n-hexane (1:1)] $R_f$=0.1 (blue fluorescence at 254 nm); $^1$H-NMR (400 MHz, $d_6$-DMSO) 4.92 (2H, s), 5.06 (2H, s), 5.07 (2H, s), 6.72–6.76 (3H, m); 6.94 (1H, d, J=8.2), 7.01 (1H, d, J=2.2), 7.28–7.42 (10H, m), 7.74 (2H, AA'BB'), 8.65 (2H, s). MS (FAB+) 488 (M+H, 45%), 419 (M+H-triazole, 21), 91 (Bn, 100%); Acc MS for $C_{30}H_{26}N_5O_2$ (Required, 488.2096; Found, 488.2087); LC-MS (Waters 2790 Alliance HPLC/ZQ MicroMass spectrometer with PDA detector using APCI), $t_R$ (gradient elution: 5:95 MeCN/$H_2O$—95:5 MeCN/$H_2O$ over 10 mins then 95:5 MeCN/$H_2O$—5:95 MeCN/$H_2O$ using Waters "Symmetry" C18 (packing: 3.5 μm), 100 mm column)=7.68 min (M+H=488); HPLC (Waters 717+ Autosampler with PDA detector, using Waters "Symmetry" C18 (packing: 3.5 μm), 4.6×150 mm column, 90:10 MeOH/$H_2O$) $t_R$=2.43 min (98% purity).

4-[(3,4-Bis(hydroxybenzyl)(4-cyanophenyl)amino]-4H-[1,2,4]triazole (OBS01067, STX355)

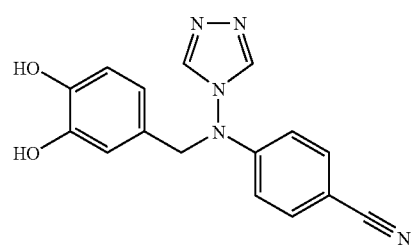

STX355

To a solution of OBS01066 (0.98 g, 2.01 mmol) in THF-MeOH (1:1) (20 mL) was added a slurry of Pd-C (10%, 0.10 g) in THF (2 mL) and the mixture stirred under an atmosphere of hydrogen (balloon) for 24 h. The suspension was filtered through Celite and the combined filtrates concentrated in vacuo to give a brown residue. Recrystallisation from MeOH gave OBS01067 (STX355) as a white solid (0.14 g, 21%). TLC [$SiO_2$, EtOAc-n-hexane (1:1)] $R_f$=0.6; $^1$H-NMR (400 MHz, $d_6$-DMSO) 4.84 (2H, s), 6.50

(1H, d, J=8.2), 6.62 (2H, m), 6.75 (2H, AA'BB'), 7.75 (2H, AA'BB'), 8.68 (2H, s); LC-MS (Waters 2790 Alliance HPLC/ZQ MicroMass spectrometer with PDA detector using APCI), $t_R$ (gradient elution: 5:95 MeCN/H$_2$O—95:5 MeCN/H$_2$O over 10 mins then 95:5 MeCN/H$_2$O—5:95 MeCN/H$_2$O using Waters "Symmetry" C18 (packing: 3.5 µm), 100 mm column)=7.68 min (M+H=488); HPLC (Waters 717+ Autosampler with PDA detector, using Waters "Symmetry" C18 (packing: 3.5 µm), 4.6×150 mm column, 70:30 MeOH/H$_2$O) $t_R$=3.02 min (99% purity).

3-Methoxy-4-benzyloxybenzaldehyde (OBS01056)

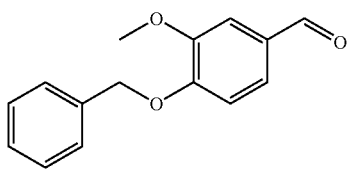

Using the procedure reported by A. I. Meyers et al., *Heterocycles*, 1989, 295.

To a solution of vanillin (7.7 g, 50.67 mmol) in EtOH (40 mL) was added potassium carbonate (7.9 g, 57.35 mmol) and benzyl bromide (6.0 mL, 50.67 mmol) and the mixture stirred at room temperature overnight. The reaction was filtered through Celite and the filtrates concentrated in vacuo. The residue was redissolved in DCM (250 mL), washed with aqueous NaOH (5% w/v, 2×100 mL) and the organic layer dried (Na$_2$SO$_4$). Concentration in vacuo and recrystallisation of the residue obtained from EtOH gave OBS01056 as a white powder (11.16 g, 91%). TLC [SiO$_2$, EtOAc-n-hexane (1:1)] R$_f$=0.8; m.p. 63–64° C. [Lit. (MeOH): 63–64° C.]; $^1$H-NMR (400 MHz, CDCl$_3$) 3.95 (3H, s), 5.25 (2H, s), 6.99 (1H, m), 7.33–7.45 (7H, m), 9.84 (1H, s)

3-Methoxy-4-benzyloxybenzyl alcohol (OBS01063)

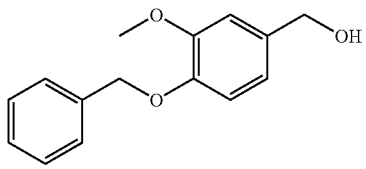

Using the procedure reported by A. van Oeveran et al., *J. Org. Chem.*, 1994, 59 (20), 5999.

To a solution of OBS01056 (5.0 g, 20.64 mmol) in anhydrous DCM (25 mL) was added a suspension of sodium borohydride (0.97 g, 25.59 mmol) in MeOH (12 mL) and the mixture stirred at room temperature for 18 h. The reaction was poured into water (50 mL) (CARE !!) and extracted with DCM (3×50 mL) and dried (MgSO$_4$). Concentration in vacuo gave a white residue. Recrystallisation from Et$_2$O-petroleum ether gave OBS01063 as colorless needles (4.91 g, 97%). TLC [SiO$_2$, EtOAc-n-hexane (1:1)] R$_f$=0.49; m.p. 72–74° C. [Lit. (Et$_2$O-Pet. ether): 72–73° C.]; $^1$H-NMR (400 MHz, d$_6$-DMSO) 3.74 (3H, s), 4.39 (2H, d, J=5.7), 5.05 (2H, s), 5.08 (1H, t, J=5.7, OH), 6.84 (1H, dd, J=2, 8.2), 6.91 (1H, d, J=8.2), 7.01 (1H, d, J=2), 7.31–7.46 (5H, m).

3-Methoxy-4-benzyloxybenzyl bromide (OBS01070)

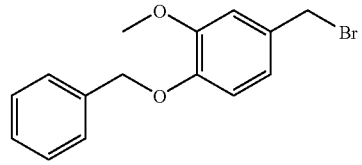

Adapting the procedure reported by A. van Oeveran et al., *J. Org. Chem.*, 1994, 59 (20), 5999.

Phosphorus tribromide (0.98 mL, 10.3 mmol) was added to a solution of OBS01063 (2.44 g, 10 mmol) in anhydrous DCM (20 mL) at 0° C. The mixture was stirred at 0° C. for 2 h and then at room temperature for 1 h. The reaction was poured onto ice water (400 mL) and allowed to warm to room temperature. The aqueous solution was extracted with DCM (5×100 mL) and the combined organic extracts dried (MgSO$_4$). Concentration in vacuo gave an off-white residue which was recrystallised from n-hexane to give OBS01070 as colourless needles (2.52 g, 82%). TLC [SiO$_2$, EtOAc-n-hexane (1:1)] R$_f$=0.92; m.p. 73–74° C. [Lit. (Pet. ether): 73° C.]; $^1$H-NMR (400 MHz, CDCl$_3$) 3.91 (3H, s), 4.49 (2H, s), 5.16 (2H, s), 6.81 (1H, d, J=8.2), 6.88 (1H, dd, J=8.2, 2), 6.94 (1H, d, J=2), 7.28–7.44 (5H, m).

4-[(3-Benzyloxy-4-methoxybenzyl)(4-cyanophenyl)amino]-4H-[1,2,4]triazole (OBS01071, STX677)

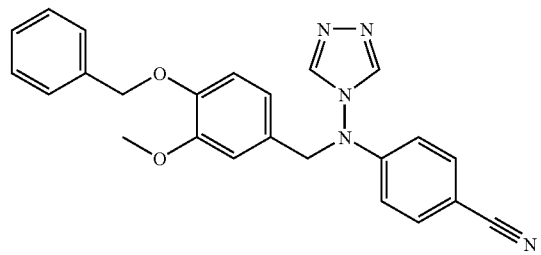

To a suspension of NaH (60% dispersion in oil, 0.22 g, 5.4 mmol) in anhydrous DMF (20 mL) at room temperature was added a solution of 4-[(4-cyanophenyl)amino]-4H-[1,2,4] triazole (1.0 g, 5.68 mmol) in anhydrous DMF (4 mL) and the mixture stirred under nitrogen for 1 h. The orange-yellow suspension was then treated with a solution of OBS01071 (1.66 g, 5.4 mmol) in anhydrous DMF (5 mL) and the mixture stirred at room temperature overnight. The mixture was transferred to a separating funnel and diluted with EtOAc (200 mL). The organic layer was washed with water (4×200 mL), brine (200 mL), and dried (MgSO$_4$). Concentration in vacuo gave a residue which was recystallised from i-PrOH to give OBS01071 (STX677) as an off-white powder (769 mg, 35%). TLC [SiO$_2$, EtOAc-n-hexane (1:1)] R$_f$=0.15 (blue fluorescence at 254 nm); $^1$H-NMR (400 MHz, d$_6$-DMSO) 3.80 (3H, s), 4.79 (2H, s), 5.12 (2H, s), 6.64 (1H, d, J=2), 6.66 (1H, dd, J=8.2, 2), 6.70 (2H, AA'BB'), 6.81 (1H, d, J=8.2), 7.29–7.42 (5H, m), 7.59 (2H, AA'BB'), 8.06 (2H, s); MS (FAB+)=412 (M+H, 100%), 343 (40), 275 (20), 227 (20); Ace MS for C$_{24}$H$_{22}$N$_5$O$_2$ (Required, 412.1779; Found, 412.1773); LC-MS (Waters 2790 Alliance HPLC/ZQ MicroMass spectrometer with PDA detector using APCI), $t_R$ (gradient elution: 5:95 MeCN/H$_2$O—95:5 MeCN/H$_2$O over 10 mins then 95:5 MeCN/H$_2$O—5:95 MeCN/H$_2$O using Waters "Symmetry" C18 (packing: 3.5 µm), 100 mm column)=6.61 min (M+H=412);

HPLC (Waters 717+ Autosampler with PDA detector, using Waters "Symmetry" C18 (packing: 3.5 μm), 4.6×150 mm column, 90:10 MeOH/H$_2$O) $t_R$=2.19 min (95% purity).

4-[(3-Hydroxy-4-methoxybenzyl)(4-cyanophenyl)amino]-4H-[1,2,4]triazole (OBS01076, STX362)

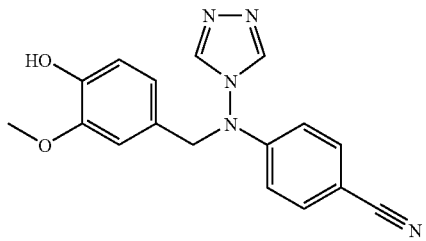

STX362

To a solution of OBS01071 (411 mg, 999 μmol) in THF-MeOH (1:1) (20 mL) was added a slurry of Pd—C (10%. 42 mg) in THF (2 mL) and the mixture stirred under an atmosphere of hydrogen (balloon) for 48 h. The mixture was filtered through Celite and the combined filtrates concentrated in vacuo to give a brown residue which solidified on standing. Recrystallisation from i-PrOH gave OBS01076 (STX362) as a colourless powder (232 mg, 72%). TLC [SiO$_2$, EtOAc-n-hexane (1:1)] R$_f$=0.52; $^1$H-NMR (400 MHz, d$_6$-DMSO) 3.71 (3H, s), 4.90 (2H, s), 6.61 (1H, dd, J=7.8, 2), 6.65 (1H, d, J=7.8), 6.79 (2H, AA'BB'), 6.80 (1H, d, J=2), 7.76 (2H, AA'BB'), 8.72 (2H, s), 9.06 (1H, br s, OH); MS (FAB+)=322 (M+H, 100%), 253 (64); Ace MS for C$_{17}$H$_{16}$N$_5$O$_2$ (Required, 322.1303; Found, 322.1304); HPLC (Waters 717+ Autosampler with PDA detector, using Waters "Symmetry" C18 (packing: 3.5 μm), 4.6×150 mm column, 80:20 MeOH/H$_2$O) $t_R$=2.59 min (95% purity).

4-[(4-Methoxy-3-O-sulfamoylbenzyl)(4-cyanophenyl) amino]-4H-[1,2,4]triazole (OBS01135, STX660)

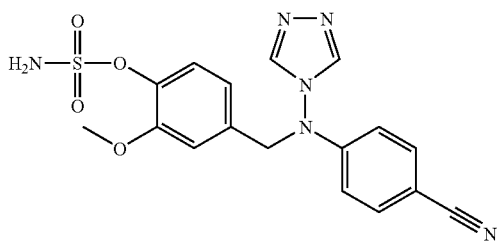

STX660

To an ice-cooled solution of OBS01076 (100 mg, 310 μmol) in DMA (10 mL) was added sulfamoyl chloride (0.69 M solution toluene, 2.71 mL—the toluene was removed in vacuo (not allowing the temperature of the water bath to exceed 30° C.) prior to addition, 8.1 mmol) and the mixture stirred under nitrogen overnight. The mixture was diluted with EtOAc (100 mL) and washed with water (3×100 mL) and brine (100 mL). The organic solution was dried (MgSO$_4$) and concentrated in vacuo to give OBS01135 (STX660) as a white residue which was precipitated from EtOAc solution by addition of n-hexane (40 mg, 32%). TLC [SiO$_2$, EtOAc-n-hexane (1:1)] R$_f$=0.52; $^1$H-NMR (400 MHz, d$_6$-DMSO) 3.77 (3H, s), 5.06 (2H, s), 6.76 (2H, AA'BB'), 6.89 and 6.91 (1H, dd, J=8.2, 2.3), 7.08 (1H, d, J=2.3), 7.23 (1H, d, J=8.2), 7.78 (2H, AA'BB'), 7.95 (2H, s), 8.87 (2H, s); LC-MS (Waters 2790 Alliance HPLC/ZQ MicroMass spectrometer with PDA detector using APCI), $t_R$ (gradient elution: 5:95 MeCN/H$_2$O—95:5 MeCN/H$_2$O over 10 min then 95:5 MeCN/H$_2$O—5:95 MeCN/H$_2$O using Waters "Symmetry" C18 (packing: 3.5 μm), 100 mm column)=4.29 min (M+H=401); HPLC (Waters 717+ Autosampler with PDA detector, using Waters "Symmetry" C18 (packing: 3.5 μm), 4.6×150 mm column, 80:20 MeOH/H$_2$O) $t_R$=3.95 min (88% purity).

4-Methoxy-3-benzyloxybenzaldehyde (OBS01054)

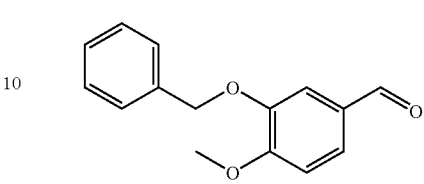

Using the procedure reported by A. I. Meyers et al., *Heterocycles*, 1989, 295.

To a suspension of isovanillin (7.7 g, 50.67 mmol) in water (50 mL) was added potassium hydroxide (3.4 g, 60 mmol) and the mixture stirred for 0.25 h. The now homogenous solution was then treated with benzyl bromide (6.0 mL, 50.67 mmol) and the mixture heated at reflux for 5 h. The reaction was diluted with DCM (200 mL), washed with water (2×100 mL) and brine (100 mL) and dried (Na$_2$SO$_4$). Concentration in vacuo and recrystallisation of the yellow residue obtained from EtOH gave OBS01054 as a colourless powder (11.28 g, 92%). TLC [SiO$_2$, EtOAc-n-hexane (1:1)] R$_f$=0.8; m.p. 62–63° C. [Lit. (EtOH): 62° C.]; $^1$H-NMR (400 MHz, d$_6$-DMSO) 3.88 (3H, s), 5.17 (2H, s), 7.21 (1H, d, J=8.2), 7.33–7.49 (6H, m), 7.58 (1H, d, J=8.2), 9.83 (1H, s).

4-Methoxy-3-benzyloxybenzyl alcohol (OBS01062)

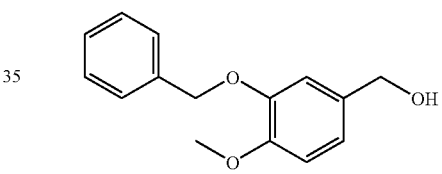

Using the procedure reported by A. I. Meyers et al., *Heterocycles*, 1989, 295.

To a solution of OBS01054 (5.0 g, 20.64 mmol) in EtOH (60 mL) was added sodium borohydride (1.23 g, 32.40 mmol) and the mixture stirred at room temperature for 18 h. The reaction was heated at relux for 1 h, cooled and decanted into aqueous ammonium chloride (50% w/v, 250 mL) (CARE !!). The aqueous solution was extracted with Et$_2$O (3×100 mL), washed with brine (100 mL) and dried (Na$_2$SO$_4$). Concentration in vacuo gave a white residue. Recrystallisation from EtOAc-petroleum ether gave OBS01062 as colorless needles (4.91 g, 97%). TLC [SiO$_2$, EtOAc-n-hexane (1:1)] R$_f$=0.48; m.p. 73–74° C. [Lit. (EtOAc-Pet. ether): 73° C.]; $^1$H-NMR (400 MHz, d$_6$-DMSO) 3.74 (3H, s), 4.39 (2H, d, J=5.7), 5.05 (2H, s), 5.08 (1H, t, J=5.7, OH), 6.84 (1H, dd, J=2, 8.2), 6.91 (1H, d, J=8.2), 7.01 (1H, d, J=2), 7.33–7.49 (5H, m).

4-Methoxy-3-benzyloxybenzyl bromide (OBS01068)

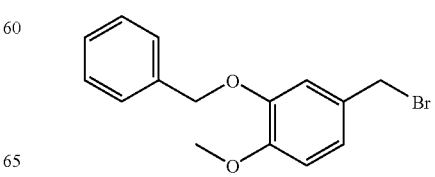

Using the procedure reported by A. I. Meyers et al., *Heterocycles*, 1989, 295.

Phosphorus tribromide (0.98 mL, 10.3 mmol) was added to a solution of OBS01062 (2.44 g, 10 mmol) in anhydrous THF (20 mL) at 0° C. The mixture was stirred at 0° C. for 2 h and then at room temperature for 1 h. Concentration in vacuo gave an off-white residue which was recrystallised from DCM-n-hexane to give OBS01068 as a white powder (2.95 g, 96%). TLC [SiO$_2$, EtOAc-n-hexane (1:1)] R$_f$=0.9; m.p. 86–88° C. [Lit. (DCM-hexane): 86–87° C.]; $^1$H-NMR (400 MHz, d$_6$-DMSO) 3.74 (3H, s), 4.39 (2H, s), 5.05 (2H, s), 6.83 (1H, dd, J=2, 8.2), 6.90 (1H, d, J=8.2), 7.01 (1H, d, J=2), 7.30–7.47 (5H, m).

4-[(3-Benzyloxy-4-methoxybenzyl)(4-cyanophenyl)amino]-4H-[1,2,4]triazole (OBS01069)

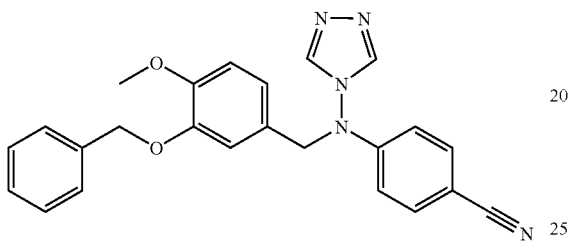

To a suspension of NaH (60% dispersion in oil, 220 mg, 5.4 mmol) in anhydrous DMF (20 mL) at room temperature was added a solution of 4-[(4-cyanophenyl)amino]-4H-[1,2,4]triazole (1.0 g, 5.68 mmol) in anhydrous DMF (4 mL) and the mixture stirred under nitrogen for 1 h. The orange-yellow suspension was then treated with a solution of OBS01068 (1.66 g, 5.4 mmol) in anhydrous DMF (5 mL) and the mixture stirred at room temperature overnight. The mixture was transferred to a separating funnel and diluted with EtOAc (200 mL). The organic layer was washed with water (4×200 mL), brine (200 mL), and dried (MgSO$_4$). Concentration in vacuo gave a residue which was recystallised from EtOH to give OBS01069 as an off-white powder (970 mg, 44%). TLC [SiO$_2$, EtOAc-n-hexane (1:1)] R$_f$=0.12 (blue fluorescence at 254 nm); $^1$H-NMR (400 MHz, CDCl$_3$) 3.89 (3H, s), 4.72 (2H, s), 5.12 (2H, s), 6.59 (2H, AA'BB'), 6.62 (1H, d, J=2), 6.64 (1H, dd, J=7.8, 2), 6.79 (1H, d, J=7.8), 7.28–7.34 (5H, m), 7.57 (2H, AA'BB'), 7.74 (2H, s); MS (FAB+) 412 (M+H, 100%), 343 (51), 227 (72); Acc MS for C$_{24}$H$_{22}$N$_5$O$_2$ (Required, 412.1776; Found, 412.1774).

4-[(3-Hydroxy-4-methoxybenzyl)(4-cyanophenyl)amino]-4H-[1,2,4]triazole (OBS01080, STX363)

STX363

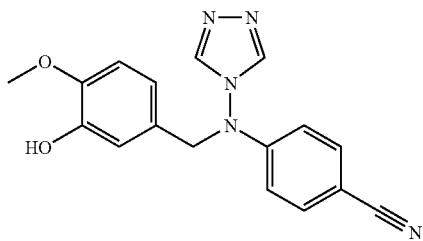

To a solution of OBS01069 (411 mg, 999 μmol) in THF-MeOH (1:1) (20 mL) was added a slurry of Pd—C (10%, 42 mg) in THF (2 mL) and the suspension stirred under an atmosphere of hydrogen (balloon) for 48 h. The suspension was filtered through Celite and the combined filtrates concentrated in vacuo to give a brown residue. Recrystallisation from i-PrOH gave OBS01080 (STX363) as a white powder (164 mg, 51%). TLC [SiO$_2$, EtOAc-n-hexane (1:1)] R$_f$=0.52; $^1$H-NMR (400 MHz, d$_6$-DMSO) 3.71 (3H, s); 4.88 (2H, s), 6.62 (1H, dd, J=8.2, 1.95), 6.68 (1H, d, J=1.95), 6.74 (2H, AA'BB'), 6.80 (1H, d, J=8.2), 7.74 (2H, AA'BB'), 8.70 (2H, s), 9.00 (1H, s, OH); MS (FAB+) 322 (M+H, 100%), 253 (61); Acc MS for C$_{17}$H$_{16}$N$_5$O$_2$ (Required, 322.1304; Found, 322.1304); HPLC (Waters 717+ Autosampler with PDA detector, using Waters "Symmetry" C18 (packing: 3.5 μm), 4.6×150 mm column, 90:10 MeOH/H$_2$O) t$_R$=2.03 min (99% purity).

4-[(4-Methoxy-3-O-sulfamoylbenzyl)(4-cyanophenyl)amino]-4H-[1,2,4]triazole (OBS01137, STX661)

STX661

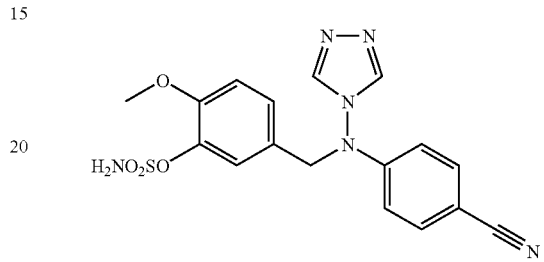

To an ice-cooled solution of OBS01080 (100 mg, 310 μmol) in DMA (10 mL) was added sulfamoyl chloride (0.69 M solution toluene, 2.71 mL—the toluene was removed in vacuo (not allowing the temperature of the water bath to exceed 30° C.) prior to addition, 8.1 mmol) and the mixture stirred under nitrogen overnight. The mixture was diluted with EtOAc (100 mL) and washed with water (3×100 mL) and brine (100 mL). The organic layer was dried (MgSO$_4$) and concentrated in vacuo to give OBS01137 (STX661) as a colourless residue which was precipitated from EtOAc solution by addition of n-hexane (40 mg, 32%). TLC [SiO$_2$, EtOAc-n-hexane (1:1)] R$_f$=0.53; $^1$H-NMR (400 MHz, d$_6$-DMSO) 3.77 (3H, s); 5.00 (2H, s), 6.79 (2H, AA'BB'), 7.06 (1H, d, J=8.6), 7.12 and 7.14 (1H, dd, J=8.2, 2.3), 7.27 (1H, d, J=2), 7.77 (2H, AA'BB'), 7.94 (2H, s), 8.75 (2H, s); LC-MS (Waters 2790 Alliance HPLC/ZQ MicroMass spectrometer with PDA detector using APCI), t$_R$ (gradient elution: 5:95 MeCN/H$_2$O—95:5 MeCN/H$_2$O over 10 mins then 95:5 MeCN/H$_2$O—5:95 MeCN/H$_2$O using Waters "Symmetry" C18 (packing: 3.5 μm), 100 mm column)=4.70 min (M+H=401); HPLC (Waters 717+ Autosampler with PDA detector, using Waters "Symmetry" C18 (packing: 3.5 μm), 4.6×150 mm column, 80:20 MeOH/H$_2$O) t$_R$=2.04 min (88% purity).

3-Bromo-4-hydroxybenzaldehyde (OBS01057)

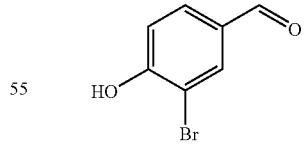

Adapting the procedure reported by S. Kelly et al., *Helv. Chim. Acta.*, 1989, 72, 594.

To a ice-cooled solution of 4-hydroxybenzaldehyde (30.0 g, 245.67 mmol) in glacial AcOH (120 mL) was added bromine (12.6 mL, 257.61 mmol). The mixture was stirred at room temperature overnight, diluted with water (600 mL) and extracted with DCM (3×120 mL). The combined organic fractions were washed with water (600 mL), dilute sodium hydrogen carbonate solution (2×600 mL) and brine (600 mL). The organic layer was dried (Na$_2$SO$_4$) and concentrated in vacuo to give a brown residue. Recrystallisation from toluene gave OBS01057 as a pink-brown crystalline solid (26.3 g, 53%). TLC [SiO$_2$, EtOAc-n-hexane (1:1)] R$_f$=0.6; m.p. 124–126° C. [Lit. (CHCl$_3$): 125–126° C.]; $^1$H-NMR (400 MHz, CDCl$_3$) 6.31 (1H, s, OH), 7.15 (1H, d, J=8.8), 7.77 (1H, dd, J=8.8, 2), 8.04 (1H, d, J=2), 9.83 (1H, s, CHO).

3-Bromo-4-benzoyloxybenzaldehyde (OBS01072)

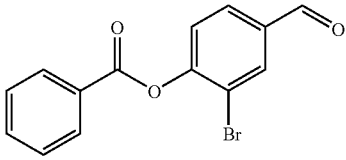

To a solution of OBS01057 (8.0 g, 40.0 mmol) in EtOAc (100 mL) was added NEt$_3$ (5.58 mL, 40.0 mmol) and the mixture stirred at room temperature for 0.5 h. Benzoyl chloride (4.64 mL, 40.0 mmol) was then added and the reaction stirred at room temperature for 5 h. The precipitated NEt$_3$.HCl was filtered off and the organic solution dried (Na$_2$SO$_4$). Concentration in vacuo gave a grey residue. Recrystallisation from EtOAc-petroleum ether gave OBS01072 as a yellow solid (10.9 g, 89%). TLC [SiO$_2$, EtOAc-n-hexane (1:1)] R$_f$=0.82; $^1$H-NMR (400 MHz, CDCl$_3$) 7.50 (1H, d, J=8.2), 7.54, 7.56 and 7.58 (2H, tt, J=7.4, 1.4), 7.68, 7.70 and 7.71 (1H, tt, J=7.4, 1.4), 7.91 and 7.93 (1H, dd, J=8.2, 1.8), 8.20 (1H, d, J=1.8), 8.24 and 8.27 (2H, dt, J=8.2, 1.4), 9.98 (1H, s, CHO).

3-Bromo-4-benzoyloxybenzyl alcohol (OBS01074)

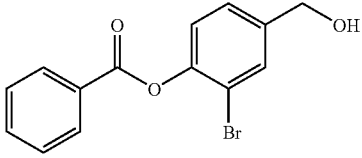

To a solution of OBS01072 (6.10 g, 19.99 mmol) in anhydrous THF (25 mL) was added sodium borohydride (1.13 g, 29.99 mmol) and the mixture stirred at room temperature for 4 h. The reaction was quenched with cautious addition of water (CARE !!), filtered through Celite and dried (MgSO$_4$). Concentration in vacuo gave a yellowish oil which crystallised on standing. Recrystallisation from Et$_2$O gave 3-bromo-4-benzoyloxybenzyl alcohol as colorless needles (5.89 g, 96%). TLC [SiO$_2$, EtOAc-n-hexane (1:1)] R$_f$=0.5; $^1$H-NMR (400 MHz, CDCl$_3$) □=4.71 (2H, s), 7.26 (1H, d, J=8.2), 7.36 (1H, dd, J=8.2, 1.95), 7.51, 7.53 and 7.55 (2H, tt, J=8.2, 1.6), 7.64–7.68 (2H, m), 8.24 (1H, t, J=1.95), 8.26 (1H, t, J=1.95).

3-Bromo-4-benzoyloxybenzyl bromide (OBS01089)

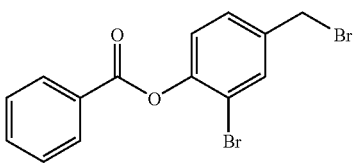

Phosphorus tribromide (0.98 mL, 10.3 mmol) was added to a solution of OBS01074 (3.07 g, 10.0 mmol) in anhydrous dichloromethane (45 mL) at 0° C. The mixture was stirred at 0° C. for 2 h and then at room temperature for 1 h. The reaction was poured onto ice water (400 mL) and allowed to warm to room temperature. The aqueous solution was extracted with diethyl ether (5×100 mL) and the combined ethereal solution dried (MgSO$_4$). Concentration in vacuo gave a yellow oil. Purification by gravity column chromatography [SiO$_2$, EtOAc-petroleum ether (1:7)] give OBS01089 as colourless needles (3.22 g, 87%). TLC [SiO$_2$, EtOAc-n-hexane (1:1)] R$_f$=0.87; $^1$H-NMR (400 MHz, CDCl$_3$) 4.47 (2H, s), 7.27 (1H, d, J=8.6), 7.41 (1H, dd, J=8.6, 2.3), 7.52, 7.54 and 7.56 (2H, tt, J=8.2, 1.56), 7.66, 7.67 and 7.69 (1H, tt, J=8.2, 1.56), 7.70 (1H, d, J=2.3), 8.24 (1H, t, J=1.2), 8.26 (1H, t, J=1.2).

4-[(4-Benzoyloxy-3-bromobenzyl)(4-cyanophenyl)amino]-4H-[1,2,4]triazole (OBS01131)

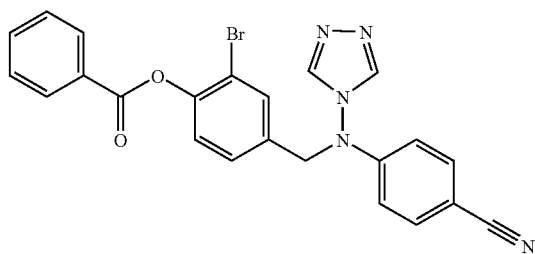

To a suspension of NaH (60% dispersion in oil, 220 mg, 5.4 mmol) in anhydrous DMF (20 mL) at room temperature was added a solution of 4-[(4-cyanophenyl)amino]-4H-[1,2,4]triazole (1.0 g, 5.68 mmol) in anhydrous DMF (4 mL) and the mixture stirred under nitrogen for 1 h. The orange-yellow suspension was then treated with a solution of OBS01089 (2.00 g, 5.4 mmol) in anhydrous DMF (5 mL) and the mixture stirred at room temperature overnight. The mixture was transferred to a separating funnel and diluted with EtOAc (200 mL). The organic layer was washed with water (4×200 mL), brine (200 mL), and dried (MgSO$_4$). Concentration in vacuo gave a residue which was recrystallised from i-PrOH to give OBS01131 as a colourless solid (1.99 g, 78%). TLC [SiO$_2$, EtOAc (100%)] R$_f$=0.5 (blue fluorescence at 254 nm); $^1$H-NMR (400 MHz, d$_6$-DMSO) 5.14 (2H, s), 6.75 (1H, t, J=2.7), 6.78 (1H, t, J=2.7), 7.44 (2H, d, J=8.2), 7.61–7.66 (2H, m), 7.76–7.80 (4H, m), 8.14 (1H, t, J=2.7), 8.16 (1H, t, J=2.7), 8.92 (2H, s); MS (FAB+) 474 (M, 100%), 405 (38); Acc MS for C$_{23}$H$_{16}$N$_5$O$_2$Br (Required, 474.0569; Found, 474.0566).

4-[(3-Bromo-4-hydroxybenzyl)(4-cyanophenyl)amino]-4H-[1,2,4]triazole (OBS01132, STX405)

STX405

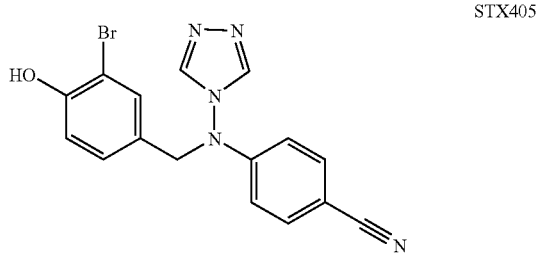

To a suspension of OBS01131 (2.0 g, 4.22 mmol) in MeOH (10 mL) was added potassium hydroxide (1.42 g, 25.3 mmol) and the mixture stirred at room temperature for 2 h. The solvents were removed in vacuo and he pH of the alkaline slurry was adjusted to ~pH 6–7 by treatment with saturated sodium hydrogen carbonate solution. The colourless precipitate was filtered off, washed with the minimum of cold water and boiled in i-PrOH to give OBS01091 (STX405) as a colourless powder (1.20 g, 77%). TLC [SiO$_2$, EtOAc-n-hexane (1:1)] R$_f$=0.43; $^1$H-NMR (400 MHz, d$_6$-DMSO) 4.93 (2H, s), 6.77 (2H, AA'BB'), 6.85 (1H, d, J=8.2), 7.06 (1H, dd, J=8.2, 1.95), 7.41 (1H, d, J=1.95), 7.76 (2H, AA'BB'), 8.76 (2H, s), 10.35 (1H, br s, OH); MS (FAB+) 370 (M, 100%), 301 (55), 260 (67), 242 (64); Acc MS for C$_{16}$H$_{12}$N$_5$OBr (Required, 370.0314; Found, 370.0304); HPLC (Waters 717+ Autosampler with PDA detector, using Waters "Symmetry" C18 (packing: 3.5 μm), 4.6×150 mm column, 94:6 MeOH/H$_2$O) t$_R$=2.73 min (96% purity).

4-[(3-Bromo-4-O-sulfamoylbenzyl)(4-cyanophenyl) amino]-4H-[1,2,4]triazole (OBS01141, STX681)

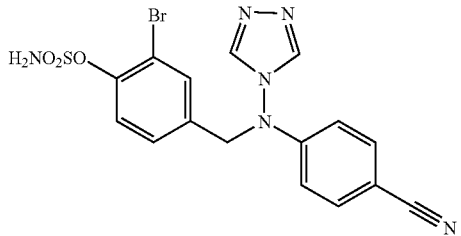

STX681

To an ice-cooled solution of OBS01132 (500 mg, 1.35 mmol) in DMA (10 mL) was added sulfamoyl chloride (0.69 M solution toluene, 11.7 mL—the toluene was removed in vacuo (not allowing the temperature of the water bath to exceed 30° C.) prior to addition, 8.1 mmol) and the mixture stirred under nitrogen overnight. The mixture was diluted with EtOAc (100 mL) and washed with water (3×100 mL) and brine (100 mL). The organic layer was dried (MgSO$_4$) and concentrated in vacuo to give a colourless residue which was precipitated from EtOAc solution by addition of n-hexane (463 mg). The white solid (200 mg) was then purified by gradient elution gravity column chromatography [SiO$_2$, EtOAc-n-hexane (1:4)—EtOAc (100%)] to give OBS01141 (STX681) as a white solid (107 mg, 44% after chromatography). TLC [SiO$_2$, EtOAc-n-hexane (1:1)] R$_f$=0.42; $^1$H-NMR (400 MHz, d$_6$-DMSO) 5.17 (2H, s), 6.80 (2H, AA'BB'), 7.50 (2H, s), 7.78 (1H, s), 7.84 (2H, AA'BB'), 8.38 (2H, s), 8.96 (2H, s); MS (FAB+) 412 (M+H, 100%), 343 (40), 275 (20), 227 (20); Acc MS for C$_{24}$H$_{22}$N$_5$O$_2$ (Required, 412.1779; Found, 412.1773); LC-MS (Waters 2790 Alliance HPLC/ZQ MicroMass spectrometer with PDA detectors using APCI), t$_R$ (gradient elution: 5:95 MeCN/H$_2$O—95:5 MeCN/H$_2$O over 10 mins then 95:5 MeCN/H$_2$O—5:95 MeCN/H$_2$O using Waters "Symmetry" C18 (packing: 3.5 μm), 100 mm column)=5.52 min (M+H= 448); HPLC (Waters 717+ Autosampler with PDA detector, using Waters "Symmetry" C18 (packing: 3.5 μm), 4.6×150 mm column, 90:10 MeOH/H$_2$O) t$_R$=1.89 min (99% purity). HPLC cannot differentiate OBS01091 (STX 405) and OBS01141 (STX 681). LC-MS/$^1$H-NMR indicates that sample of OBS01141 (STX 681) [M+H]=450 contains ca. 6.66% of starting material OBS01091 (STX 405) [M+H]= 371.

4-[(2-Bromo-ethyl)-[1,2,4]triazol-4-yl-amino]-benzonitrile (CAB03031)

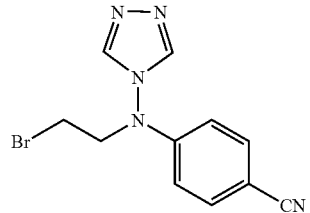

Sodium hydride (60%, 240 mg, 6.0 mmol) was added to a solution of 4-([1,2,4]triazol-4-ylamino)-benzonitrile (926 mg, 5.0 mmol) in DMSO (25 mL) at r.t. The mixture was stirred for 1 hour at this temperature and 1,2-dibromethane (5 mL) was added. The reaction mixture was stirred overnight and ethyl acetate (100 mL) was added. The mixture was transferred into a separation funnel and extracted with water (twice 100 mL) and brine (20 mL). The organic layer was dried over sodium sulphate and concentrated under reduced pressure (water bath temperature <30° C.). The resulting orange oil was mixed with diethyl ether (100 mL) and filtered through a layer of silica (ca. 5 cm). The silica was washed with more diethyl ether (ca. 100 mL) to remove the excess of 1,2-dibromoethane; the crude product was washed from the silica with acetone (120 mL). The acetone solution was concentrated under reduced pressure and the residue was purified by column-chromatography (eluent: ethyl acetate) to give the title compound as a white solid. Yield: 628 mg (43%). $^1$H-NMR (400 MHz, d$_6$-DMSO) δ=3.61 (t, J=6.2 Hz, 2H), 4.30 (t, J=6.4 Hz, 2H), 6.64 (d, J=9.0 Hz), 7.74 (d, 9.0 Hz, 2H), 8.97 (s, 2H). LRMS (FAB+):292.0 (100, [M+H]$^+$).

4-{[2-(4-Hydroxy-phenylsulfanyl)-ethyl]-[1,2,4]triazol-4-yl-amino}-benzonitrile (CAB02137, STX456)

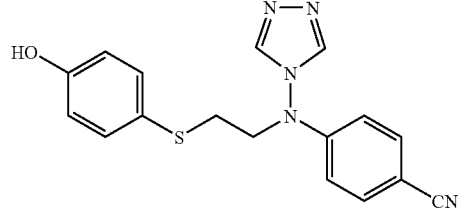

STX456

A mixture of 4-[(2-bromo-ethyl)-[1,2,4]triazol-4-yl-amino]-benzonitrile (CAB03031, 146 mg, 0.50 mmol), 4-hydroxythiophenol (126 mg, 1.0 mmol) and potassium carbonate (138 mg, 1.0 mmol) in DMF (10 mL) was stirred overnight at room temperature. The mixture was transferred into a separation funnel and ethyl acetate (50 mL) and water (50 mL) were added. The organic layer was separated, washed with brine (30 mL), dried over sodium sulphate and concentrated under reduced pressure. The residue was crystallised from methanol. Yield: 116 mg (69%) colourless crystals. $^1$H-NMR (400 MHz, d6-DMSO) δ=2.99 (t, J=7.0 Hz, 2H), 3.93 (t, J=7.0 Hz, 2H), 6.48 (d, =9.0 Hz, 2H), 6.73 (d, J=8.6 Hz, 2H), 7.21 (d, J=8.6 Hz, 2H), 7.68 (d, J=9.0 Hz, 2H), 8.89 (s, 2H), 9.66 (s, 1H, —OH). $^{13}$C-NMR (100 MHz, d6-DMSO) δ=30.62, 53.07, 102.92, 113.36, 116.86, 119.59, 122.71, 134.07, 134.49, 144.07, 151.17, 157.83. LRMS (FAB+): 338.2 (100, [M+H]$^+$). Found: C, 60.6; H, 4.57; N, 20.6%; C$_{17}$H$_{15}$N$_5$OS (337.4) requires C, 60.52; H, 4.48; N, 20.76%.

4-{[2-(3-Hydroxy-phenylsulfanyl)-ethyl]-[1,2,4]triazol-4-yl-amino}-benzonitrile (CAB02149, STX512)

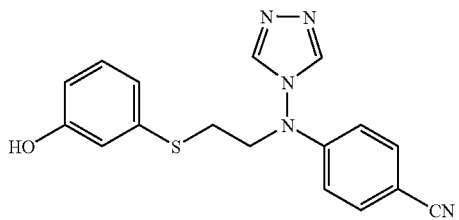

A mixture of 4-[(2-bromo-ethyl)-[1,2,4]triazol-4-yl-amino]-benzonitrile (CAB02148=CAB03031, 146 mg, 0.50 mmol), 3-(tert-butyl-dimethylsiloxy)-thiophenol (240 mg, 1.0 mmol) and potassium carbonate (276 mg, 2.0 mmol) in DMF (10 mL) was stirred for 48 hours at room temperature. The mixture was transferred into a separation funnel and ethyl acetate (50 mL) and water (50 mL) were added. The organic layer was separated, washed with brine (30 mL), dried over sodium sulphate and concentrated under reduced pressure. The residue was crystallised from methanol. Yield: 93 mg (55%) colourless crystals. $^1$H-NMR (400 MHz, d6-DMSO) δ=3.14 (t, J=7.0 Hz, 2H), 4.02 (t, J=7.0 Hz, 2H), 6.53 (d, J=9.0 Hz, 2H), 6.62 (ddd, J=7.8, 2.0, 0.8 Hz, 1H), 6.70–6.72 (m, 2H), 7.10 (dd, J=7.8, 7.8, 1H), 7.70 (d, J=9.0 Hz, 2H), 8.94 (s, 2H), 9.60 (s, 1H, —OH). $^{13}$C-NMR (100 MHz, d6-DMSO) δ=29.53, 52.46, 102.38, 112.86, 113.57, 115.36, 119.00, 130.11, 133.94, 135.82, 143.50, 150.71, 157.90, 169.59. LRMS (FAB+): 338.2 (100, [M+H]$^+$). Found: C, 60.6; H, 4.53; N, 20.8%; $C_{17}H_{15}N_5OS$ (337.4) requires C, 60.52; H, 4.48; N, 20.76%.

4-[(3-Bromo-propyl)-[1,2,4]triazol-4-yl-amino]-benzonitrile (CAB02180, STX595)

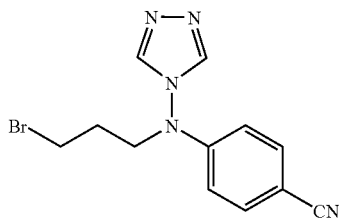

Sodium hydride (60%, 240 mg, 6.0 mmol) was added to a solution of 4-([1,2,4]triazol-4-ylamino)-benzonitrile (926 mg, 5.0 mmol) in DMSO (25 mL) at r.t. The mixture was stirred for 1 hour at this temperature and 1,3-dibromopropane (5 mL) was added. The reaction mixture was stirred overnight and ethyl acetate (100 mL) was added. The mixture was transferred into a separation funnel and extracted with water (twice 100 mL) and brine (20 mL). The organic layer was dried over sodium sulphate and concentrated under reduced pressure (water bath temperature <30° C.). The resulting orange oil was mixed with diethyl ether (100 mL) and filtered through a layer of silica (ca. 5 cm). The silica was washed with more diethyl ether (ca. 100 mL) to remove the excess of 1,3-dibromopropane, the crude product was washed from the silica with acetone (120 mL). The acetone solution was concentrated under reduced pressure and the residue was purified by column-chromatography (eluent: ethyl acetate) to give the title compound as a white solid. Yield: 792 mg (52%). $^1$H-NMR (400 MHz, d6-DMSO) δ=2.01 (tt, J=7.0, 6.6 Hz, 2H), 3.64 (t, J=6.6 Hz, 2H), 3.95 (t, J=7.0 Hz, 2H), 6.62 (d, J=9.0 Hz, 2H), to 7.74 (d, J=9.0 Hz, 2H), 9.02 (s, 2H). $^{13}$C-NMR (100 MHz, d6-DMSO) δ=30.38, 32.13, 52.72, 103.17, 113.83, 119.74, 134.63, 144.14, 151.65. LRMS (FAB+): 306.0 (100, [M+H]$^+$).

4-{[3-(4-Hydroxy-phenylsulfanyl)-propyl]-[1,2,4]triazol-4-yl-amino}-benzonitrile (CAB0182, STX596)

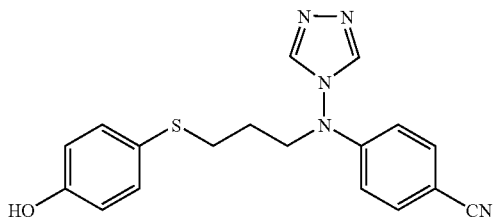

A mixture of 4-[(2-bromo-propyl)-[1,2,4]triazol-4-yl-amino]-benzonitrile (CAB02180, 146 mg, 0.50 mmol), 4-hydroxy-thiophenol (240 mg, 1.0 mmol) and potassium carbonate (276 mg, 2.0 mmol) in DMF (10 mL) was stirred for 48 hours at room temperature. The mixture was transferred into a separation funnel and ethyl acetate (50 mL) and water (50 mL) were added. The organic layer was separated, washed with brine (30 mL), dried over sodium sulphate and concentrated under reduced pressure. The residue was purified by column chromatography (eluent: ethyl acetate, Rf: 0.31) to give an yellow oil, which was crystallised from methanol. Yield: 211 mg (60%). $^1$H-NMR (400 MHz, d6-DMSO) δ=1.64 (tt, J=7.0, 7.0 Hz, 2H), 2.89 (t, J=7.0 Hz, 2H), 3.92 (t, J=7.0 Hz, 2H), 6.57 (d, J=9.0 Hz, 2H), 6.72 (d, J=9.0 Hz, 2H), 7.20 (d, J=9.0 Hz, 2H), 7.71 (d, J=9.0 Hz, 2H), 8.96 (s, 2H), 9.59 (s, 1H, —OH). LRMS (FAB+): 352.1 (100, [M+H]$^+$).

Sulfamic Acid 4-{3-[(4-cyano-phenyl)-[1,2,4]triazol-4-yl-amino]-propylsulfanyl}-phenyl ester (CAB02184, STX597)

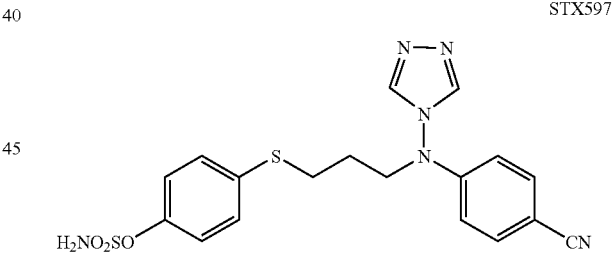

Sulphamoyl chloride solution in toluene (3 mL, 0.7 M, 2.1 mmol) was concentrated under reduced pressure (30° C. water bath temperature) to ca. 0.5 mL volume. The residue was cooled to 0° C. (ice bath) and N,N-dimethylacetamide (5 mL) was added. 4-{[3-(4-hydroxy-phenylsulfanyl)-propyl]-[1,2,4]triazol-4-yl-amino}-benzonitrile (CAB02182, 140 mg, 0.40 mmol) was added to the colourless solution and the mixture was stirred for 18 hours at room temperature. Ethyl acetate (50 mL) and water (50 mL) were added to the solution, the organic layer was separated, washed with water (2×30 mL) and brine (20 mL), dried over sodium sulphate and concentrated under reduced pressure. The residue was dissolved in a small amount of acetone and precipitated by addition of hexane. The precipitate was filtered off and dried under high vacuum. Yield: 139 mg (81%) light yellow powder. $^1$H-NMR (400 MHz, d6-DMSO) δ=1.74 (tt, J=7.0, 7.0 Hz, 2H), 3.97 (t, J=7.0 Hz, 2H), 6.62 (d, J=9.0 Hz, 2H), 7.22 (d, J=8.6 Hz, 2H), 7.43 (d, J=8.6 Hz, 2H), 7.74 (d, J=9.0 Hz, 2H), 8.03 (s, 2H, —NH$_2$), 9.00 (s, 2H). LRMS (FAB+): 431.1 (100, [M+H]$^+$).
4-[(4-Bromo-butyl)-[1,2,4]triazol-4-yl-amino]-benzonitrile (CAB03001,STX602)

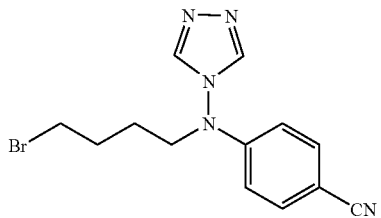

STX602

Sodium hydride (60%, 240 mg, 6.0 mmol) was added to a solution of 4-([1,2,4]triazol-4-ylamino)-benzonitrile (926 mg, 5.0 mmol) in DMSO (25 mL) at r.t. The mixture was stirred for 1 hour at this temperature and 1,4-dibromobutane (5 mL, ca 42 mmol) was added. The reaction mixture was stirred overnight and ethyl acetate (100 mL) was added. The mixture was transferred into a separation funnel and extracted with water (twice 100 mL) and brine (20 mL). The organic layer was dried over sodium sulphate and concentrated under reduced pressure (water bath temperature <30° C.). The resulting orange oil was mixed with diethyl ether (100 mL) and filtered through a layer of silica (ca. 5 cm). The silica was washed with more diethyl ether (ca. 100 mL) to remove the excess of 1,4-dibromobutane; the crude product was washed from the silica with acetone (120 mL). The acetone solution was concentrated under reduced pressure and the residue was purified by column-chromatography (eluent: ethyl acetate) to give the title compound as a white solid. Yield: 984 mg (61%). $^1$H-NMR (400 MHz, d6-DMSO) δ=1.53–1.60 (m, 2H), 1.87–1.94 (m, 2H), 3.56 (t, J=6.6 Hz, 2H), 3.87 (t, J=7.4 Hz, 2H), 6.64 (d, J=9.0 Hz, 2H), 7.73 (d, J=9.0 Hz, 2H), 8.99 (s, 2H). LRMS (FAB+): 320.0 (100, [M+H]$^+$)
4-{[4-(4-Hydroxy-phenylsulfanyl)-butyl]-[1,2,4]triazol-4-yl-amino}-benzonitrile (CAB03007)

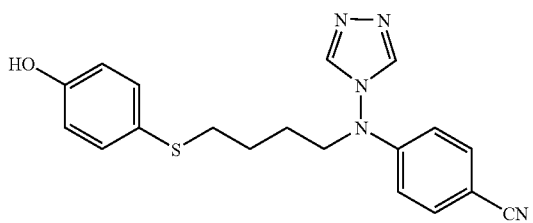

Potassium carbonate (500 mg) was added to a solution of 4-[(2-bromo-butyl)-[1,2,4]triazol-4-yl-amino]-benzonitrile (CAB03001, 384 mg, 1.2 mmol) and 4-hydroxy-thiophenol (227 mg, 1.8 mmol) in DMF (20 mL). The mixture was stirred for 18 hours at r.t., diluted with ethyl acetate (100 mL) and extracted with water (two times 30 mL) and brine (30 mL). The organic layer was dried over sodium sulphate and concentrated under reduced pressure. The residue was purified by column chromatography (eluent: ethyl acetate, Rf: 0.30). The resulting oil was dissolved in a small amount of ethyl acetate and the product was precipitated by addition of hexane. Yield: 289 mg (66%). $^1$H-NMR (400 MHz, d6-DMSO) δ=1.48–1.64 (m, 4H) 2.81 (t, J=6.6 Hz, 2H), 3.81 (t, J=6.8 Hz, 2H), 6.62 (d, J=9.0 Hz, 2H), 6.72 (d, J=8.6 Hz, 2H), 7.19 (d, J=9.0 Hz, 2H), 7.72 (d, J=9.0, 2H), 8.94 (s, 2H), 9.56 (s, 1H, —OH). LRMS (FAB+): 366.1 (100, [M+H]$^+$).

4-[(5-Bromo-pentyl)-[1,2,4]triazol-4-yl-amino]-benzonitrile (CAB03005)

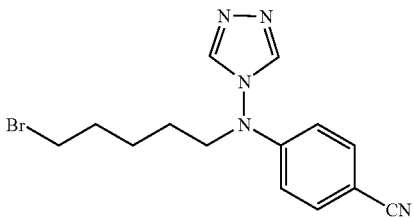

Sodium hydride (60%, 240 mg, 6.0 mmol) was added to a solution of 4-([1,2,4]triazol-4-ylamino)-benzonitrile (926 mg, 5.0 mmol) in DMSO (25 mL) at r.t. The mixture was stirred for 1 hour at this temperature and 1,5-dibromopentane (5 mL) was added. The reaction mixture was stirred overnight and ethyl acetate (100 mL) was added. The mixture was transferred into a separation funnel and extracted with water (twice 100 mL) and brine (20 mL). The organic layer was dried over sodium sulphate and concentrated under reduced pressure (water bath temperature <30° C.). The resulting orange oil was mixed with diethyl ether (100 mL) and filtered through a layer of silica (ca. 5 cm). The silica was washed with more diethyl ether (ca. 100 mL) to remove the excess of 1,5-dibromopentane. The crude product was washed from the silica with acetone (120 mL). The acetone solution was concentrated under reduced pressure and the residue was purified by column-chromatography (eluent: ethyl acetate) to give the title compound as a white solid. Yield: 1.01 g (60%). $^1$H-NMR (400 MHz, d6-DMSO) δ=1.40–1.52 (m, 2H), 1.75–1.85 (m, 2H), 3.52 (t, J=6.6 Hz, 2H), 3.78–3.89 (m, 2H), 6.64 (d, J=9.0 Hz, 2H), 7.72 (d, J=9.0 Hz, 2H), 8.97 (s, 2H). LRMS (FAB+): 334.1 (100, [M+H]$^+$).
4-{[5-(4-Hydroxy-phenylsulfanyl)-pentyl]-[1,2,4]triazol-4-yl-amino}-benzonitrile (CAB03014, STX698)

STX698

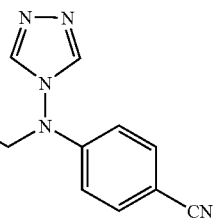

A mixture of 4-[(2-Bromo-pentyl)-[1,2,4]triazol-4-yl-amino]-benzonitrile (CAB03005, 500 mg, 1.5 mmol), 4-hydroxy-thiophenol (378 mg, 3.0 mmol) and potassium carbonate (414 mg, 3.0 mmol) in DMF (10 mL) was stirred for 12 hours at room temperature. The mixture was transferred into a separation funnel and ethyl acetate (50 mL) and water (50 mL) were added. The organic layer was separated, washed with brine (30 mL), dried over sodium sulphate and concentrated under reduced pressure. The residue was purified by column chromatography (eluent: ethyl acetate, R$_f$: 0.43). The resulting yellow oil was dissolved in ethyl acetate and precipitated by addition of hexane to give an light yellow powder. Yield: 338 mg (59%). $^1$H-NMR (400 MHz, d6-DMSO) δ=1.40–1.54 (m, 6H), 2.77 (t, J=6.8 Hz, 2H), 3.79 (t, J=6.6 Hz, 2H), 6.61 (d, J=9.0 Hz, 2H), 6.72 (d, J=9.0 Hz, 2H), 7.20 (d, J=9.0 Hz, 2H), 7.72 (d, J=9.0 Hz, 2H), 8.96 (s, 2H), 9.55 (s, 1H. —OH). $^{13}$C-NMR (100 MHz, d6-DMSO) δ=25.66, 26.67, 29.35, 35.56, 53.86, 103.06, 113.89, 116.80, 119.84, 124.54, 133.39, 134.47, 144.09, 151.89, 157.26. LRMS (FAB+): 380.0 (100, [M+H]$^+$). HRMS (FAB+) 380.15355 $C_{20}H_{22}N_5OS$ requires 380.154507.

Sulfamic Acid 4-{5-[(4-cyano-phenyl)-[1,2,4]triazol-4-yl-amino]-pentylsulfanyl}-phenyl ester (CAB03025, STX699)

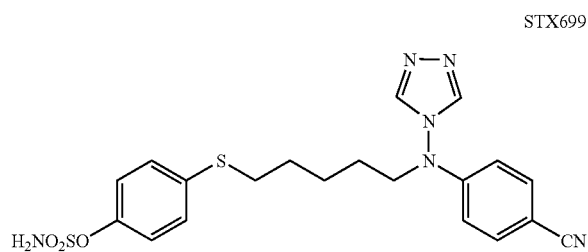

Sulphamoyl chloride solution in toluene (3 mL, 0.7 M, 2.1 mmol) was concentrated under reduced pressure (30° C. water bath temperature) to ca. 0.5 mL volume. The residue was cooled to 0° C. (ice bath) and N,N-dimethylacetamide (5 mL) was added. 4-{[3-(4-hydroxy-phenylsulfanyl)-pentyl]-[1,2,4]triazol-4-yl-amino}-benzonitrile (CAB03014, 95 mg, 0.25 mmol) was added to the colourless solution and the mixture was stirred for 18 hours at room temperature. Ethyl acetate (50 mL) and water (50 mL) were added to the solution, the organic layer was separated, washed with water (two times 30 mL) and brine (20 mL), dried over sodium sulphate and concentrated under reduced pressure. The residue was dissolved in a small amount of acetone and precipitated by addition of hexane. The precipitate was filtered off and dried under high vacuum. Yield: 103 mg (90%) light yellow powder. $^1$H-NMR (270 MHz, d6-DMSO) δ=1.35–1.63 (m, 6H), 2.95 (t, J=7.0 Hz, 2H), 3.75–3.85 (m, 2H), 6.62 (d, J=9.0 Hz, 2H), 7.20 (d, J=9.0 Hz, 2H), 7.37 (d, J=9.0 Hz, 2H), 7.71 (d, J=9.0 Hz, 2H), 7.99 (s, 2H, —NH$_2$), 8.96 (s, 2H). LRMS (FAB+): 459.1 (100, [M+H]$^+$).

4-[(10-Bromo-decyl)-[1,2,4]triazol-4-yl-amino]-benzonitrile (CAB03008)

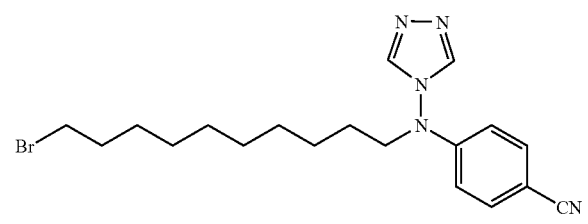

Sodium hydride (60%, 240 mg, 6.0 mmol) was added to a solution of 4-([1,2,4]triazol-4-ylamino)-benzonitrile (926 mg, 5.0 mmol) in DMSO (25 mL) at r.t. The mixture was stirred for 1 hour at this temperature and 1,10-dibromodecane (5 mL) was added. The reaction mixture was stirred overnight and ethyl acetate (100 mL) was added. The mixture was transferred into a separation funnel and extracted with water (twice 100 mL) and brine (20 mL). The organic layer was dried over sodium sulphate and concentrated under reduced pressure (water bath temperature <30° C.). The resulting orange oil was mixed with diethyl ether (100 mL) and filtered through a layer of silica (ca. 5 cm). The silica was washed with more diethyl ether (ca. 100 mL) to remove the excess of 1,10-dibromodecane. The crude product was washed from the silica with acetone (120 mL). The acetone solution was concentrated under reduced pressure and the residue was purified by column-chromatography (eluent: ethyl acetate) to give the title compound as a pale yellow solid. Yield: 1.32 g (65%). $^1$H-NMR (400 MHz, d6-DMSO) δ=1.16–1.40 (m, 14H), 1.76 (tt, J=7.0, 7.0 Hz, 2H), 3.50 (t, J=6.6 Hz, 2H), 3.79 (t, J=7.0 Hz, 2H), 6.61 (d, J=9.0 Hz, 2H), 7.70 (d, J=9.0 Hz, 2H), 8.95 (s, 2H).

4-{[10-(4-Hydroxy-phenylsulfanyl)-decyl]-[1,2,4]triazol-4-yl-amino}-benzonitrile (CAB03011, STX625)

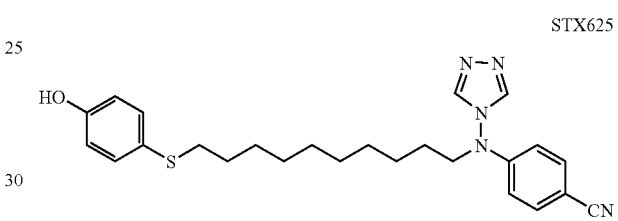

A mixture of 4-[(2-Bromo-decyl)-[1,2,4]triazol-4-yl-amino]-benzonitrile (CAB03008, 607 mg, 1.5 mmol), 4-hydroxy-thiophenol (378 mg, 3.0 mmol) and potassium carbonate (414 mg, 3.0 mmol) in DMF (10 mL) was stirred for 12 hours at room temperature. The mixture was transferred into a separation funnel and ethyl acetate (50 mL) and water (50 mL) were added. The organic layer was separated, washed with brine (30 mL), dried over sodium sulphate and concentrated under reduced pressure. The residue was purified by column chromatography (eluent: ethyl acetate, Rf: 0.71). The resulting yellow solid was dissolved in acetone and precipitated by addition of hexane to give a light yellow powder. Yield: 401 mg (59%). $^1$H-NMR (400 MHz, d6-DMSO) δ=1.16–1.52 (m, 16H), 2.76 (t, J=7.2 Hz, 2H), 3.80 (t, J=7.2 Hz, 2H), 6.62 (d, J=9.0 Hz, 2H), 6.72 (d, J=8.6 Hz, 2H), 7.19 (d, J=8.6 Hz, 2H), 7.72 (d, J=9.0 Hz, 2H), 8.97 (s, 2H), 9.53 (s, 1H, —OH). LRMS (FAB+): 450.2 (100, [M+H]$^+$). HRMS (FAB+) 450.23208 $C_{25}H_{32}N_5OS$ requires 450.232758.

Sulfamic Acid 4-{10-[(4-cyano-phenyl)-[1,2,4]triazol-4-yl-amino]-decylsulfanyl}-phenyl ester (CAB03012, STX655)

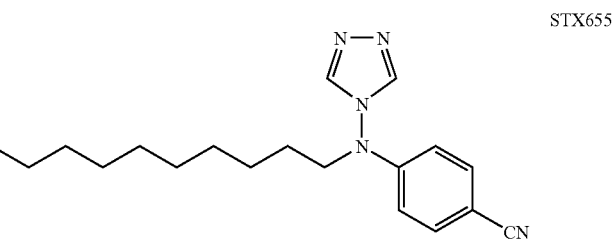

Sulphamoyl chloride solution in toluene (3 mL, 0.7 M, 2.1 mmol) was concentrated under reduced pressure (30° C. water bath temperature) to ca. 0.5 mL volume. The residue was cooled to 0° C. (ice bath) and N,N-dimethylacetamide (5 mL) was added. 4-{[3-(4-hydroxy-phenylsulfanyl)-decyl]-[1,2,4]triazol-4-yl-amino}-benzonitrile (CAB03011, 100 mg, 0.22 mmol) was added to the colourless solution and the mixture was stirred for 18 hours at room temperature. Ethyl acetate (50 mL) and water (50 mL) were added to the solution, the organic layer was separated, washed with water (two times 30 mL) and brine (20 mL), dried over sodium sulphate and concentrated under reduced pressure. The residue was dissolved in a small amount of acetone and precipitated by addition of diethyl ether and hexane. The precipitate was filtered off and dried under high vacuum. Yield: 104 mg (88%) light yellow powder. $^1$H-NMR (400 MHz, d6-DMSO) δ=1.20–1.41 (m, 14H), 1.56 (tt, J=7.0 Hz, 2H), 2.96 (t, J=7.0 Hz, 2H), 3.80 (t, J=7.0 Hz, 2H), 6.62 (d, J=9.0 Hz, 2H), 7.21 (d, J=9.0 Hz, 2H), 7.37 (d, J=9.0 Hz, 2H), 7.71 (d, J=9.0 Hz, 2H), 7.99 (s, 2H, —NH$_2$), 8.95 (s, 2H). LRMS (FAB+): 529.2 (100, [M+H]$^+$). HRMS (FAB+) 529.20425 C$_{25}$H$_{33}$N$_6$O$_3$S$_2$ requires 529.205558.

4-Benzyloxy-3,5-dichloro-benzoic acid methyl ester (CAB02115)

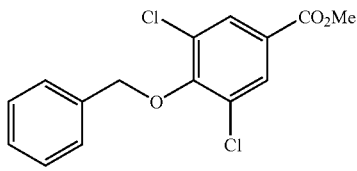

A mixture of 3,5-dichloro-4-hydroxy benzoic acid methyl ester (5.525 g, 25 mmol), benzyl bromide (5.13 g, 30 mmol) and potassium carbonate (6.91 g, 50 mmol) in N,N-dimethylformamide (100 mL) was stirred overnight at room temperature. The reaction mixture was poured into crushed ice (ca. 300 g) and the product was extracted with ethyl acetate (2×100 mL). The combined organic layers were dried over sodium sulphate and concentrated under reduced pressure. The solid residue was recrystallised from ethyl acetate and hexane. Yield: 7.47 g (96%) fine white needles. $^1$H-NMR (400 MHz, CDCl$_3$) δ=3.93 (s, 3H, —OCH$_3$), 5.12 (s, 2H, —CH$_2$Ph), 7.35–7.44 (m, 3H), 7.54–7.58 (m, 2H), 8.01 (s, 2H). $^{13}$C-NMR (100 MHz, CDCl$_3$) δ=52.66, 75.12, 127.18, 128.41, 128.48, 129.79, 130.13, 135.57, 154.57, 164.39.

(4-Benzyloxy-3,5-dichloro-phenyl)-methanol (CAB02117)

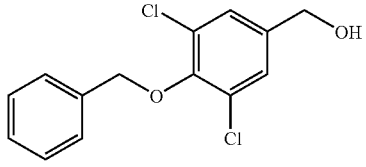

A solution of 4-benzyloxy-3,5-dichloro-benzoic acid methyl ester (CAB02115, 7.20 g, 23.14 mmol) in THF (20 mL) was added slowly with a syringe to a suspension of lithium aluminium hydride (1.50 g, 39.5 mmol) in THF (40 mL). The reaction mixture was stirred for 30 minutes at room temperature and then carefully quenched by addition of 2N sodium hydroxide solution in water. After 20 minutes stirring the colour of the mixture turned from grey to white. The white precipitate was filtered off, the filtrate was dried over sodium sulphate and concentrated under reduced pressure. The residue was recrystallised from dichloromethane/hexane. Yield: 5.83 g (89%) white powder. $^1$H-NMR (400 MHz, CDCl$_3$) δ=1.85 (t, J=5.9 Hz, 1H, —OH), 4.63 (d, J=5.9 Hz, 2H), 5.04 (s, 2H), 7.33 (s, 2H), 7.35–7.44 (m, 3H), 7.55–7.59 (m, 2H). $^{13}$C-NMR (100 MHz, CDCl$_3$) δ=64.05, 75.03, 127.36, 128.70, 128.75, 129.91, 136.39, 138.64, 150.32.

2-Benzyloxy-5-bromomethyl-1,3-dichloro-benzene (CAB02118)

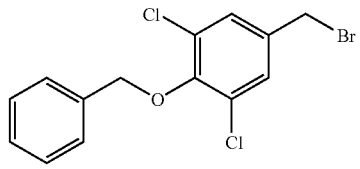

Phosphorous tribromide (2 mL) was added to a solution of (4-benzyloxy-3,5-dichloro-phenyl)-methanol (CAB02117, 5.50 g, 19.4 mmol) in dichloromethane (80 mL) at 0° C. The mixture was stirred at this temperature for 2 h, diluted with diethyl ether (150 mL), transferred into a separation funnel and washed with water (2×50 mL) and brine (50 mL). The organic layer was dried over magnesium sulphate and concentrated under reduced pressure. The residue was recrystallised from dichloromethane/hexane. $^1$H-NMR (400 MHz, CDCl$_3$) δ=4.39 (s, 2H, —CH$_2$Br), 5.05 (s, 2H, —CH$_2$Ph), 7.37 (s, 2H), 7.38–7.44 (m, 3H), 7.54–7.58 (m, 2H). $^{13}$C-NMR (100 MHz, CDCl$_3$) δ=31.48, 75.39, 128.73, 129.68, 129.70, 129.72, 130.06, 135.46, 136.27, 151.23.

4-[(4-Benzyloxy-3,5-dichloro-benzyl)-[1,2,4]triazol-4-yl-amino]-benzonitrile (CAB02119, STX434)

STX434

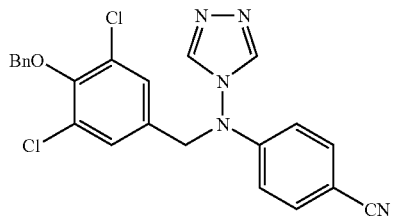

Sodium hydride (60%, 200 mg, 5.0 mmol) was added to a solution of 4-([1,2,4]triazol-4-ylamino)-benzonitrile (926 mg, 5.0 mmol) in DMF (20 mL) at r.t. The mixture was stirred for 1 h at this temperature and 2-benzyloxy-5-bromomethyl-1,3-dichloro-benzene (CAB02118, 1.73 g, 5.0 mmol) was added. The reaction mixture was stirred overnight and ethyl acetate (75 mL) was added. The mixture was transferred into a separation funnel and washed with water (2×100 mL) and brine (20 mL). The organic layer was dried over sodium sulphate and concentrated under reduced pressure. The residue was suspended in 2-propanol (20 mL) and heated to reflux for 5 minutes. The white solid was filtered off after cooling to room temperature and dried under high vacuum. Yield: 1.76 g (78%).

$^1$H-NMR (400 MHz, d6-DMSO) δ=5.00 (s, 2H), 5.07 (s, 2H), 6.74 (d, J=9.0 Hz, 2H), 7.36–7.44 (m, 3H), 7.47–7.50 (m, 2H), 7.50 (s, 2H), 7.77 (d, J=9.0 Hz, 2H), 8.92 (s, 2H). $^{13}$C-NMR (100 MHz, CDCl$_3$) δ=55.94, 74.59, 102.96, 113.61, 118.80, 128.21, 128.27, 128.63, 128.81, 133.29, 133.75, 135.69, 143.13, 149.62, 150.88. LRMS (FAB+): 450.1 (100, [M+H]$^+$).

4-[(3,5-Dichloro-4-hydroxy-benzyl)-[1,2,4]triazol-4-yl-amino]-benzonitrile (CAB02120, STX435)

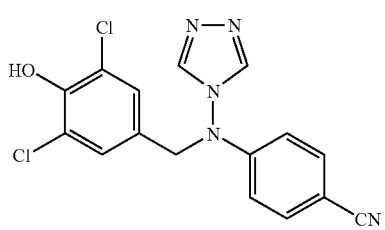

STX435

Palladium on charcoal (100 mg, 10% Pd) was added to a solution of 4-[(4-benzyloxy-3,5-dichloro-benzyl)-[1,2,4]triazol-4-yl-amino]-benzonitrile (CAB02119, 1.13 g, 2.50 mmol) in MeOH/THF/EtOAc (30 mL/30 mL/40 mL). The mixture was stirred under hydrogen atmosphere (balloon) for 18 h at room temperature. The reaction mixture was filtered through celite and the clear colourless filtrate was concentrated under reduced pressure. The residue was suspended in 2-propanol (20 mL) and heated to reflux for 5 minutes. The white solid was filtered off after cooling to room temperature and dried under high vacuum. Yield: 306 mg (34%). $^1$H-NMR (400 MHz, d6-DMSO) δ=4.97 (s, 2H, —CH$_2$Ar), 6.76 (d, J=9.0 Hz, 2H), 7.31 (s, 2H), 7.77 (d, J=9.0 Hz, 2H), 8.85 (s, 2H), 10.29 (s, 1H, —OH). $^{13}$C-NMR (100 MHz, CDCl$_3$) δ=56.57, 103.76, 114.55, 119.69, 122.89, 128.14, 129.46, 134.58, 144.03, 149.46, 151.85. LRMS (FAB+): 360.0 (100, [M+H]$^+$).

4-Benzyloxy-3-chloro-benzoic acid methyl ester (CAB02121)

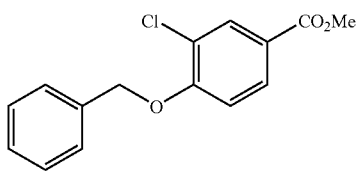

A mixture of 3-chloro-4-hydroxy benzoic acid methyl ester (4.665 g, 25 mmol), benzyl bromide (5.13 g, 30 mmol) and potassium carbonate (6.91 g, 50 mmol) in N,N-dimethylformamide (50 mL) was stirred overnight at room temperature. The reaction mixture was poured onto crushed ice (ca. 300 g) and the product was extracted with ethyl acetate (2×100 mL). The combined organic layers were dried over sodium sulphate and concentrated under reduced pressure. The residue was dissolved in dichloromethane and precipitated by addition of hexane. Yield: 6.47 g (94%) white powder. $^1$H-NMR (400 MHz, CDCl$_3$) δ=3.90 (s, 3H, —OCH$_3$), 5.23 (s, 2H, —CH$_2$Ar), 6.99 (d, J=9.0 Hz, 1H), 7.31–7.48 (m, 5H), 7.89 (dd, J=9.0, 2.3 Hz, 1H), 8.08 (d, J=2.3 Hz, 1H).

(4-Benzyloxy-3-chloro-phenyl)-methanol (CAB02127)

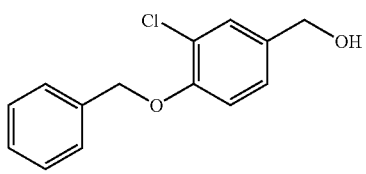

A solution of 4-benzyloxy-3-chloro-benzoic acid methyl ester (CAB02121, 4.15 g, 15.0 mmol) in THF (30 mL) was added slowly with a syringe to a suspension of lithium aluminium hydride (1.0 g, 26.3 mmol) in THF (30 mL). The reaction mixture was stirred for 30 minutes at room temperature and then carefully quenched by addition of 2N sodium hydroxide solution in water. After 20 minutes stirring the colour of the mixture turned from grey to white. The white precipitate was filtered off, the filtrate was dried over sodium sulphate and concentrated under reduced pressure to give an colourless oil, which was used without further purification. Yield: 3.61 g (97%). $^1$H-NMR (400 MHz, CDCl$_3$) δ=2.12 (s, 1H, —OH), 4.56 (s, 2H), 5.16 (s, 2H), 6.93 (d, J=8.6 Hz, 1H), 7.14 (dd, J=8.6, 2.3 Hz, 1H), 7.31–7.48 (m, 6H).

1-Benzyloxy-4-bromomethyl-2-chloro-benzene (CAB02128)

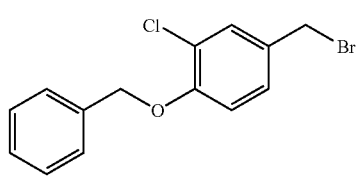

Phosphorous tribromide (2 mL) was added to a solution of (4-benzyloxy-3-chloro-phenyl)-methanol (CAB02127, 3.40 g, 13.7 mmol) in dichloromethane (50 mL) at 0° C. The mixture was stirred at this temperature for 1 h, diluted with diethyl ether (100 mL), transferred into a separation funnel and washed with water (50 mL) and brine (50 mL). The organic layer was dried over magnesium sulphate and concentrated under reduced pressure to give a white, analytical pure solid. Yield: 4.27 g (100%).

$^1$H-NMR (400 MHz, CDCl$_3$) δ=4.44 (s, 2H, —CH$_2$Br), 5.17 (s, 2H), 6.92 (d, J=8.6 Hz, 1H), 7.21 (dd, J=8.6, 2.3 Hz, 1H), 7.31–7.48 (m, 6H).

4-[(4-Benzyloxy-3-chloro-benzyl)-[1,2,4]triazol-4-yl-amino]-benzonitrile (CAB02129, STX446)

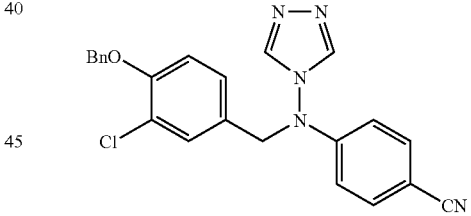

STX446

Sodium hydride (60%, 200 mg, 5.0 mmol) was added to a solution of 4-([1,2,4]triazol-4-ylamino)-benzonitrile (926 mg, 5.0 mmol) in DMF (20 mL) at r.t. The mixture was stirred for 1 hour at this temperature and 1-benzyloxy-4-bromomethyl-2-chloro-benzene (CAB02128, 1.56 g, 5.0 mmol) was added. The reaction mixture was stirred overnight and ethyl acetate (75 mL) was added. The mixture was transferred into a separation funnel and washed with water (two times 100 mL) and brine (20 mL). The organic layer was dried over sodium sulphate and concentrated under reduced pressure. The residue was suspended in 2-propanol (20 mL) and heated to reflux for 5 minutes. The white solid was filtered off after cooling to room temperature and dried under high vacuum. Yield: 1.38 g (66%). $^1$H-NMR (400 MHz, d6-DMSO) δ=4.99 (s, 2H), 5.17 (s, 2H), 6.76 (d, J=9.0 Hz, 2H), 7.16 (d, J=8.6 Hz, 1H), 7.20 (dd, J=8.6, 2.2 Hz, 1H), 7.32–7.47 (m, 6H), 7.76 (d, J=9.0 Hz, 2H), 8.81 (s, 2H). LRMS (FAB+): 416.1 (100, [M+H]$^+$).

4-[(3-Chloro-4-hydroxy-benzyl)-[1,2,4]triazol-4-yl-amino]-benzonitrile (CAB02130, STX447)

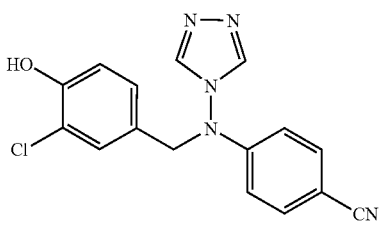

Palladium on charcoal (50 mg, 10% Pd) was added to a solution of 4-[(4-benzyloxy-3-chloro-benzyl)-[1,2,4]triazol-4-yl-amino]-benzonitrile (CAB02129, 1.04 g, 2.50 mmol) in MeOH/THF/EtOAc (25 mL/25 mL/25 mL). The mixture was stirred under hydrogen atmosphere (balloon) for 18 hours at room temperature. The reaction mixture was filtered through celite and the clear colourless filtrate was concentrated under reduced pressure. The residue was suspended in 2-propanol (20 mL) and heated to reflux for 5 minutes. The white solid was filtered off after cooling to room temperature and dried under high vacuum. Yield: 484 mg (59%). $^1$H-NMR (400 MHz, d6-DMSO) δ=4.93 (s, 2H), 6.76 (d, J=9.0 Hz, 2H), 6.86 (d, J=8.6 Hz, 1H), 7.02 (dd, J=8.2, 2.0 Hz, 1H), 7.27 (d, J=2.0 Hz, 1H), 7.76 (d, J=9.0 Hz, 2H), 8.77 (s, 2H), 10.29 (s, 1H, —OH). $^{13}$C-NMR (100 MHz, d6-DMSO) δ=56.87, 103.55, 114.48, 117.28, 119.73, 120.25, 126.72, 129.19, 130.91, 134.56, 144.02, 152.03, 153.50. LRMS (FAB+): 325.0 (100, [M+H]$^+$).

Sulfamic Acid 2-chloro-4-{[(4-cyano-phenyl)-[1,2,4]triazol-4-yl-amino]-methyl}-phenyl ester (CAB03015, STX694)

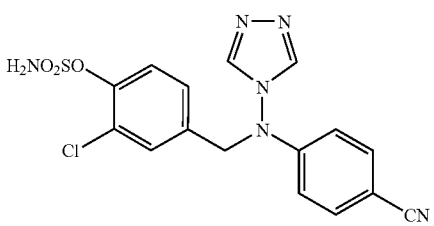

Sulphamoyl chloride solution in toluene (3 mL, 0.7 M, 2.1 mmol) was concentrated under reduced pressure (30° C. water bath temperature) to ca. 0.5 mL volume. The residue was cooled to 0° C. (ice bath) and N,N-dimethylacetamide (5 mL) was added. 4-[(3-Chloro-4-hydroxy-benzyl)-[1,2,4]triazol-4-yl-amino]-benzonitrile (CAB02130, 163 mg, 0.50 mmol) was added to the colourless solution and the mixture was stirred for 18 h at room temperature. Ethyl acetate (50 mL) and water (30 mL) were added to the solution, the organic layer was separated, washed with water (2×30 mL) and brine (20 mL), dried over sodium sulphate and concentrated under reduced pressure. The residue was dissolved in a small amount of acetone and precipitated by addition of hexane. The precipitate was filtered off and dried under high vacuum. Yield: 59 mg (29%) white powder. $^1$H-NMR (400 MHz, d6-DMSO) δ=5.11 (s, 2H), 6.72 (d, J=9.0 Hz, 2H), 7.38 (dd, J=8.2, 2.0 Hz, 1H), 7.44 (d, J=8.2 Hz, 1H), 7.59 (d, J=2.0 Hz, 1H), 7.77 (d, J=9.0 Hz, 2H), 8.31 (s, 2H, —NH$_2$), 8.91 (s, 2H). LRMS (FAB+): 405.0 (100, [M+H]$^+$). HRMS (FAB+) 405.05349 C$_{16}$H$_{14}$N$_6$O$_3$SCl requires 405.053663

Benzoic Acid 2-chloro-5-methyl-phenyl ester (CAB02124)

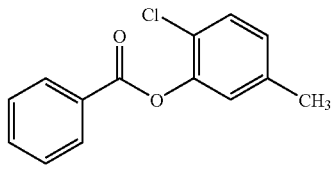

Benzoyl chloride (3.51 g, 25 mmol) was added dropwise to a solution of 2-chloro-5-methylphenol (3.92 g, 27.5 mmol) and triethylamine (5 mL) in dichloromethane (100 mL), The mixture was stirred for 18 hours at room temperature and concentrated under reduced pressure. Diethylether (200 mL) and water (100 mL) were added. The organic layer was separated and extracted with 2N NaOH (2×100 mL) and brine (50 mL), dried over sodium sulphate and concentrated under reduced pressure. The resulting colourless oil solidified in the freezer. Yield: 5.82 g (94%). $^1$H-NMR (400 MHz, CDCl$_3$) δ=2.38 (s, 3H, —CH$_3$), 7.05 (d, J=8.2 Hz, 1H), 7.11 (s, 1H), 7.36 (d, J=8.2 Hz, 1H), 7.51–7.56 (m, 2H), 7.64–7.7.70 (m, 1H), 8.22–8.28 (m, 2H). $^{13}$C-NMR (100 MHz, CDCl$_3$) δ=21.41, 123.97, 124.58, 128.07, 128.85, 129.15, 130.07, 130.55, 134.01, 138.38, 146.98, 164.51.

Benzoic Acid 5-bromomethyl-2-chloro-phenyl ester (CAB02138)

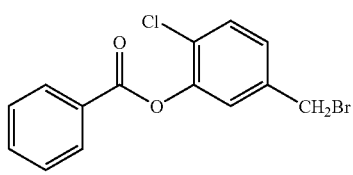

A mixture of benzoic acid 2-chloro-5-methyl-phenyl ester (CAB02124, 2.47 g, 10.0 mmol), N-bromo-succinimide (1.96 g, 11.0 mmol) and dibenzoyl peroxide (10 mg) in carbon tetrachloride (25 mL) was heated to reflux for 1 hour (TLC-control). After cooling to room temperature water (50 mL) and diethyl ether (100 mL) were added. The organic layer was separated, washed with brine (20 mL), dried over sodium sulphate and concentrated under reduced pressure. The residue was purified by column chromatography (EtOAc:hexane, 1:40, Rf: 0.21). Yield: 2.012 g (62%) colourless oil, which solidified after a few hours (contains ca. 10% benzoic acid 5-dibromomethyl-2-chloro-phenyl ester).

$^1$H-NMR (400 MHz, CDCl$_3$) δ=4.48 (s, 2H, —CH$_2$Br), 7.27 (dd, J=8.2, 2.0 Hz, 1H), 7.36 (d, J=2.0 Hz, 1H), 7.46 (d, J=8.2 Hz, 1H), 7.50–7.58 (m, 2H), 7.64–7.71 (m, 1H), 8.22–8.28 (m, 2H). LRMS (FAB+): 325.0 (81, [M+H]$^+$), 327.0 (100, [M+H]$^+$).

Benzoic Acid 2-chloro-5-{[(4-cyano-phenyl)-[1,2,4]triazol-4-yl-amino]methyl}-phenyl ester (CAB02139)

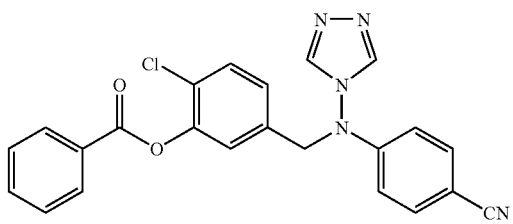

Sodium hydride (60%, 200 mg, 5.0 mmol) was added to a solution of 4-([1,2,4]triazol-4-ylamino)-benzonitrile (926 mg, 5.0 mmol) in DMF (20 mL) at r.t. The mixture was stirred for 1 hour at this temperature and benzoic acid 5-bromomethyl-2-chloro-phenyl ester (CAB02138, 1.63 g, 5.0 mmol) was added. The reaction mixture was stirred overnight and ethyl acetate (75 mL) was added. The mixture was transferred into a separation funnel and washed with water (2×50 mL) and brine (20 mL). The organic layer was dried over sodium sulphate and concentrated under reduced pressure. The residue was purified by column chromatography (EtOAc, Rf: 0.31) to give a white solid. Yield: 1.773 g (82%). $^1$H-NMR (400 MHz, CDCl$_3$) δ=4.93 (s, 2H), 6.66 (d, 9.0 Hz, 2H), 7.06 (dd, J=8.2, 2.0 Hz, 1H), 7.27 (d, J=2.0 Hz, 1H), 7.45 (d, J=8.2 Hz, 1H), 7.47–7.58 (m, 4H), 7.60–7.69 (m, 1H), 8.16–8.21 (m, 2H), 8.24 (s, 2H). LRMS (FAB+): 430.1 (100, [M+H]$^+$).

4-[(4-Chloro-3-hydroxy-benzyl)-[1,2,4]triazol-4-yl-amino]-benzonitrile (CAB02141, STX483)

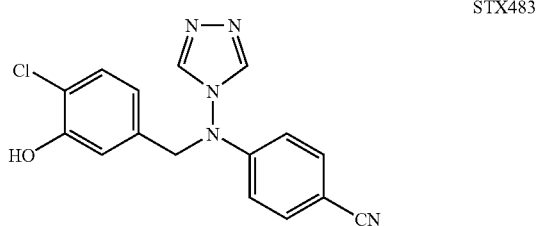

STX483

A solution of benzoic acid 2-chloro-5-{[(4-cyano-phenyl)-[1,2,4]triazol-4-yl-amino]methyl}-phenyl ester (CAB02139, 1.13 g, 2.63 mmol) and sodium methoxide (500 mg) in methanol (20 mL) and water (5 mL) was heated to reflux for 30 minutes. After cooling to room temperature most of the solvent was removed under reduced pressure and concentrated sodium bicarbonate solution (20 mL) and ethyl acetate (50 mL) were added. The organic layer was separated, dried over sodium sulphate and the solvent was removed under reduced pressure. The resulting white powder was refluxed in ethyl acetate (10 mL, product did not dissolve completely). After cooling to room temperature the product was filtered off and dried under high vacuum. Yield: 412 mg (48%) white powder. $^1$H-NMR (400 MHz, d6-DMSO) δ=4.97 (s, 2H), 6.71–6.75 (m, 3H), 6.84 (d, J=2.0 Hz, 1H), 7.25 (d, J=8.2 Hz, 1H), 7.75 (d, J=9.0 Hz, 2H), 8.76 (s, 2H), 10.21 (s, 1H, —OH). LRMS (FAB+): 326.1 (100, [M+H]$^+$).

Sulfamic Acid 2-chloro-5-{[(4-cyano-phenyl)-[1,2,4]triazol-4-yl-amino]-methyl}-phenyl ester (CAB02176, STX559)

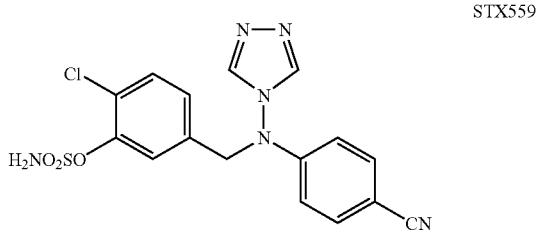

STX559

Sulphamoyl chloride solution in toluene (3 mL, 0.7 M, 2.1 mmol) was concentrated under reduced pressure (30° C. water bath temperature) to ca. 0.5 mL volume. The residue was cooled to 0° C. (ice bath) and N,N-dimethylacetamide (5 mL) was added. 4-[(4-Chloro-3-hydroxy-benzyl)-[1,2,4] triazol-4-yl-amino]-benzonitrile (CAB02141, 200 mg, 0.614 mmol) was added to the colourless solution and the mixture was stirred for 18 hours at room temperature. Ethyl acetate (50 mL) and water (30 mL) were added to the solution, the organic layer was separated, washed with water (2×30 mL) and brine (20 mL), dried over sodium sulphate and concentrated under reduced pressure. The residue was dissolved in a small amount of acetone and precipitated by addition of diethyl ether and hexane. The precipitate was filtered off and dried under high vacuum. Yield: 136 mg (55%) white powder. $^1$H-NMR (400 MHz, d6-DMSO) δ=5.11 (s, 2H), 6.75 (d, J=9.0 Hz, 2H), 7.25 (dd, J=8.2, 2.0 Hz, 1H), 7.46 (d, J=2.0 Hz, 1H), 7.54 (d, J=8.2 Hz, 1H), 7.77 (d, J=9.0 Hz, 2H), 8.32 (s, 2H, —NH$_2$), 8.82 (s, 2H). LRMS (FAB+): 87.0 (100), 404.9 (40, [M+H]$^+$). HRMS (FAB+): 405.05338 C$_{16}$H$_{14}$N$_6$O$_3$SCl requires 405.053663.

4-Benzyloxy-3-chloro-5-methoxy-benzoic acid benzyl ester (CAB02162)

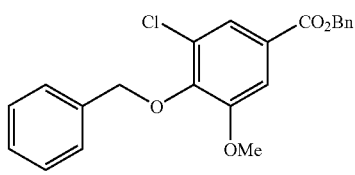

A mixture of 5-chloro-vanillic acid (4.05 g, 20 mmol), benzyl bromide (8.55 g, 50 mmol) and potassium carbonate (6.90 g, 50 mmol) in DMF (60 mL) was stirred at room temperature for 18 hours. The mixture was transferred into a separation funnel and ethyl acetate (100 mL) and water (100 mL) were added, the organic layer was separated, washed with water (2×50 mL) and brine (50 mL), dried over sodium sulphate and concentrated under reduced pressure. The residue was crystallised from dichloromethane/hexane. Yield: 7.34 g (96%) colourless needles. $^1$H-NMR (400 MHz, CDCl$_3$) δ=3.92 (s, 3H, —OCH$_3$), 5.13 (s, 2H), 5.36 (s, 2H), 7.31–7.51 (m, 10H), 7.53 (d, J=2.0 Hz, 1H), 7.73 (d, J=2.0 Hz, 1H). LRMS (FAB+): 91.0 (100), 382.1 (15, [M+H]$^+$).

(4-Benzyloxy-3-chloro-5-methoxy-phenyl)-methanol (CAB02170)

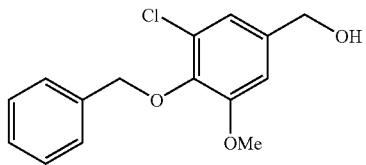

A solution of 4-benzyloxy-3-chloro-5-methoxy-benzoic acid benzyl ester (CAB02162, 3.83 g, 10.0 mmol) in THF (20 mL) was added dropwise with a syringe to a suspension of lithium aluminium hydride (500 mg, 13.15 mmol) in THF (30 mL). The mixture was stirred at room temperature for 30 minutes and 2N NaOH (5 mL) was added. The mixture was stirred for another hour, the aluminium salts were filtered off, the filtrate was dried over sodium sulphate and concentrated under reduced pressure. The resulting oil was heated to 120° C. under high vacuum in a kugelrohr-destillation-apparatus to remove benzyl alcohol for 10 h. The product was obtained as a light yellow oil and was used without any further purification. Yield: 2.70 g (97%). $^1$H-NMR (400 MHz, CDCl$_3$) δ=2.09 (2, 1H, —OH), 3.86 (s, 3H, —OCH$_3$), 4.56 (s, 2H), 5.02 (s, 2H), 6.83 (d, J=2.0 Hz, 1H), 6.95 (d, J=2.0 Hz, 1H), 7.31–7.41 (m, 3H), 7.52–7.55 (m, 2H).

2-Benzyloxy-1-chloro-5-chloromethyl-3-methoxy-benzene (CAB02174)

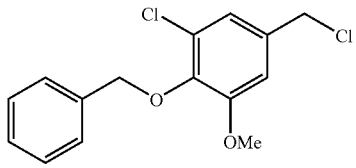

Thionyl chloride (2 mL) was added to solution of (4-benzyloxy-3-chloro-5-methoxy-phenyl)-methanol (CAB02170, 2.703 g, 9.7 mmol) in dichloromethane (10 mL). The solution was stirred for 1 h at room temperature, then diethyl ether (50 mL) and water (20 mL) were added. The organic layer was separated, washed with conc. sodium bicarbonate solution (10 mL), dried over sodium sulphate and concentrated under reduced pressure. The residue was dissolved in dichloromethane (5 mL) and precipitated by addition of hexane (ca. 50 mL). Yield: 2.730 g (95%) white powder. $^1$H-NMR (400 MHz, CDCl$_3$) δ=3.89 (s, 3H, —OCH$_3$), 4.52 (s, 2H), 5.07 (s, 2H), 6.87 (d, J=2.0 Hz, 1H), 7.03 (d, J=2.0 Hz, 1H), 7.33–7.43 (m, 3H), 7.53–7.58 (m, 2H). LRMS (FAB+): 91.0 (100), 296.0 (17, [M+H]$^+$).

4-[(4-Benzyloxy-3-chloro-5-methoxy-benzyl)-[1,2,4]triazol-4-yl-amino]-benzonitrile (CAB02177, STX599)

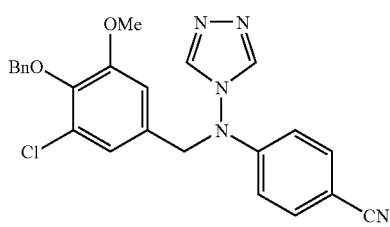

Sodium hydride (60%, 200 mg, 5.0 mmol) was added to a solution of 4-([1,2,4]triazol-4-ylamino)-benzonitrile (926 mg, 5.0 mmol) in DMF (20 mL) at r.t. The mixture was stirred for 1 h at this temperature and 2-benzyloxy-1-chloro-5-chloromethyl-3-methoxy-benzene (CAB02174, 1.49 g, 5.0 mmol) was added. The reaction mixture was stirred overnight and ethyl acetate (100 mL) and water (50 mL) were added. The organic layer was separated and washed with water (2×50 mL) and brine (30 mL). The organic layer was dried over sodium sulphate and concentrated under reduced pressure. The residue was suspended in 2-propanol (20 mL) and heated to reflux for 5 minutes. The white solid was filtered off after cooling to room temperature and dried under high vacuum. Yield: 1.76 g (79%).

$^1$H-NMR (400 MHz, d6-DMSO) δ=3.78 (s, 3H, —OCH$_3$), 4.80 (s, 2H), 5.05 (s, 2H), 6.52 (d, J=2.0 Hz, 1H), 6.67 (d, J=9.0 Hz, 2H), 6.89 (d, J=2.0 Hz, 1H), 7.32–7.40 (m, 3H), 7.46–7.50 (m, 2H), 7.61 (d, J=9.0 Hz, 2H), 8.75 (s, 2H). LRMS (FAB+): 91.0 (100), 446.0 (65, [M+H]$^+$). HRMS (FAB+): 446.13840 C$_{24}$H$_{21}$N$_5$O$_2$Cl requires 446.138378.

4-[(3-chloro-4-hydroxy-5-methoxy-benzyl)-[1,2,4]triazol-4-yl-amino]-benzonitrile (CAB02179, STX600)

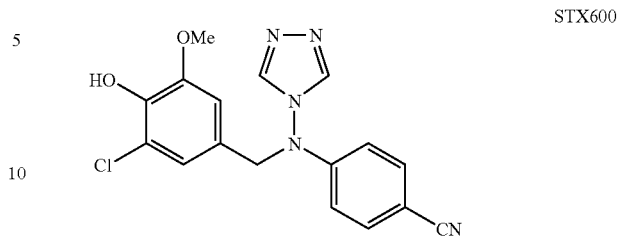

Palladium on charcoal (100 mg, 5% Pd) was added to a solution of 4-[(4-benzyloxy-3-chloro-5-methoxy-benzyl)-[1,2,4]triazol-4-yl-amino]-benzonitrile (CAB02177, 1.34 g, 3.0 mmol) in ethanol (60 mL) and THF (40 mL). The mixture was stirred under hydrogen atmosphere (balloon) for 24 h (TLC monitored), then filtered through celite and concentrated under reduced pressure. The residue was dried under high vacuum. Yield: 1.06 g (99%), white powder. $^1$H-NMR (400 MHz, d6-DMSO) δ=3.77 (s, 3H, —OCH$_3$), 4.92 (s, 2H), 6.79 (d, J=9.0 Hz, 2H), 6.81 (d, J=1.8 Hz, 1H), 6.85 (d, J=1.8 Hz, 1H), 7.77 (d, J=9.0 Hz, 2H), 8.79 (s, 2H), 9.49 (s, 1H, —OH). LRMS (FAB+): 356.0 (100, [M+H]$^+$). HRMS (FAB+): 356.09234 C$_{17}$H$_{15}$N$_5$O$_2$Cl requires 356.091428.

Sulfamic Acid 2-chloro-4-{[(4-cyano-phenyl)-[1,2,4]triazol-4-yl-amino]-methyl}-6-methoxy-phenyl ester (CAB02181, STX601)

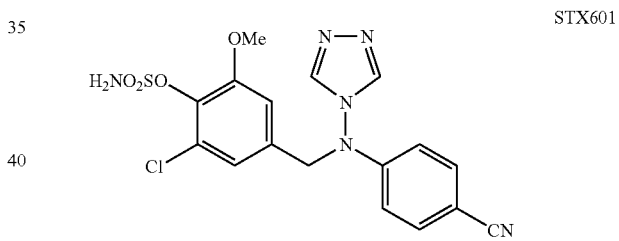

Sulphamoyl chloride solution in toluene (3 mL, 0.7 M, 2.1 mmol) was concentrated under reduced pressure (30° C. water bath temperature) to ca. 0.5 mL volume. The residue was cooled to 0° C. (ice bath) and N,N-dimethylacetamide (5 mL) was added. 4-[(3-Chloro-4-hydroxy-5-methoxy-benzyl)-[1,2,4]triazol-4-yl-amino]-benzonitrile (CAB02179, 212 mg, 0.596 mmol) was added to the colourless solution and the mixture was stirred for 18 hours at room temperature. Ethyl acetate (50 mL) and water (30 mL) were added to the solution, the organic layer was separated, washed with water (2×30 mL) and brine (20 mL), dried over sodium sulphate and concentrated under reduced pressure. The residue was dissolved in a small amount of acetone and precipitated by addition of hexane. The precipitate was filtered off and dried under high vacuum. Yield: 219 mg (84%) white powder. $^1$H-NMR (400 MHz, d6-DMSO) δ=3.78 (s, 3H, —OCH$_3$), 6.74 (d, J=9.0 Hz, 2H), 7.04 (d, J=2.0 Hz, 1H), 7.07 (d, J=2.0 Hz, 1H), 7.77 (d, J=9.0 Hz, 2H), 7.98 (s, 2H, —NH$_2$), 8.91 (s, 2H). LRMS (FAB+): 435.0 (100, [M+H]$^+$). HRMS (FAB+): 435.06476 C$_{17}$H$_{16}$N$_6$O$_4$SCl requires 435.064228.

4-Benzyloxy-3-fluoro-benzaldehyde (CAB03016)

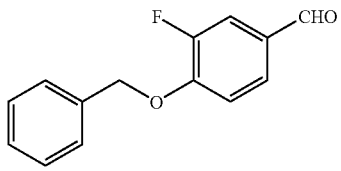

A mixture of 3-fluoro-4-hydroxy benzaldyde (4.90 g, 35.0 mmol), benzyl bromide (6.84 g, 40.0 mmol, 4.80 mL) and potassium carbonate (9.66 g, 70.0 mmol) in DMF (50 mL) was stirred for 18 h at room temperature. The reaction mixture was transferred into a separation funnel and ethyl acetate (100 mL) and water (50 mL) were added. The organic layer was separated, washed with water (2×50 mL) and brine (30 mL), dried over sodium sulphate and concentrated under reduced pressure. The white solid residue was recrystallised from dichloromethane/hexane. Yield: 7.65 g (95%). $^1$H-NMR (400 MHz, CDCl$_3$) δ=5.24 (s, 2H), 7.12 (dd, J=8.2, 8.2 Hz, 1H), 7.34–7.48 (m, 5H), 7.59–7.66 (m, 2H), 9.85 (d, J=2.0 Hz, 1H, —CHO). LRMS (FAB+): 91 (100), 231.1 (100, [M+H]$^+$).

(4-Benzyloxy-3-fluoro-phenyl)-methanol (CAB03017)

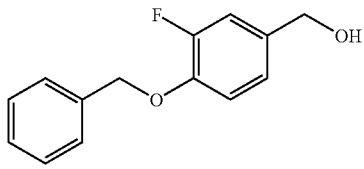

Sodium borohydride (500 mg, 13.2 mmol) was added to a solution of 4-benzyloxy-3-fluoro-benzaldehyde (CAB03016, 7.32 g, 31.8 mmol) in ethanol (40 mL) and THF (40 mL) at 0° C. The clear and colourless solution was allowed to warm to room temperature and stirred for 12 h at this temperature. Ethyl acetate (150 mL) and water (50 mL) were added to the solution, the organic layer was separated, washed with water (2×50 mL) and brine (50 mL), dried over sodium sulphate and concentrated under reduced pressure. The white solid residue was dissolved in dichloromethane and precipitated by addition of hexane. The white powder was filtered off and dried under high vacuum. Yield: 7.16 g (97%). $^1$H-NMR (400 MHz, CDCl$_3$) δ=1.71 (s, 1H, —OH), 4.61 (s, 2H, —CH$_2$OH), 5.15 (s, 2H), 6.97 (dd, J=8.6, 8.6 Hz, 1H), 7.02 (dd, J=8.6, 1.9 Hz, 1H), 7.13 (dd, J=11.7, 1.9 Hz, 1H), 7.30–7.46 (m, 5H). LRMS (FAB+): 91 (100), 215.1 (40), 232.1 (100, [M]$^+$).

1-Benzyloxy-4-chloromethyl-2-fluoro-benzene (CAB03018)

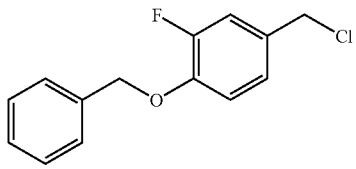

Thionyl chloride (5 mL) was added to solution of (4-benzyloxy-3-fluoro-phenyl)-methanol (CAB03017, 6.80 g, 29.28 mmol) in dichloromethane (50 mL). The solution was stirred for 1 h at room temperature and concentrated under reduced pressure. Then diethyl ether (100 mL) and water (20 mL) were added. The organic layer was separated, washed with conc. sodium bicarbonate solution (10 mL), dried over sodium sulphate and concentrated under reduced pressure. The residue was dissolved in dichloromethane (5 mL) and precipitated by addition of hexane (ca. 50 mL). The precipitate was filtered off and dried under high vacuum. Yield: 7.01 g (95%) white powder. $^1$H-NMR (400 MHz, CDCl$_3$) δ=4.52 (s, 2H, —CH$_2$Cl), 5.15 (s, 2H), 6.96 (dd, J=8.2, 8.2 Hz, 1H), 7.04–7.06 (m, 1H), 7.15 (dd, J=11.7, 2.4 Hz, 1H), 7.31–7.45 (m. 5H). LRMS (FAB+): 91 (100), 215.0 (10), 250.0 (16, [M]$^+$).

4-[(4-Benzyloxy-3-fluoro-benzyl)-[1,2,4]triazol-4-yl-amino]-benzonitrile (CAB03019, STX695)

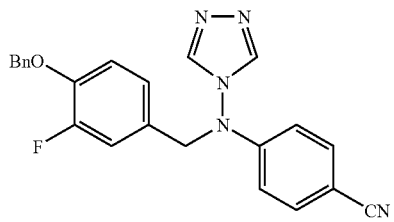

STX695

Sodium hydride (60%, 400 mg, 10.0 mmol) was added to a solution of 4-([1,2,4]triazol-4-ylamino)-benzonitrile (1.852 g, 10.0 mmol) in DMF (50 mL) at room temperature. The mixture was stirred for 1 h at this temperature and 1-benzyloxy-4-chloromethyl-2-fluoro-benzene (CAB03018, 2.51 g, 10.0 mmol) was added. The reaction mixture was stirred overnight and ethyl acetate (200 mL) and water (50 mL) were added. The mixture was transferred into a separation funnel and washed with water (2×50 mL) and brine (30 mL). The organic layer was dried over sodium sulphate and concentrated under reduced pressure. The residue was suspended in 2-propanol (40 mL) and heated to reflux for 5 minutes. The white solid was filtered off after cooling to room temperature and dried under high vacuum. Yield: 3.12 g (78%). $^1$H-NMR (400 MHz, d6-DMSO) δ=4.97 (s, 2H), 5.12 (s, 2H), 6.73 (d, J=9.0 Hz, 2H), 7.01 (dd, J=8.2, 1.2 Hz, 1H), 7.16 (dd, J=8.6, 8.6 Hz 1H), 7.21 (dd, J=8.6, 2.4 Hz, 1H), 7.30–7.44 (m, 5H), 7.75 (d, J=9.0 Hz, 2H), 8.80 (s, 2H). LRMS (FAB+): 400.1 (100, [M+H]$^+$).

HRMS (FAB+): 400.15800 $C_{23}H_{19}N_5OF$ requires 400.157364.

4-[(3-Fluoro-4-hydroxy-benzyl)-[1,2,4]triazol-4-yl-amino]-benzonitrile (CAB03020, STX696)

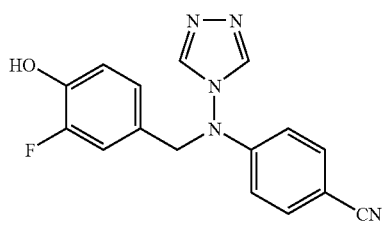

STX696

4-[(4-Benzyloxy-3-fluoro-benzyl)-[1,2,4]triazol-4-yl-amino]-benzonitrile (CAB03019, 2.83 g, 7.09 mmol) was dissolved in a mixture of ethanol (50 mL), THF (50 mL) and ethyl acetate (50 mL) by heating and palladium on charcoal (150 mg, 5% Pd) was added. The mixture was stirred under hydrogen-atmosphere (balloon) for 18 h, filtered through a 3 cm layer of celite and concentrated under reduced pressure. The residue was suspended in 2-propanol (30 mL), the mixture was heated to reflux for 5 minutes. After cooling room temperature the white precipitate was filtered off and dried under high vacuum. Yield: 2.13 g (97%). ¹H-NMR (400 MHz, d6-DMSO) δ=4.93 (s, 2H), 6.75 (d, J=9.0 Hz, 2H), 6.82–6.89 (m, 2H), 7.07–7.12 (m, 1H), 7.76 (d, J=9.0 Hz, 2H), 8.77 (s, 2H), 9.95 (s, 1H, —OH).

Sulfamic Acid 4-{[(4-cyano-phenyl)-[1,2,4]triazol-4-yl-amino]-methyl}-2-fluoro-phenyl ester (CAB03021, STX700)

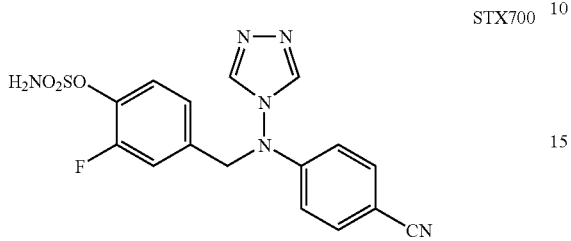

Sulphamoyl chloride solution in toluene (3 mL, 0.7 M, 2.1 mmol) was concentrated under reduced pressure (30° C. water bath temperature) to ca. 0.5 mL volume. The residue was cooled to 0° C. (ice bath) and N,N-dimethylacetamide (5 mL) was added. 4-[(3-Fluoro-4-hydroxy-benzyl)-[1,2,4] triazol-4-yl-amino]-benzonitrile (CAB03020, 220 mg, 0.71 mmol) was added to the colourless solution and the mixture was stirred for 4 h at room temperature. Ethyl acetate (50 mL) and water (30 mL) were added to the solution, the organic layer was separated, washed with water (2×25 mL) and brine (25 mL), dried over sodium sulphate and concentrated under reduced pressure. The residue was dissolved in acetone (5 mL) and precipitated by addition of diethyl ether. The precipitate was filtered off and dried under high vacuum. Yield: 228 mg (83%) white powder. ¹H-NMR (400 MHz, d6-DMSO) δ=5.11 (s, 2H), 6.71 (d, J=9.0 Hz, 2H), 7.23 (dd, 8.2, 1.2 Hz, 1H), 7.39 (dd, J=8.2, 8.2 Hz, 1H), 7.43 (dd, J=11.1, 2.1 Hz, 1H), 7.77 (d, J=9.0 Hz, 2H), 8.28 (s, 2H, —NH₂), 8.92 (s, 2H). LRMS (FAB+): 389.1 (100, [M+H]⁺). HRMS (FAB+): 389.08298 $C_{16}H_{14}N_6O_3SF$ requires 389.083214.

Benzoic Acid 2-fluoro-5-methyl-phenyl ester (CAB02145)

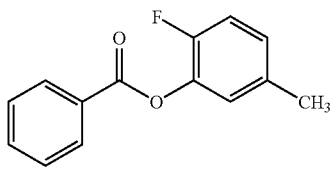

Benzoyl chloride (4.22 g, 30 mmol) was added dropwise with a syringe to a solution of 2-fluoro-5-methylphenol (3.784 g, 30 mmol) and triethylamine (5 mL) in dichloromethane (50 mL), The mixture was stirred for 18 h at room temperature and concentrated under reduced pressure. Diethyl ether (200 mL) and water (100 mL) were added, the organic layer was separated and extracted with 2N NaOH (2×30 mL) and brine (20 mL), dried over sodium sulphate and concentrated under reduced pressure to give a white solid. Yield: 6.601 g (96%). ¹H-NMR (400 MHz, CDCl₃) δ=2.36 (s, 3H, —CH₃), 7.01–7.12 (m, 3H), 7.49–7.55 (m, 2H), 7.63–7.68 (m, 1H), 8.19–8.23 (m, 2H). LRMS (FAB+): 231.1 (100, [M+H]⁺).

Benzoic Acid 5-bromomethyl-2-fluoro-phenyl ester (CAB02146)

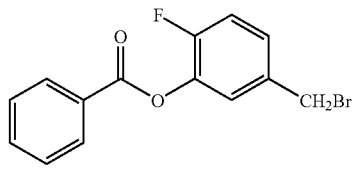

A mixture of benzoic acid 2-fluoro-5-methyl-phenyl ester (CAB02145, 2.47 g, 10.0 mmol), N-bromo-succinimide (1.96 g, 11.0 mmol) and dibenzoylperoxide (10 mg) in carbon tetrachloride (25 mL) was heated to reflux for 2 h (TLC monitored). After cooling to room temperature, water (50 mL) and diethyl ether (100 mL) were added. The organic layer was separated, washed with brine (20 mL), dried over sodium sulphate and concentrated under reduced pressure. The residue was purified by column chromatography (EtOAc:hexane, 1:25, $R_f$: 0.28). Yield: 1.80 g (58%), white solid. ¹H-NMR (400 MHz, CDCl₃) δ=4.48 (s, 2H, —CH₂Br), 7.18 (dd, J=9.8, 8.6 Hz, 1H), 7.28 (ddd, J=8.6, 4.3, 2.3 Hz, 1H), 7.34 (dd, J=7.0, 2.3 Hz, 1H), 7.50–7.55 (m, 2H), 7.64–7.69 (m, 1H), 8.18–8.23 (m, 2H). LRMS (FAB+): 229.1 (95), 309.0 (100, [M+H]⁺). Found: C 54.1, H 3.22%; $C_{14}H_{10}BrFO_2$ (309.13) requires C 54.39, H 3.26%.

Benzoic Acid 5-{[(4-cyano-phenyl)-[1,2,4]triazol-4-yl-amino]methyl}-2-fluoro-phenyl ester (CAB02147)

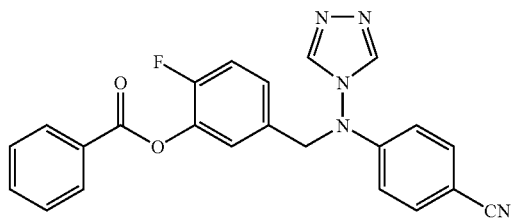

Sodium hydride (60%, 200 mg, 5.0 mmol) was added to a solution of 4-([1,2,4]triazol-4-ylamino)-benzonitrile (926 mg, 5.0 mmol) in DMF (20 mL) at r.t. The mixture was stirred for 1 h at this temperature and benzoic acid 5-bromomethyl-2-fluoro-phenyl ester (CAB02146, 1.55 g, 5.0 mmol) was added. The reaction mixture was stirred overnight and ethyl acetate (75 mL) and water (50 mL) were added. The mixture was transferred into a separation funnel and washed with water (2×50 mL) and brine (20 mL). The organic layer was dried over sodium sulphate and concentrated under reduced pressure. The residue was purified by column chromatography (EtOAc, $R_f$: 0.32) to give a white solid. Yield: 1.16 g (56%). ¹H-NMR (400 MHz, CDCl₃) δ=4.91 (s, 2H), 6.67 (d, J=9.0 Hz, 2H), 7.07 (ddd, J=8.2, 4.3, 2.0 Hz, 1H), 7.18 (dd, J=9.4, 8.6 Hz, 1H), 7.24 (dd, J=7.0, 2.3 Hz, 1H), 7.49–7.56 (m, 2H), 7.58 (d, J=9.0 Hz, 2H), 7.62–7.70 (m, 1H), 8.15–8.20 (m, 2H), 8.21 (s, 2H). LRMS (FAB+): 414.2 (100, [M+H]⁺).

4-[(4-Fluoro-3-hydroxy-benzyl)-[1,2,4]triazol-4-yl-amino]-benzonitrile (CAB02154, STX488)

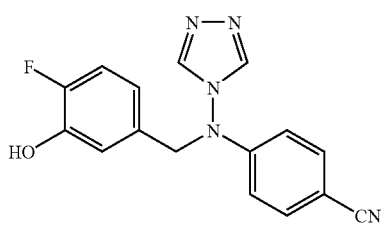

A solution of sodium hydroxide (250 mg, 6.25 mmol) in water (5 mL) was added to a solution of benzoic acid 5-{[(4-cyano-phenyl)-[1,2,4]triazol-4-yl-amino]methyl}-2-fluoro-phenyl ester (CAB02147, 958 mg, 2.32 mmol) in methanol (10 mL). The solution was heated to reflux for 5 minutes and concentrated under reduced pressure. Water (10 mL) was added and the milky suspension was neutralised (pH 7–8) with 2N hydrochloric acid. The white precipitate was filtered off, washed with a small amount of water (5 mL) and dried under high vacuum. Yield: 476 mg (66%). $^{1}$H-NMR (400 MHz, d6-DMSO) δ=4.95 (s, 2H), 6.70 (ddd, J=11.4, 8.4, 2.4 Hz, 1H), 6.75 (d, J=9.0 Hz, 2H), 6.84 (dd, J=8.4, 2.4 Hz, 1H), 7.06 (dd, J=11.3, 8.4 Hz, 1H), 7.76 (d, J=9.0 Hz, 2H), 8.75 (s, 2H), 9.90 (s, 1H, —OH). LRMS (FAB+): 310.1 (100, [M+H]$^{+}$).

4-Benzyloxy-3-trifluoromethyl-benzoic acid (CAB03046)

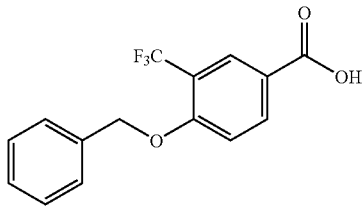

Sodium hydride (60%, 1.80 g, 45 mmol) was added to a solution of 4-fluoro-3-trifluoromethyl benzoic acid (4.162 g, 20 mmol) and benzyl alcohol (3.25 g, 30 mmol) in DMSO (50 mL). The mixture was stirred overnight at room temperature, poured into water (50 mL) and acidified with concentrated hydrochloric acid. The white precipitate was filtered off, dissolved in ethyl acetate (ca. 50 mL), dried over sodium sulphate and concentrated under reduced pressure. The residue was recrystallised from ethyl acetate/hexane. Yield: 4.252 g (72%). $^{1}$H-NMR (400 MHz, CDCl$_{3}$) δ=5.37 (s, 2H), 7.32–7.48 (m, 6H), 8.12 (d, J=2.0 Hz, 1H), 8.18 (dd, J=8.6, 2.0 Hz, 1H), 13.16 (br s, 1H, —COOH). LRMS (FAB+): 91.1 (100), 297.1(18, [M+H]$^{+}$).

(4-Benzyloxy-3-trifluoromethyl-phenyl)-methanol (CAB03047)

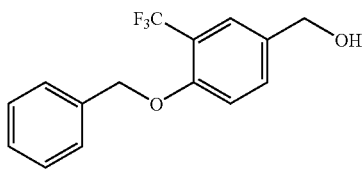

4-Benzyloxy-3-trifluoromethyl-benzoic acid (CAB03046, 3.555 g, 12 mmol) in THF (20 mL) was added dropwise to a suspension of lithium aluminium hydride (1.0 g, 26.3 mmol) in THF (20 mL). The mixture was stirred for another 30 minutes at room temperature and then quenched by addition of 2N NaOH (5 mL). The white preciptate was filtered off and washed with dichloromethane (100 mL), the filtrate was dried over sodium sulphate and concentrated under reduced pressure. The resulting oil was crystallised from diethyl ether/hexane. Yield: 3.31 g (98%). $^{1}$H-NMR (400 MHz, CDCl$_{3}$) δ=1.72 (t, J=5.9 Hz, 1H, —OH), 4.66 (d, J=5.9 Hz, 2H, —CH$_{2}$OH), 5.21 (s, 2H, —CH$_{2}$Ph), 7.02 (d, J=8.2 Hz, 1H), 7.30–7.48 (m, 6H), 7.61 (d, J=2.3 Hz, 1H). LRMS (FAB+): 91.1 (100), 265.2 (45), 282.2 (40, [M+H]$^{+}$).

1-Benzyloxy-4-chloromethyl-2-trifluoromethyl-benzene (CAB03050)

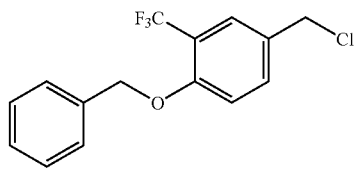

Thionyl chloride (2.0 mL) was added to solution of (4-benzyloxy-3-trifluoromethyl-phenyl)-methanol (CAB03047, 3.10 g, 11.0 mmol) in dichloromethane (20 mL). The solution was stirred for 1 h at room temperature and concentrated under reduced pressure. Then diethyl ether (100 mL) and water (20 mL) were added. The organic layer was separated, washed with conc. sodium bicarbonate solution (10 mL), dried over sodium sulphate and concentrated under reduced pressure. The resulting oil solidified after a few minutes and was dried under high vacuum. Yield: 3.25 g (98%). $^{1}$H-NMR (400 MHz, CDCl$_{3}$) δ=4.57 (s, 2H, —CH$_{2}$Cl), 5.22 (s, 2H, —OCH$_{2}$Ph), 7.02 (d, J=8.5 Hz, 1H), 7.31–7.52 (m, 6H), 7.63 (d, J=2.0 Hz, 1H). LRMS (FAB+): 91.1 (100), 265.2 (8), 300.1 (10, [M]$^{+}$).

4-[(4-Benzyloxy-3-trifluoromethyl-benzyl)-[1,2,4]triazol-4-yl-amino]-benzonitrile (CAB03054, STX719)

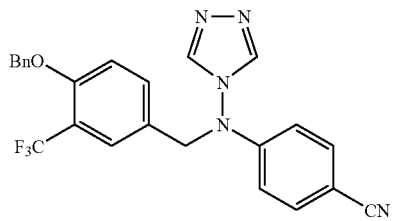

Sodium hydride (60%, 200 mg, 5.0 mmol) was added to a solution of 4-([1,2,4]triazol-4-ylamino)-benzonitrile (926 mg, 5.0 mmol) in DMF (50 mL) at room temperature. The mixture was stirred for 1 h at this temperature and 1-benzyloxy-4-chloromethyl-2-trifluoromethyl-benzene (CAB03050, 1.50 g, 5.0 mmol) was added. The reaction mixture was stirred overnight and ethyl acetate (100 mL) and water (30 mL) were added. The mixture was transferred into a separation funnel and washed with water (2×30 mL) and brine (20 mL). The organic layer was dried over sodium sulphate and concentrated under reduced pressure. The residue was suspended in 2-propanol (40 mL) and heated to reflux for 5 minutes. The white solid was filtered off after cooling to room temperature and dried under high vacuum. Yield: 1.87 g (83%). $^{1}$H-NMR (400 MHz, d6-DMSO) δ=5.05 (s, 2H), 5.23 (s, 2H), 6.78 (d, J=9.0 Hz, 2H), 7.26 (d, J=8.6 Hz, 1H), 7.30–7.44 (m, 5H), 7.51 (dd, J=8.6, 2.0 Hz, 1H), 7.56 (d, J=2.0 Hz, 1H), 7.77 (d, J=9.0 Hz, 2H), 8.79 (s, 2H). LRMS (FAB+): 450.2 (100, [M+H]$^{+}$). HRMS (FAB+): 450.15404 C$_{24}$H$_{19}$N$_{5}$OF$_{3}$ requires 450.154170

4-[(4-Hydroxy-3-trifluoromethyl-benzyl)-[1,2,4]triazol-4-yl-amino]-benzonitrile (CAB03059, STX781)

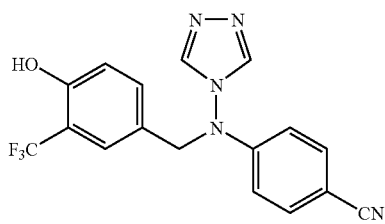

Palladium on charcoal (100 mg, 10% Pd) was added to a solution of 4-[(4-benzyloxy-3-trifluoromethyl-benzyl)-[1,2,4]triazol-4-yl-amino]-benzonitrile (CAB03054, 1.75 g, 3.89 mmol) in EtOH/THF/MeCN (50 mL/50 mL/30 mL). The mixture was stirred under hydrogen atmosphere (balloon) for 18 h at room temperature. The reaction mixture was filtered through celite and the clear colourless filtrate was concentrated under reduced pressure. The residue was suspended in 2-propanol (20 mL) and heated to reflux for 5 minutes. The white solid was filtered off after cooling to room temperature and dried under high vacuum. Yield: 1.31 g (94%). $^1$H-NMR (400 MHz, d6-DMSO) δ=4.98 (s, 2H), 6.78 (d, J=9.0 Hz, 2H), 6.91 (d, J=8.6 Hz, 1H), 7.31 (dd, J=8.6, 2.0 Hz, 1H), 7.39 (d, J=2.0 Hz, 1H), 7.76 (d, J=9.0 Hz, 2H), 8.74 (s, 2H), 10.66 (s, 1H, —OH). LRMS (FAB+): 360.2 (100, [M+H]$^+$).

3-Benzyloxy-phenol (JRL01015)

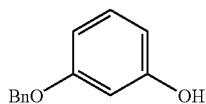

To a stirred solution of resorcinol (7.05 g, 63.4 mmol) in DMF (100 mL) at 0° C. under nitrogen was added NaH (60%, 2.54 g, 63.4 mmol). After stirring for 30 min, benzyl bromide (7.72 mL, 63.4 mmol) was added and the resulting mixture was stirred for 4 h at room temperature. The reaction mixture was diluted with ethyl acetate (300 mL) and the organic layer separated washed with brine (300 mL, 4×100 mL), dried (Na$_2$SO$_4$), filtered and evaporated to give the crude product which was fractionated by flash chromatography (hexane/EtOAc 3:1) to give JRL01015 as a pale yellow solid (4.06 g, 32%); R$_f$ 0.50 (Hexane/EtOAc 3:1); $^1$H (400 MHz CDCl$_3$) 4.97 (1H, s OH), 5.01 (2H, s, CH$_2$), 6.42 (1H, dd, J 2.3 and 8.0 Hz), 6.47 (1H, t, J 2.3 Hz), 6.56 (1H, dd, J 2.3 and 8.0 Hz), 7.12 (1H, t, J 8.0 Hz) and 7.28–7.46 (5H, m).

5-Benzyloxy-2-nitro-phenol (JRL01017A)

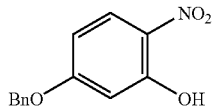

To a stirred solution of JRL01015 (4.0 g, 20.0 mmol) in AcOH (40 mL) at 5–10° C. was added HNO$_3$ (69%, 2.74 g, 30.0 mmol) in AcOH (1.80 g, 30.0 mmol). After stirring for 4 h at room temperature, the reaction mixture was diluted EtOAc (150 mL) and the organic layer separated washed with brine (200 mL, 4×100 mL), dried (Na$_2$SO$_4$), filtered and evaporated to give the crude product which was fractionated by a flash chromatography (hexane/EtOAc 3:1) to give JRL01017 as a yellow solid (1.88 g, 38.5%); R$_f$ 0.65 (hexane/EtOAc 3:1); $^1$H (400 MHz, CDCl$_3$) 5.13 (2H, s, CH$_2$), 6.59 (1H, dd, J 2.4 and 9.0 Hz), 6.62 (1H, d, J 2.4 Hz), 7.34–7.45 (5H, m), 8.04 (1H, d, J 9.0 Hz) and 11.00 (1H, s, OH).

2-Amino-5-benzyloxy-phenol (JRL01022)

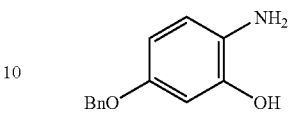

To a stirred solution of JRL01017 (500 mg, 2.04 mmol) in EtOH/H$_2$O (1:1, 50 mL) was added sodium hydrosulfite (Na$_2$S$_2$O$_4$, ~85%, 1.67 g, 8.16 mmol) and the yellow suspension resulted was heated at 75° C. After 1 h at this temperature, the reaction mixture had become colorless and it was then cooled to room temperature. The reaction mixture was diluted with EtOAc (100 mL) and the organic layer separated washed with brine (4×50 mL), dried (Na$_2$SO$_4$), filtered and evaporated to give the crude product which was purified by a flash chromatography (hexane/EtOAc 3:1) to give JRL01022 as a dark pink solid (418 mg, 95%); R$_f$ 0.50 (hexane/EtOAc, 3:1); $^1$H (400 MHz, DMSO-d$_6$) ~4.0 (2H, v br s), 4.90 (2H, s), 6.24 (1H, dd, J 2.7 and 8.4 Hz), 6.37 (1H, d, J 2.7 Hz), 6.49 (1H, d, J 8.4 Hz), 7.28–7.46 (5H, m) and ~11.0 (1H, v br s).

6-Benzyloxy-2-bromomethyl-benzooxazole (JRL01026)

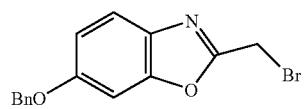

To a stirred mixture of JRL01022 (773 mg, 3.60 mmol) in trimethylsilylpolyphosphate (PPSE)/1,2-dichlorobenzene (1:5, 60 mL) under nitrogen was added bromoacetic acid (400 mg, 2.88 mmol) and the resulting purple mixture was heated at 150° C. for 1 h. After cooling to room temperature, the reaction mixture was diluted with EtOAc (100 mL) and the organic layer separated washed with brine (4×50 mL), dried (Na$_2$SO$_4$), filtered and evaporated to an oil which was fractionated by flash chromatography (hexane/EtOAc 5:1) to give JRL01026 as a white solid (369 mg, 40%); R$_f$ 0.28 (hexane/EtOAc 5:1); $^1$H (400 MHz, CDCl$_3$) 4.55 (2H, s), 5.10 (2H, s), 7.03 (1H, dd, J 2.2 and 8.6 Hz), 7.10 (1H, d, J 2.2 Hz), 7.30–7.46 (5H, m) and 7.59 (1H, d, J 8.6 Hz).

4-[(6-Benzyloxy-benzooxazol-2-ylmethyl)-[1,2,4]triazol-4-yl-amino]-benzonitrile (JRL01029)

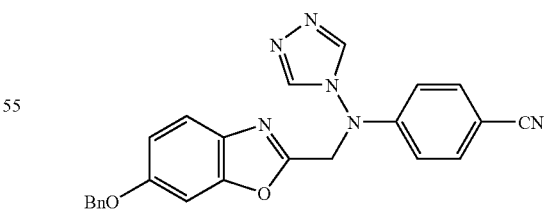

To a stirred solution of NaH (60%, 12 mg, 300 μmol) in DMF (10 mL) at 0° C. under nitrogen was added 4-[(1,2,4)triazol-4-amino]benzonitrile (55 mg, 300 μmol) in DMF (10 mL). After stirring at 40–50° C. under nitrogen for 1 h, the orange reaction mixture was cooled to room temperature and JRL01026 (100 mg, 310 μmol) was added. The resulting mixture was stirred overnight at room temperature under nitrogen. After diluting the reaction mixture with CH$_2$Cl$_2$ (50 mL), the organic layer was washed with brine (100 mL, 3×50 mL), dried (Na$_2$SO$_4$), filtered and evaporated to give a crude product which was fractionated by flash chromatography (EtOAc) to give JRL01029 as a white solid (80 mg, 63%); R$_f$ 0.24 (EtOAc); $^1$H (400 MHz, CDCl$_3$) 5.11 (2H, s), 5.19 (2H, s), 6.59 (2H AA'BB'; 7.05 (1H, dd, J 2.2 and 8.8 Hz), 7.11 (1H, d, J 2.2 Hz), 7.30–7.60 (8H, m) and 8.65 (2H, s).

4-[(6-Hydroxy-benzooxazol-2-ylmethyl)-[1,2,4]triazol-4-yl-amino]-benzonitrile (JRL01035, STX357)

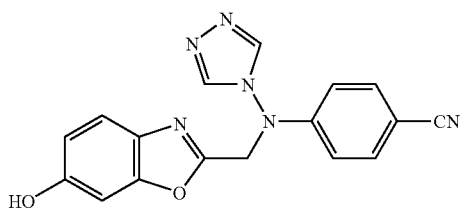

To a stirred solution of JRL01029 (235 mg, 5.56 mmol) in THF/MeOH 1:1 (60 mL) was added Pd—C 10% (65 mg) and the resulting suspension was stirred under an atmosphere of H$_2$ (balloon) overnight. After filtration on celite, the filtrate collected was evaporated to give a grey solid which was purified by trituration in hot EtOAc to produce JRL01035 as a white solid (128 mg, 69%); R$_f$ 0.38 (Acetone/EtOAc, 1:2); $^1$H (400 MHz, DMSO-d, 400 MHz) 5.47 (2H, s), 6.70 (2H, d, J 9 Hz),6.80 (1H, dd, J 2.1 and 8.6 Hz), 7.02 (1H, d, J 2.1 Hz), 7.48 (1H, d, J 8.6 Hz), 7.74 (2H, d, J 9 Hz), 8.95 (2H, s) and 9.86 (1H, br s).

4-Benzyloxy-phenol (JRL01016)

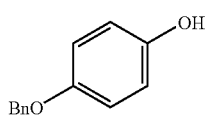

To a stirred solution of hydroquinone (7.00 g, 63.4 mmol) in DMF (100 mL) at 0° C. under nitrogen was added NaH (60%, 2.54 g, 63.4 mmol). After stirring for 30 min, benzyl bromide (7.72 mL, 63.4 mmol) was added and the resulting mixture was stirred for 4 h at room temperature. The reaction mixture was diluted with ethyl acetate (300 mL) and the organic layer separated was washed with brine (300 mL, 4×100 mL), dried (Na$_2$SO$_4$), filtered and evaporated to give the crude product which was fractionated by flash chromatography (hexane/EtOAc 3:1) to give JRL01016 as a white solid (3.11 g, 25%); R$_f$ 0.35 (Hexane/EtOAc 3:1); $^1$H (400 MHz CDCl$_3$) 4.61 (1H, s OH), 5.01 (2H, s, CH$_2$), 6.74 (2H, AA'BB'), 6.85 (2H, AA'BB'), and 7.28–7.44 (5H, m).

4-Benzyloxy-2-nitro-phenol (JRL01023)

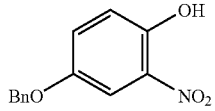

To a stirred solution of JRL01016 (500 mg, 2.50 mmol) in ethylene glycol dimethyl ether (10 mL) at −50° C. under nitrogen was added in one portion tetraborofluoruate nitronium in sulpholane (0.5 M, 5.1 mL, 2.55 mmol). After 1 h of stirring at −50° C., the reaction mixture at room temperature was filtered through a short silica column. The eluate collected was evaporated to give the crude product which was fractionated by flash chromatography (hexane/EtOAc 10:1). The first fractionation gave some pure JRL01023 as a yellow solid. The mixture of fractions retrieved from the first column was fractionated again to give more JRL01023 (total amount isolated: 186 mg, combined yield: 30%); R$_f$ 0.33 (hexane/EtOAc, 10:1); $^1$H (400 MHz, CDCl$_3$) 5.05 (2H, s), 7.09 (1H, d, J 9.0 Hz), 7.28 (1H, dd, J 3.0 and 9.0 Hz), 7.32–7.44 (5H, m), 7.59 (1H, d, J 3.0 Hz) and 10.34 (1H, s, OH).

2-Amino-4-benzyloxy-phenol (JRL01028)

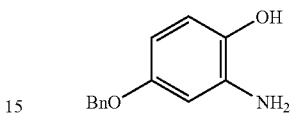

To a stirred solution of JRL01023 (1.33 g, 5.44 mmol) in EtOH/H$_2$O (1:1, 150 mL) was added sodium hydrosulfite (Na$_2$S$_2$O$_4$, ~85%, 4.45 g, 21.74 mmol) and the yellow suspension resulted was heated at 75° C. After 1 h at this temperature, the reaction mixture had become colorless and it was then cooled to room temperature. The reaction mixture was diluted with EtOAc (150 mL) and the organic layer separated washed with brine (4×100 mL), dried (Na$_2$SO$_4$), filtered and evaporated to give the crude product which was purified by a flash chromatography (hexane/EtOAc 2:1) to give JRL01028 as a brown solid (700 mg, 62%); R$_f$ 0.20 (hexane/EtOAc, 2:1); $^1$H (400 MHz, DMSO-d$_6$) 4.54 (2H, s), 4.90 (2H, s), 6.02 (1H, dd, J 2.8 and 8.6 Hz), 6.28 (1H, d, J 2.8 Hz), 6.52 (1H, d, J 8.6 Hz), 7.25–7.45 (5H, m) and 8.50 (1H, s).

5-Benzyloxy-2-bromomethyl-benzooxazole (JRL01030)

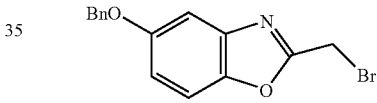

To a stirred mixture of JRL01028 (663 mg, 3.08 mmol) in trimethylsilylpolyphosphate (PPSE)/1,2-dichlorobenzene (1:5, 60 mL) under nitrogen was added bromoacetic acid (333 mg, 2.40 mmol) and the resulting purple mixture was heated at 150° C. for 1 h. After cooling to room temperature, the reaction mixture was diluted with EtOAc (100 mL) and the organic layer separated washed with brine (4×50 mL), dried (Na$_2$SO$_4$), filtered and evaporated to an oil which was fractionated by flash chromatography (hexane/EtOAc 7:1) to give JRL01026 as a red solid (228 mg, 30%); R$_f$ 0.21 (hexane/EtOAc 7:1); $^1$H (400 MHz, CDCl$_3$) 4.56 (2H, s), 5.10 (2H, s), 7.06 (1H, dd, J 2.4 and 8.8 Hz), 7.25 (1H, d, J 2.4 Hz) and 7.30–7.46 (6H, m).

2-Methyl-benzothiazol-6-ol (JRL01040)

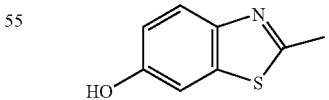

BBr$_3$ (1M in CH$_2$Cl$_2$, 7.7 mL, 7.7 mmol) was slowly added to a stirred solution of 6-methoxybenzothiazol (950 mg, 5.14 mmol) in dichloromethane (30 mL) at 0° C. under nitrogen and the reaction mixture became a dark brown suspension. After stirring at room temperature overnight, the reaction was quenched with ice/brine and diluted with EtOAc (100 mL). The organic layer that separated was washed with brine (4×50 mL), dried (Na$_2$SO$_4$), filtered and evaporated to give light brown residue which was fractionated by flash chromatography (hexane/EtOAc 3:1) to give JRL01040 as a white powder (600 mg, 71%); $R_f$ 0.16 (hexane/EtOAc 3:1); $^1$H (400 MHz, acetone-d) 2.72 (3H, s), 6.99 (1H, dd, J 2.4 and 8.6 Hz), 7.35 (1H, d, J 2.4 Hz), 7.70 (1H, d, J 8.6 Hz) and 8.70 (1H, br s).

6-Benzyloxy-2-methyl-benzothiazole (JRL01053)

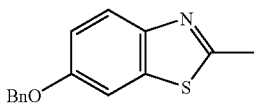

To a stirred solution of JRL01040 (1.47 g, 8.93 mmol) in DMF (30 mL) at 0° C. under nitrogen was added NaH (60%, 393 mg, 9.83 mmol). After stirring for 30 min, benzyl bromide (1.2 mL, 9.83 mmol) was added and the resulting mixture was stirred for 4 h at room temperature. The reaction mixture was diluted with ethyl acetate (100 mL) and the organic layer separated washed with brine (100 mL, 4×50 mL), dried (Na$_2$SO$_4$), filtered and evaporated to give the crude product which was fractionated by flash chromatography (hexane/EtOAc 6:1) to give JRL01053 as a pale yellow solid (2.20 g, 96%); $R_f$ 0.15 (Hexane/EtOAc 6:1); $^1$H (400 MHz CDCl$_3$) 2.75 (3H, s), 5.06 (2H, s), 7.10 (1H, dd, J 2.2 and 8.8 Hz) 7.28–7.45 (6H, m) and 7.82 (1H, d, J 9 Hz).

6-Benzyloxy-2-bromomethyl-benzothiazole (JRL01071)

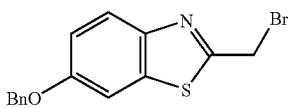

To a stirred solution of JRL01053 (2.1 g, 8.22 mmol) in CCl$_4$ (50 mL) was added NBS (1.55 g, 8.64 mmol) and dibenzoyl peroxide (32 mg). The pale yellow suspension was refluxed for 2 h, cooled to room temperatue and filtered. The filtrate was diluted with EtOAc (100 mL), washed with NaOH (5%, 1×100 mL) and then brine (3×50 mL) dried (Na$_2$SO$_4$), filtered and evaporated to give the crude product which was fractionated by flash chromatography (Hexane/EtOAc 7:1) to give JRL01071 as a white solid (1.05 g, 39%); m.p. 93–96° C.; $R_f$ 0.23 (hexane/EtOAc 7:1); $^1$H (400 MHz, CDCl$_3$) 4.76 (2H, s), 5.10 (2H, s), 7.15 (1H, dd, J 2.7 and 9.0 Hz), 7.30–7.46 (6H, m) and 7.89 (1H, d, J 9.0 Hz); LRMS (FAB+) 333.9 [55, (M+H)$^+$], 255.0 [17, (M+H−$^{79}$Br)$^+$], 91.0 {100, Bn$^+$}; HRMS (FAB+) 333.98873, C$_{15}$H$_{13}$BrNOS requires 333.99012.

4-[(6-Benzyloxy-benzothiazol-2-ylmethyl)-[1,2,4]triazol-4-yl-amino]-benzonitrile (JRL01074)

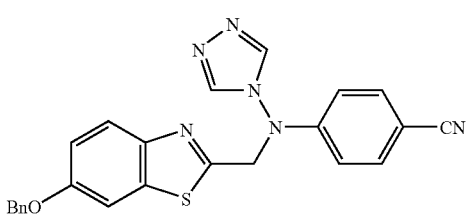

To a stirred mixture of NaH (60%, 57 mg, 1.42 mol) in DMF (5 mL) at 0° C. under nitrogen was added 4-[(1,2,4)triazol-4-amino]benzonitrile (264 mg, 1.42 mol) in DMF (5 mL). After stirring at 40–50° C. under nitrogen for 1 h, the orange reaction mixture was cooled to room temperature and JRL01071 (500 mg, 1.50 mol) was added. The resulting mixture was stirred overnight at room temperature under nitrogen. After diluting the reaction mixture with CH$_2$Cl$_2$ (50 mL), the organic layer was washed with brine (100 mL, 3×50 mL), dried (Na$_2$SO$_4$), filtered and evaporated to give a crude product which was fractionated by flash chromatography (EtOAc) to give JRL01071 as a pale yellow solid (320 mg, 51%); $R_f$ 0.26 (EtOAc); $^1$H (400 MHz, CDCl$_3$) 5.12 (2H, s), 5.30 (2H, s), 6.60 (2H AA'BB'), 7.18 (1H, dd, J 2.6 and 9.0 Hz), 7.30–7.50 (6H, m), 7.54 (2H AA'BB'), 7.85 (1H, d, J 9.0 Hz) and 8.57 (2H, s).

5-Benzyloxy-2-methyl-benzothiazole (JRL01052)

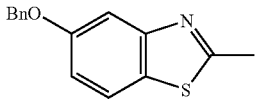

To a stirred solution of 2-Methylbenzothiazol-5-ol (4.0 g, 23.48 mmol) in DMF (40 mL) at 0° C. under nitrogen was added NaH (60%, 1.03 g, 25.75 mmol). After stirring for 30 min, benzyl bromide (3.2 mL, 25.83 mmol) was added and the resulting mixture was stirred for 4 h at room temperature. The reaction mixture was diluted with ethyl acetate (300 mL) and the organic layer separated washed with brine (300 mL, 4×100 mL), dried (Na$_2$SO$_4$), filtered and evaporated to give the crude product which was fractionated by flash chromatography (hexane/EtOAc 6:1) to give JRL01052 as a pale yellow solid (5.63 g, 94%); $R_f$ 0.15 (Hexane/EtOAc 6:1); $^1$H (400 MHz CDCl$_3$) 2.80 (3H, s), 5.14 (2H, s), 7.00–7.70 (8H, m).

5-Benzyloxy-2-bromomethyl-benzothiazole (JRL01064)

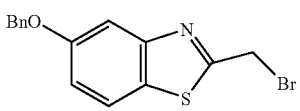

To a stirred solution of JRL01052 (3.6 g, 14.10 mmol) in CCl$_4$ (100 mL) was added NBS (2.66 g, 14.80 mmol) and dibenzoyl peroxide (55 mg). The pale yellow suspension was refluxed for 2 h, cooled to room temperatue and filtered. The filtrate was diluted with EtOAc (200 mL), washed with NaOH (5%, 1×200 mL) and then brine (3×100 mL) dried (Na$_2$SO$_4$), filtered and evaporated to give the crude product which was fractionated by flash chromatography (hexane/EtOAc 7:1) to give JRL01064 as a white solid with (1.81 g, 38%); m.p. 87–89° C.; $R_f$ 0.25 (hexane/EtOAc 7:1); $^1$H (400 MHz, CDCl$_3$) 4.77 (2H, s), 5.13 (2H, s), 7.14 (1H, dd, J 2.5 and 8.6 Hz), 7.30–7.48 (5H, m), 7.55 (1H, d, J 2.5 Hz) and 7.71 (1H, d, J 8.6 Hz); LRMS (FAB+) 333.9 [50, (M+H)$^+$], 255.0 [17, (M+H−$^{79}$Br)$^+$], 91.0 {100, Bn$^+$}; HRMS (FAB+) 333.98946, C$_{15}$H$_{13}$BrNOS requires 333.99012.

4-[(5-Benzyloxy-benzothiazol-2-ylmethyl)-[1,2,4]triazol-4-yl-amino]-benzonitrile (JRL01078)

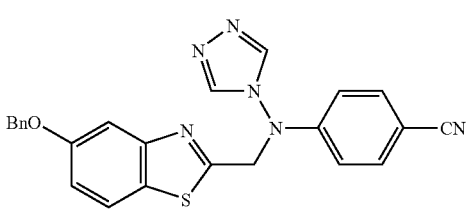

A suspension of JRL01064 (500 mg, 1.5 mmol), 4-[(1,2,4)triazol-4-amino]benzonitrile (277 mg, 1.5 mmol) and anhydrous potassium carbonate (207 mg, 1.5 mmol) in acetonitrile (10 mL) was stirred at room temperature under nitrogen overnight. The resulting reaction mixture was diluted with EtOAc (50 mL) and the organic layer was washed with brine (4×50 mL), dried (Na$_2$SO$_4$), filtered and evaporated to give the crude product which was fractionated by flash chromatography (EtOAc/acetone. 4:1) to give JRL01078 as a yellow solid (98 mg, 15%); R$_f$ 0.24 (EtOAc); $^1$H (400 MHz, CDCl$_3$) 5.12 (2H, s), 5.33 (2H, s), 6.58 (2H AA'BB'; 7.13 (1H, dd, J 2.6 and 9.0 Hz), 7.30–7.48 (5H, m), 7.50–7.56 (3H, m), 7.71 (1H, d, J 9.0 Hz) and 8.61 (2H, s).

4-(3-Hydroxy-propylsulfanyl)-phenol (CAB02029)

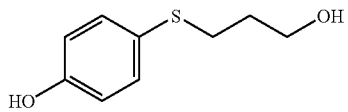

4-Hydroxythiophenol (6.31 g, 50 mmol) was dissolved in ethanol (100 mL) and potassium tert.-butoxide (6.72 g, 60 mmol) was added. The mixture was stirred stirred until a clear, yellow solution was obtained. Then 3-chloro-1-propanol (4.20 mL, 50 mmol) was added with a syringe. The reaction mixture was stirred overnight at room temperature, the potassium chloride precipitate was filtered off and the filtrate was concentrated under reduced pressure. The residue was dissolved in ethyl acetate (150 mL) and the organic layer was extracted with water (2×100 mL) and brine (100 mL), dried over sodium sulphate and concentrated under reduced pressure. The resulting oil was dissolved in dichloromethane (50 mL) and hexane (100 mL) and left standing open overnight. The solid product was filtered off and dried under high vacuum. Yield: 5.34 g (58%) pale yellow solid.

$^1$H-NMR (400 MHz, CD$_3$OD) δ=1.71–1.77 (m, 2H), 2.82–2.86 (m, 2H), 3.60–3.64 (m, 2H), 6.73 (d, J=8.6 Hz, 2H), 7.24 (d, J=8.6 Hz, 2H).

3-(4-Benzyloxy-phenylsulfanyl)-propan-1-ol (CAB02032)

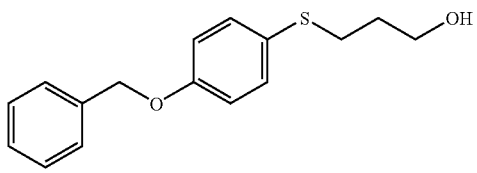

4-(3-Hydroxy-propylsulfanyl)-phenol (CAB02029, 3.686 g, 20 mmol) was dissolved in ethanol (50 mL) and potassium tert-Butoxide (2.80 g, 25 mmol) and benzyl bromide (3.0 mL, ca. 25 mmol) were added. The mixture was stirred overnight at room temperature, the precipitated potassium bromide was filtered off and the filtrate was concentrated under reduced pressure. The resulting yellow solid was dissolved in ethyl acetate (100 mL), the solution was washed with water (100 mL) and brine (100 mL), dried over sodium sulphate and concentrated under reduced pressure. The residue was dissolved in dichloromethane (ca. 10 mL) and the product was precipitated by addition of hexane (ca. 200 mL). The crystalline product was collected and dried under high vacuum. Yield: 4.481 g (82%) colourless, small plates. $^1$H-NMR (400 MHz, CDCl$_3$) δ=1.45 (br s, 1H, —OH), 1.82–1.87 (m, 2H), 2.84 (t, J=7.4 Hz, 2H), 3.74–3.78 (m, 2H), 5.05 (s, 2H, —OCH$_2$Ph), 6.90–6.93 (m, 2H), 7.31–7.44 (m, 7H).

1-Bromo-3-(4-benzyloxy-phenylsulfanyl)-propane (CAB02037)

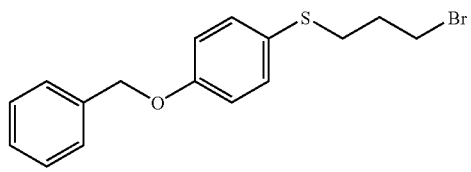

Triphenylphosphine (7.90 g, 30.0 mmol) was added to a solution of 3-(4-benzyloxy-phenylsulfanyl)-propan-1-ol (CAB02032, 4.12 g, 15.0 mmol) and carbon tetrabromide (4.98 g, 18.0 mmol) in dichloromethane (120 mL) at 0° C. (ice/water bath). The reaction mixture was allowed to warm up to room temperature and was stirred for another hour. The solution was transferred into a separation funnel and conc. NaHCO$_3$-solution (50 mL) was added. The organic layer was separated, dried over sodium sulphate ad concentrated under reduced pressure. The residue was dissolved in ethyl acetate (25 mL) and hexane (100 mL) was added with stirring. The precipitated triphenylphosphine oxide was filtered off and washed with more EtOAc/hexane-mixture (1:4, 100 mL). The organic solutions were concentrated and the residue was purified by column chromatography (ethyl acetate/hexane, 1:10, Rf: 0.48). Yield: 4.96 g (98%) colourless oil, which becomes a solid after a couple of days. $^1$H-NMR (400 MHz, CDCl$_3$) δ=2.07 (tt, J=7.0, 7.0 Hz, 2H), 2.95 (t, J=7.0 Hz, 2H), 3.50 (t, J=7.0 Hz, 2H), 5.04 (s, 2H, —OCH$_2$Ph), 6.92 (d, J=9.0 Hz, 2H), 7.27–7.44 (m, 7H). $^{13}$C-NMR (100.5 MHz, CDCl$_3$) δ=32.30, 32.50, 34.41, 70.44, 115.84, 126.15, 127.72, 128.31, 128.86, 133.65, 136.89, 158.43.

4-{[3-(4-Benzyloxy-phenylsulfanyl)-propyl]-[1,2,4]triazol-4-yl-amino}-benzonitrile (CAB02038)

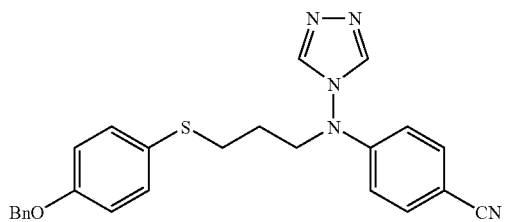

Sodium hydride (60%, 200 mg, 5.0 mmol) was added to a solution of 4-([1,2,4]triazol-4-ylamino)-benzonitrile (926 mg, 5.0 mmol) in DMF (10 mL) at 0° C. The mixture was stirred for 30 min at 50° C., cooled to room temperature and 1-bromo-3-(4-benzyloxy-phenylsulfanyl)-propane (CAB02037, 1.686 g, 5.0 mmol) was added. The reaction mixture was stirred for 15 h and ethyl acetate (100 mL) was added. The mixture was transferred into a separation funnel and extracted with water (2×50 mL) and brine (20 mL). The organic layer was dried over sodium sulphate and concentrated under reduced pressure. The residue was purified by column-chromatography (eluent: ethyl acetate, Rf: 0.41). Yield: 1.724 g (78%) colourless oil. The oil was crystallised from a small amount of methanol. Yield: 1.517 g (68%). $^1$H-NMR (400 MHz, CDCl$_3$) δ=1.84 (tt, J=6.4, 6.4 Hz, 2H), 2.90 (t, J=6.4 Hz, 2H), 3.90 (t, J=6.4 Hz, 2H), 5.06 (s, 2H, —OCH$_2$Ph), 6.52 (d, J=9.0 Hz, 2H), 6.93 (d, J=9.0 Hz, 2H), 7.31 (d, J=9.0 Hz, 2H), 7.33–7.44 (m, 5H), 7.52 (d, J=9.0 Hz, 2H), 8.26 (s, 2H). LRMS (FAB+): 442.2 (100, [M+H]$^+$)

4-{[3-(4-Benzyloxy-benzenesulfonyl)-propyl]-[1,2,4]triazol-4-yl-amino}-benzonitrile (CAB02168)

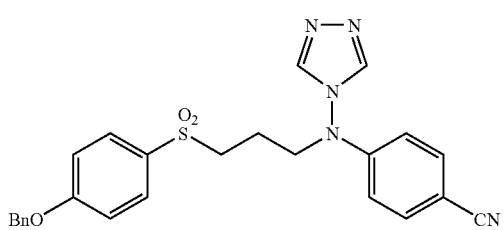

m-Chloroperbenzoic acid (259 mg, 1.50 mmol) was added to a solution of 4-{[3-(4-Benzyloxy-phenylsulfanyl)-propyl]-[1,2,4]triazol-4-yl-amino}-benzonitrile (CAB02038, 221 mg, 0.50 mmol) in dichloromethane (10 mL) at room temperature. The mixture was stirred for 1 h, then ethyl acetate (50 mL) and concentrated NaHCO$_3$-solution (20 mL) were added. The mixture was transferred into a separation funnel, the organic layer was separated, washed with brine (20 mL), dried over sodium sulphate and concentrated under reduced pressure. The residue was purified by column chromatography (ethyl acetate, R$_f$: 0.22). Yield: 186 mg (78%) pale yellow foam. $^1$H-NMR (400 MHz, CDCl$_3$) δ=2.08 (tt, J=7.0, 7.0 Hz, 2H), 3.15 (t, J=7.0 Hz, 2H), 4.04 (t, J=7.0 Hz, 2H), 5.16 (s, 2H, —OCH$_2$Ph), 6.61 (d, J=9.0 Hz, 2H), 7.11 (d, J=9.0 Hz, 2H), 7.34–7.44 (m, 5H), 7.58 (d, J=9.0 Hz, 2H), 7.81 (d, J=9.0 Hz, 2H), 8.30 (s, 2H). LRMS (FAB+): 474.1 (100, [M+H]$^+$).

HRMS (FAB+) 474.16010 C$_{25}$H$_{24}$N$_5$O$_3$S requires 474.159987

4-{[3-(4-Hydroxy-benzenesulfonyl)-propyl]-[1,2,4]triazol-4-yl-amino}-benzonitrile (CAB02169, STX541)

STX541

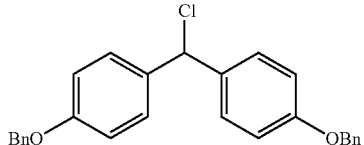

Palladium on charcoal (50 mg, 10% Pd) was added to a solution of 4-{[3-(4-Benzyloxy-benzenesulfonyl)-propyl]-[1,2,4]triazol-4-yl-amino}-benzonitrile (CAB02168, 118 mg, 0.25 mmol) in THF (10 mL) and ethanol (10 mL). The mixture was stirred under hydrogen atmosphere (balloon) for 18 h at room temperature. The reaction mixture was filtered through celite and the clear colourless filtrate was concentrated under reduced pressure. The residue was crystallised from acetone/water. Yield: 68 mg (71%) colourless crystals. $^1$H-NMR (400 MHz, d6-DMSO) δ=1.68–1.76 (m, 2H), 3.38 (t, J=7.6 Hz, 2H), 3.92 (t, J=7.2 Hz, 2H), 6.57 (d, J=9.0 Hz, 2H), 6.95 (d, J=9.0 Hz, 2H), 7.68 (d, J=9.0 Hz, 2H), 7.73 (d, J=9.0 Hz, 2H), 8.97 (s, 2H), 10.64 (s, 1H, —OH). LRMS (FAB+): 384.0 (100, [M+H]$^+$). HRMS (FAB+): 384.11248 C$_{18}$H$_{18}$N$_5$O$_3$S requires 384.11304.

Bis-(4,4'-benzyloxy)phenyl-chloromethane (CAB02062)

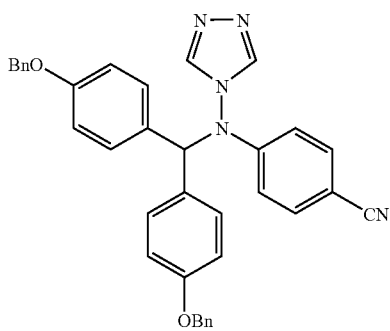

Thionylchloride (3.0 mL) was added to bis-(4-benzyloxy-phenyl)-methanol (1.982 g, 5.0 mmol). The resulting pink solution was stirred at room temperature until the production of sulphur dioxide and hydrogen chloride ceased (ca. 1.5 h). The excess of thionyl chloride was removed under reduced pressure, the crude product was used without any further purification. Yield: 2.075 g (100%). $^1$H-NMR (400 MHz, CDCl$_3$) δ=5.06 (s, 4H, 2×—OCH$_2$Ph), 6.11 (s, 1H, Ar$_2$CHCl), 6.94 (d, J=8.6 Hz, 4H), 7.30–7.46 (m, 14H).

4-{[Bis-(4-benzyloxy-phenyl)-methyl]-[1,2,4]triazol-4-yl-amino}-benzonitrile (CAB02068)

Sodium hydride (60%, 200 mg, 5.0 mmol) was added to a solution of 4-([1,2,4]triazol-4-ylamino)-benzonitrile (926 mg, 5.0 mmol) in DMF (10 mL) at 0° C. The mixture was stirred for 1 h at room temperature and Bis-(4,4-benzyloxy)phenyl-chloromethane (CAB02062, 2.075 g, 5.0 mmol) was added. The reaction mixture was stirred for 15 h and ethyl acetate (100 mL) was added. The mixture was transferred into a separation funnel and extracted with water (2×50 mL) and brine (20 mL). The organic layer was dried over sodium sulphate and concentrated under reduced pressure. The residue was purified by column-chromatography (ethyl acetate, R$_f$: 0.41). Yield: 1.319 g (47%) white solid. $^1$H-NMR (400 MHz, CDCl$_3$) δ=5.02 (s, 4H, 2×—OCH$_2$Ph), 6.28 (s, 1H), 6.54 (d, J=9.0 Hz, 2H), 6.90 (d, J=8.6 Hz, 4H), 7.06 (d, J=8.6 Hz, 4H), 7.30–7.44 (m, 10H), 7.51 (d, J=9.0 Hz, 2H), 7.88 (s, 2H). $^{13}$C-NMR (100.5 MHz, CDCl$_3$) δ=69.89, 70.44, 104.68, 113.48, 115.63, 118.93, 127.76, 128.39, 128.86, 129.31, 129.76, 134.19, 136.56, 143.92, 150.39, 159.19. LRMS (FAB+): 564.2 (100, [M+H]$^+$).

4-{[Bis-(4-hydroxy-phenyl)-methyl]-[1,2,4]triazol-4-yl-amino}-benzonitrile (CAB02070, STX340)

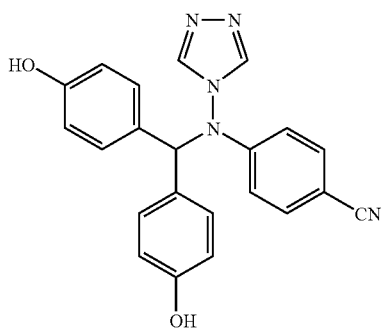

4-{[Bis-(4-benzyloxy-phenyl)-methyl]-[1,2,4]triazol-4-yl-amino}-benzonitrile (CAB02068, 564 mg, 1.0 mmol) was dissolved in ethanol (50 mL) and palladium on charcoal (50 mg, 10% Pd) was added. The mixture was stirred under hydrogen atmosphere (balloon) for 48 h (TLC monitored) until all starting material was consumed. The Pd/C was filtered off (celite) and the solution was concentrated under reduced pressure. A yellow solid was obtained, which was dissolved in ethyl acetate (10 mL) upon heating. After cooling to room temperature the white precipitate was filtered off and dried under high vacuum. Yield: 312 mg (81%). $^1$H-NMR (400 MHz, d6-DMSO) δ=5.74 (s, 2H, 2×—OH), 6.28 (s, 1H), 6.53 (d, J=9.0 Hz, 2H), 6.61 (d, J=8.6 Hz, 4H), 7.10 (d, J=8.6 Hz, 4H), 7.65 (d, J=9.0 Hz, 2H), 8.83 (s, 2H). LRMS (FAB+): 199.1 (100), 384.1 (50, [M+H]$^+$). LRMS (FAB−): 184.1 (100), 382.1 (41, [M−H]$^−$).

4-{[Bis-(4-sulphamoyloxy-phenyl)-methyl]-[1,2,4]triazol-4-yl-amino}-benzonitrile (CAB02075)

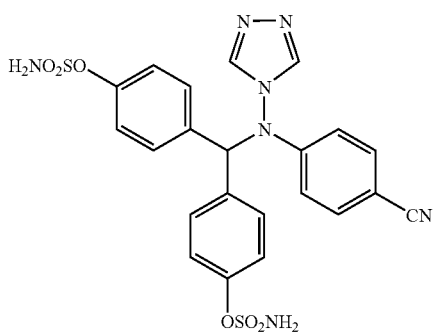

Sulphamoyl chloride solution in toluene (5 mL, 0.7 M, 3.5 mmol) was concentrated under reduced pressure (30° C. water bath temperature) to ca. 1 mL volume. The residue was cooled to 0° C. (ice bath) and N,N-dimethylacetamide (5 mL) was added. 4-{[Bis-(4-hydroxy-phenyl)-methyl]-[1,2,4]triazol-4-yl-amino}-benzonitrile (CAB02070, 250 mg, 0.65 mmol) was added to the colourless solution and the mixture was stirred for 18 h at room temperature. Ethyl acetate (50 mL) and water (30 mL) were added to the solution, the organic layer was separated, washed with water (2×30 mL) and brine (20 mL), dried over sodium sulphate and concentrated under reduced pressure to give a white solid. The solid was dissolved in ethyl acetate and precipitated by addition of hexane. The white powder was filtered off and dried under high vacuum. Yield: 299 mg (85%).

$^1$H-NMR (400 MHz, d6-DMSO) δ=6.67 (s, 1H), 6.67 (d, J=8.6 Hz, 2H), 7.17 (d, J=8.6 Hz, 4H), 7.47 (d, J=8.6 Hz, 4H), 7.70 (d, J=8.6 Hz, 2H), 8.02 (s, 4H, 2×—NH$_2$), 8.77 (s, 2H). LRMS (FAB+): 542.1 (50, [M+H]$^+$). LRMS (FAB−): 184.1 (100), 540.0 (85, [M−H]$^−$).

Dimethylsulfamic Acid 4-formyl-phenyl ester (JRL01114) (We followed the synthetic method described in the 1957 German patent no. 1 016 256)

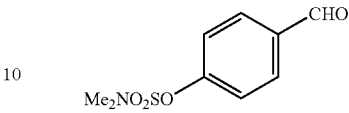

A stirred solution of 4-hydroxybenzaldehyde (1.0 g, 8.02 mmol) in N,N-dimethylcyclohexylamine (7 mL) was heated to 90–95° C. and at this temperature ClSO$_2$NMe$_2$ (0.87 mL, 8.02 mL) was added dropwise. The reaction mixture was then heated at 90–95° C. for 3 h. After cooling to room temperatue, EtOAc (100 mL) was added and the organic layer was washed with 1M hydrochloric acid (2×100 mL) and then brine (3×50 mL), dried (Na$_2$SO$_4$), filtered and evaporated to give a yellow oil which solidified to a yellow wax upon storage in the refrigerator (1.82 g, 99%); $^1$H (270 MHz, CDCl$_3$) 3.08 (6H, s), 7.46 (2H AA'BB'), 7.94 (2H AA'BB') and 10.0 (1H, s).

Dimethyl-sulfamic Acid 4-hydroxymethyl-phenyl ester (JRL01115)

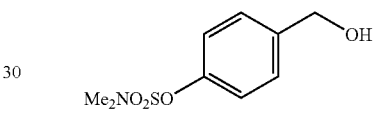

To a stirred solution of JRL01114 (1.81 g, 7.90 mmol) in THF (50 mL) was added at 0° C. NaBH$_4$ (305 mg, 7.90 mmol). After 2 h of stirring, the initial yellow mixture became a white suspension and the reaction mixture was then poured into ice/water (~100 mL). The aqueous layer was extracted with chloroform (4×50 mL). The combined organic extracts was dried (Na$_2$SO$_4$), filtered and evaporated to give a yellow oil (1.0 g) which was purified by flash chromatography (ethyl acetate) to give JRL01115 as a clear pale yellow oil (820 mg, 45%); $^1$H (400 MHz, CDCl$_3$) 1.76 (~1H, br s, exchanged with D$_2$O), 2.98 (6H, s), 4.70 (2H, s), 7.27 (2H AA'BB') and 7.39 (2H AA'BB'); LRMS (FAB+) 385.1 [7, (M+H+NBA)$^+$], 231.0 (50, M+), 214.0 [100, (M+H−H$_2$O)$^+$], 202.0 (10); HRMS (FAB+) 231.05557, C$_9$H$_{13}$NO$_4$S requires 231.05653.

Dimethyl-sulfamic Acid 4-chloromethyl-phenyl ester (LWO02144)

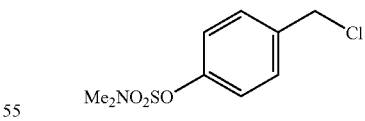

To a solution of JRL01115 (725 mg, 3.135 mmol) in dichloromethane (10 mL) at ice/water temperature was added thionyl chloride (0.35 mL, 4.703 mmol). After stirring at room temperature for 1 h, the volatiles were removed from the reaction mixture and the oil resulted co-evaporated 3 times with chloroform (3×30 mL) to give to LWO02144 as a yellow oil (767 mg, 98%); R$_f$ 0.52 (EtOAc/hexane, 1:1), c.f. 0.19 (JRL01115); $^1$H (400 MHz, CDCl$_3$) 2.99 (6H, s, NMe$_2$), 4.58 (2H, s), 7.28 (2H AA'BB') and 7.42 (2H, AA'BB'); LRMS (FAB+) 403.0 [18, (M+H+NBA)$^+$], 391.2 (21), 249.9 [100, (M+H)$^+$], 214.0 [45, (M+H−Cl)$^+$], 113.0

(17); HRMS (FAB+) 249.02239, $C_9H_{12}ClNO_3S$ requires 249.02264. LWO02144 was very pure and hence was used without further purification.

Dimethyl-sulfamic Acid 4-{[(4-cyano-phenyl)-[1,2,4]triazol-4-yl-amino]-methyl}-phenyl ester (LWO02145, STX636)

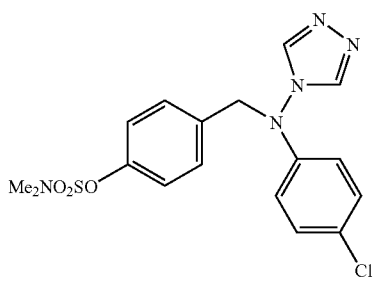

To a stirred solution of 4-[(1,2,4)triazol-4-amino] benzonitrile (538 mg, 2.903 mol) in anhydrous DMF (10 mL) at ice/water temperature was added MaH (60%, 128 mg, 3.193 mmol). The pale orange brown mixture that formed was stirred under nitrogen at 50° C. for 10 min. After cooling to room temperature, LWO02144 (725 mg, 2.903 mmol) in DMF (total 5 mL) was added to the reaction mixture. The resulting orange/brown suspension was stirred and heated at 50–60° C. for 4 h. The cooled reaction mixture was diluted with ethyl acetate (100 mL) and the organic layer that separated washed with brine (100 mL, 4×50 mL), dried ($MgSO_4$), filtered and evaporated to give an orange/brown syrup (1.15 g). This crude product was fractionated on silica by flash chromatography (neat ethyl acetate initially followed by neat acetone after the first fraction has been collected) and the second fraction that collected upon evaporation gave LWO02145 as a clear bright yellow syrup which solidified upon standing at room temperature overnight to give a light yellow wax (803 mg, 69%); m.p. crystals broke up and scattered intensively at around 150° C. and beyond, crystals melted at 195–202° C.; $R_f$ 0.36 (EtOAc), c.f. 0.13 (LWO02144); $^1H$ (400 MHz, $CDCl_3$) 2.98 (6H, s, $NMe_2$), 4.90 (2H, s), 6.68 (2H AA'BB'), 7.27 (4H, m), 7.60 (2H, AA'BB') and 8.13 (2H, s, triazole-H); LRMS (FAB+) 399.2 [100, (M+H)$^+$], 330.1 [43, (M-triazole)$^+$]; HRMS (FAB+) 399.12458, $C_{18}H_{19}N_6O_3S$ requires 399.12394. Found: C, 53.9; H, 4.62; N, 22.7%; $C_{18}H_{18}N_6O_3S$ requires C, 54.26; H, 4.55; N, 21.09%.

3-Bromo-4-(N,N-dimethylsulfamoyl)benzaldehyde (OBS02001)

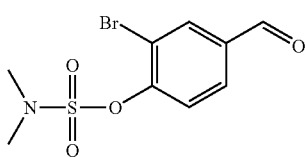

To a solution of OBS01057 (6.0 g, 30 mmol) in N,N-dimethylcyclohexylamine (30 mL) at 80–90° C., was added N,N-dimethylsulfamoyl chloride (3.79 mL, 35.27 mmol). The mixture was stirred at this temperature for 4 h, transferred to a separating funnel and diluted with EtOAc (100 mL). The organic layer was washed with water (2×200 mL), 6M HCl (aq.) (200 mL), brine (2×200 mL), dried ($Na_2SO_4$) and filtered. Concentration in vacuo of the filtrates gave an orange oil which solidified on standing. The product was stirred in n-hexane, filtered and air-dried to give OBS02001 as a pale yellow solid (8.21 g, 89%). TLC [$SiO_2$, EtOAc-n-hexane (1:1)] $R_f$=0.9; $^1H$-NMR (270 MHz, $CDCl_3$)=3.09 (6H, s), 7.68 (1H, d, J=8.4), 7.84 (1H, dd, J=1.8, 8.4), 8.12 (1H, d, J=1.8), 9.93 (1H, s).

3-Bromo-4-(N,N-dimethylsulfamoyl)benzyl alcohol (OBS02002)

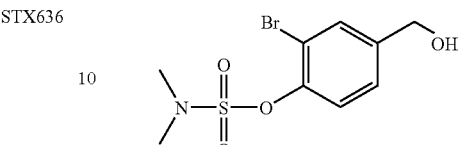

To a solution of OBS02001 (6.0 g, 19.47 mmol) in anhydrous THF (50 mL) was added sodium borohydride (0.81 g, 21.42 mmol). The mixture was stirred at room temperature for 4 h, quenched with water (CARE!!) and filtered through a Celite pad. The filtrate was concentrated in vacuo and re-dissolved in DCM (200 mL). The organic layer was washed with brine (2×200 mL), dried ($Na_2SO_4$) and filtered. Concentration in vacuo of the filtrates gave OBS02002 as a pale yellow oil (5.54 g, 92%). TLC [$SiO_2$, EtOAc-n-hexane (1:1)] $R_f$=0.47; $^1H$-NMR (270 MHz, $CDCl_3$)=2.97 (6H, s), 3.14 (1H, bs, OH), 4.51 (2H, s), 7.19 (1H, dd, J=1.5, 8.1), 7.37 (1H, d, J=8.4), 7.52 (1H, d, J=1.8).

3-Bromo-4-(N,N-dimethylsulfamoyl)benzyl chloride (OBS02003)

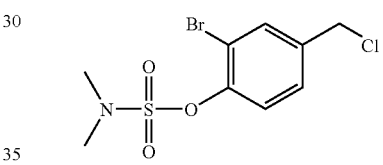

To a solution of OBS02002 (5.0 g, 16.12 mmol) in anhydrous DCM (50 mL) was added thionyl chloride (1.76 mL, 24.18 mmol). The mixture was stirred at room temperature for 2 h and the volatiles removed in vacuo. The residue was re-dissolved and co-evaporated three times with DCM (3×20 mL) to give a yellow oil which solidified on standing. The solid was stirred in n-hexane, filtered and air-dried to give OBS02003 as an off-white solid (5.01 g, 95%). TLC [$SiO_2$, EtOAc-n-hexane (1:1)] $R_f$=0.79; $^1H$-NMR (270 MHz, $CDCl_3$)=3.05 (6H, s), 4.51 (2H, s), 7.32 (1H, dd, J=2.2, 8.4), 7.48 (1H, d, J=8.4), 7.62 (1H, d, J=2.2).

Dimethylsulfamic Acid 2-bromo-4-{[(4-cyano-phenyl)-[1,2,4]triazol-4-ylamino]methyl}phenyl ester (OBS02005, STX732)

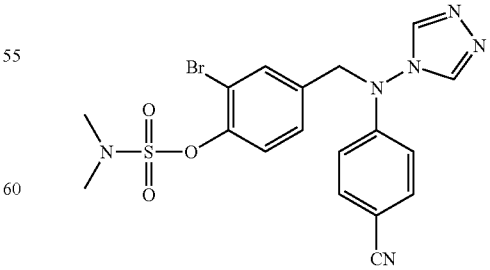

To a suspension of NaH (60% dispersion in oil, 0.44 g, 11.36 mmol) in anhydrous DMF (30 mL) at room temperature was added a solution of 4-[(4-cyanophenyl)amino]-4H-

[1,2,4]triazole (2.0 g, 10.8 mmol) in anhydrous DMF (10 mL) and the mixture stirred under nitrogen for 1 h. The orange-yellow suspension was then treated with a solution of OBS02003 (3.73 g, 11.36 mmol) in anhydrous DMF (5 mL) and the mixture stirred at 80–90° C. overnight. The mixture was transferred to a separating funnel and diluted with EtOAc (200 mL). The organic layer was washed with water (4×200 mL), brine (200 mL), dried (MgSO$_4$) and filtered. Concentration in vacuo of the combined filtrates gave a residue which was recystallised from i-PrOH to give OBS02005 as a colourless solid (3.34 g, 65%). TLC [SiO$_2$, EtOAc (100%)] R$_f$=0.32 (blue fluorescence at 254 nm); Anal. Calcd. for C$_{18}$H$_{17}$N$_6$SO$_3$Br: C, 45.3; H, 17.6; N, 3.6%; Found: C. 45.4; H, 17.5; N, 3.6%; $^1$H-NMR (400 MHz, d$^6$-DMSO)=2.98 (6H, s), 5.11 (2H, s), 6.75 (2H, AA'BB'), 7.43 (2H, s), 7.74 (1H, s), 7.78 (2H, AA'BB'), 8.88 (2H, s); $^{13}$C-NMR (400 MHz, d$^6$-DMSO)=39.4 (2×CH$_3$), 56.9 (CH$_2$), 103.8, 114.5 (2×CH), 116.1, 119.7, 123.9 (CH), 129.9 (CH), 134.3 (CH), 134.6 (2×CH), 136.0, 144.0 (2×CH), 146.9, 151.7; MS (FAB+)=477 (100%), 410 (30), 274 (22), 113 (32); Acc. MS for C$_{18}$H$_{17}$N$_6$SO$_3$Br (Required, 477.03445; Found, 477.03282); LC-MS (Waters 2790 Alliance HPLC/ZQ MicroMass spectrometer with PDA detector using APCI), t$_R$ (gradient elution: 5:95 MeCN/H$_2$O—95:5 MeCN/H$_2$O over 10 min then 95:5 MeCN/H$_2$O—5:95 MeCN/H$_2$O using Waters "Symmetry" C18 (packing: 3.5 μm), 100 mm column)=6.24 min (M+H=478.19); HPLC (Waters 717+ Autosampler with PDA detector, using Waters "Symmetry" C18 (packing: 3.5 μm), 4.6×150 mm column, 90:10 MeOH/H$_2$O) t$_R$=1.98 min (99.8% purity).

3,5-Dibromo-4-(N,N-dimethylsulfamoyl)benzaldehyde (OBS02013)

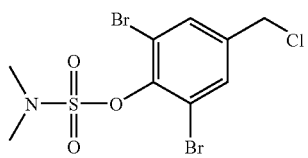

To a solution of 3,5-dibromo-4-hydroxybenzaldehyde (5.0 g, 17.86 mmol) in N,N-dimethylcyclohexylamine (30 mL) at 80–90° C., was added N,N-dimethylsulfamoyl chloride (30 mL). The mixture was stirred at this temperature for 4 h, transferred to a separating funnel and diluted with EtOAc (100 mL). The organic layer was washed with water (2×200 mL), 6M HCl (aq.) (200 mL), brine (2×200 mL), dried (Na$_2$SO$_4$) and filtered. Concentration in vacuo of the combined filtrates gave a dark amber oil which solidified on standing. The product was stirred in n-hexane, filtered and air-dried to give OBS02013 as a pale cream solid (6.09 g, 88%). TLC [SiO$_2$, EtOAc-n-hexane (1:1)] R$_f$=0.73; $^1$H-NMR (270 MHz, CDCl$_3$)=3.14 (6H, s), 8.06 (2H, s), 9.88 (1H, s).

3,5-Dibromo-4-(N,N-dimethylsulfamoyl)benzyl alcohol (OBS02015)

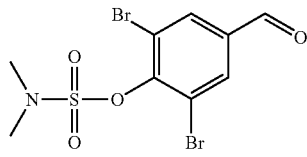

To a solution of OBS02013 (5.5 g, 14.21 mmol) in anhydrous THF (50 mL) was added sodium borohydride (0.59 g, 15.63 mmol). The mixture was stirred at room temperature for 4 h, quenched with water (CARE!!) and filtered through a Celite pad. The filtrate was concentrated in vacuo and re-dissolved in DCM (200 mL). The organic layer was washed with brine (2×200 mL), dried (Na$_2$SO$_4$) and filtered. Concentration in vacuo of the combined filtrates gave OBS02015 as a pale yellow oil (5.21 g, 94%). TLC [SiO$_2$, EtOAc-n-hexane (1:1)] R$_f$=0.55; $^1$H-NMR (270 MHz, CDCl$_3$)=1.97 (1H, bs, OH), 3.11 (6H, s), 4.63 (2H, s), 7.55 (2H, t, J=1.5).

3,5-Dibromo-4-(N,N-dimethylsulfamoyl)benzyl chloride (OBS02018)

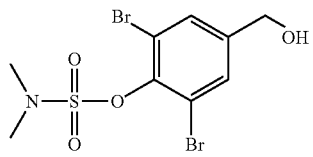

To a solution of OBS02015 (3.93 g, 10.10 mmol) in anhydrous DCM (50 mL) was added thionyl chloride (1.11 mL, 15.15 mmol). The mixture was stirred at room temperature for 2 h and the volatiles removed in vacuo. The residue was re-dissolved and co-evaporated three times with DCM (3×20 mL) to give OBS02018 as a brown oil which solidified on standing (3.93 g, 96%). TLC [SiO$_2$, EtOAc-n-hexane (1:1)] R$_f$=0.83; $^1$H-NMR (270 MHz, CDCl$_3$)=3.11 (6H, s), 4.46 (2H, s), 7.59 (2H, s).

Dimethylsulfamic Acid 2,6-dibromo-4-{[(4-cyano-phenyl)-[1,2,4]triazol-4-ylamino]methyl}phenyl ester (OBS02019, STX740)

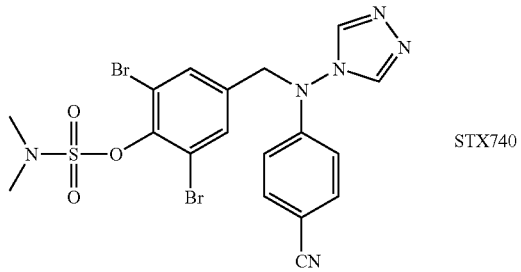

STX740

To a suspension of NaH (60% dispersion in oil, 0.22 g, 5.67 mmol) in anhydrous DMF (20 mL) at room temperature was added a solution of 4-[(4-cyanophenyl)amino]-4H-[1,2,4]triazole (1.0 g, 5.4 mmol) in anhydrous DMF (5 mL) and the mixture stirred under nitrogen for 1 h. The orange-yellow suspension was then treated with a solution of OBS02018 (2.31 g, 5.67 mmol) in anhydrous DMF (5 mL) and the mixture stirred at 80–90° C. overnight. The mixture was transferred to a separating funnel and diluted with EtOAc (200 mL). The organic layer was washed with water (4×200 mL), brine (200 mL), and dried (MgSO$_4$). Concentration in vacuo gave a residue which was recystallised from i-PrOH to give OBS02019 as a white solid (2.06 g, 69%). TLC [SiO$_2$, EtOAc (100%)] R$_f$=0.53 (blue fluorescence at 254 nm); Anal. Calcd. for C$_{18}$H$_{16}$N$_6$SO$_3$Br$_2$: C, 53.3; H, 4.7; N, 19.6%; Found: C. 53.1; H, 4.7; N, 19.3%; $^1$H-NMR (270 MHz, d$^6$-DMSO)=3.02 (6H, s), 5.09 (2H, s), 6.81 (2H, AA'BB'), 7.73 (2H, s), 7.76 (2H, AA'BB'), 8.93 (2H, s); $^{13}$C-NMR (400 MHz, d$^6$-DMSO)=39.3 (2×CH$_3$), 56.7 (CH$_2$), 103.9, 114.5 (2×CH), 118.7, 119.7, 133.6 (2×CH), 134.6 (2×CH), 137.6, 144.0, 145.1 (2×CH), 151.7; MS (FAB)=557 (M+H, 100%), 488 (20), 113 (28); Acc. MS for C$_{18}$H$_{16}$N$_6$SO$_3$Br$_2$ (Required, 556.9442; Found, 556.9429); LC-MS (Waters 2790 Alliance HPLC/ZQ MicroMass spectrometer with PDA detector using APCI), $t_R$ (gradient elution: 5:95 MeCN/H$_2$O—95:5 MeCN/H$_2$O over 10 mins then 95:5 MeCN/H$_2$O—5:95 MeCN/H$_2$O using Waters "Symmetry" C18 (packing: 3.5 μm), 100 mm column)=6.46 min (M+2H=558.17); HPLC (Waters 717+ Autosampler with PDA detector, using Waters "Symmetry" C18 (packing: 3.5 μm), 4.6×150 mm column, 90:10 MeOH/H$_2$O) $t_R$=2.01 min (98.7% purity).

3-Bromo-4-(N,N-dimethylsulfamoyl)-5-methoxybenzaldehyde (OBS02022)

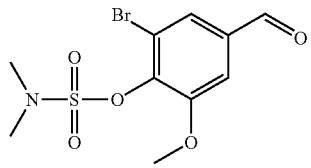

To a solution of 5-bromovanillin (3.0 g, 12.98 mmol) in N,N-dimethylcyclohexylamine (30 mL) at 80–90° C., was added N,N-dimethylsulfamoyl chloride (1.64 mL, 15.26 mmol). The mixture was stirred at this temperature for 4 h, transferred to a separating funnel and diluted with EtOAc (100 mL). The organic layer was washed with water (2×200 mL), 6M HCl (aq.) (200 mL), brine (2×200 mL), dried (Na$_2$SO$_4$) and filtered. Concentration in vacuo of the combined filtrates gave a golden-brown oil which solidified on standing. The product was stirred in n-hexane, filtered and air-dried to give OBS02022 as a cream solid (3.22 g, 73%). TLC [SiO$_2$, EtOAc-n-hexane (1:1)] R$_f$=0.88; $^1$H-NMR (270 MHz, CDCl$_3$)=3.07 (6H, s), 3.96 (3H, s), 7.43 (1H, d, J=1.8), 7.68 (1H, d, J=1.8), 9.87 (1H, s).

3-Bromo-4-(N,N-dimethylsulfamoyl)-5-methoxybenzyl alcohol (OBS02023)

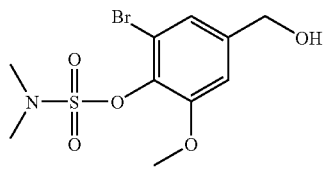

To a solution of OBS02022 (3.0 g, 8.87 mmol) in anhydrous THF (50 mL) was added sodium borohydride (0.37 g, 9.76 mmol). The mixture was stirred at room temperature for 4 h, quenched with water (CARE!!) and filtered through a Celite pad. The filtrate was concentrated in vacuo and re-dissolved in DCM (200 mL). The organic layer was washed with brine (2×200 mL), dried (Na$_2$SO$_4$) and filtered. Concentration in vacuo of the combined filtrates gave OBS02023 as a pale yellow oil (1.71 g, 57%). TLC [SiO$_2$, EtOAc-n-hexane (1:1)] R$_f$=0.68; $^1$H-NMR (270 MHz, CDCl$_3$)=1.94 (1H, bs, OH), 3.07 (6H, s), 3.91 (3H, s), 4.65 (2H, s), 6.96 (1H, d, J=2), 7.17 (1H, d, J=2).

3-Bromo-4-(N,N-dimethylsulfamoyl)-5-methoxybenzyl chloride (OBS02026)

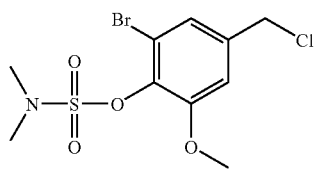

To a solution of OBS02023 (1.56 g, 4.59 mmol) in anhydrous DCM (50 mL) was added thionyl chloride (0.5 mL, 6.88 mmol). The mixture was stirred at room temperature for 2 h and the volatiles removed in vacuo. The residue was re-dissolved and co-evaporated three times with DCM (3×20 mL) to give OBS02026 as a brown oil (0.79 g, 48%). TLC [SiO$_2$, EtOAc-n-hexane (1:1)] R$_f$=0.89; $^1$H-NMR (270 MHz, CDCl$_3$)=3.00 (6H, s), 3.85 (3H, s), 4.46 (2H, s), 6.92 (1H, d, J=1.8), 7.16 (1H, d, J=1.8).

Dimethylsulfamic Acid 2-bromo-4-{[(4-cyano-phenyl)-[1,2,4]triazol-4-ylamino]methyl}-6-methoxyphenyl ester (OBS02028, STX747)

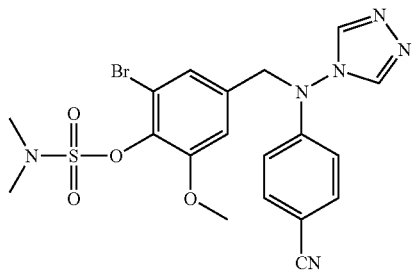

To a suspension of NaH (60% dispersion in oil, 0.07 g, 1.73 mmol) in anhydrous DMF (20 mL) at room temperature was added a solution of 4-[(4-cyanophenyl)amino]-4H-[1,2,4]triazole (0.31 g, 1.65 mmol) in anhydrous DMF (5 mL) and the mixture stirred under nitrogen for 1 h. The orange-yellow suspension was then treated with a solution of OBS02026 (0.62 g, 1.73 mmol) in anhydrous DMF (5 mL) and the mixture stirred at 80–90° C. overnight. The mixture was transferred to a separating funnel and diluted with EtOAc (200 mL). The organic layer was washed with water (4×200 mL), brine (200 mL), dried (MgSO$_4$) and filtered. Concentration in vacuo of the combined filtrates gave a residue which was recystallised from i-PrOH to give OBS02028 as an off-white solid (0.50 g, 59%). TLC [SiO$_2$, EtOAc (100%)] R$_f$=0.63 (blue fluorescence at 254 nm); Anal. Calcd. for C$_{19}$H$_{19}$N$_6$SO$_4$Br: C, 45.0; H, 3.8; N, 16.6%; Found: C. 44.9; H, 3.8; N, 15.8%; $^1$H-NMR (400 MHz, d$^6$-DMSO)=2.93 (6H, s), 3.86 (3H, s), 5.07 (2H, s), 6.77 (2H, AA'BB'), 7.11 (1H, d, J=1.6), 7.24 (1H, d, J=1.6), 7.79 (2H, AA'BB'), 8.9 (2H, s); $^{13}$C-NMR (400 MHz, d$^6$-DMSO)=39.0 (2×CH$_3$), 57.31 (CH$_2$), 57.31 (CH$_3$), 103.9, 113.3 (CH), 114.5 (CH), 118.3, 119.7, 125.1 (CH), 134.6 (CH), 136.3, 137.3, 144.0 (CH), 152.0, 153.4; MS (FAB+)=509 (M+2H, 100%), 440 (31), 215 (19), 113 (19); Acc. MS for Cl$_{19}$H$_{19}$N$_6$SO$_4$Br (Required, 507.04323; Found, 507.04501); LC-MS (Waters 2790 Alliance HPLC/ZQ MicroMass spectrometer with PDA detector using APCI), $t_R$ (gradient elution: 5:95 MeCN/H$_2$O—95:5 MeCN/H$_2$O over 10 mins then 95:5 MeCN/H$_2$O—5:95 MeCN/H$_2$O using Waters "Symmetry" C18 (packing: 3.5 μm), 100 mm column)=6.16 min (M+H=508.29); HPLC (Waters 717+ Autosampler with PDA detector, using Waters "Symmetry" C18 (packing: 3.5 μm), 4.6×150 mm column, 90:10 MeOH/H$_2$O) $t_R$=1.96 min (97.5% purity).

3-Chloro-4-(N,N-dimethylsulfamoyl)benzaldehyde (OBS02043)

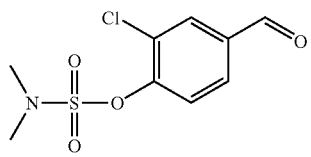

To a solution of 3-chloro-4-hydroxybenzaldehyde (6.0 g, 38.32 mmol) in N,N-dimethylcyclohexylamine (30 mL) at 80–90° C., was added N,N-dimethylsulfamoyl chloride (4.84 mL, 45.05 mmol). The mixture was stirred at this temperature for 4 h, transferred to a separating funnel and diluted with EtOAc (100 mL). The organic layer was washed with water (2×200 mL), 6M HCl (aq.) (200 mL), brine (2×200 mL), dried ($Na_2SO_4$) and filtered. Concentration in vacuo of the combined filtrates gave a brown oil which solidified on standing. The product was stirred in n-hexane, filtered and air-dried to give OBS02043 as a beige solid (5.36 g, 53%). TLC [$SiO_2$, EtOAc-n-hexane (1:1)] $R_f$=0.92; $^1$H-NMR (270 MHz, $CDCl_3$)=3.06 (6H, s), 7.67 (1H, d, J=8.4), 7.79 (1H, dd, J=2.2, 8.4), 7.95 (1H, d, J=1.8), 9.93 (1H, s).

3-Chloro-4-(N,N-dimethylsulfamoyl)benzyl alcohol (OBS02046)

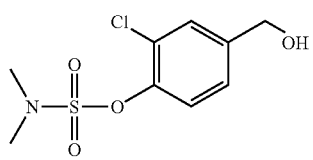

To a solution of OBS02043 (5.0 g, 18.96 mmol) in anhydrous THF (50 mL) was added sodium borohydride (0.79 g, 20.86 mmol). The mixture was stirred at room temperature for 4 h, quenched with water (CARE!!) and filtered through a Celite pad. The filtrate was concentrated in vacuo and re-dissolved in DCM (200 mL). The organic layer was washed with brine (2×200 mL), dried ($Na_2SO_4$) and filtered. Concentration in vacuo of the combined filtrates gave OBS02046 as a golden-brown oil (3.81 g, 76%). TLC [$SiO_2$, EtOAc-n-hexane (1:1)] $R_f$=0.64; $^1$H-NMR (270 MHz, $CDCl_3$)=2.04 (1H, bs, OH), 3.05 (6H, s), 4.66 (2H, s), 7.25 (1H, dd, J=2.2, 8.4), 7.46 (1H, d, J=2.2), 7.47 (1H, d, J=8.1).

3-Chloro-4-(N,N-dimethylsulfamoyl)benzyl chloride (OBS02052)

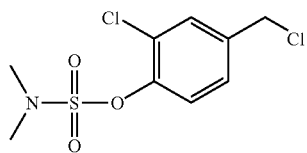

To a solution of OBS02046 (3.02 g, 11.37 mmol) in anhydrous DCM (50 mL) was added thionyl chloride (1.24 mL, 17.05 mmol). The mixture was stirred at room temperature for 2 h and the volatiles removed in vacuo. The residue was re-dissolved and co-evaporated three times with DCM (3×20 mL) to give OBS02052 as an amber oil (2.68 g, 83%). TLC [$SiO_2$, EtOAc-n-hexane (1:1)] $R_f$=0.91; $^1$H-NMR (270 MHz, $CDCl_3$)=3.04 (6H, s), 4.52 (2H, s), 7.28 (1H, dd, J=2.2, 8.4), 7.47 (1H, d, J=8.5), 7.47 (1H, d, J=2.2).

Dimethylsulfamic Acid 2-chloro-4-{[(4-cyano-phenyl)-[1,2,4]triazol-4-ylamino]methyl}phenyl ester (OBS02054, STX787)

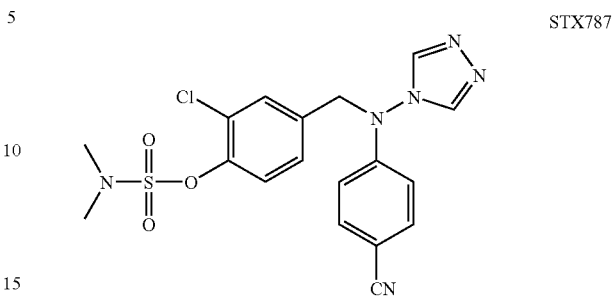

STX787

To a suspension of NaH (60% dispersion in oil, 0.34 g, 8.95 mmol) in anhydrous DMF (20 mL) at room temperature was added a solution of 4-[(4-cyanophenyl)amino]-4H-[1,2,4]triazole (1.66 g, 8.95 mmol) in anhydrous DMF (5 mL) and the mixture stirred under nitrogen for 1 h. The orange-yellow suspension was then treated with a solution of OBS02052 (2.67 g, 9.4 mmol) in anhydrous DMF (5 mL) and the mixture stirred at 80–90° C. overnight. The mixture was transferred to a separating funnel and diluted with EtOAc (200 mL). The organic layer was washed with water (4×200 mL), brine (200 mL), dried ($MgSO_4$) and filtered. Concentration in vacuo of the combined filtrates gave a residue which was recystallised from i-PrOH to give OBS02054 as a pale cream solid (2.03 g, 52%). TLC [$SiO_2$, EtOAc (100%)] $R_f$=0.53 (blue fluorescence at 254 nm); Anal. Calcd. for $C_{18}H_{17}N_6SO_3Cl$ : C, 49.9; H, 4.0; N, 19.4%; Found: C, 49.7; H, 4.0; N, 19.2%; $^1$H-NMR (270 MHz, $CDCl_3$)=3.01 (6H, s), 4.87 (2H, s), 6.62 (2H, AA'BB'), 7.15 (1H, dd, J=2.2, 8.4), 7.32 (1H, d, J=2.2), 7.46 (1H, d, J=8.4), 7.55 (2H, AA'BB'), 8.18 (2H, s); $^{13}$C-NMR (400 MHz, $d^6$-DMSO)=38.3 (2×$CH_3$), 56.0 ($CH_2$), 102.9, 113.5 (2×CH), 118.7, 123.4 (CH), 125.8, 128.3 (CH), 130.3 (CH), 133.7 (2×CH), 134.9, 143.0 (2×CH), 144.7, 150.9; MS (FAB)=433 (M+H, 100%), 364 (37); Acc. MS for $C_{18}H_{17}N_6SO_3Cl$ (Required M+H, 433.08476; Found M+H, 433.08496); LC-MS (Waters 2790 Alliance HPLC/ZQ MicroMass spectrometer with PDA detector using APCI), $t_R$ (gradient elution: 5:95 MeCN/$H_2O$—95:5 MeCN/$H_2O$ over 10 min then 95:5 MeCN/$H_2O$—5:95 MeCN/$H_2O$ using Waters "Symmetry" C18 (packing: 3.5 μm), 100 mm column)=6.18 min (M+H=434.18); HPLC (Waters 717+ Autosampler with PDA detector, using Waters "Symmetry" C18 (packing: 3.5 μm), 4.6×150 mm column, 90:10 MeOH/$H_2O$) $t_R$=1.98 min (99.9% purity).

4-(N,N-Dimethylsulfamoyl)-3-methoxybenzaldehyde (OBS02011)

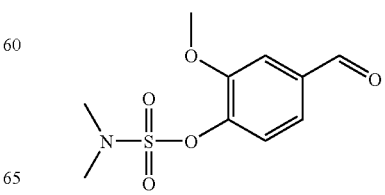

To a solution of vanillin (4.56 g, 30 mmol) in N,N-dimethylcyclohexylamine (30 mL) at 80–90° C., was added N,N-dimethylsulfamoyl chloride (3.79 mL, 35.27 mmol). The mixture was stirred at this temperature for 4 h, transferred to a separating funnel and diluted with EtOAc (100 mL). The organic layer was washed with water (2×200 mL), 6M HCl (aq.) (200 mL), brine (2×200 mL), dried (Na$_2$SO$_4$) and filtered. Concentration in vacuo of the combined filtrates gave a golden-yellow oil which solidified on standing. The product was stirred in n-hexane, filtered and air-dried to give OBS02011 as yellow plates (6.92 g, 89%). TLC [SiO$_2$, EtOAc-n-hexane (1:1)] R$_f$=0.65; $^1$H-NMR (270 MHz, CDCl$_3$)=2.98 (6H, s), 3.93 (3H, s), 7.44 (1H, d, J=1.6), 7.48 (1H, dd, J=1.6, 8.1), 7.53 (1H, d, J=8.1), 9.92 (1H, s).

4-(N,N-Dimethylsulfamoyl)-3-methoxybenzyl alcohol (OBS02014)

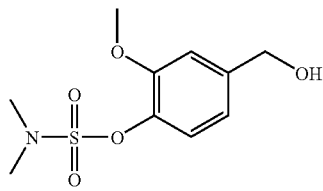

To a solution of OBS02011 (5.5 g, 21.21 mmol) in anhydrous THF (50 mL) was added sodium borohydride (0.88 g, 23.33 mmol). The mixture was stirred at room temperature for 4 h, quenched with water (CARE!!) and filtered through a Celite pad. The filtrate was concentrated in vacuo and re-dissolved in DCM (200 mL). The organic layer was washed with brine (2×200 mL), dried (Na$_2$SO$_4$) and filtered. Concentration in vacuo of the combined filtrates gave OBS02014 as a pale yellow oil (5.12 g, 92%). TLC [SiO$_2$, EtOAc-n-hexane (1:1)] R$_f$=0.18; $^1$H-NMR (270 MHz, CDCl$_3$)=2.44 (1H, bs, OH), 2.92 (6H, s), 3.84 (3H, s), 4.60 (2H, s), 6.85 (1H, dd, J=2.2, 8.4), 6.97 (1H, d, J=1.8), 7.25 (1H, d, J=8.1).

4-(N,N-Dimethylsulfamoyl)-3-methoxybenzyl chloride (OBS02016)

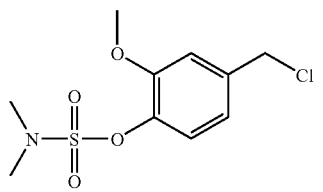

To a solution of OBS02014 (2.76 g, 10.55 mmol) in anhydrous DCM (50 mL) was added thionyl chloride (1.15 mL, 15.82 mmol). The mixture was stirred at room temperature for 2 h and the volatiles removed in vacuo. The residue was re-dissolved and co-evaporated three times with DCM (3×20 mL) to give OBS02016 as a brown oil (2.91 g, 99%). TLC [SiO$_2$, EtOAc-n-hexane (1:1)] R$_f$=0.84; $^1$H-NMR (270 MHz, CDCl$_3$)=2.96 (6H, s), 3.90 (3H, s), 4.55 (2H, s), 6.95 (1H, dd, J=1.8, 8.0), 7.01 (1H, d, J=1.8), 7.32 (1H, d, J=8.0).

Dimethylsulfamic Acid 4-{[(4-cyano-phenyl)-[1,2,4]triazol-4-ylamino]methyl}-2-methoxyphenyl ester (OBS02017, STX739)

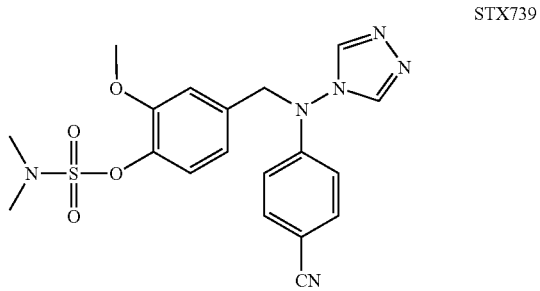

To a suspension of NaH (60% dispersion in oil, 0.22 g, 5.67 mmol) in anhydrous DMF (20 mL) at room temperature was added a solution of 4-[(4-cyanophenyl)amino]-4H-[1,2,4]triazole (1.0 g, 5.4 mmol) in anhydrous DMF (5 mL) and the mixture stirred under nitrogen for 1 h. The orange-yellow suspension was then treated with a solution of OBS02016 (1.59 g, 5.67 mmol) in anhydrous DMF (5 mL) and the mixture stirred at 80–90° C. overnight. The mixture was transferred to a separating funnel and diluted with EtOAc (200 mL). The organic layer was washed with water (4×200 mL), brine (200 mL), dried (MgSO$_4$) and filtered. Concentration in vacuo of the combined filtrates gave a residue which was recystallised from i-PrOH to give OBS02017 as a cream solid (1.07 g, 46%). TLC [SiO$_2$, EtOAc (100%)] R$_f$=0.26 (blue fluorescence at 254 nm); Anal. Calcd. for C$_{19}$H$_{20}$N$_6$SO$_4$: C, 38.9; H, 2.9; N, 15.1%; Found: C, 38.9; H, 3.0; N, 14.8%; $^1$H-NMR (400 MHz, d$^6$-DMSO)=2.83 (6H, s), 3.84 (3H, s), 5.07 (2H, s), 6.80 (2H, AA'BB'), 6.90 (1H, dd, J=2, 8), 7.12 (1H, d, J=2), 7.23 (1H, d, J=8), 7.79 (2H, AA'BB'), 8.83 (2H, s); $^{13}$C-NMR (400 MHz, d 6-DMSO)=39.1 (2×CH$_3$), 56.8 (CH$_3$), 57.6 (CH$_2$), 103.7, 114.1 (2×CH), 114.5 (CH), 119.7, 121.5 (CH), 124.1 (CH), 134.6 (2×CH), 135.2, 138.8, 144.0 (2×CH), 151.8, 152.0; MS (FAB+)=429 (M+H, 100%), 360 (36), 321 (6), 244 (15), 113 (5); Ace. MS for C$_{19}$H$_{20}$N$_6$SO$_4$ (Required, 429.1341; Found, 429.1345); LC-MS (Waters 2790 Alliance HPLC/ZQ MicroMass spectrometer with PDA detector using APCI), t$_R$ (gradient elution: 5:95 MeCN/H$_2$O—95:5 MeCN/H$_2$O over 10 min then 95:5 MeCN/H$_2$O—5:95 MeCN/H$_2$O using Waters "Symmetry" C18 (packing: 3.5 μm), 100 mm column)=5.83 min (M+2H=430.27); HPLC (Waters 717+ Autosampler with PDA detector, using Waters "Symmetry" C18 (packing: 3.5 μm), 4.6×150 mm column, 90:10 MeOH/H$_2$O) t$_R$=1.94 min (99.5% purity).

3-(N,N-Dimethylsulfamoyl)-4-methoxybenzaldehyde (OBS02049)

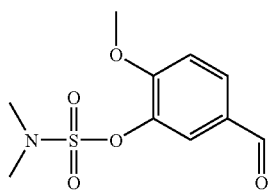

To a solution of isovanillin (4.56 g, 30 mmol) in N,N-dimethylcyclohexylamine (30 mL) at 80–90° C., was added N,N-dimethylsulfamoyl chloride (3.79 g, 35.27 mmol). The mixture was stirred at this temperature for 4 h, transferred to a separating funnel and diluted with EtOAc (100 mL). The organic layer was washed with water (2×200 mL), 6M HCl (aq.) (200 mL), brine (2×200 mL), dried (Na$_2$SO$_4$) and filtered. Concentration in vacuo of the combined filtrates gave a brown oil which solidified on standing. The product was stirred in n-hexane, filtered and air-dried to give OBS02049 as a pale yellow solid (6.91 g, 89%). TLC [SiO$_2$, EtOAc-n-hexane (1:1)] R$_f$=0.57; $^1$H-NMR (270 MHz, CDCl$_3$)=2.98 (6H, s), 3.95 (3H, s), 7.07 (1H, d, J=8.4), 7.77 (1H, dd, J=1.8, 8.4), 7.83 (1H, d, J=2.2), 9.84 (1H, s).

3-(N,N-Dimethylsulfamoyl)-4-methoxybenzyl alcohol (OBS02053)

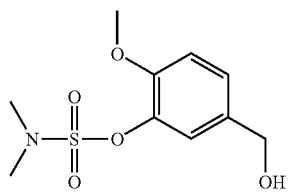

To a solution of OBS02049 (5.5 g, 21.21 mmol) in anhydrous THF (50 mL) was added sodium borohydride (0.88 g, 23.33 mmol). The mixture was stirred at room temperature for 4 h, quenched with water (CARE!!) and filtered through a Celite pad. The filtrate was concentrated in vacuo and re-dissolved in DCM (200 mL). The organic layer was washed with brine (2×200 mL), dried (Na$_2$SO$_4$) and filtered. Concentration in vacuo of the combined filtrates gave OBS02053 as a golden-yellow oil (3.26 g, 59%). TLC [SiO$_2$, EtOAc-n-hexane (1:1)] R$_f$=0.36; $^1$H-NMR (270 MHz, CDCl$_3$)=1.73 (1H, bs, OH), 2.97 (6H, s), 3.88 (3H, s), 4.62 (2H, s), 6.95 (1H, d, J=8.4), 7.23 (1H, dd, J=2.2, 8.4), 7.36 (1H, d, J=2.2).

3-(N,N-Dimethylsulfamoyl)-4-methoxybenzyl chloride (OBS02058)

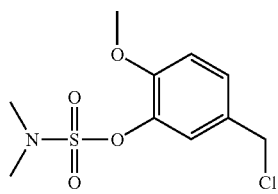

To a solution of OBS02053 (2.33 g, 8.89 mmol) in anhydrous DCM (50 mL) was added thionyl chloride (0.97 mL, 13.34 mmol). The mixture was stirred at room temperature for 2 h and the volatiles removed in vacuo. The residue was re-dissolved and co-evaporated three times with DCM (3×20 mL) to give OBS02058 as a light-sensitive brown oil (2.07 g, 83%); $^1$H-NMR (270 MHz, CDCl$_3$)=2.98 (6H, s), 3.89 (3H, s), 4.54 (2H, s), 6.94 (1H, d, J=8.4), 7.25 (1H, dd, J=2.2, 8.4), 7.40 (1H, d, J=2.2).

Dimethylsulfamic Acid 5-{[(4-cyano-phenyl)-[1,2,4]triazol-4-ylamino]methyl}-2-methoxyphenyl ester (OBS02060, STX796)

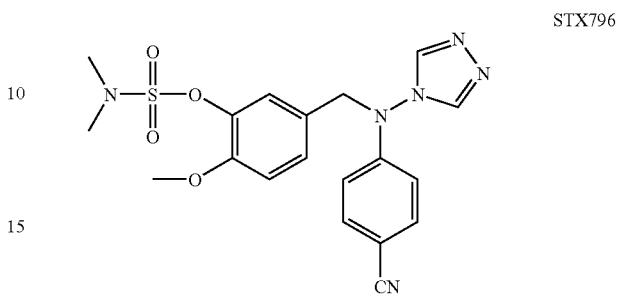

STX796

To a suspension of NaH (60% dispersion in oil, 0.28 g, 6.91 mmol) in anhydrous DMF (20 mL) at room temperature was added a solution of 4-[(4-cyanophenyl)amino]-4H-[1,2,4]triazole (1.28 g, 6.91 mmol) in anhydrous DMF (5 mL) and the mixture stirred under nitrogen for 1 h. The orange-yellow suspension was then treated with a solution of OBS02058 (2.03 g, 7.26 mmol) in anhydrous DMF (5 mL) and the mixture stirred at 80–90° C. overnight. The mixture was transferred to a separating funnel and diluted with EtOAc (200 mL). The organic layer was washed with water (4×200 mL), brine (200 mL), dried (MgSO$_4$) and filtered. Concentration in vacuo of the combined filtrates gave a residue which was recystallised from EtOAc-n-hexane to give OBS02060 as a pale cream solid (2.24 g, 76%); $^1$H-NMR (270 MHz, CHCl$_3$)=2.88 (6H, s), 3.82 (3H, s), 4.79 (2H, s), 6.66 (2H, AA'BB'), 6.83 (1H, d, J=8.4), 6.94 (1H, dd, J=2.2, 8.4), 7.30 (1H, d, J=1.8), 7.53 (2H, AA'BB'), 8.12 (2H, s); $^{13}$C-NMR (270 MHz, CHCl$_3$)=38.7 (2×CH$_3$), 56.1 (CH$_3$), 57.2 (CH$_2$), 105.1, 112.9 (CH), 113.6 (2×CH), 118.5, 123.9 (CH), 125.7 (CH), 127.6 (CH), 133.9 (2×CH), 139.4, 142.6 (2×CH), 150.4, 151.8; MS (FAB+)=429 (M+H, 100%), 360 (50), 321 (6), 244 (43); Acc. MS for C$_{19}$H$_{20}$N$_6$SO$_4$ (Required, 429.1343; Found, 429.1345); LC-MS (Waters 2790 Alliance HPLC/ZQ MicroMass spectrometer with PDA detector using APCI), t$_R$ (gradient elution: 5:95 MeCN/H$_2$O—95:5 MeCN/H$_2$O over 10 min then 95:5 MeCN/H$_2$O—5:95 MeCN/H$_2$O using Waters "Symmetry" C18 (packing: 3.5 µm), 100 mm column)=5.80 min (M+2H=430.27); HPLC (Waters 717+ Autosampler with PDA detector, using Waters "Symmetry" C18 (packing: 3.5 µm), 4.6×150 mm column, 90:10 MeOH/H$_2$O) t$_R$=1.96 min (99.8% purity).

Synthesis of STX258, 265, 273, 287, 288, 290, 291, 292

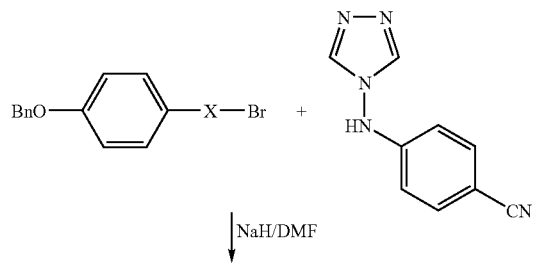

-continued
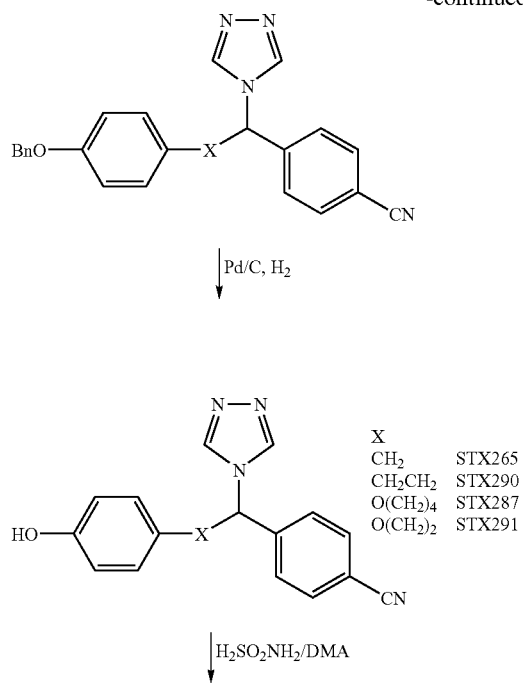
| X | |
|---|---|
| CH₂ | STX265 |
| CH₂CH₂ | STX290 |
| O(CH₂)₄ | STX287 |
| O(CH₂)₂ | STX291 |
↓ H₂SO₂NH₂/DMA
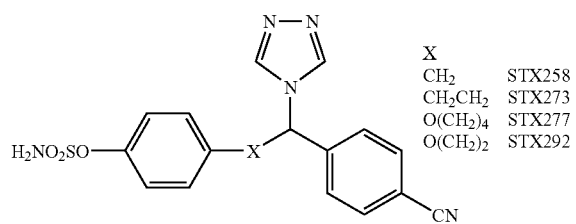
| X | |
|---|---|
| CH₂ | STX258 |
| CH₂CH₂ | STX273 |
| O(CH₂)₄ | STX277 |
| O(CH₂)₂ | STX292 |
Synthesis of STX300 and STX301
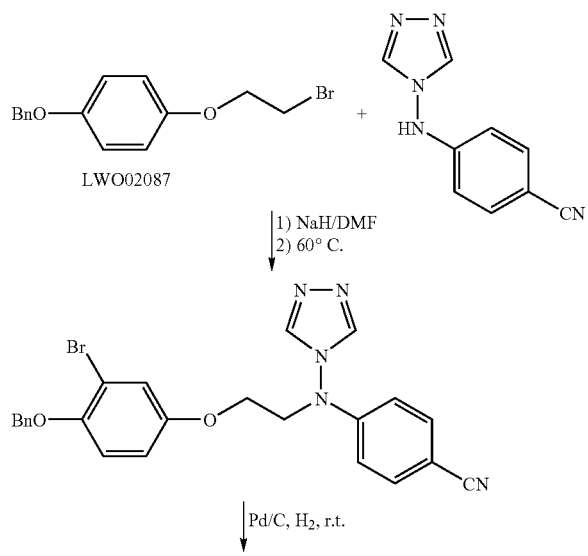

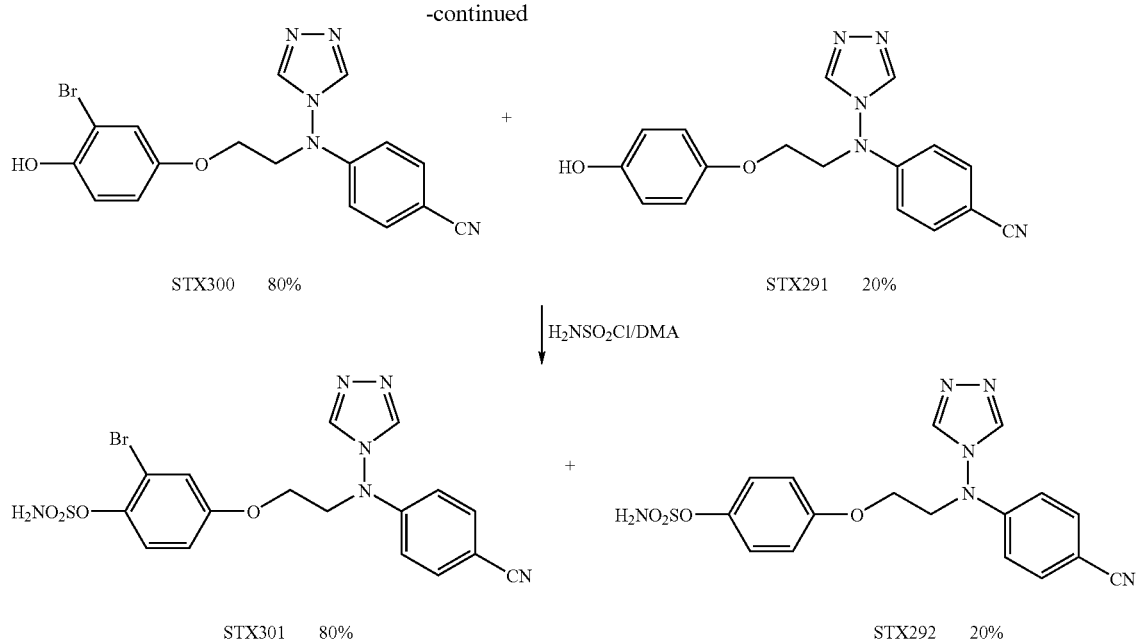

STX300 80% + STX291 20%

H₂NSO₂Cl/DMA ↓

STX301 80% + STX292 20%

Compounds of Formula IV
Bis-(4-Benzyloxyphenyl)methanone (LWO02007A)

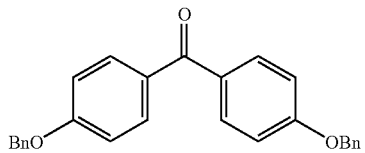

To a solution of 4,4'-dihydroxybenzophenone (5.0 g, 23.34 mmol) in anhydrous DMF (150 mL) at 0° C. was added sodium hydride (60% in mineral oil, 2.1 g, 51.35 mmol), in two portions. After stirring for 20 min at which no more evolution of hydrogen was observed, benzyl bromide (8.96 g, 51.35 mmol) was added. The resulting yellow suspension was then stirred under an atmosphere of nitrogen at 100° C. for 1 h. Upon cooling to room temperature, water (500 mL) was added to the suspension and the precipitate that formed was filtered and washed exhaustively with water. After air-drying overnight at room temperature, the white solid (10.1 g) that collected was recrystallised from hot toluene to give LWO02007A as white flaky plate crystals (8.92 g, 22.61 mmol, 96.9%); m.p. 188–190° C.
Bis-(4-Benzyloxyphenyl)methanol (LWO02018)

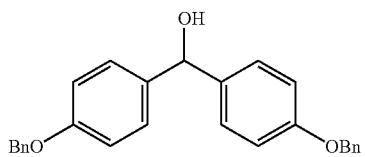

To a solution of LWO02007A (3.50 g, 8.873 mmol) in anhydrous THF (250 mL) at 0° C. was added a suspension of lithium aluminium hydride (95%, 425 mg, 10.65 mmol) in anhydrous THF (20 mL). After stirring for 30 min at room temperature, the grey suspension/mixture was concentrated and ethyl acetate (200 mL) was added the wet residue that obtained. The organic layer was washed with 1M HCl (200 mL), then brine (4×100 mL), dried (MgSO₄), filtered and evaporated to give LWO02018 as a white/pale yellow residue (3.56 g); m.p. 113–120° C.; $\delta_H$ (400 MHz, DMSO-d₆) 5.06 (4H, s, OCH₂), 5.58 (1H, d, J=4.3 Hz, CH), 5.67 (1H, d, J=4.3 Hz, exchanged with D₂O, OH), 6.93 (4H, AA'BB'), 7.23 (4H, AA'BB') and 7.38 (10H, m, Bn).
1-[Bis-(4-Benzyloxyphenyl)methyl]-1H-[1,2,4]triazole (LWO02019)

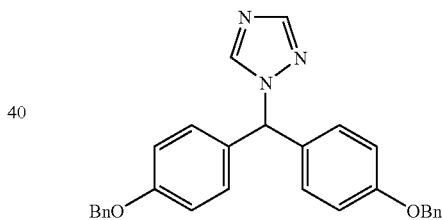

A mixture of LWO02018 (3.26 g, 8.222 mmol) and 1H-1,2,4-triazole (695 mg, 9.866 mmol) in toluene (350 mL) in the presence of p-toluenesulphonic acid (650 mg) was heated under Dean Stark conditions overnight. After cooling to room temperature and evaporation of solvent, the light yellow residue that obtained was dissolved in ethyl acetate (300 mL). The organic layer was washed with 1M NaOH (2×100 mL), then brine (3×50 mL), dried (MgSO₄), filtered and evaporated to give a light yellow/brown residue (3.36 g). This crude was dissolved in hot ethyl acetate (30 mL) and hexane (15 mL) was added portionwise. Upon cooling to room temperature, LWO02019A was obtained as yellow crystals (2.50 g, 5.586 mmol, 68%); m.p. 134–137° C.; $\delta_H$ (400 MHz, DMSO-d₆) 5.09 (4H, s, 2×OCH₂), 6.94 (1H, s, CH), 7.01 (4H, AA'BB'), 7.14 (4H, AA'BB'), 7.29–7.47 (10H, m, Bn), 8.03 (~1H, s, C3'-H) and 8.53 (1H, s, C5'-H); LRMS (FAB+) 447.3[17, M⁺],379.3[100, (M-triazole)⁺], 288,2[8, (M-triazole-Bn)⁺], 91.1[75, Bn⁺]; LRMS (FAB−): no peak was observed; HRMS (FAB+) 447.19588 $C_{29}H_{25}N_3O_2$ requires 447.19468. Found: C, 77.6, H 5.63; N, 9.26; $C_{29}H_{25}N_3O_2$ requires C 77.83, H 5.63, N 9.37.

1-[Bis-(4-Hydroxyphenyl)methyl]-1H-[1,2,4]triazole (LWO02020, STX267)

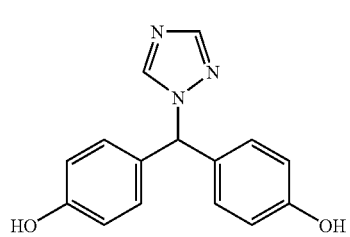

To a solution of LWO02019 (1.50 g, 3.356 mmol) in distilled THF (50 mL) was added methanol (30 mL) and Pd/C (10%, 75 mg). The black suspension was stirred at room temperature under an atmosphere of hydrogen (balloon) over weekend. After removal by filtration and exhaustive washings of the supported catalyst with distilled THF, the filtrate was evaporated to give a frothy light yellow residue (839 mg, 3.319 mmol, 93.5%). This crude was dissolved in hot THF (15 mL) and hexane (10 mL) was added portionwise. Upon cooling, LWO02020A was obtained as white crystals (483 mg); m.p. 230° C.; $\delta_H$ (400 MHz, DMSO-$d_6$) 6.73 (4H, AA'BB'), 6.79 (1H, s, CH), 6.99 (4H, AA'BB'), 8.01 (~1H, s, C3'-H), 8.45 (1H, s, C5'-H) and 9.52 (~2H, s, exchanged with $D_2O$, 2×OH); $\delta_C$ (100.4 MHz, DMSO-$d_6$) 65.2 (d, CH), 115.3 (d, Ar), 129.3 (d, Ar), 129.9 (s, Ar), 144.0 (d, C5'), 151.8 (d, C3'), 157.1 (s, Ar—OH). Found: C 67.2, H 5.08, N 15.4; $C_{15}H_{13}N_3O_2$ requires C, 67.4; H 4.90; N 15.72.

1-[Bis-(4-sulfamoyloxyphenyl)methyl]-1H-[1,2,4]triazole (LWO02021, STX268)

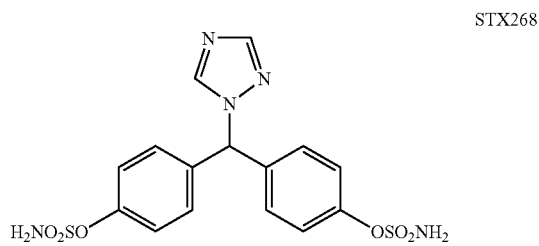

To a solution of LWO02020 (257 mg, 1.336 mmol) in N,N-dimethylacetamide (20 mL) at room temperature under an atmosphere of nitrogen was added sulfamoyl chloride in toluene (ca. 0.68 M, 7.8 mL). After stirring the reaction mixture overnight, it was diluted with ethyl acetate (100 mL). The organic layer that separated was washed with brine (100 mL, 4×50 mL), dried ($MgSO_4$), filtered and evaporated to give a light brown syrup/residue (612 mg). This crude was purified by flash chromatography (ethyl acetate) and the second fraction that collected gave LWO02021A as white residue (310 mg, 728.7 μmol, 54.5%); m.p. 70–85° C.; $\delta_H$ (400 MHz, DMSO-$d_6$) 7.19 (1H, s, CH), 7.30 (4H, AA'BB'), 7.36 (4H, AA'BB'), 8.03 (~4H, br s, exchanged with $D_2O$, $H_2NSO_2$), 8.10 (~1H, s, C3'-H) and 8.63 (1H, s, C5'-H); LRMS (FAB+): 851.2[6, $(2M+H)^+$], 579.2[10, (M+H+NBA)$^+$], 426.2[60, $(M+H)^+$], 357.2[100, (M-triazole)$^+$]; (FAB−): 849.1[16, $(2M-H)^-$], 578.1[35, $(M+NBA)^-$], 424.1 [100, $(M-H)^-$], 345.2[25, $(M-H_2NSO_2)^-$]; HRMS (FAB+) 426.05452 $C_{15}H_{16}N_5O_6S_2$ requires 426.05420.

1-[Bis-(3-bromo-4-hydroxyphenyl)methyl]-1H-[1,2,4]triazole (JRL01105, STX356)

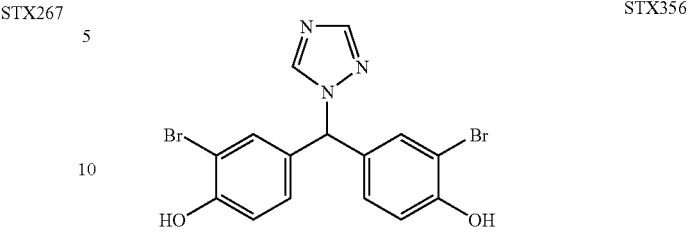

To a stirred solution of 1-[Bis-(4-hydroxyphenyl)methyl]-1H-[1,2,4]triazole (STX267, 500 mg, 1.87 mmol) in $CH_2Cl_2$/MeOH 1:1 (40 ml) at −78° C. under nitrogen, a solution of benzyltrimethylammonium tribromide (1.49 g, 3.74 mmol) in $CH_2Cl_2$/MeOH 1:1 (10 ml) was added dropwise over 45 min. The orange mixture was kept at 0° C. for 7 h and then at room temperature overnight, at which time the solution had become colorless. The reaction mixture was evaporated and the residue that obtained was dissolved in a mixture water (100 mL) and EtOAc (100 mL). The aqueous layer was separated and was further extracted with EtOAc (2×50 mL). The organic extracts were combined and washed with brine, dried ($Na_2SO_4$) and evaporated. The crude product was fractionated by flash chromatography (hexane/ethyl acetate, 1:3) and the second fraction that collected gave JRL01105 (STX356) (485 mg) as white solid at about 97% purity; $\delta_H$ (400 MHz, DMSO-$d_6$) 6.90 (1H, s, CH), 6.93 (2H, d, J 8.6 Hz), 7.03 (2H, dd, J 2.1 and 8.6 Hz), 7.30 (2H, d, J 2.1 Hz), 8.06 (1H, s), 8.56 (1H, s) and 10.45 (2H, br s, exchanged with $D_2O$, 2×OH). The main impurity was the mono-brominated derivative of STX356. A small quantity of this fraction was further purified by semi-preparative HPLC (Waters PrepLC RP18, 25×10 mm, flow rate: 10 mL/min, mobile phase: MeOH/$H_2O$, 60:40). The fraction with a retention time of 5.5 min was collected and upon evaporation gave a white solid; m.p. 198–205° C. (dec.). Found: C, 42.2, H, 2.65; N, 9.79; $C_{15}H_{11}Br_2N_3O_2$ requires C 42.38, H 2.61, N 9.89.

1-[Bis-(3-bromo-4-sulfamoyloxyphenyl)methyl]-1H-[1,2,4] triazole (JRL01109, STX566)

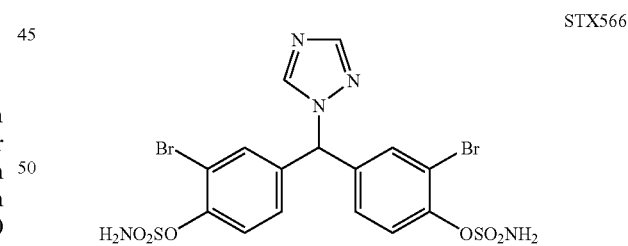

To a solution of JRL01105 (175 mg, 412 μmol) in N,N-dimethylacetamide (15 mL) at room temperature under an atmosphere of nitrogen was added sulfamoyl chloride (4.4 eq.). After stirring the reaction mixture overnight, it was diluted with ethyl acetate (30 mL) and the resulting mixture was washed with brine (50 mL, 4×20 mL), dried ($MgSO_4$), filtered and evaporated to give JRL01109 as a pale yellow residue (210 mg); m.p. 98–102° C.; $\delta_H$ (270 MHz, DMSO-$d_6$) 7.21 (1H, s, CH), 7.38 (2H, dd, J 2.1 and 8.4 Hz), 7.55 (2H, d, J 8.4 Hz), 7.66 (2H, d, J 2.1 Hz), 8.15 (1H, s), 8.32 (4H, br s) and 8.69 (1H, s); LRMS (FAB+): 584.0[10, $(M+H)^+$], 515.0(10), 391.0[100, $(M-2H_2NSO_2O)^+$]; HRMS (FAB+): 583.87219 $C_{15}H_{14}Br_2N_5O_6S_2$ requires 583.87318.

1-[Bis-(3,5-dibromo-4-sulfamoyloxyphenyl)methyl]-1H-[1,2,4]triazole (LWO02128A, STX414)

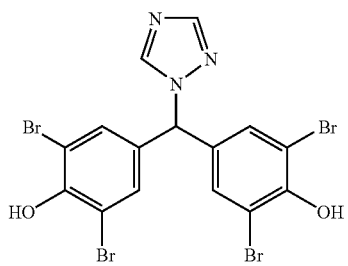

1-[Bis-(4-hydroxyphenyl)methyl]-1H-[1,2,4]triazole (450 mg, 1.684 mmol) was dissolved in hot acetic acid (100 mL). Upon cooling to ice/water temperature, potassium acetate (3.3 g, 33.67 mmol) was added to the yellow mixture followed by a solution of bromine in acetic acid dropwise (1.1 g/10 mL acetic acid, 7.5 mL, 5.061 mmol) over a period of 30 min. After stirring for another 30 min, water (20 mL) was added to the pale yellow gel/solid that resulted and the whole mixture was evaporated to give a wet pale yellow/beige residue. This crude was diluted with ethyl acetate (150 mL) and the blue green organic layer was washed with brine (4×100 mL), dried (MgSO$_4$), filtered and evaporated to give a slightly wet yellow residue (1.2 g). Upon standing in the round-bottomed flask unstoppered at room temperature overnight, a yellow/brown residue (850 mg) was obtained which upon trituration with acetone (10 mL) gave yellow deposits. After filtration and washing with more acetone, the pale yellow powder collected was air-dried to give LWO02128A (205 mg, 21%); m.p. 223–235° C. (dec.); $^1$H (400 MHz, CDCl$_3$) 6.97 (1H, s, CH), 7.40 (4H, s, Ar), 8.11 (1H, s, triazole-H), 8.64 (1H, s, triazole-H) and 10.23 (2H, br s, exchanged with D$_2$O, 2×OH); LRMS (FAB+) 584.0 [48, (M+H)$^+$], 513.0 [68, (M-triazole)$^+$], 427.4 (95), 260.1 (88), 193.2 [100, ((M-4Br-triazole)$^+$]; LRMS (FAB−) 579.8 (100, M$^-$), 455.1 (40), 276.1 (70), 195.1 (60); HRMS (FAB−) 579.73119, C$_{15}$H$_8$$^{79}$Br$_3$$^{81}$BrN$_3$O$_2$ requires 579.73295.

Synthesis of STX267 and STX268

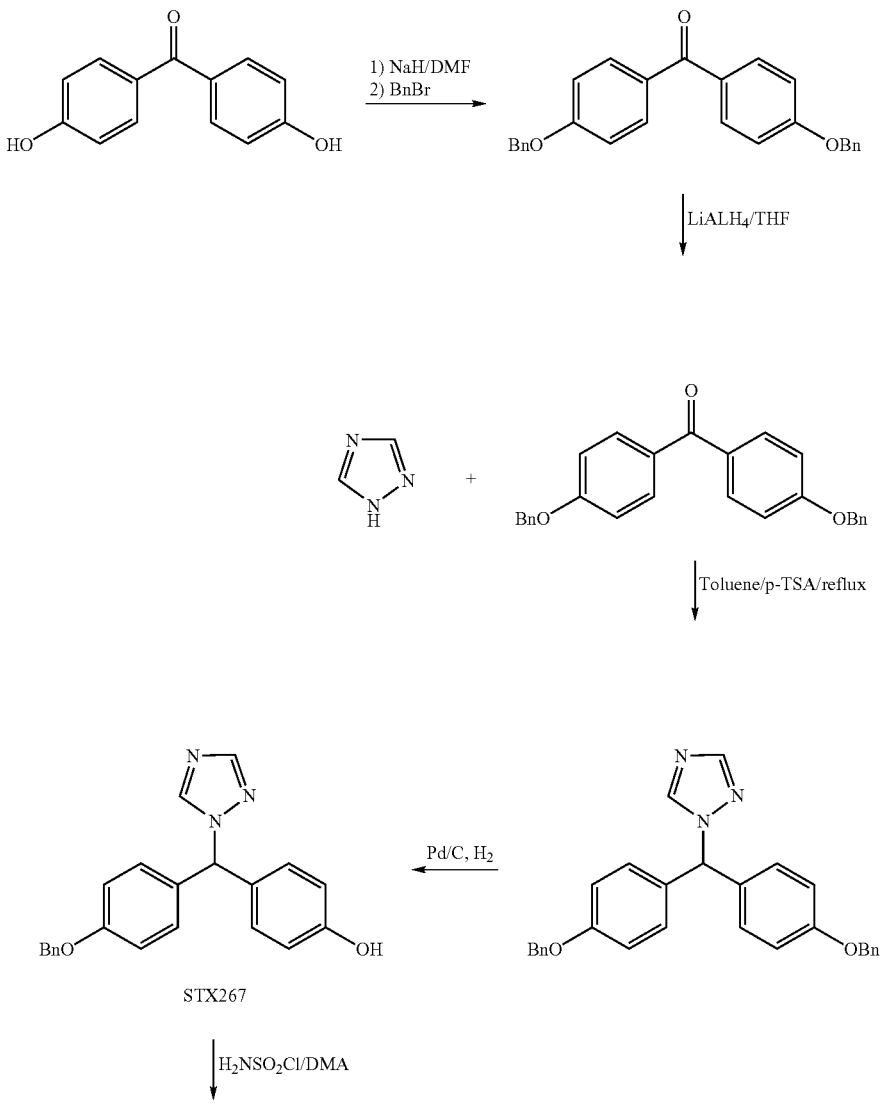

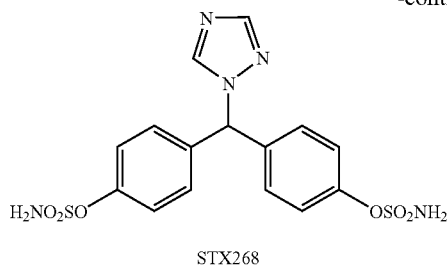

STX268

Compounds of Formula V
4-Benzyloxybenzyl chloride (LWO02011)

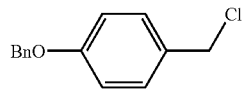

To a solution of 4-benzyloxybenzyl alcohol (5.0 g, 22.64 mmol) in dichloromethane (100 mL) at ice/water temperature was added dropwise thionyl chloride (2.5 mL, 33.96 mmol). The resulting clear pink/red solution was stirred at 0° C. for another 40 min before being evaporated to give a light green/yellow residue. After co-evaporation of the crude with dichloromethane three times, a creamy residue (5.77 g) was obtained which was dissolved in hot toluene (3 mL) and treated portionwise with hexane (60 mL). Upon standing at room temperature, LWO02011A was obtained as white crystals (2.89 g, 12.42 mmol). A second crop (LWO02011B, 1.41 g, 6.06 mmol, total yield: 81.6%) of the product was obtained from the residue of the mother liquor of the first crop after it has been recrystallised from hot hexane (20 mL); m.p. 74–80° C.; $\delta_H$ (400 MHz, DMSO-d$_6$) 4.72 (2H, s, CH$_2$Cl), 5.11 (2H, s, OCH$_2$), 7.01 (2H, m, Ar) and 7.39 (7H, m, Ar).

1-(4-Benzyloxybenzyl)-1H-[1,2,4]triazole (A) and 4-(4-Benzyloxybenzyl)-4H-[1,2,4]triazole (B) (LWO02013)

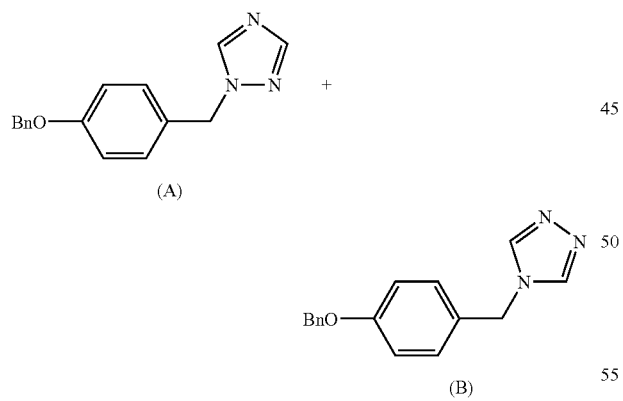

A suspension of (1H)-1,2,4-triazole (890 mg, 12.89 mmol), 4-benzyloxybenzyl chloride (2.0 g, 8.594 mmol), anhydrous potassium carbonate (1.19 g) in N,N-dimethylformamide (20 mL) was stirred at 90–95° C. for 4 h under an atmosphere of nitrogen. After cooling to room temperature, the reaction mixture was diluted with ethyl acetate (100 mL) and washed with 1M sodium hydroxide (150 mL) and then brine (4×50 mL). The organic layer was then dried (MgSO$_4$), filtered and evaporated to give a white residue (2.16 g). This crude was dissolved in hot ethyl acetate (15 mL) and hexane was added portionwise to the resulting solution. Upon cooling, LWO02013 was obtained as white crystals (1.34 g, 5.051 mmol). $^1$H NMR has suggested LWO02013 contains a 1:1 mixture of the above isomers (A and B).

4-[1,2,4]Triazol-1-ylmethylphenol (LWO02015A, STX269)

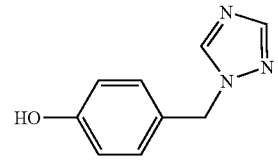

STX269

To a solution of LWO02013 (1.25 g, 4.711 mmol) in distilled THF (50 mL) was added absolute ethanol (10 mL) and Pd/C (10%, 70 mg). The resulting black suspension was stirred at room temperature for 72 h under an atmosphere of hydrogen (balloon). After removal by filtration and washings of the supported catalyst exhaustively with distilled THF, the filtrate was evaporated to give a white residue (580 mg) which was recrystallised from acetone/hexane to give LWO02015A as off white crystals (298 mg, 1.701 mmol). A second crop (LWO02015B, 77 mg, 439.5 µmol, total yield: 45.4%) of the product was obtained from the residue of the mother liquor when it was recrystallised in the same manner; m.p. 145–148° C. [Lit.[1] 143–146° C. (chloroform/Pet ether)]; $\delta_H$ (400 MHz, DMSO-d$_6$) 5.26 (2H, s, CH$_2$), 6.73 (2H, m, Ar), 7.13 (2H, m, Ar), 7.94 (1H, s, C3'-H), 8.58 (1H, s, C5'-H) and 9.50 (1H, s, exchanged with D$_2$O, OH); LRMS (FAB+): 351.2[10, (2M+H)$^+$], 176.2[100, (M+H)$^+$], 107.1 [47, (M-Triazole)$^+$], (FAB–): 481.3[30, (M+2NBA)$^-$], 349.2 [27, (2M–H)$^-$], 328.2[100, (M+NBA)$^-$], 221.2(23), 174.2 [100, (M–H)$^-$];

HRMS (FAB+) 176.08183 C$_9$H$_{10}$N$_3$O requires 176.08239. Found: C 61.6, H 5.11, N 23.6; C$_9$H$_9$N$_3$O requires C, 61.70; H, 5.18; N, 23.99.

[1] Abdreubu et. Al. (1989) Farmaco 44(9) 831–842.

Sulfamic Acid 4-[1,2,4]triazol-1-ylmethylphenyl ester (LWO02017A, STX270)

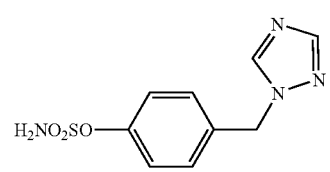

STX270

To a solution of LWO02015A (150 mg, 856.2 µmol) in distilled THF (10 mL) at 0° C. was added sodium hydride (60% in mineral oil, 36 mg, 899 µmol). After stirring for 10 min at which no more evolution of hydrogen was observed, sulfamoyl chloride in toluene (ca. 0.68M, 2.5 mL) was added under an atmosphere of nitrogen and the resulting thin white suspension was stirred at room temperature for 3 h. The reaction mixture was then diluted with ethyl acetate (70 mL) and washed with brine (100 mL, 3×50 mL). The organic layer that separated was dried (MgSO$_4$), filtered and evaporated to give a white residue (144 mg) which was recrystallised from acetone/hexane to give LWO02017A as white crystals (71 mg, 279.2 μmol, 32.6%); $v_{max}$ (KBr) 3352, 3127, 2880, 2646, 1509, 1369, 1183, 1158 cm$^{-1}$; $\delta_H$ (400 MHz, DMSO-d$_6$) 5.44 (2H, s, CH$_2$), 7.27 (2H, AA'BB'), 7.38 (2H, AA'BB'), 8.0 (~2.7H, m, reduced to one proton, singlet, after D$_2$O exchange, C3'-H and H$_2$NSO$_2$) and 8.68 (1H, s, C5'-H); Found: C, 42.6; H, 4.01; N, 21.7; C$_9$H$_{10}$N$_4$O$_3$S requires C, 42.51; H, 3.96; N, 22.03.

Synthesis of STX269 and STX270

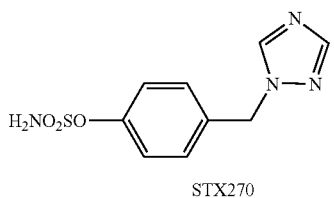

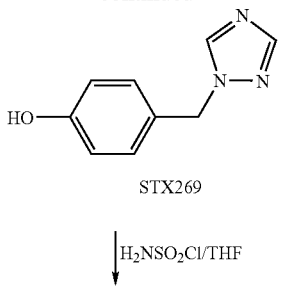

Biological Data

Compounds were tested for aromatase and steroid sulphatase inhibition in accordance with the above Protocols. Each compound in accordance with the present invention is found to inhibit steroid sulphatase and aromatase.

The following in vitro data were recorded.

| Compound | Structure | AROMATASE IC$_{50}$ (nM) | SULPHATASE IC$_{50}$ (nM) |
|---|---|---|---|
| H340F1 | 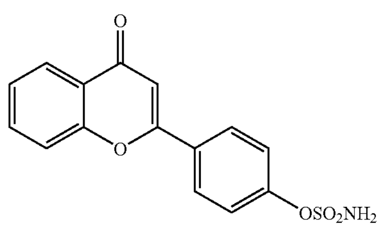 | (59% inhibition at 10 μM) IC$_{50}$ > 10 μM | 10 μM |
| H342F1 | 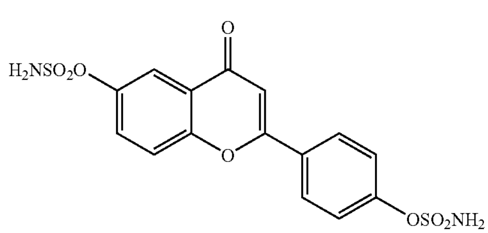 | (No inhibition seen) | 90 |

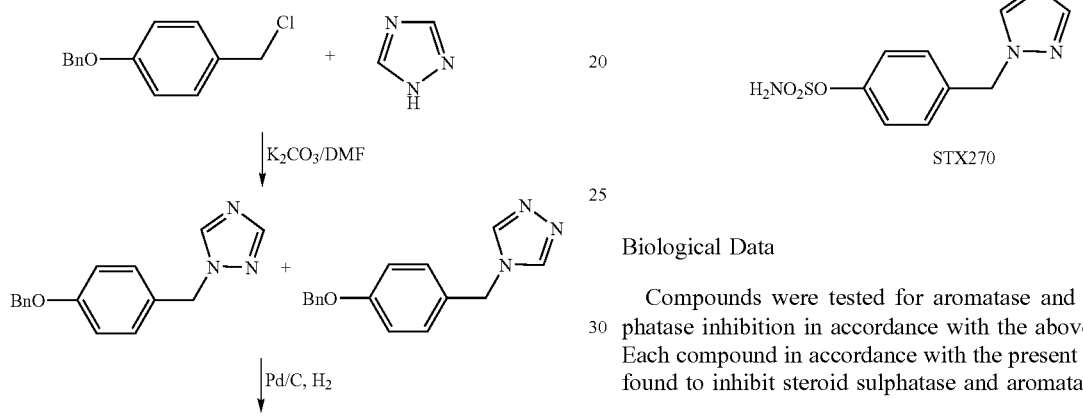

-continued

| Compound | Structure | AROMATASE IC$_{50}$ (nM) | SULPHATASE IC$_{50}$ (nM) |
| --- | --- | --- | --- |
| STX258 | 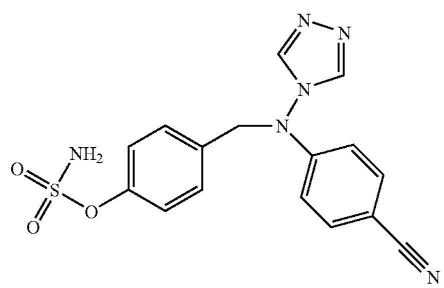 | 100 | 227 |
| STX265 | 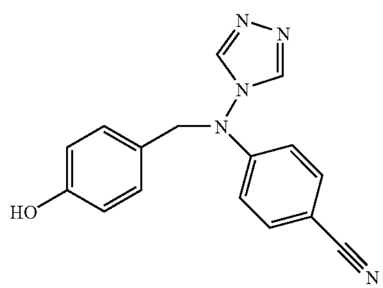 | 23 | n.d. |
| STX268 | 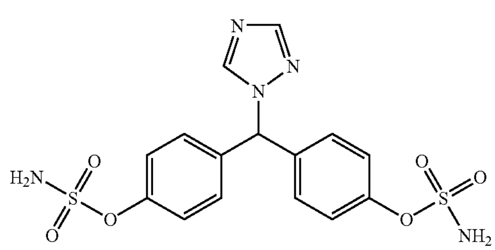 | 3044 | >10000 (31% at 10 μM) |
| STX269 | 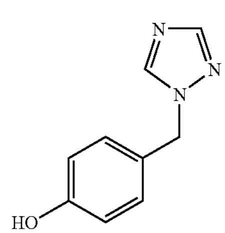 | 41% inhibition at 10 μM | n.d. |
| STX270 | 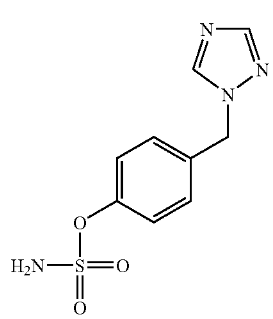 | 62% inhibition at 10 μM | 14% inhibition at 10 μM in placental microsomes |

-continued

| Compound | Structure | AROMATASE IC$_{50}$ (nM) | SULPHATASE IC$_{50}$ (nM) |
|---|---|---|---|
| STX273 | 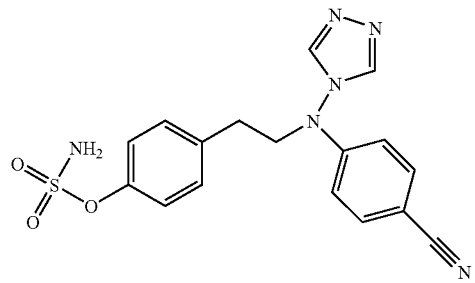 | 69% inhibition at 0.1 µM | n.d. |
| STX287 | 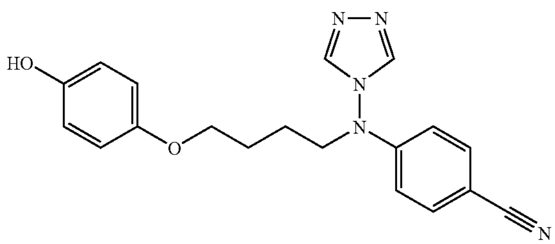 | 4.4 | n.d. |
| STX288 | 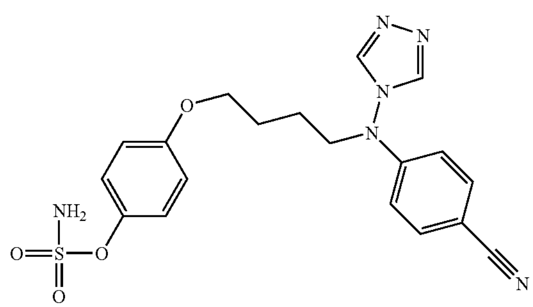 | 31 | >10 µM |
| STX290 | 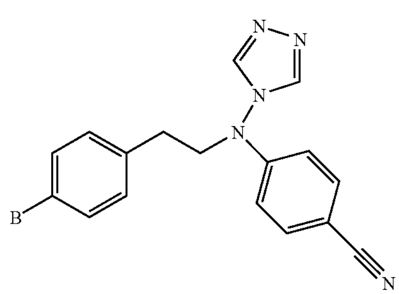 | 1.3 | n.d. |
| STX291 | 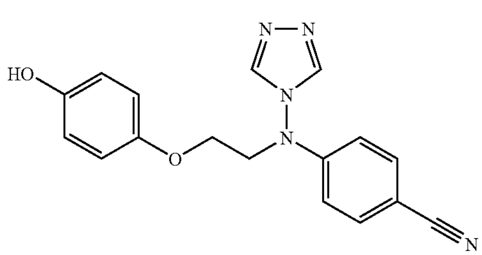 | 26 | n.d. |

| Compound | Structure | AROMATASE IC$_{50}$ (nM) | SULPHATASE IC$_{50}$ (nM) |
|---|---|---|---|
| STX292 | 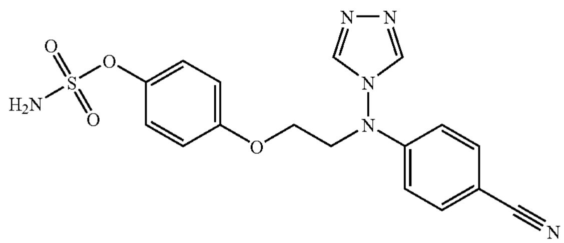 | 767 | >10 μM |
| STX300 | 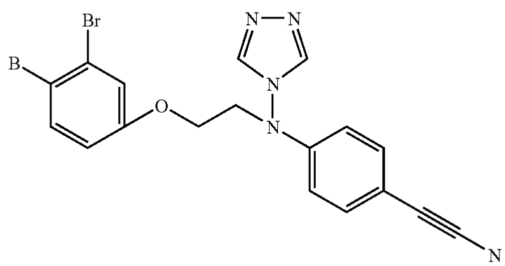 | 1.6 | n.d. |
| STX301 | 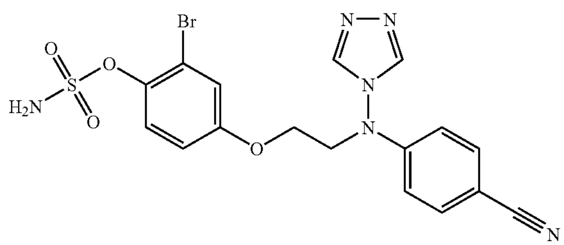 | 119 | n.d. |
| STX310 | 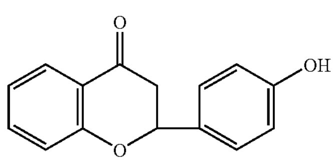 | (42% inhibition at 10 μM) IC$_{50}$ > 10 μM | n.d. |
| STX566 | 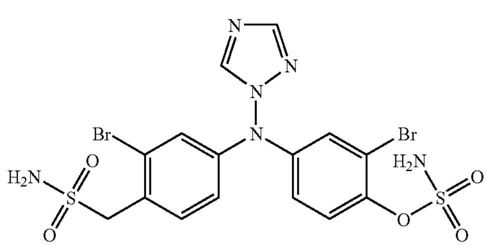 | 4.9 | 476 |
| STX597 | 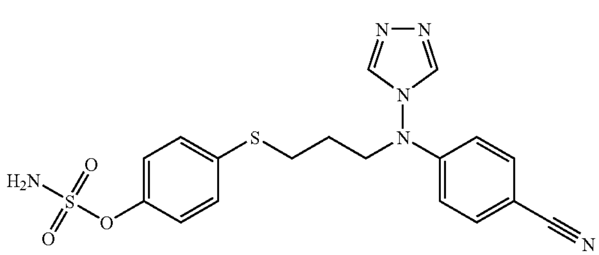 | 0.51 | >10000 |

-continued
| Compound | Structure | AROMATASE IC$_{50}$ (nM) | SULPHATASE IC$_{50}$ (nM) |
|---|---|---|---|
| STX636 | 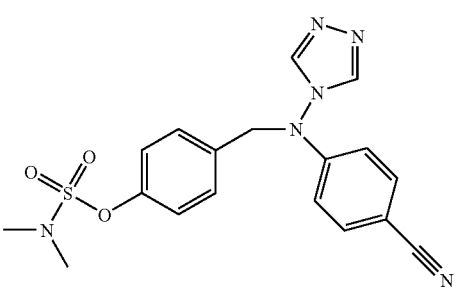 | 9 | >10000 (6.6% at 10 μM) |
| STX681 | 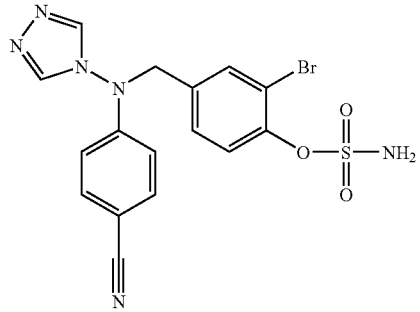 | 0.82 | 39 |
| STX694 | 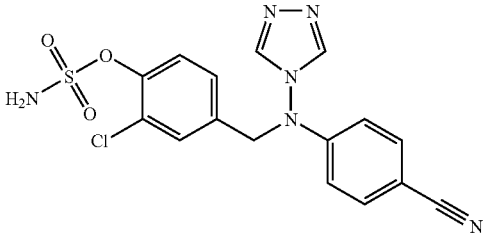 | 2.3 | 20 |
| STX699 | 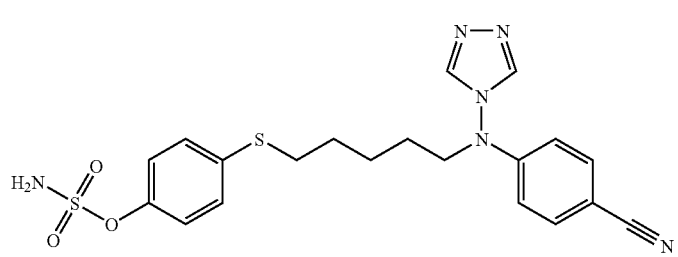 | 0.73 | 1000 |
| STX700 | 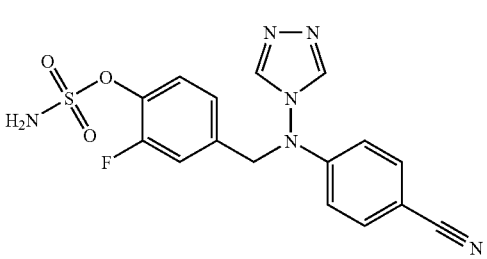 | 12 | 40 |

| Compound | Structure | AROMATASE IC$_{50}$ (nM) | SULPHATASE IC$_{50}$ (nM) |
|---|---|---|---|
| STX732 | 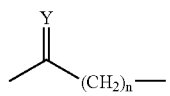 | 19 | >10000 (12% at 10 μM) |

In vivo data were recorded using the above described aromatase and STS animals assays. The relevant compounds were administered and for each animal both aromatase and STS activities were determined. The data are shown in FIGS. 3 and 4.

All publications and patents and patent applications mentioned in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

What is claimed is:

1. A compound of Formula IIId

Formula IIId

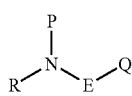

wherein E is an optional linker group;
  wherein R is a 5, 6, or 7-membered carbocyclic ring system;
  wherein P is 4H-1,2,4-triazole and;
  wherein Q is a polycyclic ring system and
  at least Q comprises a sulphamate group.

2. A compound according to claim 1 wherein P, is 4H-1,2,4-triazole and Q and R are independently selected from or comprise carbocyclic ring systems selected from the group consisting of aryl groups, cycloalkyl groups, substituted and unsubstituted aromatic rings, and substituted and unsubstituted benzyl rings.

3. A compound according to claim 2 wherein P is 4H-1,2,4-triazole and Q and R are independently selected from or comprise carbocyclic ring systems consisting of substituted and unsubstituted benzyl rings.

4. A compound according to claim 1 wherein E is present.

5. A compound according to claim 1, wherein E is selected from C=O and hydrocarbyl groups.

6. A compound according to claim 1, wherein E is selected from C=O and linear or branched hydrocarbon groups having a carbon chain of from 1 to 6 carbon atoms and a group of the formula $$\underset{(CH_2)_n}{\overset{Y}{\bigtriangleup}}-$$

wherein n is 1 to 6 and Y=Oxygen, Sulphur or CH$_2$.

7. A compound according to claim 2, wherein Q and R are independently selected from or comprise an aromatic ring.

8. A compound according to claim 2, wherein Q and R are independently selected from or comprise substituted and unsubstituted aromatic rings.

9. A compound according to claim 1, wherein P, Q and R are independently selected from or comprise ring systems comprising from 3 to 10 members.

10. A compound according to claim 1, wherein Q is a polycyclic ring systems comprising carbon and optionally one or more hetero atoms.

11. A compound according to claim 1, wherein Q is a polycyclic ring systems comprising carbon and optionally one, two or three hetero atoms.

12. A compound according to claim 1, wherein Q is a polycyclic ring systems comprising carbon and one or more hetero atoms.

13. A compound according to claim 1, wherein Q is a polycyclic ring systems comprising carbon and one or more hetero atoms selected from Nitrogen, Sulphur and Oxygen.

14. A compound according to claim 1 wherein R is substituted by a halogen.

* * * * *